(12) United States Patent
Schneider et al.

(10) Patent No.: US 12,247,045 B2
(45) Date of Patent: Mar. 11, 2025

(54) MAP4K4 INHIBITORS

(71) Applicant: Imperial College Innovations Limited, London (GB)

(72) Inventors: Michael Schneider, London (GB); Gary Newton, Saffron Walden (GB); Kathryn Chapman, Saffron Walden (GB); Ashley Jarvis, Abingdon (GB); Rehan Aqil, Saffron Walden (GB); Tifelle Reisinger, Saffron Walden (GB); Melanie Bayford, Saffron Walden (GB); Nicholas Chapman, Saffron Walden (GB); Nicholas Martin, Saffron Walden (GB); David Middlemiss, Heartfordshire (GB)

(73) Assignee: Imperial College Innovations Limited, London (GB)

( * ) Notice: Subject to any disclaimer, the term of this patent is extended or adjusted under 35 U.S.C. 154(b) by 755 days.

(21) Appl. No.: 17/298,870

(22) PCT Filed: Dec. 4, 2019

(86) PCT No.: PCT/GB2019/053429
§ 371 (c)(1),
(2) Date: Jun. 1, 2021

(87) PCT Pub. No.: WO2020/115481
PCT Pub. Date: Jun. 11, 2020

(65) Prior Publication Data
US 2023/0055250 A1 Feb. 23, 2023

(30) Foreign Application Priority Data
Dec. 5, 2018 (GB) ..................... 1819839

(51) Int. Cl.
*C07F 9/6561* (2006.01)
*C07D 471/04* (2006.01)
*C07D 487/04* (2006.01)

(52) U.S. Cl.
CPC .......... *C07F 9/6561* (2013.01); *C07D 471/04* (2013.01); *C07D 487/04* (2013.01)

(58) Field of Classification Search
None
See application file for complete search history.

(56) References Cited

U.S. PATENT DOCUMENTS 11,795,169 B2 * 10/2023 Schneider ............. C07F 9/6561
2020/0339583 A1 10/2020 Schneider et al.
(Continued)

FOREIGN PATENT DOCUMENTS

EP 0482804 4/1992
WO WO-1997/049706 12/1997
(Continued)

OTHER PUBLICATIONS

Tintori et al., European Journal of Medicinal Chemistry, vol. 44, Issue 3, 2009, p. 990-1000 (Year: 2009).*
(Continued)

*Primary Examiner* — Jeffrey S Lundgren
*Assistant Examiner* — Anthony Joseph Seitz
(74) *Attorney, Agent, or Firm* — Mintz, Levin, Cohn, Ferris, Glovsky and Popeo, P.C.

(57) ABSTRACT

This invention relates to compounds that may be useful as inhibitors of Mitogen-activated Protein Kinase Kinase Kinase Kinase-4 (MAP4K4). The invention also relates to the use these compounds, for example in a method of treatment of cardiac conditions. In particular, the present invention relates to compounds of formula (I):
(Continued)

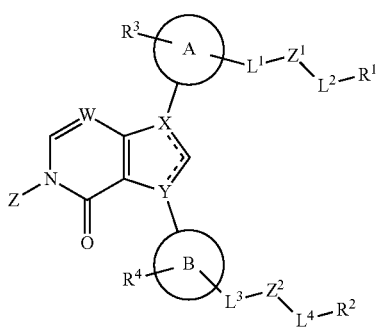

(I)

30 Claims, 19 Drawing Sheets

(56) References Cited

U.S. PATENT DOCUMENTS

| | | | |
|---|---|---|---|
| 2023/0055250 A1* | 2/2023 | Schneider | ............ A61P 9/00 |
| 2024/0199621 A1 | 6/2024 | Schneider et al. | |

FOREIGN PATENT DOCUMENTS

| | | | | |
|---|---|---|---|---|
| WO | WO-9749706 A1 * | 12/1997 | ......... | C07D 487/04 |
| WO | WO-2013/113669 | 8/2013 | | |
| WO | WO-2013/180265 | 12/2013 | | |
| WO | WO-2019/073253 | 4/2019 | | |

OTHER PUBLICATIONS

St-Gallay, S. A., et al. "A high-throughput screening triage workflow to authenticate a novel series of PFKFB3 inhibitors," SLAS Discovery: Advancing Life Sciences R&D, 2018, 23(1), 11-22.

Altmann et al., "N7-Substituted-5-aryl-pyrrolo[2,3-d]pyrimidines Represent a Versatile Class; of Potent Inhibitors of the Tyrosine Kinase c-Src," Mini Reviews in Medicinal Chemistry, 2, pp. 201-208 (2002).

Augustine and Agrawal, "Syntheses of 1,3-disubstituted-5a-hydropyrrolo[2,3-d]quinazolino[3,2-e]pyrimidin-6(5H)-ones: A comparison of conventional and microwave technique," Indian Journal of Chemistry, 44B, pp. 1653-1658 (2005).

Chow et al., "Human Induced Pluripotent Stem Cell-Derived Cardiomyocyte Encapsulating Bioactive Hydrogels Improve Rat Heart Function Post Myocardial Infarction," Stem Cell Reports, 9, pp. 1415-1422 (2017).

Dave and Desai, "Synthesis and Reactions of Fluoroaryl Substituted 2-Amino-3-cyanopyrroles and Pyrrolo[2,3-d]pyrimidines," J. Heterocyclic Chem., 36, pp. 729-733 (1999).

Dave and Patel, "Synthesis of 5,7-Disubstituted 7H-Pyrrolo[2,3-d]Pyrimidin-4(3H)-ones and Their N-Alkylation's under Phase Transfer Conditions," J. Heterocyclic Chem., 51, pp. 943-947 (2014).

Desai, "Synthesis of Fused Tetrazolo[1,5-c] pyrrolo[3,2-e]pyrimidines and Their Reductive Conversion to New 4-Aminopyrrolo [2,3-d]pyrimidines," Synthetic Communications, 36, pp. 2169-2182 (2006).

El-Bayouki et al., "Pyrrolo[2,3-d]Pyrimidines. I: Synthesis of Novel Pyrrolo[2,3-d]pyrimidine Derivatives With Anti-microbial Activity," Journal of Chemical Research. Minipr, Scientific Reviews, 8(1) pp. 1901-1912 (1995).

El-Bayouki et al., "Synthesis of new pyrrole and pyrrolo[2,3-d]pyrimidine derivatives of potential antioxidant activity," Collect. Czech. Chem. Commun., 75(8), pp. 813-834 (2010).

Ghorab et al., "Computer-Based Ligand Design and Synthesis of Some New Sulfonamides Bearing Pyrrole or Pyrrolopyrimidine Moieties Having Potential Antitumor and Radioprotective Activities," Phosphorus, Sulfur, and Silicon and the Related Elements, 183(1), pp. 90-104 (2008).

Ghorab et al., "Novel Antitumor and Radioprotective Sulfonamides Containing Pyrrolo[2,3-d]pyrimidines," ArzneimForschDrugRes, 56(6), pp. 405-413 (2006).

Ghorab et al., "Synthesis and Molecular Docking of Some Novel Anticancer Sulfonamides Carrying a Biologically Active Pyrrole and Pyrrolopyrimidine Moieties," Acta Poloniae Pharmaceutica—Drug Research, 71(4) pp. 603-614 (2014).

Ghorab et al., "Synthesis of novel pyrrole and pyrrolo[2,3-d]pyrimidine derivatives bearing sulfonamide moiety for evaluation as anticancer and radiosensitizing agents," Bioorganic & Medicinal Chemistry Letters, 20, pp. 6316-6320 (2010).

Hassan et al., "Heteroaromatization with Sulfonamido Phenyl Ethanone, Part I: Synthesis of Novel Pyrrolo [2,3-D]Pyrimidine and Pyrrolo[3,2-E] [1,2,4]Triazolo[1,5-C]Pyrimidine Derivatives Containing Dimethylsulfonamide Moiety," Phosphorus, Sulfur, and Silicon, 184(2), pp. 291-308 (2009).

Hussein et al., "Synthesis and Kinetic Testing of Tetrahydropyrimidine-2-thione and Pyrrole Derivatives as Inhibitors of the Metallo-β-lactamase from *Klebsiella pneumonia* and *Pseudomonas aeruginosa*," Chem. Biol. Drug Des., 80, pp. 500-515 (2012).

International Search Report and Written Opinion for International Patent Application No. PCT/GB2018/052936, mailed Dec. 19, 2018 (17 pages).

International Search Report and Written Opinion for International Patent Application No. PCT/GB2019/053429, mailed Jun. 11, 2020 (8 pages).

Mohamed et al., "Synthesis and kinetic testing of new inhibitors for a metallo-β-lactamase from *Klebsiella pneumonia* and *Pseudomonas aeruginosa*," European Journal of Medicinal Chemistry, 46, pp. 6075-6082 (2011).

Sarg et al., "Synthesis of Pyrroles and Condensed Pyrroles as Anti-Inflammatory Agents with Multiple Activities and Their Molecular Docking Study," Open Journal of Medicinal Chemistry, 5, pp. 49-96 (2015).

Tintori et al., "Docking, 3D-QSAR studies and in silico ADME prediction on c-Src tyrosine kinase inhibitors," European Journal of Medicinal Chemistry, 44, pp. 990-1000 (2009).

Virbasius and Czech, "Map4k4 Signaling Nodes in Metabolic and Cardiovascular Diseases," Trends in Endocrinology & Metabolism, 27(7), pp. 484-492 (2016).

Chemistry Abstracts Registry No. 1348286-95-2, Indexed in the Registry file on STN CAS Online on Dec. 4, 2011.

Missbach Martin et al: "Substituted 5,7-diphenyl-pyrrolo[2,3d]pyrimidines: potent inhibitors of the tyrosine kinase c-Src", Bioorganic & Medicinal Chemistry Letters, vol. 10, No. 9, Jun. 5, 2017, pp. 945-949.

Ndubaku et al: "Structure-based design of GNE-495, a Potent and Selective MAP4K4 inhibitor with efficacy in retinal angiogenesis", ACS Med. Chem. Lett., 2015, 6, 913-918.

Wang et al: "Fragment-based identification and optimization of a class potent pyrrolo [2,1-f][1,2,4]triazine MAP4K4 inhibitors", Bioorganic & Medicinal Chemistry Letters, 2014, 24, 4546-4552.

Chemical Abstracts Registry No. 1348789-28-5, Indexed in the Registry file on STN CAS Online on Dec. 5, 2011, 1 page.

* cited by examiner

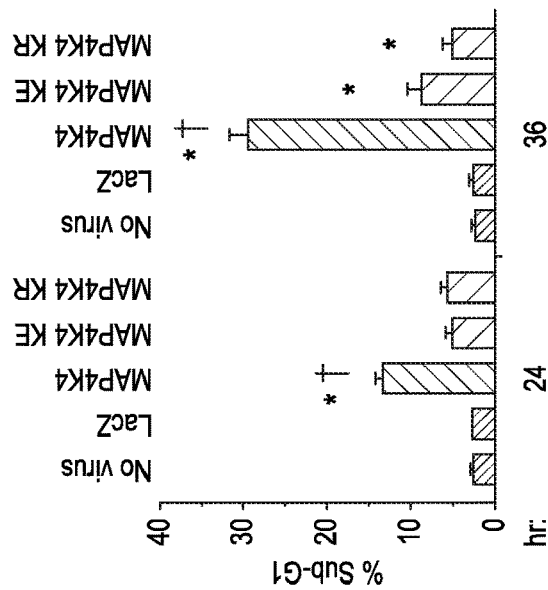
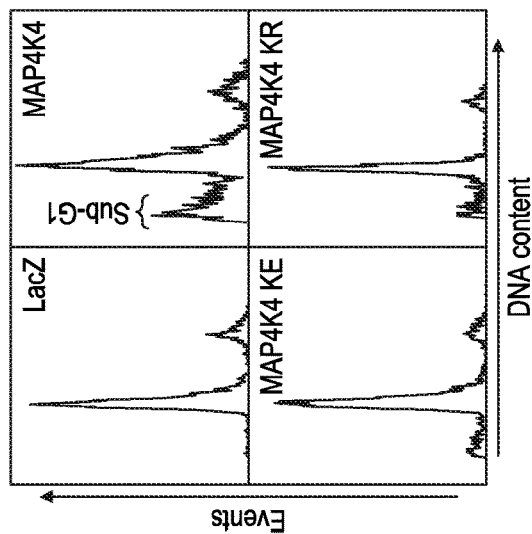
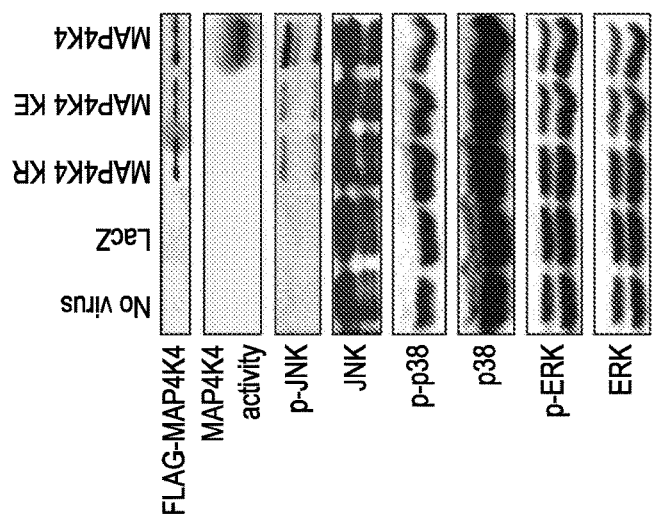
FIG. 2A
FIG. 2B

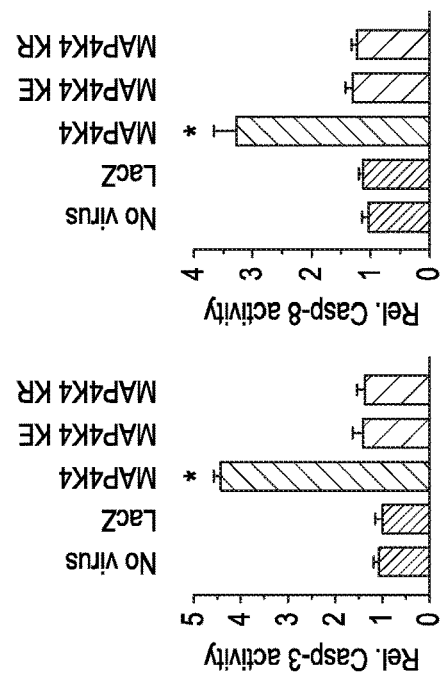
FIG. 2E
FIG. 2D
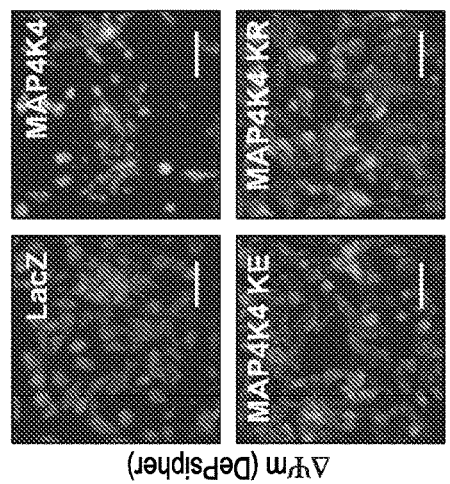
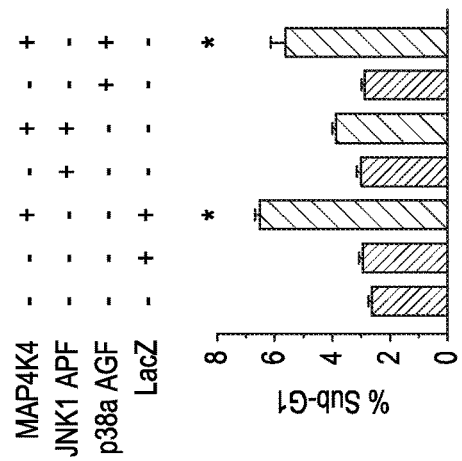
FIG. 2C

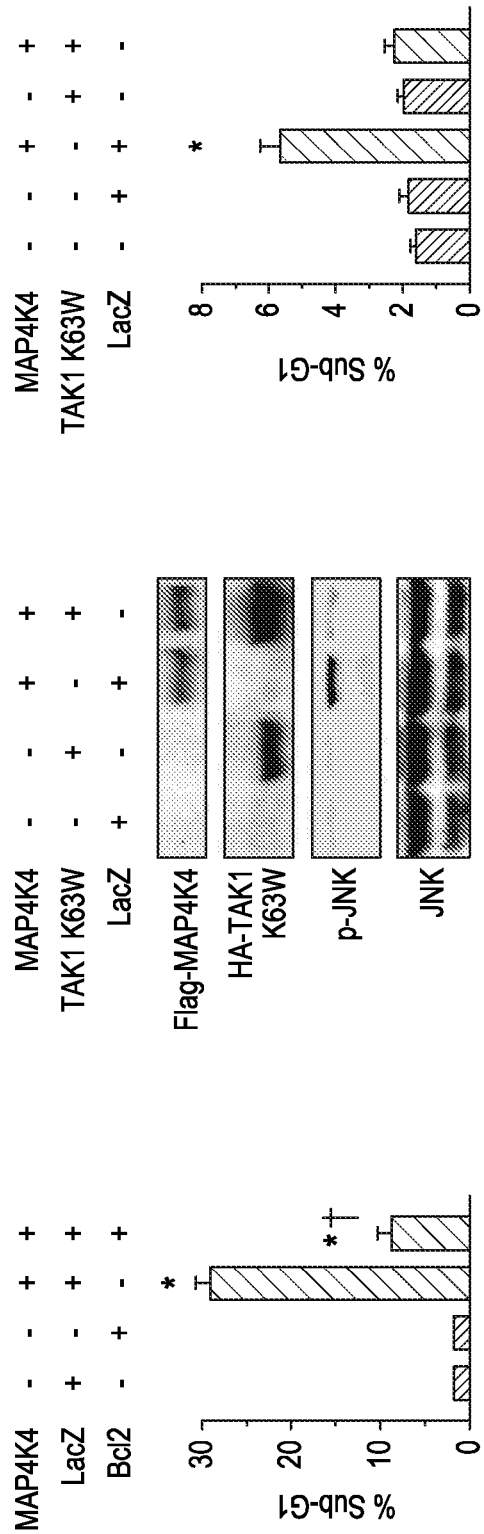

MAP4K4 INHIBITORS

This application is the national stage entry of PCT Application No. PCT/GB2019/053429, filed Dec. 4, 2019, which claims priority to British Application No. 1819839.0, filed Dec. 5, 2018, each of which is incorporated herein in its entirety for all purposes.

This invention relates to compounds that may be useful as inhibitors of Mitogen-activated Protein Kinase Kinase Kinase Kinase-4 (MAP4K4). The invention also relates to the use of these compounds, for example in a method of treatment. There are also provided processes for producing compounds of the present invention and method of their use. In particular, the present invention relates to compounds of formula (I).

BACKGROUND

Heart disease remains the single commonest cause of death and disability worldwide and is projected to increase as the population ages, its socio-economic burden consequently rising for the foreseeable future. Cardiac muscle cell death is an instrumental component of both acute ischemic injury and also chronic heart failure. In preclinical models, the molecular and genetic dissection of cardiac cell death suggests potential nodal control points, among them, signaling pathways controlled by mitogen-activated protein kinases (MAPKs), especially Jun N-terminal Kinase (JNK) and p38 MAPK (Dorn, 2009; Fiedler et al., 2014; Rose et al., 2010; Whelan et al., 2010). Directly suppressing cardiomyocyte death is logical; however, no clinical counter-measures target the relevant intracellular pathways. Furthermore, to date few human trials for heart disease seek to enhance cardiomyocyte survival directly, and several promising strategies have failed (Hausenloy and Yellon, 2015; Heusch, 2013; Newby et al., 2014a; Piot et al., 2008).

Human induced pluripotent stem cell-derived cardiomyocytes (hiPSC-CM) have already gained wide acceptance as predictive in the case of cardiotoxicity and patient-specific pathways, and provide a potentially transformative means to enhance target validation and improve cardiac drug discovery (Beilin et al., 2012; Blinova et al., 2017; Mathur et al., 2015; Matsa et al., 2014).

Because the "terminal" MAPKs p38 and JNK receive inputs from multiple signals, both protective and adverse, it is logical to consider targeting specific proximal kinases that might couple these MAPKs to cell death more selectively. MAP kinase kinase kinase kinases (MAP4Ks) are the most proximal protein kinases in the MAPK superfamily. MAP4K4 (HPK/GCK-like Kinase [HGK]; NCK-Interacting Kinase [NIK]) is a serine-threonine kinase related to Ste20 in *S. cerevisiae*. Like their yeast orthologue, the mammalian Ste20 kinases control cell motility, fate, proliferation and stress responses (Dan et al., 2001). With the cloning of human MAP4K4 came the first such evidence, namely, a key role coupling pro-inflammatory cytokines to JNK (Yao et al., 1999). MAP4K4 is now appreciated as a mediator of inflammation, cytoskeletal function, and, notably, cell death, with well-established contributions to cancer and diabetes (Chen et al., 2014; Lee et al., 2017a; Miled et al., 2005; Vitorino et al., 2015; Yang et al., 2013; Yue et al., 2014).

A pathobiological role for MAP4K4 has been suggested by its engagement of transforming growth factor-β-activated kinase-1 (TAK1/MAP3K7), JNK (Yao et al., 1999) and p38 MAPK (Zohn et al., 2006), these downstream MAPKs all having reported pro-death functions in cardiac muscle cells (Fiedler et al., 2014; Jacquet et al., 2008; Rose et al., 2010; Zhang et al., 2000). By contrast, the Raf-MEK-ERK pathway is cardioprotective (Fiedler et al., 2014; Lips et al., 2004; Rose et al., 2010).

Mitogen-activated Protein Kinase Kinase Kinase Kinase-4 (MAP4K4) is activated in failing human hearts and relevant rodent models. Using human induced pluripotent stem cell-derived cardiomyocytes (hiPSC-CM), we demonstrate that death induced by oxidative stress requires MAP4K4. Notably, gene silencing by means of MAP4K4 short hairpin RNA confers protection to hiPSC-CMs. Thus, we demonstrate MAP4K4 to be a relevant target in cardiac injury.

Certain embodiments of the present invention aim to provide pharmacological MAP4K4 inhibitors. An aim of the present invention is to rescue cell survival, mitochondrial function, and calcium cycling in cardiomyocytes. The present invention specifically aims to suppress human cardiac muscle cell death. The present invention further has the aim of reducing injury during "heart attacks" (ischemic injury or ischemia-reperfusion injury) for example in the adult human heart. Certain embodiments of the present invention provide selective modulation of MAP4K4 over other kinases and biological targets. In certain embodiments, the compounds of the present invention provide selectivity towards MAP4K4 over the kinases listed in Table 42, presented in the experimental section. Certain embodiments seek to achieve one or more of the aims discussed herein.

The present invention provides pharmacological inhibitors of MAP4K4, and demonstrates that inhibiting MAP4K4 effectively protects both the intact adult myocardium and, specifically, cardiomyocytes from injury. Further suggested functions of MAP4K4 in disease and, hence, therapeutic indications for a MAP4K4 inhibitor, include neurodegeneration and skeletal muscle disorders (Loh et al., 2008; Yang et al., 2013; Schroder et al., 2015; Wang et al., 2013).

BRIEF SUMMARY OF THE DISCLOSURE

In accordance with the present inventions there is provided a compound of formula (I) or a pharmaceutically acceptable salt thereof:

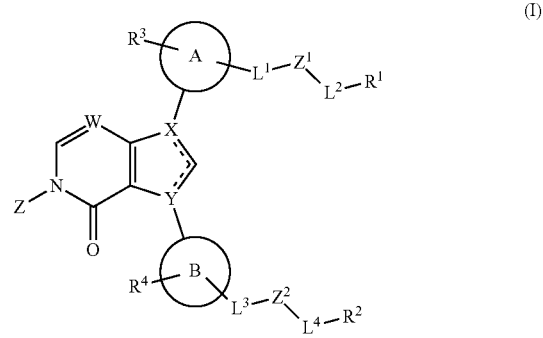

wherein
W is independently selected from N or C;
Z is independently selected from H or —CH$_2$OP(=O)(OH)$_2$;
either X is N and Y is C, or Y is N and X is C;
ring A is independently selected from an aryl and a 5 to 10 membered heterocyclic ring containing 1, 2 or 3 heteroatoms selected from N, O and S;

ring B is independently selected from an aryl and a 5 or 6 membered heterocyclic ring containing 1, 2 or 3 heteroatoms selected from N, O and S;

provided that ring A and ring B of the compound of formula (I) are not both phenyl;

$L^1$ and $L^3$ are independently selected from a bond, —$(CR^aR^b)_m$—, —$O(CR^aR^b)_m$— or —$NH(CR^aR^b)_m$—, wherein m is at each occurrence independently selected from 1, 2, 3, or 4;

$Z^1$ is a bond, —$NR^{5a}$—, —O—, —C(O)—, —$SO_2$—, —$SO_2NR^{5a}$—, —$NR^{5a}SO_2$—, —$C(O)NR^{5a}$—, —$NR^{5a}C(O)$—, —C(O)O—, or —$NR^{5a}C(O)NR^{5a}$—;

$Z^2$ is a bond, —$NR^{5b}$—, —O—, —C(O)—, —$SO_2$—, —$SO_2NR^{5a}$—, —$NR^{5a}SO_2$—, —$C(O)NR^{5a}$—, —$NR^{5b}C(O)$—, or —C(O)O—;

$L^2$ and $L^4$ are independently either a bond or —$(CR^cR^d)_n$—, wherein n is at each occurrence independently selected from 1, 2, 3, or 4;

$R^1$ is selected from H, halo, $C_{1-6}$ alkyl, $C_{2-6}$ alkenyl, $C_{1-6}$ haloalkyl, —$NR^{6a}R^{6b}$, —$OR^{6a}$, OP(=O)(OH)$_2$, —C(O)$R^{6a}$, 5 or 6 membered heteroaryl rings, or 3 to 8 membered heterocycloalkyl ring systems, wherein the heteroaryl and heterocycloalkyl rings are unsubstituted or substituted with 1 or 2 groups selected from: $C_{1-6}$ alkyl, oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —C(O)$R^7$, and —$NR^8C(O)R^7$;

$R^2$ is selected from H, halo, $C_{1-6}$ alkyl, $C_{2-6}$ alkenyl, $C_{1-6}$ haloalkyl, —$NR^{6a}R^{6b}$, —$OR^{6a}$, OP(=O)(OH)$_2$, —C(O)$R^{6a}$, —$NR^{5b}C(O)O$—$C_{1-6}$ alkyl, phenyl, 5 or 6 membered heteroaryl rings, 3 to 8 membered cycloalkyl rings, or 3 to 8 membered heterocycloalkyl ring systems, wherein the phenyl, heteroaryl, cycloalkyl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, C(O)$R^{6a}$, —C(O)$OR^g$, and —$NR^8C(O)R^7$;

$R^3$ and $R^4$ are independently selected from H, halo, —CN and $C_{1-6}$ alkyl;

$R^{5a}$ and $R^{5b}$ are independently selected at each occurrence, from: H, $C_{1-6}$ alkyl, or C3-6 cycloalkyl;

$R^{6a}$ and $R^{6b}$ are, independently selected at each occurrence, from: H, $C_{1-6}$ alkyl, $C_{1-6}$ alkyl substituted with —$OR^e$, $C_{1-6}$ alkyl substituted with —$NR^eR^f$, and C3-6 cycloalkyl;

$R^7$ is selected from H, —$OR^g$, $C_{1-6}$ alkyl and C3-6 cycloalkyl;

$R^8$ is selected from H and $C_{1-6}$ alkyl;

$R^a$, $R^b$, $R^c$ and $R^d$ are, at each occurrence, independently selected from: H, halo, $C_{1-6}$ alkyl, and —$OR^h$, or $R^a$ and $R^b$ or $R^c$ and $R^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and $R^e$, $R^f$, $R^g$ and $R^h$ are each independently selected at each occurrence from H or $C_{1-6}$ alkyl.

The dotted bonds in formula (I) represent the possibility for a double bond to be present. As the skilled person will appreciate both dotted bonds cannot represent a double bond at the same time; one dotted bond will be a double bond whilst the other bill be a single bond. The double bond will originate from X or Y when X or Y is C. For the avoidance of doubt, compounds of formula (I) may be compounds of formulae (Ia) or (Ib) which demonstrate the two possible configurations for the dotted bonds in formula (I):

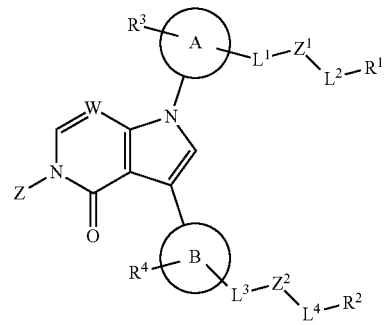

(Ia)

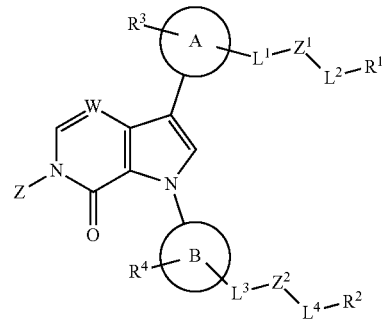

(Ib)

In some embodiments the compound of formula (I) is not the following compound:

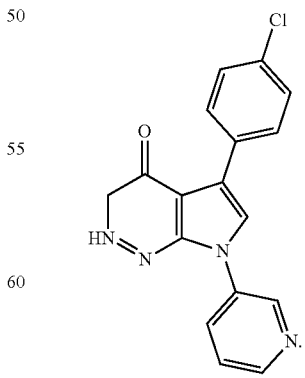

In some embodiments W is C. In some embodiments W is N.

In some embodiments W is N and the compound of formula (I) is a compound according to formula (Ic) and (Id):

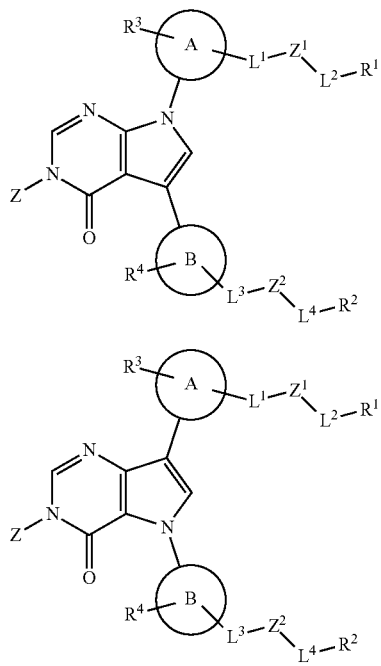

When W is C the atom represented by W is C and to comply with valence the C atom is substituted by a H atom. Thus, where W is C the compound of formula (I) is a compound according to formula (Ie) and (If):

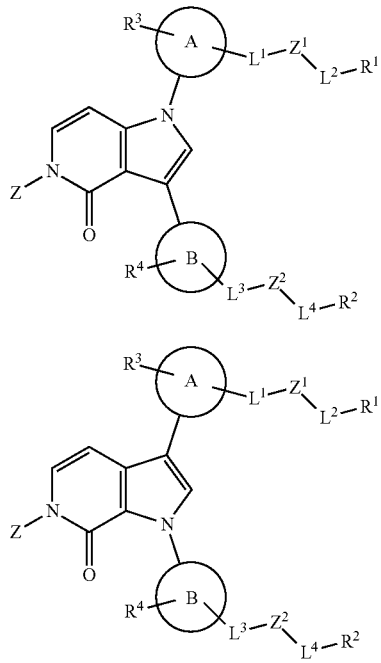

In some embodiments Z is —CH$_2$OP(=O)(OH)$_2$. In embodiments, Z is H.

In embodiments ring A is independently selected from phenyl and a 5 to 10 membered heteroaryl ring containing 1, 2 or 3 heteroatoms selected from N, O and S. In embodiments ring B is independently selected from phenyl and a 5 or 6 membered heteroaryl ring containing 1, 2 or 3 heteroatoms selected from N, O and S.

In embodiments ring A is independently selected from phenyl and a 5 to 10 membered heteroaryl ring containing 1, 2 or 3 heteroatoms selected from N, O and S; and ring B is independently selected from phenyl and a 5 or 6 membered heteroaryl ring containing 1, 2 or 3 heteroatoms selected from N, O and S.

In embodiments ring A is a 5, 6 or 9 membered heterocyclic ring.

In embodiments ring A is a 5 or 6 membered heteroaryl.

In embodiments ring A is a 6 or 9 membered heteroaryl (optionally wherein the 9 membered ring is a fused bicyclic system comprising a 6 membered and 5 membered ring).

In embodiments A may be a fused bicyclic system comprising a 6 and 5 membered heteroaryl. Optionally, A may be a fused 6,5 ring system wherein the 6 membered ring is a phenyl ring and the 5 membered ring is a heteroaryl ring having 1 or 2 N atoms.

In embodiments ring A is an aryl.

In embodiments ring A is independently selected from pyrrole, 2H-pyrrole, furan, pyrrolidine, pyrroline, tetrahydrofuran, thiophene, tetrahydrothiophene, pyrazole, imidazole, oxazole, isoxazole, pyrazoline, imidazoline, pyrazolidine, imidazolidine, thiazole, isothiazole, thiazolidine, isoxazolidine, triazole, oxadiazole, furazan, thiadiazole, pyridine, pyridine N-oxide, pyran, dihydropyran, piperidine, pyridazine, pyrimidine, pyrazine, oxazine, dioxine, piperazine, morpholine, dioxane, thiazine, thiomorpholine, oxathiane, dithiane, triazine, phenyl, naphthalene, benzimidazole, and indazole.

In embodiments ring A is independently selected from pyrrole, 2H-pyrrole, furan, pyrroline, thiophene, pyrazole, imidazole, oxazole, isoxazole, pyrazoline, imidazoline, thiazole, isothiazole, triazole, oxadiazole, furazan, thiadiazole, pyridine, pyridine N-oxide, pyran, dihydropyran, piperidine, pyridazine, pyrimidine, pyrazine, oxazine, dioxine, piperazine, thiazine, oxathiane, dithiane, triazine, phenyl, naphthalene, benzimidazole, and indazole.

In embodiments ring A is independently selected from pyrrole, pyrazole, imidazole, oxazole, isoxazole, thiazole, isothiazole, pyridine, pyridine N-oxide, pyridazine, pyrimidine, pyrazine, phenyl, benzimidazole, and indazole.

In embodiments ring A is independently selected from pyrrole, pyrazole, isoxazole, pyridine, pyridine N-oxide, pyridazine, pyrazine, pyrimidine and phenyl.

In embodiments ring A is independently selected from pyrrole, pyrazole, isoxazole, pyridazine, pyrazine, pyridine, pyridine N-oxide, pyrimidine, benzimidazole, and indazole.

In embodiments ring A is pyridine.

In embodiments when ring A is pyridine, the

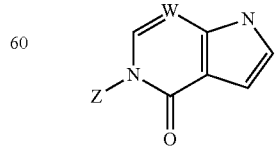

moiety is attached to ring A at the para position relative to the nitrogen atom on the pyridine ring.

In embodiments when ring A is pyridine, the

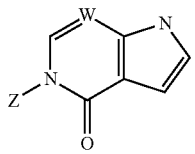

moiety is attached to ring A at the meta position relative to the nitrogen atom on the pyridine ring.

In embodiments ring A is pyrazole. In embodiments ring A is pyrimidine. In embodiments ring A is pyridazine. In embodiments ring A is pyrazine. In embodiments ring A is pyrrole. In embodiments ring A is phenyl. In embodiments ring A is pyridine N-oxide. In embodiments ring A is benzimidazole. In embodiments ring A is indazole.

In embodiments ring B is a 5 or 6 membered heterocyclic.

In embodiments ring B is a 5 or 6 membered heteroaryl.

In embodiments ring B is aryl.

In embodiments ring B is selected from pyrrole, 2H-pyrrole, furan, pyrrolidine, pyrroline, tetrahydrofuran, thiophene, tetrahydrothiophene, pyrazole, imidazole, oxazole, isoxazole, pyrazoline, imidazoline, pyrazolidine, imidazolidine, thiazole, isothiazole, thiazolidine, isoxazolidine, triazole, oxadiazole, furazan, thiadiazole, pyridine, pyran, dihydropyran, piperidine, pyridazine, pyrimidine, pyrazine, oxazine, dioxine, piperazine, morpholine, dioxane, thiazine, thiomorpholine, oxathiane, dithiane, triazine, phenyl and naphthalene.

In embodiments ring B is independently selected from pyrrole, 2H-pyrrole, pyrroline, thiophene, pyrazole, imidazole, oxazole, isoxazole, pyrazoline, imidazoline, thiazole, isothiazole, triazole, oxadiazole, furazan, thiadiazole, pyridine, pyridine N-oxide, pyran, dihydropyran, piperidine, pyridazine, pyrimidine, pyrazine, oxazine, dioxine, piperazine, thiazine, oxathiane, dithiane, triazine, phenyl, naphthalene, benzimidazole, and indazole.

In embodiments ring B is selected from pyrrole, pyrazole, imidazole, oxazole, isoxazole, thiazole, isothiazole, pyridine, pyridazine, pyrimidine, pyrazine and phenyl.

In embodiments ring B is selected from pyrrole, pyrazole, isoxazole, pyridine, pyridazine, pyrazine, pyrimidine and phenyl.

In embodiments ring B is selected from pyrrole, pyrazole, isoxazole, pyridazine, pyrazine, pyridine and pyrimidine.

In embodiments ring B is pyridine.

In embodiments when ring B is pyridine, the

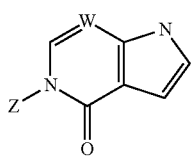

moiety is attached to ring B at the para position relative to the nitrogen atom on the pyridine ring.

In embodiments when ring B is pyridine, the

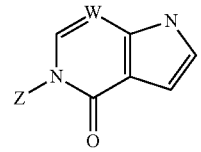

moiety is attached to ring B at the meta position relative to the nitrogen atom on the pyridine ring.

In embodiments ring B is pyrazole. In embodiments ring B is not pyrazole. In embodiments ring B is pyrimidine. In embodiments ring B is pyridazine. In embodiments ring B is pyrazine. In embodiments ring B is pyrrole. In embodiments ring B is phenyl.

In embodiments ring A is independently selected from pyrrole, pyrazole, imidazole, oxazole, isoxazole, thiazole, isothiazole, pyridine, pyridine N-oxide, pyridazine, pyrimidine, pyrazine, benzimidazole, indazole, and phenyl and ring B is independently selected from pyrrole, pyrazole, imidazole, oxazole, isoxazole, thiazole, isothiazole, pyridine, pyridazine, pyrimidine, pyrazine and phenyl, with the proviso that ring A and ring B are not both phenyl.

In some embodiments, it should be understood that ring A or ring B may be an alcohol-substituted heteroaryl. Alcohol substituted heteroaryl rings may exist in one of at least two tautomeric forms. Accordingly, an alcohol substituted heteroaryl can exist in the alcohol form and also in the keto form. For example, ring A or ring B may be pyridine substituted with an OH group. Such an OH substituted pyridine may be considered to be pyridone. Accordingly, in some embodiments ring A or ring B is pyridone.

In embodiments ring A is selected from:

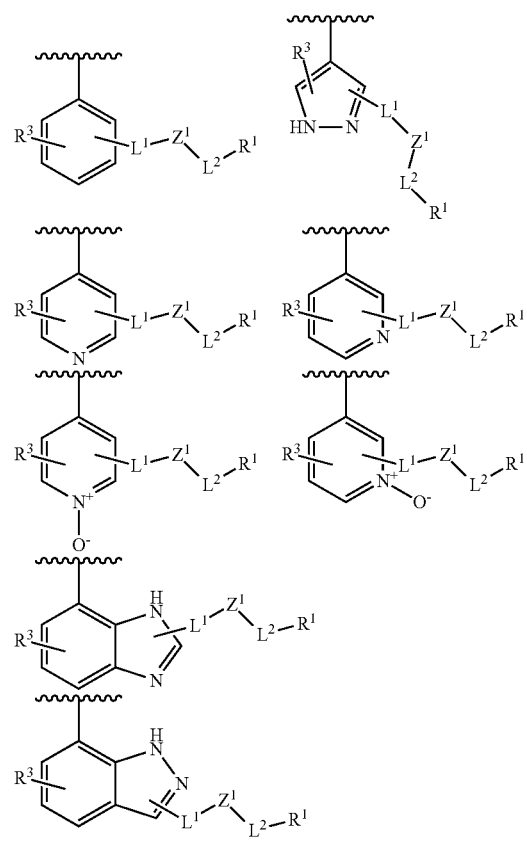

-continued
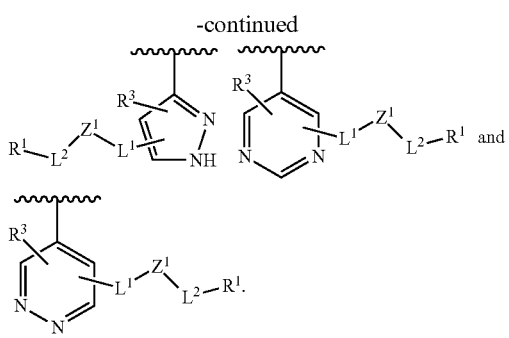
In embodiments ring B is selected from:
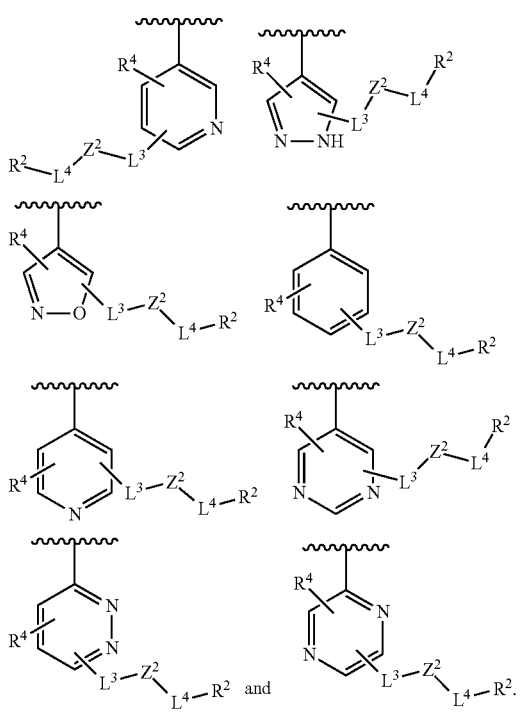
In embodiments ring A is selected from:
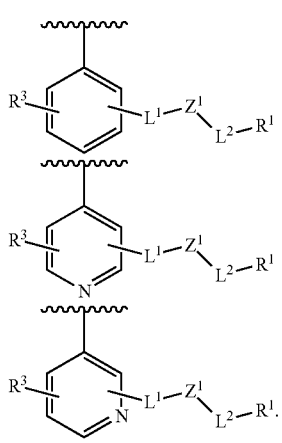
In embodiments ring A is
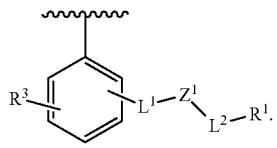
In embodiments ring A is
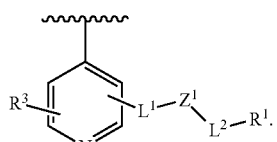
In embodiments ring A is
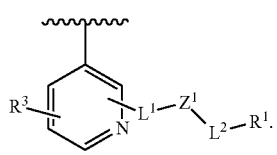
In embodiments ring A is
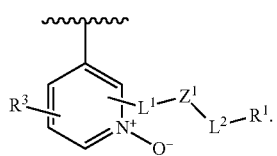
In embodiments ring A is
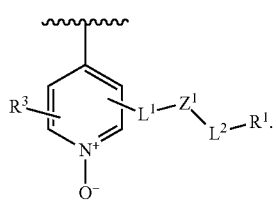
In embodiments ring B is selected from:
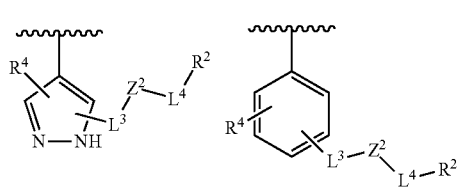

-continued
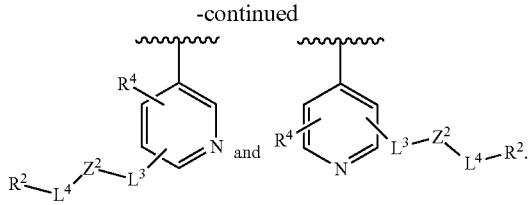
In embodiments ring B is
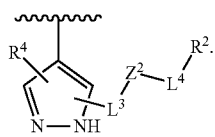
In embodiments ring B is
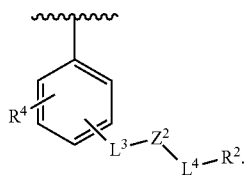
In embodiments ring B is L
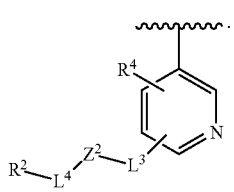
In embodiments ring B is N
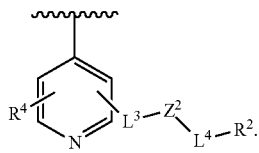
In embodiments ring A is
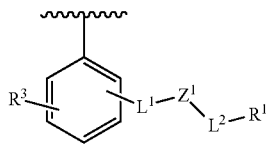
and ring B is selected from
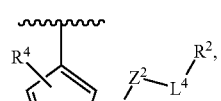 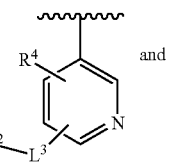
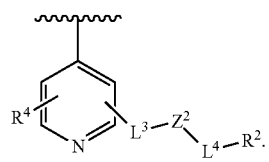
In embodiments ring A is
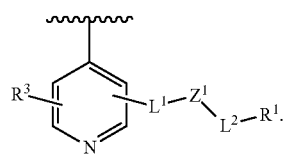
and ring B is selected from
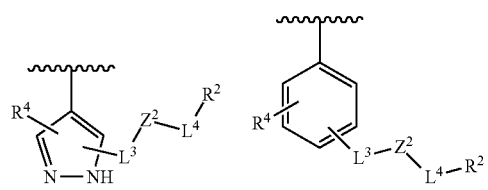
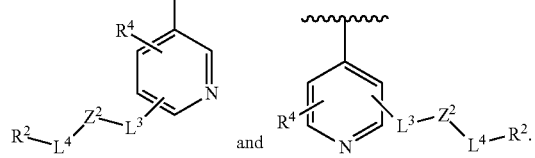
In embodiments ring A is
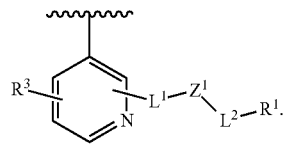
and ring B is selected from
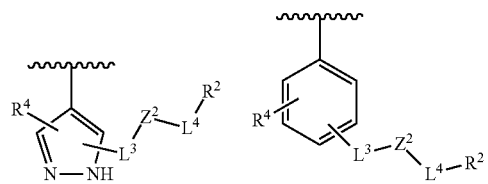

-continued

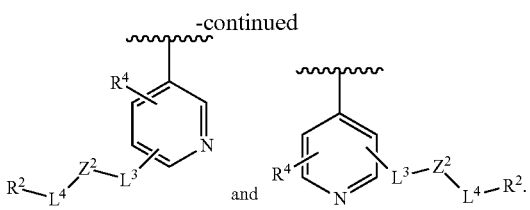
and

In embodiments ring A is

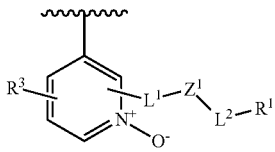

and ring B is selected from

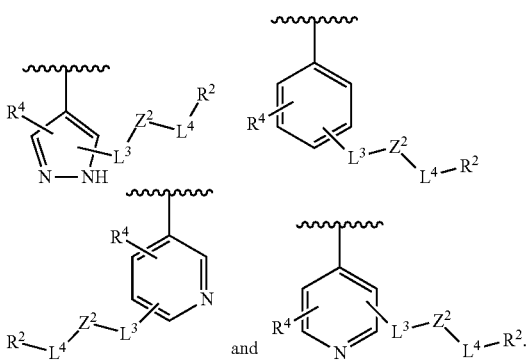
and

In embodiments ring A is

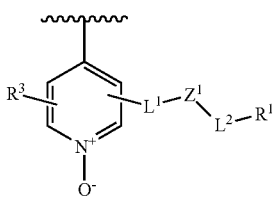

and ring B is selected from

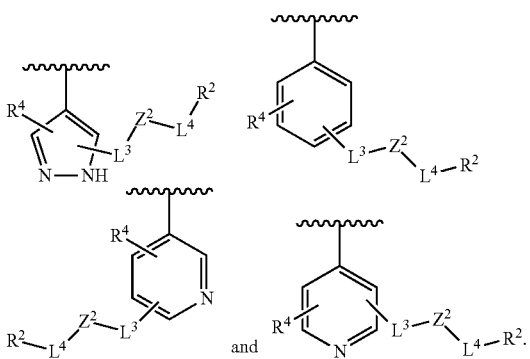
and

In embodiments $L^1$ is represented by a bond or —CH$_2$—.
In embodiments $Z^1$ is a bond, —O—, —C(O)—, —SO$_2$—, or —NR$^{5a}$C(O)—.
In embodiments $L^2$ is bond, —CH$_2$—, —CH$_2$CH$_2$—, —(CH$_2$)$_3$—, —CH$_2$CH(OH)CH$_2$—, —CH$_2$CH(OH)C(CH$_3$)$_2$—, —CH$_2$CH(OCH$_3$)CH$_2$—, —CH$_2$C(CH$_3$)$_2$CH$_2$—, —CH$_2$C(CH$_3$)$_2$—, —CF$_2$CH$_2$—,

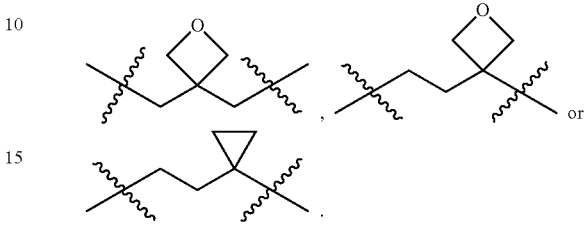

In embodiments $R^1$ is selected from H, halo, $C_{1-6}$ alkyl, $C_{2-6}$ alkenyl, halo, $C_{1-6}$ alkyl, 5 or 6 membered heteroaryl rings, or 3 to 8 membered heterocycloalkyl ring systems (optionally 5 or 6 membered), wherein the heteroaryl and heterocycloalkyl rings are unsubstituted or substituted with 1 or 2 groups selected from: $C_{1-6}$ alkyl and oxo.

In embodiments $L^1$ is represented by a bond or —CH$_2$—; $Z^1$ is a bond, —O—, —C(O)—, —SO$_2$—, or —NR$^{5a}$C(O)—; $L^2$ is bond, —CH$_2$—, —CH$_2$CH$_2$—, —(CH$_2$)$_3$—, or —CH$_2$CH(OH)CH$_2$—; and $R^1$ is selected from H, halo, $C_{1-6}$ alkyl, $C_{2-6}$ alkenyl, —NR$^{6a}$R$^{6b}$, —OR$^{6a}$, 5 or 6 membered heteroaryl rings, or 3 to 8 membered heterocycloalkyl ring systems (optionally 5 or 6 membered), wherein the heteroaryl and heterocycloalkyl rings are unsubstituted or substituted with 1 or 2 groups selected from: $C_{1-6}$ alkyl and oxo.

In embodiments $L^1$ is represented by a bond or —CH$_2$—; $Z^1$ is a bond, —O—, —C(O)—, —SO$_2$—, or —NR$^{5a}$C(O)—; $L^2$ is bond, —CH$_2$—, —CH$_2$CH$_2$—, —(CH$_2$)$_3$—, or —CH$_2$CH(OH)CH$_2$—, —CH$_2$CH(OH)C(CH$_3$)$_2$—, —CH$_2$CH(OCH$_3$)CH$_2$—, —CH$_2$C(CH$_3$)$_2$CH$_2$—, —CH$_2$C(CH$_3$)$_2$—, —CF$_2$CH$_2$—,

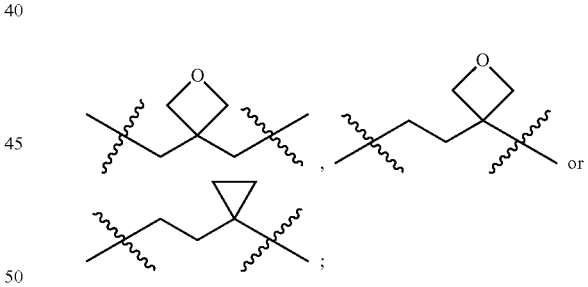

and $R^1$ is selected from H, halo, $C_{1-6}$ alkyl, $C_{2-6}$ alkenyl, —NR$^{6a}$R$^{6b}$, —OR$^{6a}$, 5 or 6 membered heteroaryl rings, or 3 to 8 membered heterocycloalkyl ring systems (optionally 5 or 6 membered), wherein the heteroaryl and heterocycloalkyl rings are unsubstituted or substituted with 1 or 2 groups selected from: $C_{1-6}$ alkyl and oxo.

In embodiments $L^1$ is represented by a bond.
In embodiments $Z^1$ is represented by a bond or —O—.
In embodiments $L^2$ is a bond, —CH$_2$—, —CH$_2$CH$_2$—, —(CH$_2$)$_3$—, or —CH$_2$CH(OH)CH$_2$—.
In embodiments $R^1$ is selected from H, halo, —NR$^{6a}$R$^{6b}$ or —OR$^{6a}$. Optionally, R$^{6a}$ and R$^{6b}$ may be independently selected from: H or $C_{1-6}$ alkyl.
In embodiments $R^1$ is H, F, —OH, or —NMe$_2$.
In embodiments $L^1$ is represented by a bond; $Z^1$ is represented by a bond or —O—; $L^2$ is bond, —CH$_2$—, —CH$_2$CH$_2$—, —(CH$_2$)$_3$—, or —CH$_2$CH(OH)CH$_2$—; and R$^1$ is selected from H, halo, —NR$^{6a}$R$^{6b}$, or —OR$^{6a}$. Optionally, R$^{6a}$ and R$^{6b}$ may be independently selected from: H or C$_{1-6}$ alkyl, optionally R$^1$ is H, F, —OH, or —NMe$_2$.

In embodiments L$^3$ is represented by a bond or —CH$_2$—.

In embodiments Z$^2$ is a bond, —NR$^{5b}$—, —O—, —C(O)—, or —NR$^{5a}$C(O)—.

In embodiments L$^4$ is represented by a bond, —CH$_2$—, —CH$_2$CH$_2$—, —CH$_2$C(Me)$_2$-, —CH$_2$CH$_2$C(Me)$_2$-, —(CH$_2$)$_3$—, —CH$_2$CH(OH)CH$_2$—, —CH$_2$CH(OMe)CH$_2$—, —CH$_2$CH(OH)C(CH$_3$)$_2$—, —CH$_2$CH(OCH$_3$)CH$_2$—, —CH$_2$C(CH$_3$)$_2$CH$_2$—, —CH$_2$C(CH$_3$)$_2$—, —CF$_2$CH$_2$—,

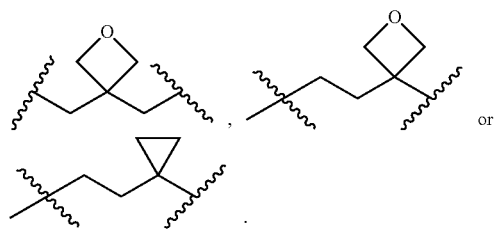

In embodiments R$^2$ is selected from H, C$_{1-6}$ alkyl, C$_{2-6}$ alkenyl, C$_{1-6}$ haloalkyl, —NR$^{6a}$R$^{6b}$, —OR$^{6a}$, OP(=O)(OH)$_2$, —C(O)R$^{6a}$, —NR$^{5b}$C(O)O—C$_{1-6}$ alkyl, phenyl, 5 or 6 membered heteroaryl rings, 3 to 8 membered cycloalkyl rings, or 3 to 8 membered heterocycloalkyl ring systems,
 wherein the phenyl, heteroaryl, cycloalkyl and heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, C(O)R$^{6a}$, —C(O)OR$^g$, and —NR$^8$C(O)R$^7$.

In embodiments R$^2$ is selected from: H, halo, C$_{1-6}$ alkyl, C$_{2-6}$ alkenyl, —NR$^{6a}$R$^{6b}$, —OR$^{6a}$, —C(O)R$^{6a}$, —NR$^{5b}$C(O)O—C$_{1-6}$ alkyl, and 3 to 8 membered heterocycloalkyl ring systems,
 wherein the heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$C(O)R$^7$.

In embodiments R$^2$ is selected from: H, C$_{1-6}$ alkyl, C$_{2-6}$ alkenyl, —NR$^{6a}$R$^{6b}$, —OR$^{6a}$, —C(O)R$^{6a}$, —NR$^{5b}$C(O)O—C$_{1-6}$ alkyl, and 3 to 8 membered heterocycloalkyl ring systems,
 wherein the heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$C(O)R$^7$.

In embodiments L$^3$ is represented by a bond or —CH$_2$—; Z$^2$ is a bond, —NR$^{5b}$—, —O—, —C(O)—, or —NR$^{5a}$C(O)—; L$^4$ is represented by a bond, —CH$_2$—, —CH$_2$CH$_2$—, —CH$_2$C(Me)$_2$-, —CH$_2$CH$_2$C(Me)$_2$-, —(CH$_2$)$_3$—, —CH$_2$CH(OH)CH$_2$—, —CH$_2$CH(OMe)CH$_2$—, —CH$_2$CH(OH)C(CH$_3$)$_2$—, —CH$_2$CH(OCH$_3$)CH$_2$—, —CH$_2$C(CH$_3$)$_2$CH$_2$—, —CH$_2$C(CH$_3$)$_2$—, —CF$_2$CH$_2$—,

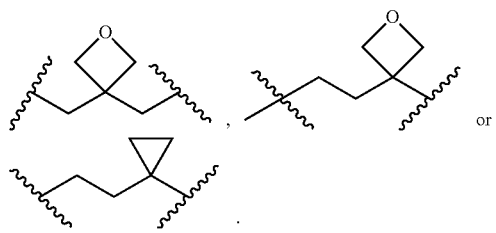

and R$^2$ is selected from: H, halo, C$_{1-6}$ alkyl, C$_{2-6}$ alkenyl, —NR$^{6a}$R$^{6b}$, —OR$^{6a}$, —C(O)R$^{6a}$, —NR$^{5b}$C(O)O—C$_{1-6}$ alkyl, and 3 to 8 membered heterocycloalkyl ring systems,
 wherein the heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$C(O)R$^7$.

In embodiments L$^3$ is represented by a bond or —CH$_2$—; Z$^2$ is a bond, —NR$^{5b}$—, —O—, —C(O)—, or —NR$^{5a}$C(O)—; L$^4$ is represented by a bond, —CH$_2$—, —CH$_2$CH$_2$—, —CH$_2$C(Me)$_2$-, —CH$_2$CH$_2$C(Me)$_2$-, —(CH$_2$)$_3$—, —CH$_2$CH(OH)CH$_2$—, —CH$_2$CH(OMe)CH$_2$—, —CH$_2$CH(OH)C(CH$_3$)$_2$—, —CH$_2$CH(OCH$_3$)CH$_2$—, —CH$_2$C(CH$_3$)$_2$CH$_2$—, —CH$_2$C(CH$_3$)$_2$—, —CF$_2$CH$_2$—,

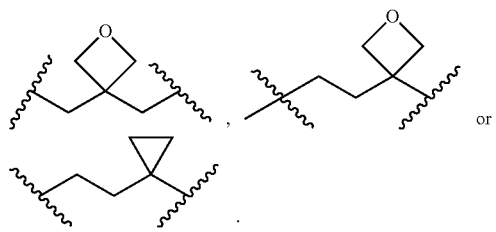

and R$^2$ is selected from: H, C$_{1-6}$ alkyl, C$_{2-6}$ alkenyl, —NR$^{6a}$R$^{6b}$, —OR$^{6a}$, —C(O)R$^{6a}$, —NR$^{5b}$C(O)O—C$_{1-6}$ alkyl, and 3 to 8 membered heterocycloalkyl ring systems,
 wherein the heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$C(O)R$^7$.

In embodiments L$^3$ is represented by a bond.

In embodiments Z$^2$ is a bond or —O—.

In embodiments L$^4$ is represented by a bond, —CH$_2$CH$_2$—, —CH$_2$CH(OH)CH$_2$—, —CH$_2$CH$_2$C(Me)$_2$-, or —(CH$_2$)$_3$—.

In embodiments R$^2$ is selected from: —OR$^{6a}$, —NR$^{6a}$R$^{6b}$, 3 to 8 membered cycloalkyl ring, 3 to 8 membered heterocycloalkyl ring systems, and 8 membered fused bicyclic heterocycloalkyl ring systems wherein the cycloalkyl rings and heterocycloalkyl rings are unsubstituted or substituted with 1 or 2 groups selected from: oxo, C$_{1-6}$ alkyl, C(O)R$^{6a}$, C$_{1-6}$ alkyl substituted with NR$^{6a}$R$^{6b}$, and C$_{1-6}$ alkyl substituted with OR$^{6a}$. Optionally, R$^{6a}$ and R$^{6b}$ may be independently selected from: H or C$_{1-6}$ alkyl.

In embodiments L$^3$ is represented by a bond; Z$^2$ is a bond or —O—; L$^4$ is represented by a bond, —CH$_2$CH$_2$—, —CH$_2$CH(OH)CH$_2$—, —CH$_2$CH$_2$C(Me)$_2$-, or —(CH$_2$)$_3$—; and R$^2$ is selected from: —OR$^{6a}$, —NR$^{6a}$R$^{6b}$, and 3 to 8 membered (optionally 5 or 6 membered) heterocycloalkyl ring systems wherein the heterocycloalkyl rings are unsubstituted or substituted with 1 or 2 groups selected from: oxo, $C_{1-6}$ alkyl, $C_{1-6}$ alkyl substituted with $NR^{6a}R^{6b}$, and $C_{1-6}$ alkyl substituted with $OR^{6a}$. Optionally, $R^{6a}$ and $R^{6b}$ may be independently selected from: H or $C_{1-6}$ alkyl.

In embodiments when ring A is a 5,6 fused bicyclic ring system, the groups, $-L^1-Z^1-L^2-R^1$, or $R^3$ are independently substituted on either the 5 or 6 membered ring of the fused 5 and 6 membered heteroaryl.

In embodiments when ring A or ring B is a 9 membered heteroaryl (e.g. indazole or benzimidazole), the $-L^1-Z^1-L^2-R^1$, $-L^3-Z^2-L^4-R^2$, $R^3$, or $R^4$ substituents may be independently selected from H and methyl.

In embodiments compounds of formula (I) may be compounds of formulae (IIa) or (IIb):

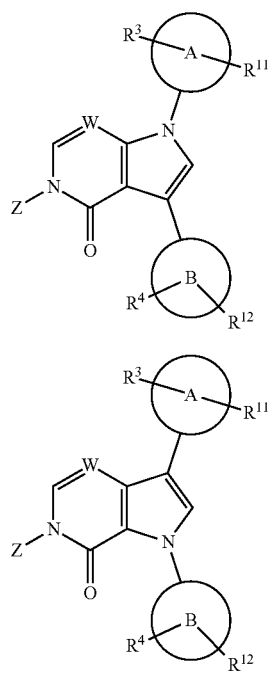

(IIa)

(IIb)

wherein
$R^{11}$ is selected from: H, halo, $C_{1-6}$ alkyl, $C_{2-6}$ alkenyl, $-(CH_2)_oR^Y$, $-(CH_2)_oNR^ZR^{6a}$, $-(CH_2)_oOR^Z$, $-(CH_2)_oSO_2R^{6a}$, $-(CH_2)_oC(O)NR^ZR^{6a}$, or $-(CH_2)_oC(O)OR^Z$,
$R^Y$ is selected from 5 or 6 membered heteroaryl rings;
$R^Z$ is selected from H, $C_{1-6}$ alkyl, $-C(O)R^{6a}$, $-C(O)OR^{6a}$, $-C(O)(CR^aR^b)_pNR^{6a}R^{6b}$, $(CR^aR^b)_pOR^{6a}$, $(CR^aR^b)_pNR^{6a}R^{6b}$, $(CR^aR^b)_pR^V$; and
$R^V$ is selected from 3 to 8 membered heterocycloalkyl ring systems, wherein the heterocycloalkyl ring is unsubstituted or substituted with 1 or 2 groups selected from: oxo, $C_{1-6}$ alkyl or halo, and
$R^{12}$ is selected from: H, halo, $C_{1-6}$ alkyl, $C_{2-6}$ alkenyl, $-(CH_2)_oR^{Y2}$, $-(CH_2)_oNR^{Z2}R^{6a}$, $-(CH_2)_oOR^{Z2}$, $-(CH_2)_oC(O)NR^{Z2}R^{6a}$, or $-(CH_2)_oC(O)OR^{Z2}$,
$R^{Y2}$ is selected from 5 or 6 membered heteroaryl rings;
$R^{Z2}$ is selected from H, $C_{1-6}$ alkyl, $-C(O)R^{6a}$, $-C(O)OR^{6a}$, $-C(O)(CR^aR^b)_nNR^{6a}R^{6b}$, $(CR^aR^b)_pOR^{6a}$, $(CR^aR^b)_pNR^{6a}R^{6b}$, $(CR^aR^b)_pR^{V2}$ or $-C(O)(CR^aR^b)_pR^{V2}$;
$R^{V2}$ is selected from 3 to 8 membered heterocycloalkyl ring systems, wherein the heterocycloalkyl ring is unsubstituted or substituted with 1 or 2 groups selected from: oxo, halo, $C_{1-6}$ alkyl, $C_{1-6}$ alkyl substituted with $NR^{6a}R^{6b}$, or $C_{1-6}$ alkyl substituted with $OR^{6a}$;
is selected from 0, 1, 2 or 3; and
p is selected from 0, 1, 2 or 3.

In embodiments $L^1-Z^1-L^2-R^1$ is $R^{11}$. Equally, $R^{11}$ may represent $L^1-Z^1-L^2-R^1$.

In embodiments $L^3-Z^2-L^4-R^2$ is $R^{12}$. Equally, $R^{12}$ may represent $L^3-Z^2-L^4-R^2$.

The skilled person will recognise that $L^1-Z^1-L^2-R^1$ or $R^{11}$ are substituted on to a phenyl ring or a heteroaryl ring, represented in the structure as ring A. The phenyl ring or heteroaryl ring is also substituted by the bicyclic ring that contains Y and X. Substitution of the $-L^1-Z^1-L^2-R^1$ or $R^{11}$ group on the phenyl ring or heteroaryl ring is defined relative to the bicyclic ring containing Y and X. As such, $L^1-Z^1-L^2-R^1$ or $R^{11}$ may be substituted at the 2, 3 or 4 position of the phenyl ring (also referred to as the ortho, meta or para positions respectively).

Preferably, the $-L^1-Z^1-L^2-R^1$ or $R^{11}$ is substituted at the 3 or 4 position of the phenyl ring or heteroaryl ring. Accordingly, compounds of formula (I) may be compounds of formulae (IIIa), where $R^{11}$ (or $-L^1-Z^1-L^2-R^1$ in place of $R^{11}$) is substituted at the 4 position, or (111 b), where $R^{11}$ (or $-L^1-Z^1-L^2-R^1$ in place of $R^{11}$) is substituted at the 3 position:

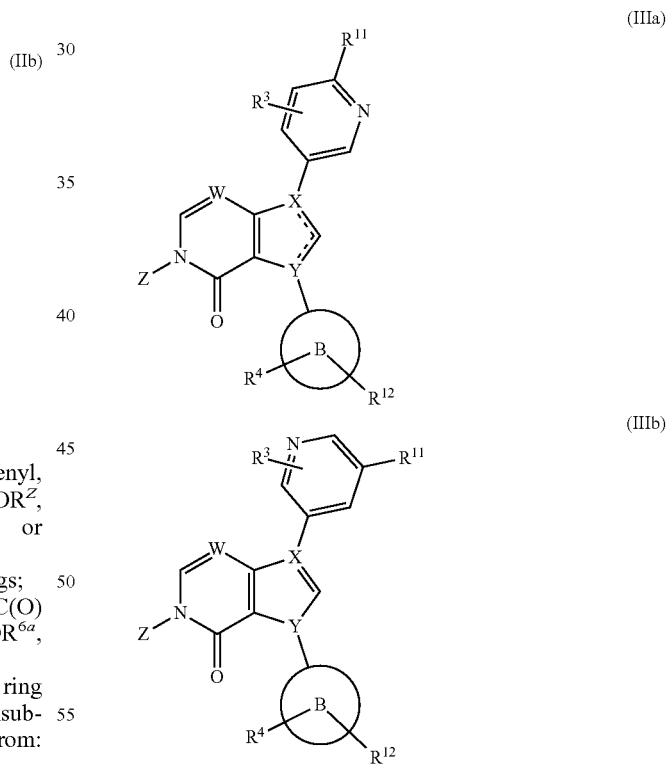

(IIIa)

(IIIb)

Equally, the skilled person will recognise that $-L^3-Z^2-L^4-R^2$ or $R^{12}$ are substituted on to a phenyl ring or a heteroaryl ring, represented in the structure as ring A. The phenyl ring or heteroaryl ring is also substituted by the bicyclic ring that contains Y and X. Substitution of the $-L^3-Z^2-L^4-R^2$ or $R^{12}$ group on the phenyl ring is defined relative to the bicyclic ring containing Y and X. As such, $-L^3-Z^2-L^4-R^2$ or $R^{12}$ may be substituted at the 2, 3 or 4 position of the phenyl ring (also referred to as the ortho, meta or para positions respectively).

Preferably, the -L³-Z²-L⁴-R² or R¹² is substituted at the 3 or 4 position of the phenyl ring. Accordingly, compounds of formula (I) may be compounds of formulae (IVa), where R¹² (or -L³-Z²-L⁴-R² in place of R¹²) is substituted at the 4 position, or (IVb), where R¹² (or -L³-Z²-L⁴-R² in place of R¹²) is substituted at the 3 position:

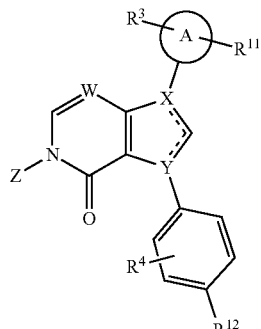

(IVa)

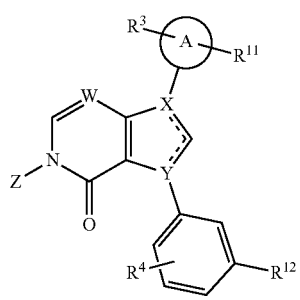

(IVb)

In embodiments-L¹-Z¹-L²-R¹ or R¹¹ is selected from: H, C$_{1-6}$ alkyl, —(CR$^a$R$^b$)$_m$OR$^{6a}$, halo, —OR$^{6a}$, —(CR$^a$R$^b$)$_m$-5 or 6 membered heteroaryl rings, —SO$_2$—C$_{1-6}$ alkyl, —C(O)OR$^{6a}$, —C(O)NR$^{6a}$R$^{6b}$, —O(CR$^a$R$^b$)$_n$—NR$^{6a}$R$^{6b}$, and —O(CR$^a$R$^b$)$_n$-3 to 8 membered heterocycloalkyl ring, wherein the heteroaryl and heterocycloalkyl rings are unsubstituted or substituted with 1 or 2 groups selected from: C$_{1-6}$ alkyl, oxo or halo. Optionally, -L³-Z²-L⁴-R² or R¹² may also be H.

Preferably, in embodiments-L¹-Z¹-L²-R¹ or R¹¹ is selected from: H, C$_{1-6}$ alkyl, halo, —(CR$^a$R$^b$)$_m$OR$^{6a}$, —OR$^{6a}$, and —O(CR$^a$R$^b$)$_m$—NR$^{6a}$R$^{6b}$.

In embodiments-L¹-Z¹-L²-R¹ or R¹¹ is selected from: H, C$_{1-6}$ alkyl, halo and —(CR$^a$R$^b$)$_m$OR$^{6a}$.

In embodiments-L¹-Z¹-L²-R¹ or R¹¹ is selected from: H, C$_{1-6}$ alkyl, fluoro and —(CR$^a$R$^b$)$_m$OR$^{6a}$.

In embodiments-L¹-Z¹-L²-R¹ or R¹¹ is selected from: H, methyl, ethyl, propyl, butyl, fluoro and —(CR$^a$R$^b$)$_m$OR$^{6a}$.

In embodiments-L¹-Z¹-L²-R¹ or R¹¹ is selected from: H, methyl, ethyl, propyl, butyl, fluoro and —(CH$_2$)$_m$OR$^{6a}$.

In embodiments-L¹-Z¹-L²-R¹ or R¹¹ is selected from: H, methyl, ethyl, propyl, butyl, fluoro and —(CH$_2$)$_m$OH.

In embodiments-L²-Z¹-L²-R¹ or R¹¹ is selected from: H, methyl, fluoro and —(CH$_2$)$_2$OH.

Optionally, -L¹-Z¹-L²-R¹ or R¹¹ is selected from: H, C$_{1-6}$ alkyl, halo, —(CR$^a$R$^b$)$_m$OR$^{6a}$, —OR$^{6a}$, and —O(CR$^a$R$^b$)$_m$—NR$^{6a}$R$^{6b}$; and -L³-Z²-L⁴-R² or R¹² are H.

In embodiments-L³-Z²-L⁴-R² or R¹² is selected from: halo, C$_{1-6}$ alkyl, C$_{2-6}$ alkenyl, —OR$^{6a}$, —NR$^{6a}$R$^{6b}$, —(CR$^a$R$^b$)$_m$-phenyl, —(CR$^a$R$^b$)$_m$-5 or 6 membered heteroaryl rings, —(CR$^a$R$^b$)$_m$NR$^{6a}$R$^{6b}$, —(CR$^a$R$^b$)$_m$OR$^{6a}$, —(CR$^a$R$^b$)$_m$OC(O)R$^{6a}$, —(CR$^a$R$^b$)$_m$C(O)R$^{6a}$, —(CR$^a$R$^b$)$_m$C(O)NR$^{6a}$R$^{6b}$, —(CR$^a$R$^b$)$_m$NR$^{5a}$C(O)—C$_{1-6}$ alkyl, —(CR$^a$R$^b$)$_m$NR$^{5a}$C(O)OR$^{6a}$, —O(CR$^a$R$^b$)$_n$OR$^{6a}$, —O(CR$^a$R$^b$)$_n$NR$^{5b}$C(O)OC$_{1-6}$ alkyl, 3 to 8 membered heterocycloalkyl ring, —O(CR$^a$R$^b$)$_n$-3 to 8 membered heterocycloalkyl ring, —O(CR$^a$R$^b$)$_n$—NR$^{6a}$R$^{6b}$, —NR$^{5a}$(CR$^c$R$^d$)$_n$OR$^{6a}$, —C(O)NR$^{6a}$R$^{6b}$, —NR$^{5b}$C(O)—C$_{1-6}$ alkyl, —NR$^{5b}$C(O)(CR$^c$R$^d$)$_n$NR$^{6a}$R$^{6b}$, —NR$^{5b}$C(O)(CR$^c$R$^d$)$_n$OR$^{6a}$, and —NR$^{5b}$C(O)(CR$^c$R$^d$)$_n$-3 to 8 membered heterocycloalkyl ring, wherein the phenyl, heteroaryl and heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$C(O)R$^7$. Optionally, -L¹-Z¹-L²-R¹ or R¹¹ may be H.

Preferably, in embodiments-L³-Z²-L⁴-R² or R¹² is selected from: —O(CR$^a$R$^b$)$_n$OR$^{6a}$; —O(OR$^a$R$^b$)$_n$—NR$^{6a}$R$^{6b}$; 3 to 8 membered heterocycloalkyl ring substituted with 1 or 2 groups selected from: oxo, C$_{1-6}$ alkyl, C$_{2-6}$ alkenyl, C$_{1-6}$ alkyl substituted with NR$^{6a}$R$^{6b}$, or C$_{1-6}$ alkyl substituted with OR$^{6a}$; —O(CR$^a$R$^b$)$_n$-3 to 8 membered heterocycloalkyl ring substituted with 1 or 2 groups selected from: oxo, or C$_{1-6}$ alkyl. Optionally, -L¹-Z¹-L²-R¹ or R¹¹ may also be H.

In embodiments L¹-Z¹-L²-R¹ or R¹¹ is selected from. H, F, —OMe, —C(O)OH, —C(O)OEt, —C(O)NHMe, —C(O)NH$_2$, —SO$_2$Me, —CH$_2$-imidazolyl —O(OH$_2$)$_3$NMe$_2$, —OCH$_2$-pyrolidinyl, —OCH$_2$—N-methylpyrolidinyl, —O(CH$_2$)$_3$-morpholinyl, or —OCH$_2$CH(OH)CH$_2$-morpholinyl.

In embodiments L¹-Z¹-L²-R¹ or R¹¹ is selected from H, —C(O)OH, —C(O)OEt, —O(OH$_2$)$_3$NMe$_2$, —OCH$_2$-pyrolidinyl, —OCH$_2$—N-methylpyrolidinyl, —O(CH$_2$)$_3$-morpholinyl, or —OCH$_2$CH(OH)CH$_2$-morpholinyl. Optionally, L¹-Z¹-L²-R¹ or R¹¹ has the definition in the preceding sentence when X is C and Y is N. For example, in embodiments where the compounds are compounds of formula (Ib), L¹-Z¹-L²-R¹ or R¹¹ is selected from the groups recited in this paragraph.

In embodiments-L¹-Z¹-L²-R¹ or R¹¹ is selected from H, F, —OMe, —C(O)OH, —C(O)NHMe, —C(O)NH$_2$, —SO$_2$Me, or —CH$_2$-imidazolyl. Optionally, L¹-Z¹-L²-R¹ or R¹¹ is selected from F, OMe, —C(O)OH, —O(O)NHMe, —O(O)NH$_2$, —SO$_2$Me, or —CH$_2$-imidazolyl, when X is N and Y is C. For example, in embodiments where the compounds are compounds of formula (Ia) L¹-Z¹-L²-R¹ or R¹¹ is selected from the groups recited in this paragraph.

In embodiments-L³-Z²-L⁴-R² or R¹² is selected from: H, F, Cl, —OMe, methyl, NH$_2$, —CH$_2$-phenyl, —CH$_2$-imidazolyl, —CH$_2$NH$_2$, —CH$_2$NMe$_2$, —CH$_2$NHMe, —CH$_2$NHC(O)Me, —CH$_2$N(Me)C(O)Ot-Bu, —CH$_2$OH, —CH$_2$CH$_2$OH, —CH$_2$CH$_2$CH$_2$OH, —CH$_2$CH$_2$OMe, —CH$_2$CH$_2$CH$_2$OCH$_3$, —CH$_2$CH$_2$NHMe, —(CH$_2$)$_3$OH, —(CH$_2$)$_3$OMe, —CH$_2$C(Me$_2$)OH, —CH$_2$CH$_2$OC(O)Me, —CH$_2$C(O)OMe, —CH$_2$C(O)OH, —CH$_2$C(O)OEt, —CH$_2$C(O)NH$_2$, —OMe, —OCH$_2$CH$_2$OH, —OCH$_2$CH$_2$OMe, —OCH$_2$C(Me)$_2$OH, —OCH$_2$CH$_2$C(Me)$_2$OH, —OCH$_2$CH(OH)CH$_2$OH, —OCH$_2$C(Me$_2$)OH, —OCH$_2$CH$_2$NH$_2$, —OCH$_2$CH$_2$NMe$_2$, —O(CH$_2$)$_3$NMe$_2$, —OCH$_2$CH(OH)CH$_2$NMe$_2$, —OCH$_2$CH$_2$NHC(O)O$^t$Bu, —OCH$_2$-azetidinyl, —OCH$_2$—N-methylazetindinyl, —O—N-ethylpiperadinyl, —O(CH$_2$)$_3$-morpholinyl, —OCH$_2$CH(OH)CH$_2$-morpholinyl, —OCH$_2$CH(OMe)CH$_2$-morpholinyl, —O(CH$_2$)$_3$—N-methylpiperazinyl, —OCH$_2$CH(OH)CH$_2$—N-methylpiperazinyl, —OCH$_2$CH(OH)CH$_2$—N-methylpiperazinonyl, —O(CH$_2$)$_3$—N-methylpiperazinonyl, —OCH$_2$CH(OH)CH$_2$-morpholinonyl, —OCH₂CH(OH)CH₂-morpholinonyl, —OCH₂CH(OH)CH₂-thiomorpholin-dionyl, —NHCH₂CH₂OH, —N(Me)CH₂CH₂OH, —NHCH₂CH₂OMe, —C(O)NHCH₂CH₂NMe₂, —C(O)NHCH₂CH₂OH, —NHC(O)Me, —NHC(O)CH₂OH, —NHC(O)CH₂NH₂, —NHC(O)CH₂NHMe, —NHC(O)CH₂NMe₂, —NHC(O)CH₂CH₂NHMe, —NHC(O)(CH₂)₃NMe₂, —NHC(O)CH₂-morpholinyl, —NHC(O)CH₂—N-oxetanyl, azetidinyl, hydroxypyrolidinyl, methylpiperazinyl, pyrolidinonyl, imidazolidinonyl, N-methylimidazolidinonyl, piperidinonyl, ylpiperazinonyl, —O(CH₂)₃N(CH₃)₂, —NHCH₂CH₂OH, —N(CH₃)CH₂CH₂OH—NHCH₂CH₂OCH₃, NHC(O)CH₃, NHC(O)CH₂CH₂NHCH₃, oxelane, azetidine, azetidine substituted with C(O)OC(CH₃)₃, azetidine substituted with C(O)CH₃, azetidine substituted with C(O)cyclopropyl, cyclobutyl substituted with NHC(O)CH₃, azetidine substituted with OH, azetidine substituted with CH₂OH, pyrrolidine substituted with OH,

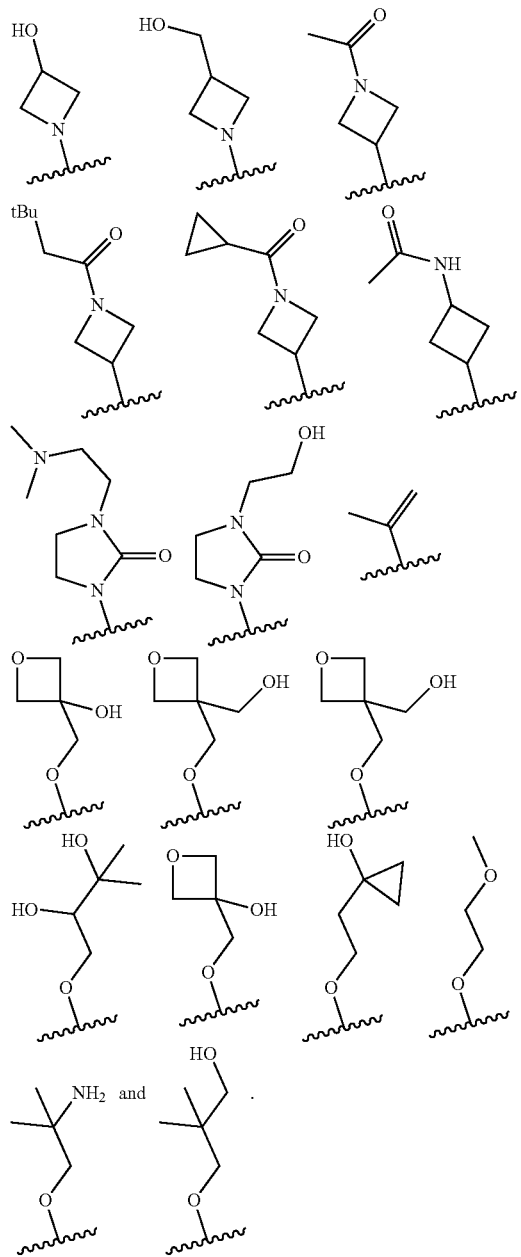
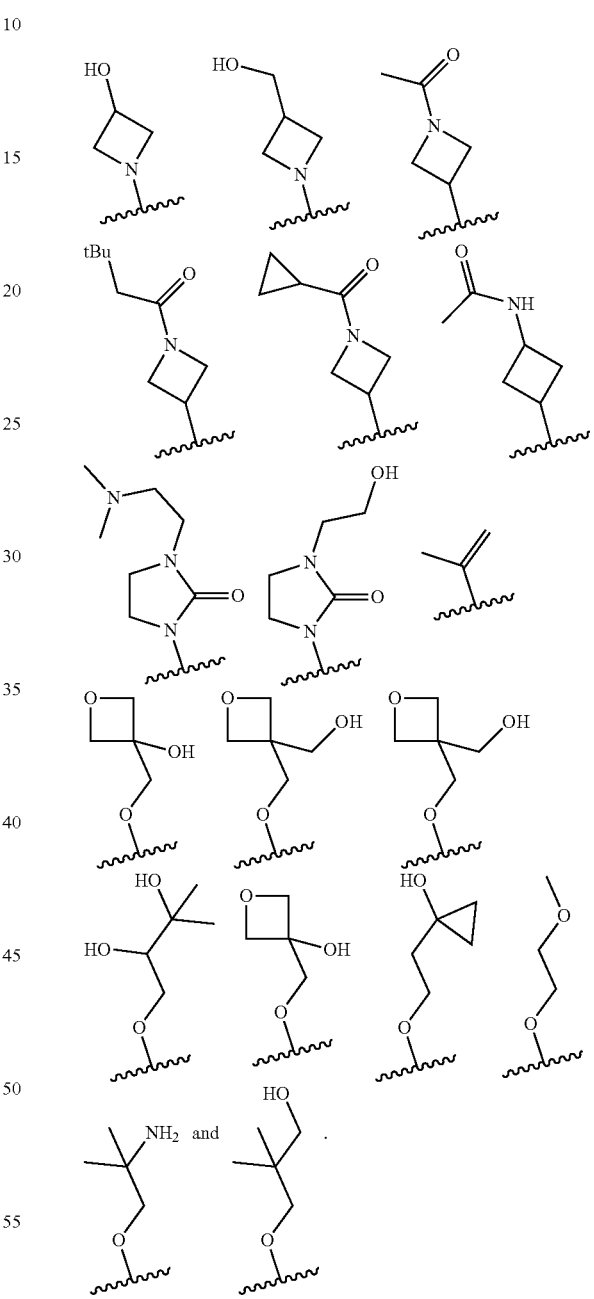

In embodiments-L³-Z²-L⁴-R² or R¹² is selected from: H, F, —OMe, methyl, NH₂, —CH₂-phenyl, —CH₂(O)OCH₃, —CH₂CH₂OH, —CH₂CH₂CH₂OH, —CH₂CH₂OCH₃, —CH₂CH₂CH₂OCH₃, —CH₂CH₂NHCH₃, —CH₂CH₂OC(O)CH₃, —CH₂C(O)OCH₃, —OCH₂CH₂OCH₃, —OCH₂C(CH₃)₂OH, —O(CH₂)₃-morpholinyl, —O(CH₂)₃—N-meth- In embodiments-L³-Z²-L⁴-R² or R¹² is selected from: H, F, Cl, —OMe, —CH₂-imidazolyl, —CH₂OH, —CH₂NH₂, —CH₂NMe₂, —CH₂NHMe, —CH₂C(O)OH, —CH₂C(O)OEt, —CH₂C(O)NH₂, —CH₂NHC(O)Me, —CH₂N(Me)C(O)Ot-Bu, —OMe, —OCH₂CH₂OH, —OCH₂CH₂OMe, —OCH₂C(Me)₂OH, —OCH₂CH₂C(Me)₂OH, —OCH₂CH₂NH₂, —OCH₂CH₂NMe₂, —OCH₂CH(OH)CH₂NMe₂, —OCH₂CH₂NHC(O)Oᵗالبu, —OCH₂-azetidinyl, —OCH$_2$—N-methylazetindinyl, —O—N-ethylpiperadinyl, —O(CH$_2$)$_3$-morpholinyl, —OCH$_2$CH(OH)CH$_2$-morpholinyl, —OCH$_2$CH(OMe)CH$_2$-morpholinyl, —O(CH$_2$)$_3$—N-methylpiperazinyl, —C(O)NHCH$_2$CH$_2$NMe$_2$, —C(O)NHCH$_2$CH$_2$OH, —NHC(O)Me, —NHC(O)CH$_2$OH, —NHC(O)CH$_2$NH$_2$, —NHC(O)CH$_2$NHMe, —NHC(O)CH$_2$NMe$_2$, —NHC(O)CH$_2$CH$_2$NHMe, —NHC(O)(CH$_2$)$_3$NMe$_2$, —NHC(O)CH$_2$-morpholinyl, —NHC(O)CH$_2$—N-methylpiperazinyl, pyrolidinonyl, imidazolidinonyl, N-methylimidazolidinonyl, piperidinonyl,

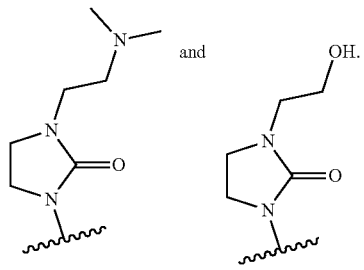 [SMILES: *N1CCN(CCN(C)C)C1=O ; *N1CCN(CCO)C1=O]

Optionally, L$^3$-Z$^2$-L$^4$-R$^2$ or R$^{12}$ has the definition in the preceding sentence when X is N and Y is C. For example, in embodiments where the compounds are compounds of formula (Ia) L$^3$-Z$^2$-L$^4$-R$^2$ or R$^{12}$ is selected from the groups recited in this paragraph.

In embodiments L$^3$-Z$^2$-L$^4$-R$^2$ or R$^{12}$ is H or OMe. Optionally, L$^3$-Z$^2$-L$^4$-R$^2$ or R$^{12}$ has the definition in the preceding sentence when X is C and Y is N. For example, in embodiments where the compounds are compounds of formula (Ib), L$^3$-Z$^2$-L$^4$-R$^2$ or R$^{12}$ is selected from the groups recited in this paragraph.

In embodiments L$^3$-Z$^2$-L$^4$-R$^2$ or R$^{12}$ is selected from: -Me, —F, —NH$_2$, —CH$_2$-phenyl, —CH$_2$CH$_2$OH, —CH$_2$CH$_2$OMe, —CH$_2$CH$_2$NHMe, —(CH$_2$)$_3$OH, —(CH$_2$)$_3$OMe, —CH$_2$CH$_2$OC(O)Me, —CH$_2$C(O)OMe, —OMe, —OCH$_2$CH$_2$OMe, —O(CH$_2$)$_3$NMe$_2$, —OCH$_2$C(Me)$_2$OH, —OCH$_2$CH$_2$C(Me)$_2$OH, —O(CH$_2$)$_3$-morpholinyl, —O(CH$_2$)$_3$—N-methylpiperazinyl, —OCH$_2$CH(OH)CH$_2$-morpholinyl, —OCH$_2$CH(OMe)CH$_2$-morpholinyl, —NHCH$_2$CH$_2$OH, —N(Me)CH$_2$CH$_2$OH, —NHCH$_2$CH$_2$OMe, —NH$_0$(O)Me, —NHC(O)CH$_2$CH$_2$NHMe, oxetanyl, azetidinyl, hydroxypyrolidinyl,

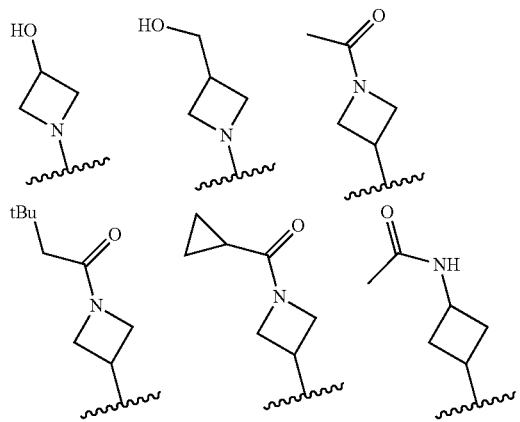

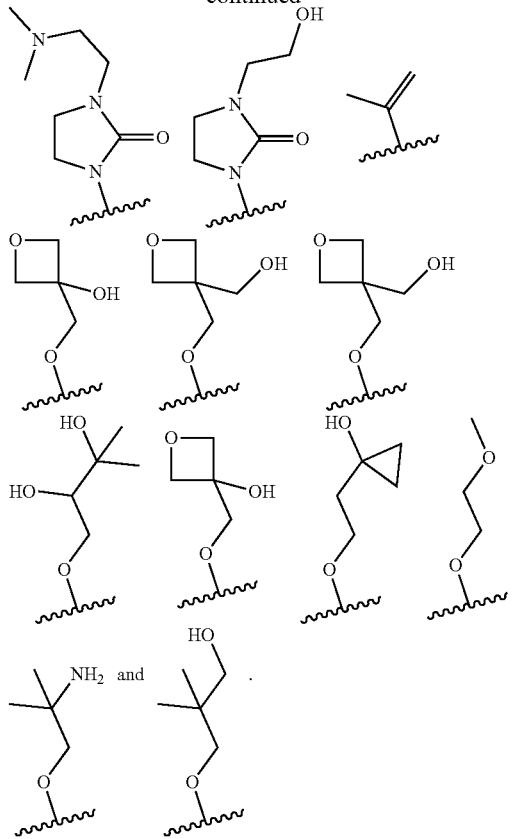

Optionally, L$^3$-Z$^2$-L$^4$-R$^2$ or R$^{12}$ has the definition in the preceding sentence when X is N and Y is C. For example, in embodiments where the compounds are compounds of formula (Ia) L$^3$-Z$^2$-L$^4$-R$^2$ or R$^{12}$ is selected from the groups recited in this paragraph.

In embodiments, -L$^3$-Z$^2$-L$^4$-R$^2$ or R$^{12}$ is —OCH$_2$CH(OH)CH$_2$OH, —OCH$_2$C(Me$_2$)OH, —CH$_2$C(Me$_2$)OH, —OCH$_2$CH(OH)CH$_2$—N-methylpiperazinyl, —OCH$_2$CH(OH)CH$_2$—N-methylpiperazinonyl, —OCH$_2$CH(OH)CH$_2$-morpholinonyl, —OCH$_2$CH(OH)CH$_2$-morpholinyl, —OCH$_2$CH(OH)CH$_2$-morpholinonyl, —OCH$_2$CH(OH)CH$_2$-thiomorpholin-dionyl or —OCH$_2$CH(OH)CH$_2$-morpholinyl.

In preferred embodiments-L$^1$-Z$^1$-L$^2$-R$^1$ or R$^{11}$ is F, —CH$_2$OH, —OCH$_2$CH$_2$NMe$_2$, —O(CH$_2$)$_3$NMe$_2$, —OCH$_2$CH(OH)CH$_2$NMe$_2$, or —OCH$_2$CH$_2$OH.

In preferred embodiments-L$^1$-Z$^1$-L$^2$-R$^1$ or R$^{11}$ is substituted at the 3 position of the phenyl ring (for example as demonstrated in formula (Nib)) and is F or —CH$_2$OH.

In preferred embodiments-L$^1$-Z$^1$-L$^2$-R$^1$ or R$^{11}$ is substituted at the 4 position of the phenyl ring (for example as demonstrated in formula (IIIa)) and is selected from: —OCH$_2$CH$_2$NMe$_2$, —O(CH$_2$)$_3$NMe$_2$, —OCH$_2$CH(OH)CH$_2$NMe$_2$, and —OCH$_2$CH$_2$OH.

In preferred embodiments-L$^3$-Z$^2$-L$^4$-R$^2$ or R$^{12}$ is selected from: —OCH$_2$CH$_2$OH, —OCH$_2$CH$_2$OMe, —OCH$_2$CH(OH)CH$_2$OH, —OCH$_2$CH$_2$C(Me)$_2$OH, pyrolidinonyl, imidazolidinonyl, N-methylimidazolidinonyl, —O(CH$_2$)$_3$-morpholinyl, —O(CH$_2$)$_3$—N-methylpiperazinyl, —O(CH$_2$)$_3$—N-methylpiperazinonyl, —OCH$_2$CH(OH)CH$_2$-morpholinonyl, —OCH$_2$CH(OH)CH$_2$—N-methylpiperazinyl, —OCH$_2$CH(OH)CH$_2$—N-methylpiperazinonyl, —O(CH$_2$)$_3$NMe$_2$, —OCH$_2$CH(OH)CH$_2$NMe$_2$,

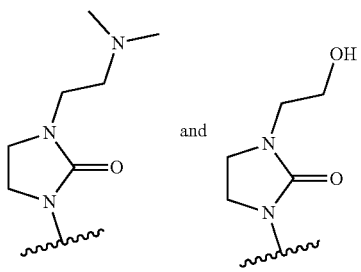 [SMILES: *N1CCN(CCN(C)C)C1=O ; *N1CCN(CCO)C1=O]

In preferred embodiments-L$^3$-Z$^2$-L$^4$-R$^4$ or R$^{12}$ is substituted at the 3 position of the phenyl ring (for example as demonstrated in formula (IVb)) and is.

In embodiments-L$^3$-Z$^2$-L$^4$-R$^2$ or R$^{12}$ is substituted at the 4 position of the phenyl ring (for example as demonstrated in formula (IVa)) and is selected from: —OCH$_2$CH$_2$OH, —OCH$_2$CH$_2$OMe, —OCH$_2$CH(OH)CH$_2$OH, —OCH$_2$CH$_2$C(Me)$_2$OH, pyrolidinonyl, imidazolidinonyl, N-methylimidazolidinonyl, —O(CH$_2$)$_3$-morpholinyl, —O(CH$_2$)$_3$—N-methylpiperazinyl, —O(CH$_2$)$_3$—N-methylpiperazinonyl, —OCH$_2$CH(OH)CH$_2$-morpholinonyl, —OCH$_2$CH(OH)CH$_2$—N-methylpiperazinyl, —OCH$_2$CH(OH)CH$_2$—N-methylpiperazinonyl, —O(CH$_2$)$_3$NMe$_2$, —OCH$_2$CH(OH)CH$_2$NMe$_2$,

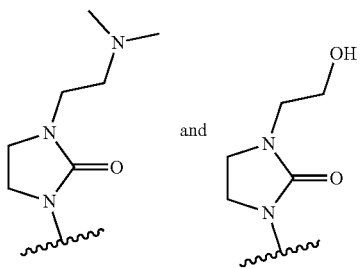 [SMILES: *N1CCN(CCN(C)C)C1=O ; *N1CCN(CCO)C1=O]

In embodiments-L$^3$-Z$^2$-L$^4$-R$^2$ or R$^{12}$ are a group other than H as defined above and -L$^1$-Z$^1$-L$^2$-R$^1$ or R$^{11}$ are H. In alternative embodiments-L$^1$-Z$^1$-L$^2$-R$^1$ or R$^{11}$ are a group other than H as defined above and -L$^3$-Z$^2$-L$^4$-R$^2$ or R$^{12}$ are H.

In embodiments-L$^1$-Z$^1$-L$^2$-R$^1$ or R$^{11}$ is —O(CR$^a$R$^b$)$_m$—R$^1$.

In preferred embodiments-L$^3$-Z$^2$-L$^4$-R$^2$ or R$^{12}$ is —O(CR$^a$R$^b$)$_m$—R$^2$.

In preferred embodiments-L$^1$-Z$^1$-L$^2$-R$^1$ or R$^{11}$ is —O(CR$^a$R$^b$)$_{1-3}$—R$^1$.

In preferred embodiments-L$^3$-Z$^2$-L$^4$-R$^2$ or R$^{12}$ is —O(CR$^a$R$^b$)$_{1-3}$—R$^2$.

In certain embodiments W is N. In certain embodiments W is C. In certain embodiments W is N and Z is —CH$_2$OP(=O)(OH)$_2$.

In an embodiment the compound of the present invention is a compound according to formula (V) and pharmaceutically acceptable salts thereof:

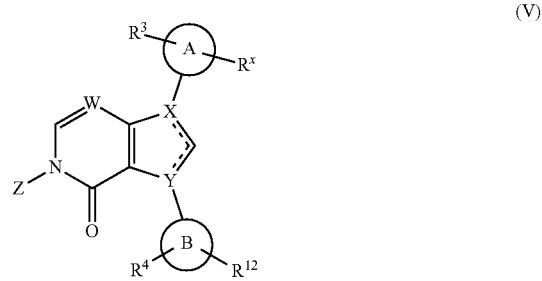

wherein
W is independently selected from N or C;
Z is independently selected from H or —CH$_2$OP(=O)(OH)$_2$;
either X is N and Y is C, or Y is N and X is C;
R$^X$ and R$^{X2}$ are either (A) or (B):
(A) R$^X$ is selected from: H, —(CH$_2$)$_m$R$^Y$, —(CH$_2$)$_m$NR$^Z$R$^{6a}$, —(CH$_2$)$_{1-3}$OR$^Z$, —(CH$_2$)$_m$SO$_2$R$^{6a}$, —(CH$_2$)$_m$C(O)NR$^Z$R$^{6a}$, —(CH$_2$)$_m$C(O)OR$^Z$,
R$^Y$ is selected from 5 or 6 membered heteroaryl rings;
R$^Z$ is selected from H, C$_{1-6}$ alkyl, —C(O)R$^{6a}$, —C(O)OR$^{6a}$, —C(O)(CR$^a$R$^b$)$_n$NR$^{6a}$R$^{6b}$, (CR$^a$R$^b$)$_n$OR$^{6a}$, (CR$^a$R$^b$)$_n$NR$^{6a}$R$^{6b}$, (CR$^a$R$^b$)$_n$R$^V$; and
R$^V$ is selected from 3 to 8 membered heterocycloalkyl ring systems, wherein the heterocycloalkyl ring is unsubstituted or substituted with 1 or 2 groups selected from: oxo, C$_{1-6}$ alkyl or halo; and
R$^{X2}$ is selected from: H, halo, C$_{1-6}$ alkyl, —(CH$_2$)$_m$R$^{Y2}$, —(CH$_2$)$_m$NR$^{Z2}$R$^{6a}$, —(CH$_2$)$_m$OR$^{Z2}$, —(CH$_2$)$_m$C(O)NR$^{Z2}$R$^{6a}$, —(CH$_2$)$_m$C(O)OR$^{Z2}$,
R$^{Y2}$ is selected from 5 or 6 membered heteroaryl rings;
R$^{Z2}$ is selected from H, C$_{1-6}$ alkyl, —C(O)R$^{6a}$, —C(O)OR$^{6a}$, —C(O)(CR$^a$R$^b$)$_n$NR$^{6a}$R$^{6b}$, (CR$^a$R$^b$)$_n$OR$^{6a}$, (CR$^a$R$^b$)$_n$NR$^{6a}$R$^{6b}$, (CR$^a$R$^b$)$_n$R$^{V2}$ or —C(O)(CR$^a$R$^b$)$_n$R$^{V2}$; and
R$^{V2}$ is selected from 3 to 8 membered heterocycloalkyl ring systems, wherein the heterocycloalkyl ring is unsubstituted or substituted with 1 or 2 groups selected from: oxo, halo, C$_{1-6}$ alkyl, C$_{1-6}$ alkyl substituted with NR$^{6a}$R$^{6b}$, or C$_{1-6}$ alkyl substituted with OR$^{6a}$;
or
(B) R$^X$ is selected from: H, halo, C$_{1-6}$ alkyl, —(CH$_2$)$_m$R$^Y$, —(CH$_2$)$_m$NR$^Z$R$^{6a}$, —(CH$_2$)$_m$OR$^Z$, —(CH$_2$)$_m$SO$_2$R$^{6a}$, —(CH$_2$)$_m$C(O)NR$^Z$R$^{6a}$, —(CH$_2$)$_m$C(O)OR$^Z$,
R$^Y$ is selected from 5 or 6 membered heteroaryl rings;
R$^Z$ is selected from H, C$_{1-6}$ alkyl, —C(O)R$^{6a}$, —C(O)OR$^{6a}$, —C(O)(CR$^a$R$^b$)$_n$NR$^{6a}$R$^{6b}$, (CR$^a$R$^b$)$_n$OR$^{6a}$, (CR$^a$R$^b$)$_n$NR$^{6a}$R$^{6b}$, (CR$^a$R$^b$)$_n$R$^V$; and
R$^V$ is selected from 3 to 8 membered heterocycloalkyl ring systems, wherein the heterocycloalkyl ring is unsubstituted or substituted with 1 or 2 groups selected from: oxo, C$_{1-6}$ alkyl or halo; and
R$^{X2}$ is selected from: H, —(CH$_2$)$_m$R$^{Y2}$, —(CH$_2$)$_m$NR$^{Z2}$R$^{6a}$, —(CH$_2$)$_{1-3}$OR$^{Z2}$, —(CH$_2$)$_m$C(O)NR$^{Z2}$R$^{6a}$, —(CH$_2$)$_m$C(O)OR$^{Z2}$, R$^{Y2}$ is selected from 5 or 6 membered heteroaryl rings;

R$^{Z2}$ is selected from H, C$_{1-6}$ alkyl, —C(O)R$^{6a}$, —C(O)OR$^{6a}$, —C(O)(CR$^a$R$^b$)$_n$NR$^{6a}$R$^{6b}$, (CR$^a$R$^b$)$_n$OR$^{6a}$, (CR$^a$R$^b$)$_n$NR$^{6a}$R$^{6b}$, (CR$^a$R$^b$)$_n$R$^{Y2}$ or —C(O)(CR$^a$R$^b$)$_n$R$^{Y2}$; and R$^{V2}$ is selected from 3 to 8 membered heterocycloalkyl ring systems, wherein the heterocycloalkyl ring is unsubstituted or substituted with 1 or 2 groups selected from: oxo, halo, C$_{1-6}$ alkyl, C$_{1-6}$ alkyl substituted with NR$^{6a}$R$^{6b}$, or C$_{1-6}$ alkyl substituted with OR$^{6a}$;

provided that R$^X$ and R$^{X2}$ are not both H and are not both halo;

m is selected from 1, 2, or 3;

n is selected from 1, 2, or 3;

R$^3$ and R$^4$ are independently selected from H, halo, —CN and C$_{1-6}$ alkyl;

R$^{6a}$ and R$^{6b}$ are, at each occurrence, independently selected from: H and C$_{1-6}$ alkyl;

R$^a$, R$^b$, R$^c$ and R$^d$ are, at each occurrence, independently selected from: H, halo, C$_{1-6}$ alkyl, and —OR$^e$; and R$^e$ is selected from H or C$_{1-6}$ alkyl.

In embodiments the compounds of the invention have the proviso that when Y is N and X is C then-L$^3$-Z$^2$-L$^4$-R$^2$ cannot be OMe when-L$^1$-Z$^1$-L$^2$-R$^1$ is H and when X is N and Y is C then-L$^1$-Z$^1$-L$^2$-R$^1$ cannot be H, halo, methyl, trifluoromethyl, OMe, OEt, —OCH$_2$CH$_2$NHCH$_2$CH$_2$OH, —SO$_2$NH$_2$, or SO$_2$NMe$_2$ when-L$^3$-Z$^2$-L$^4$-R$^2$ is H, halo, methyl, or OMe.

In embodiments the compounds of the invention have the proviso that-L$^1$-Z$^1$-L$^2$-R$^1$ and -L$^3$-Z$^2$-L$^4$-R$^2$ cannot be selected from the following definitions at the same time:

L$^1$-Z$^1$-L$^2$-R$^1$ cannot be selected from: H, halo, C$_{1-6}$ alkyl, —SO$_2$NR$^{6a}$R$^{6b}$, or —O—C$_{1-6}$ alkyl; and L$^3$-Z$^2$-L$^4$-R$^2$ cannot be selected from: H, halo, C$_{1-6}$ alkyl, —SO$_2$NR$^{6a}$R$^{6b}$, or —O—C$_{1-6}$ alkyl.

In a preferred embodiment of the invention, the compound of formula (I) is a compound selected from:

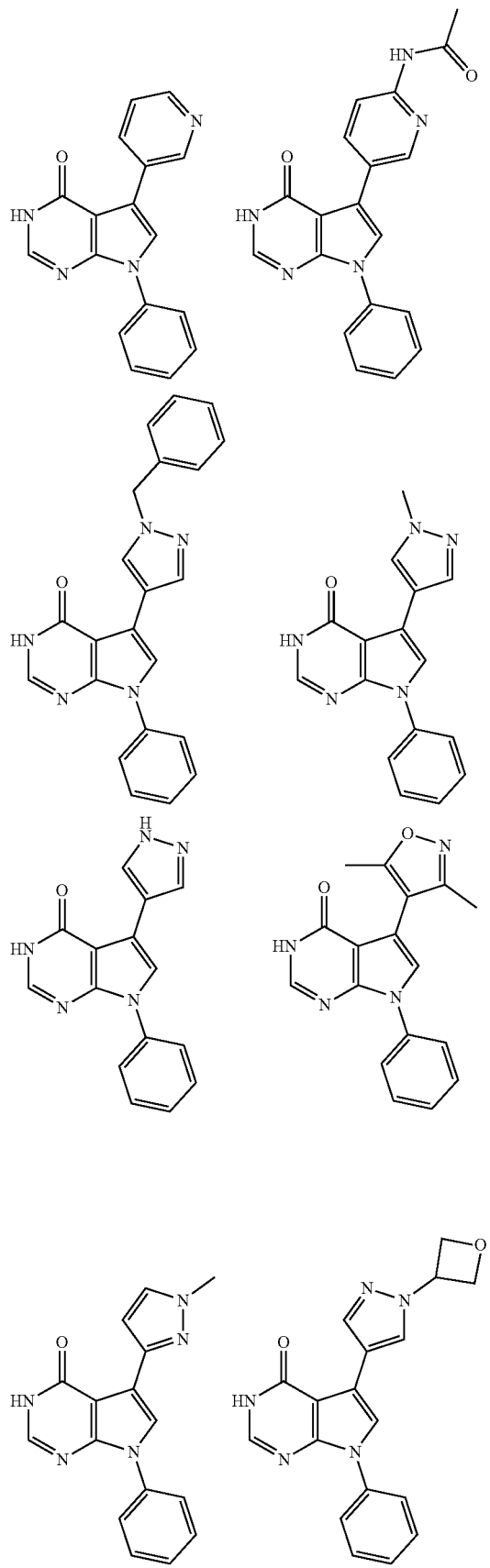

-continued

-continued
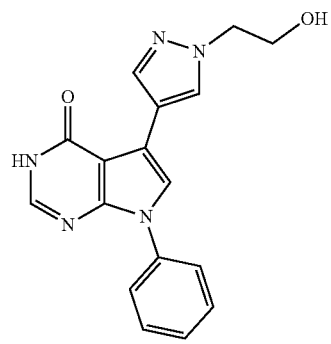
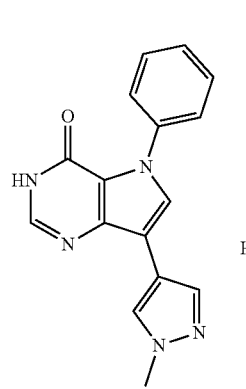
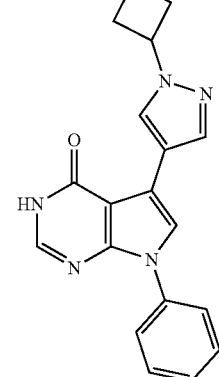
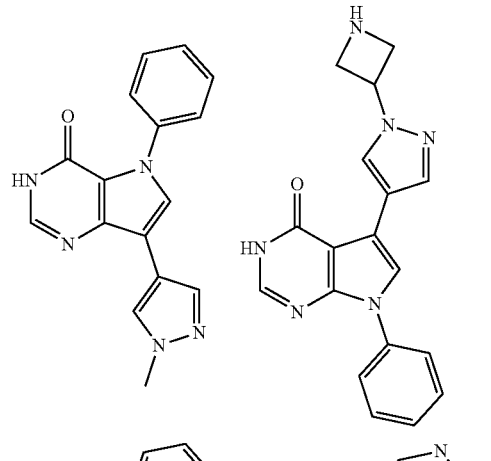
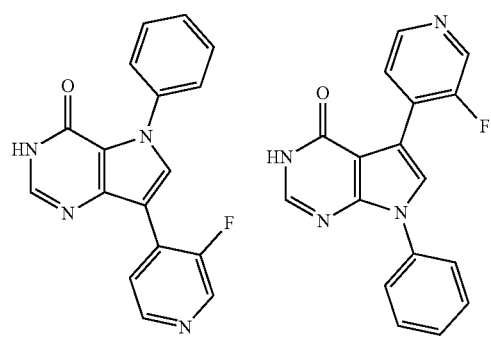
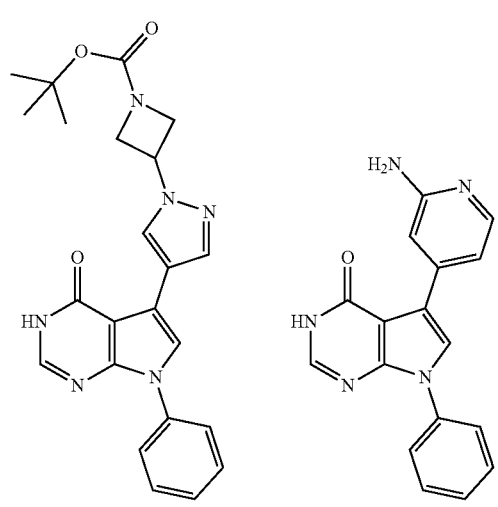
-continued
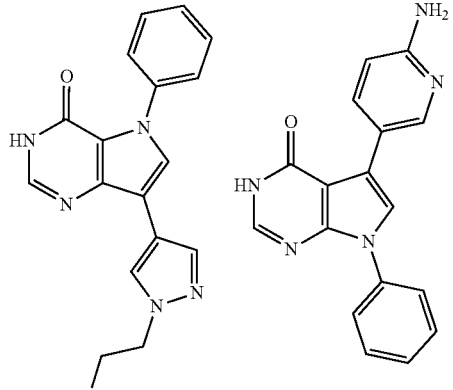
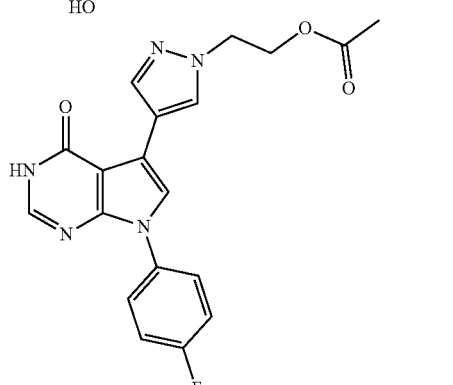
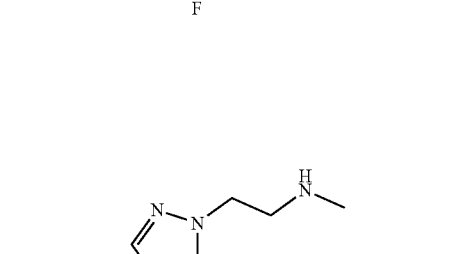
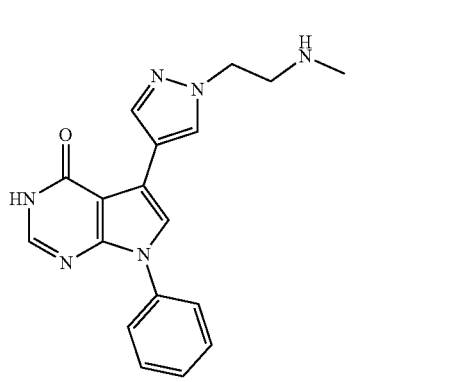
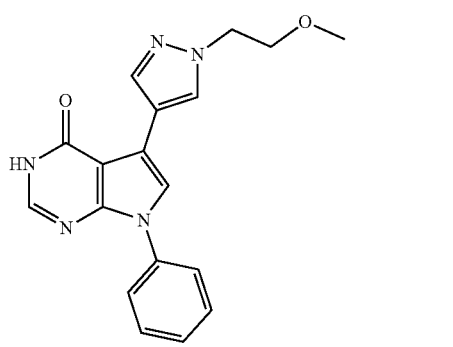

31
-continued
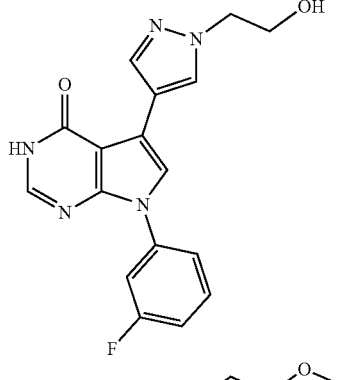
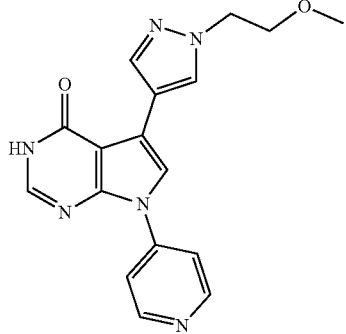
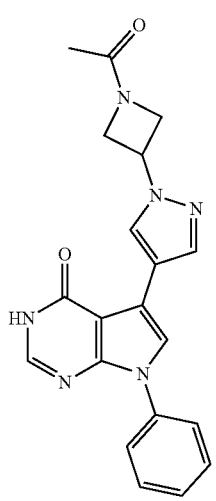
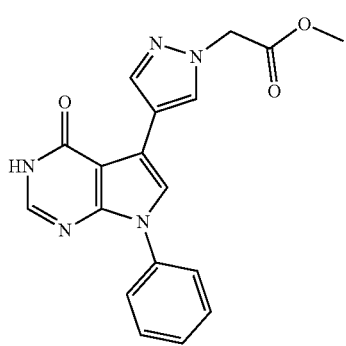
32
-continued
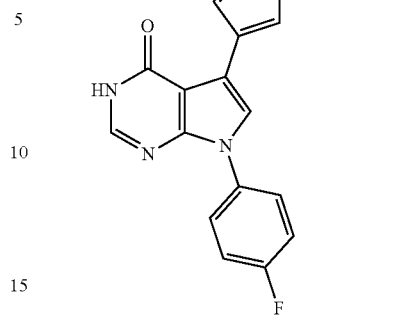
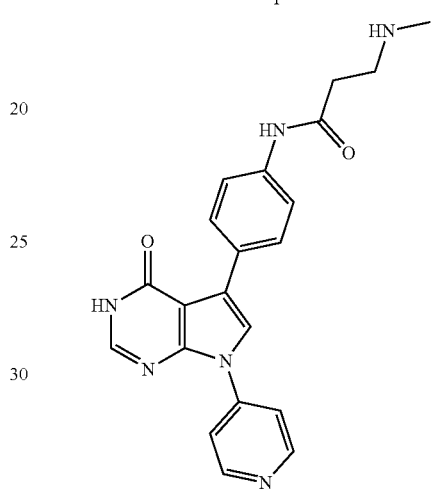
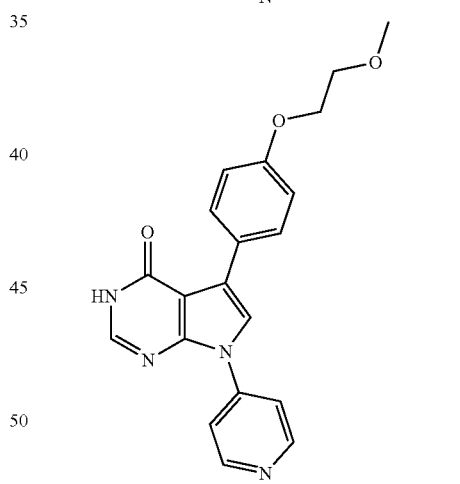
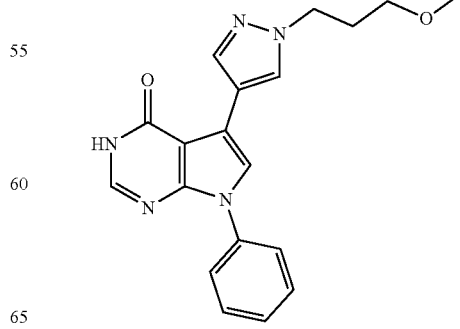

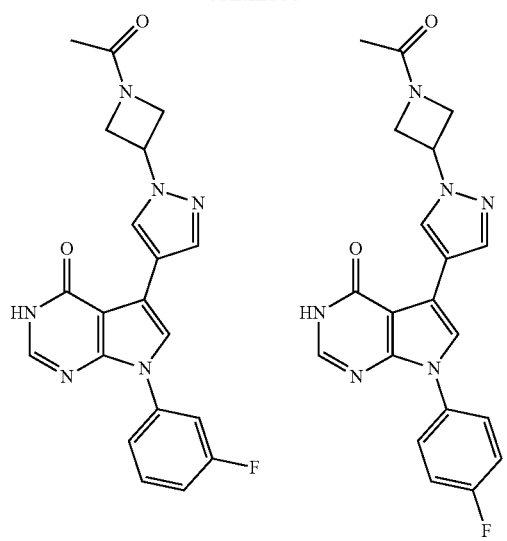
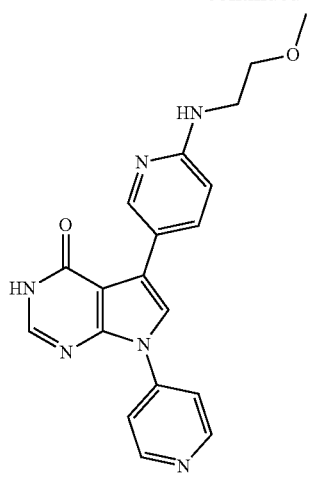
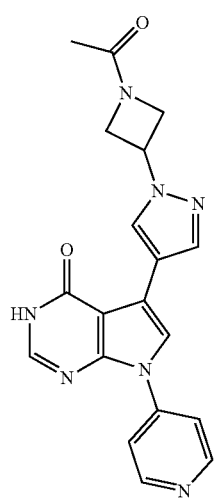
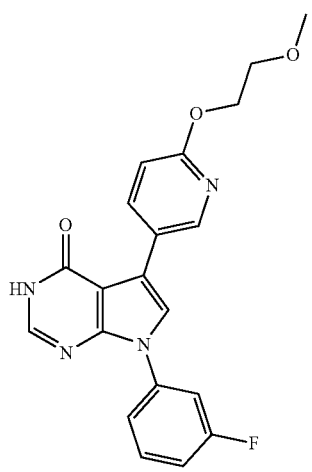
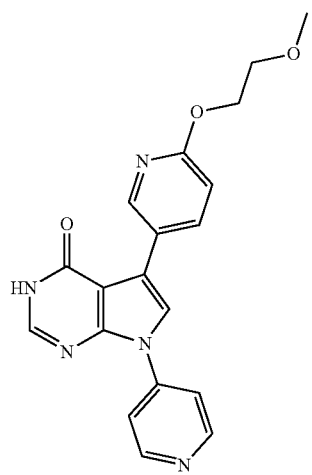
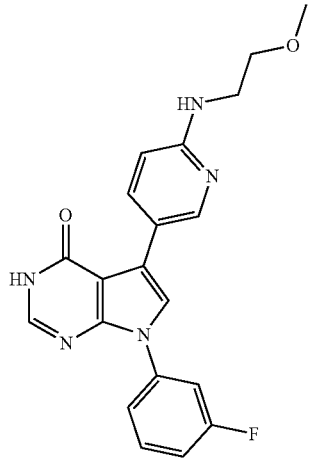

-continued
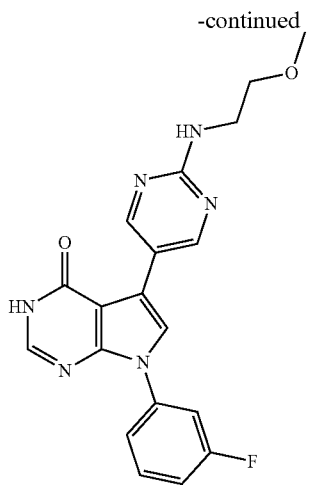
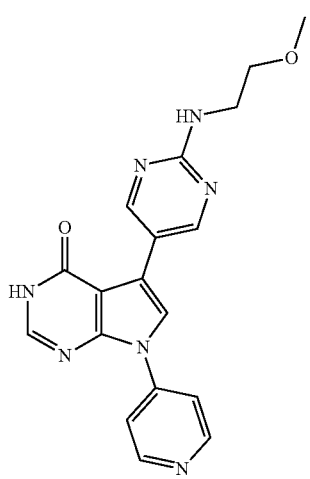
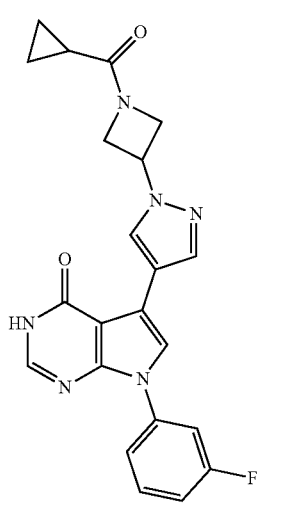
-continued
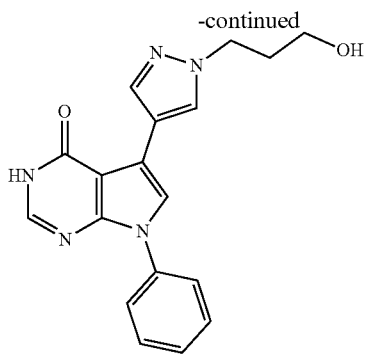
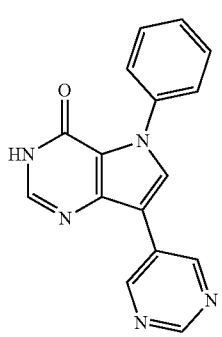 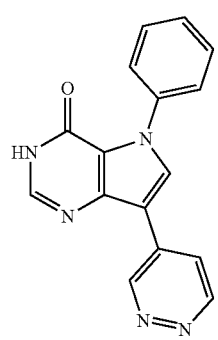
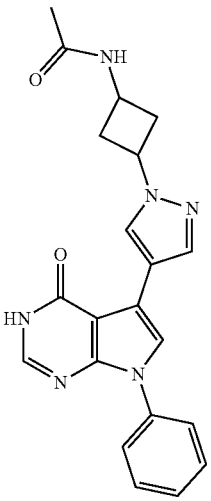
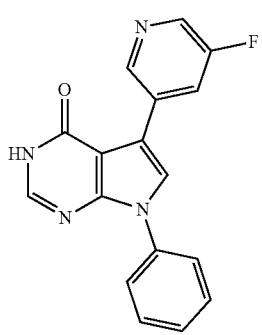

37
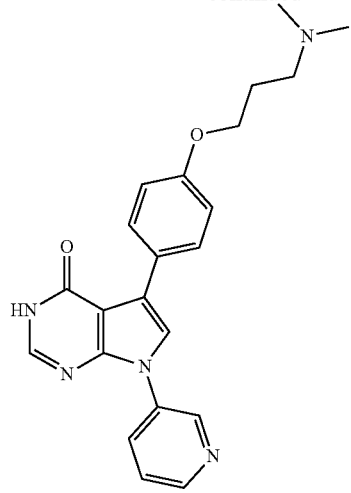
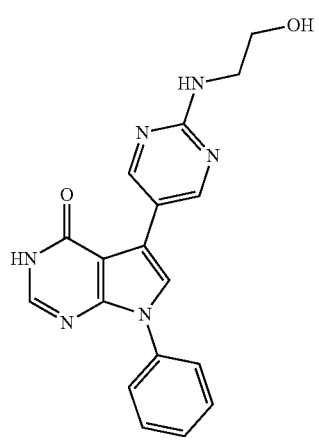
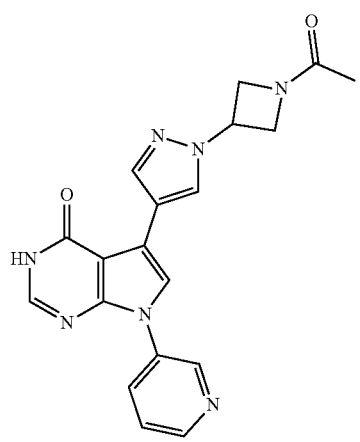
38
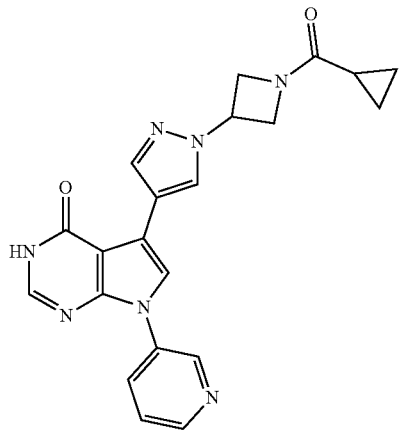
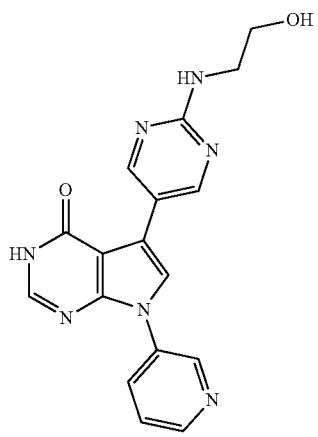
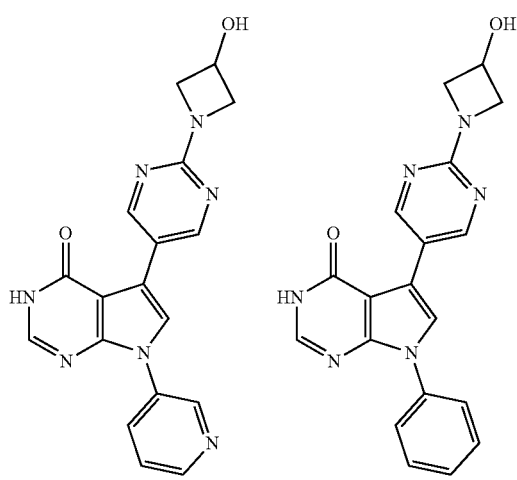

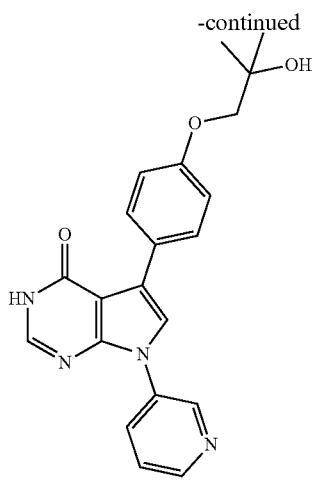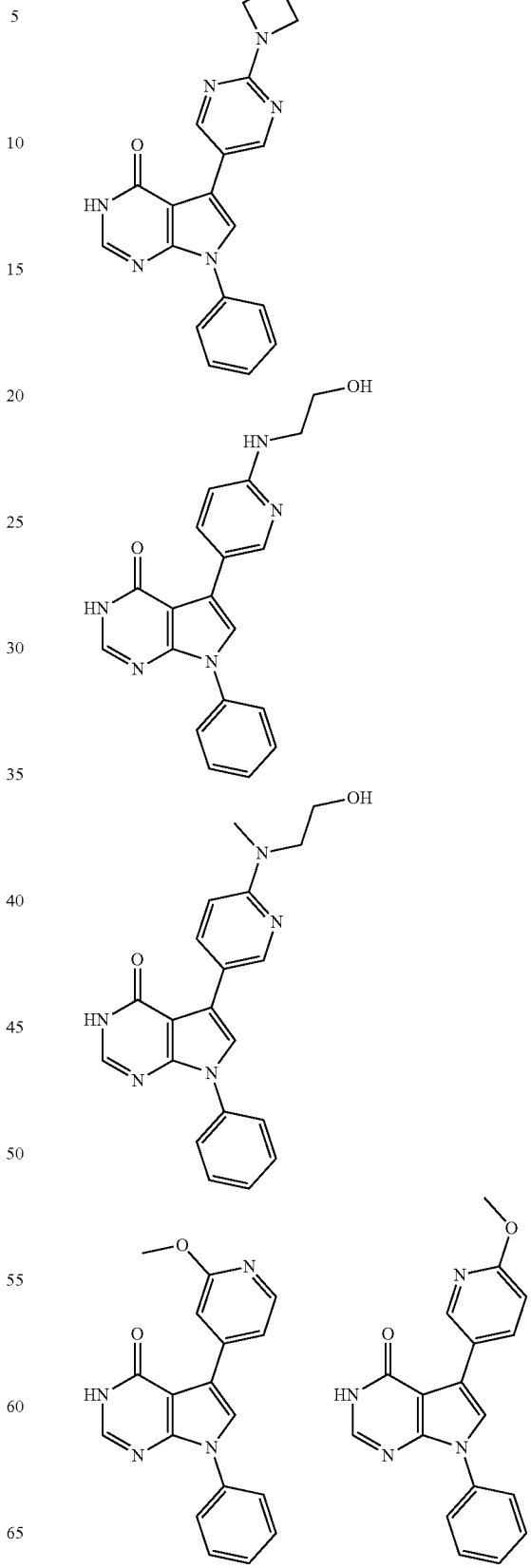

-continued
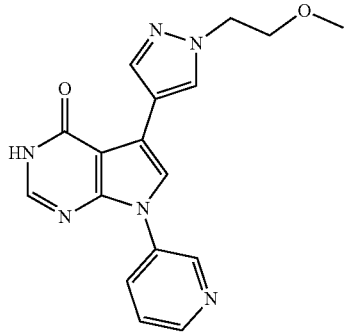
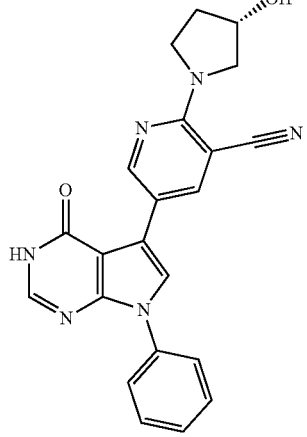
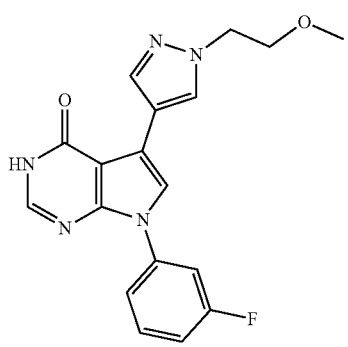
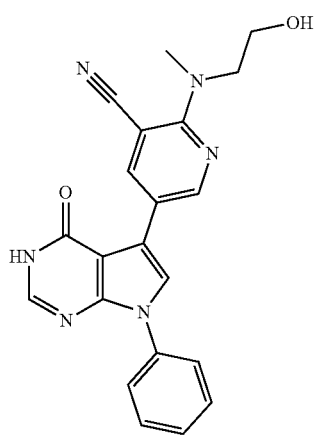
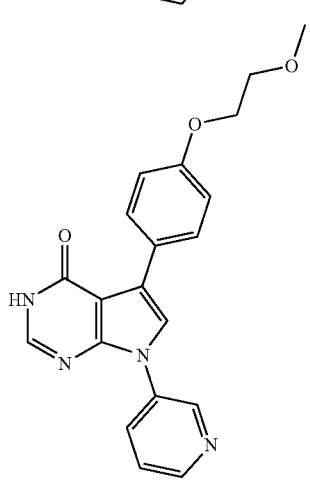
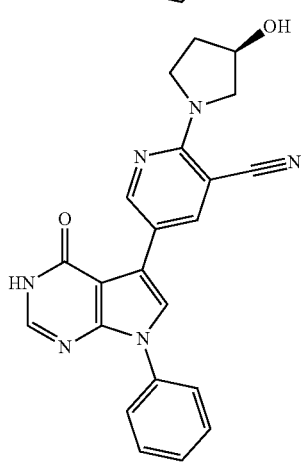
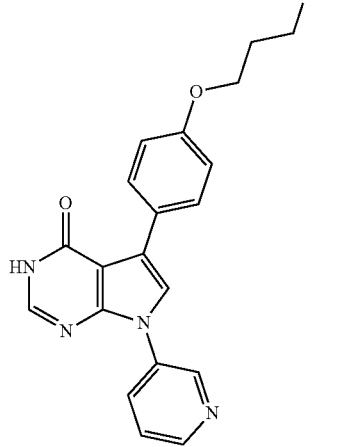

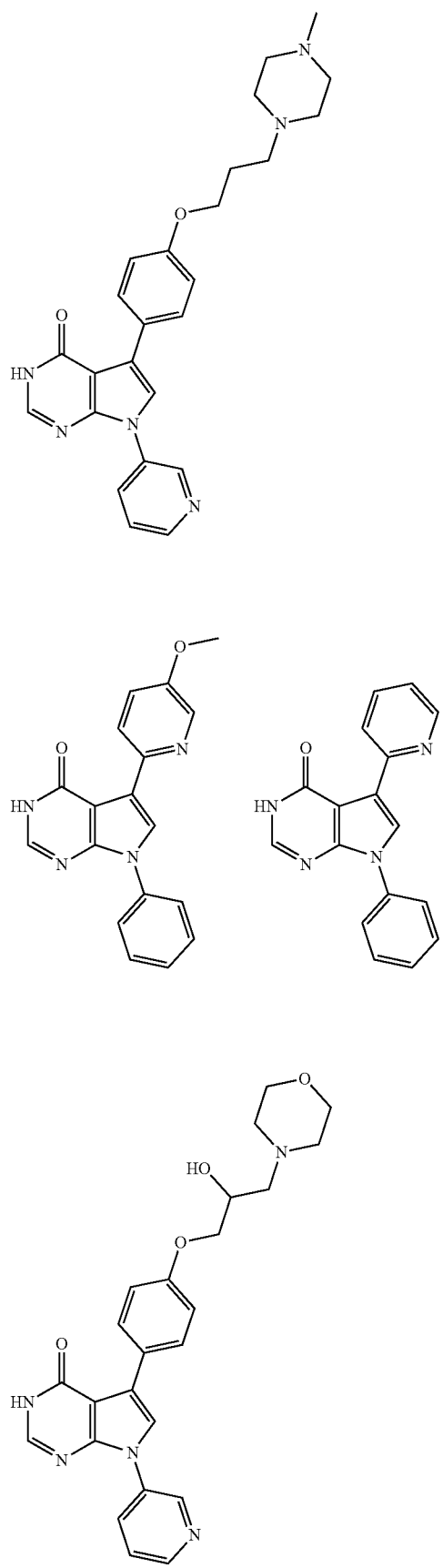
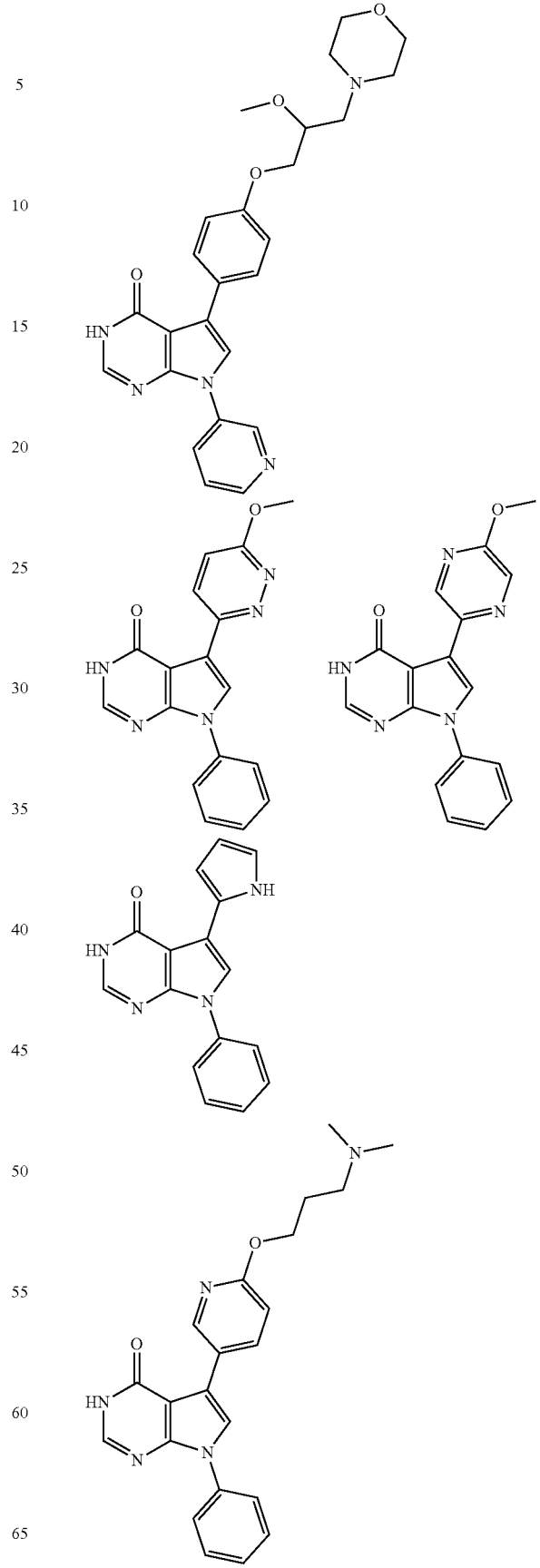

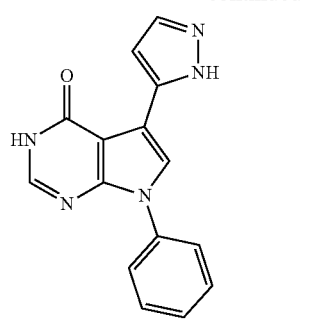
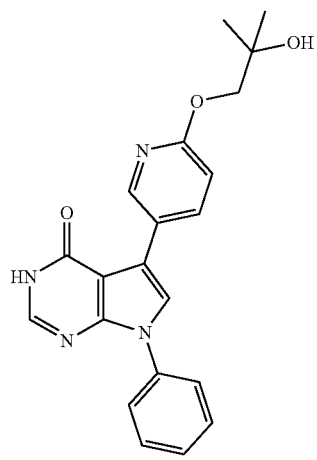

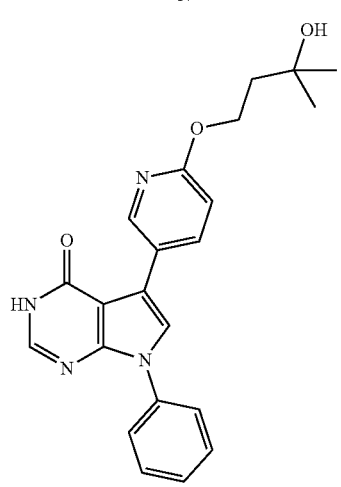
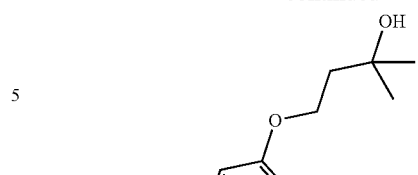
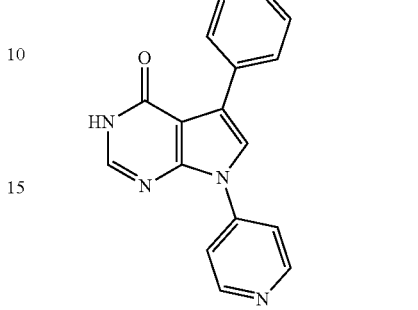
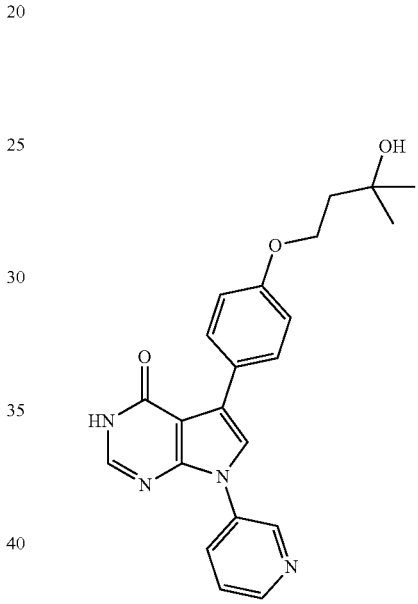
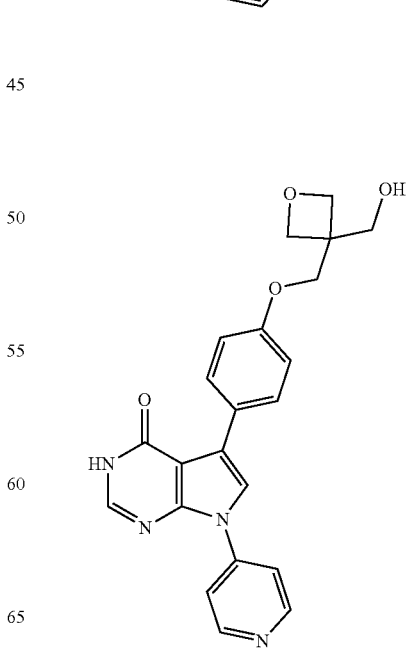

-continued
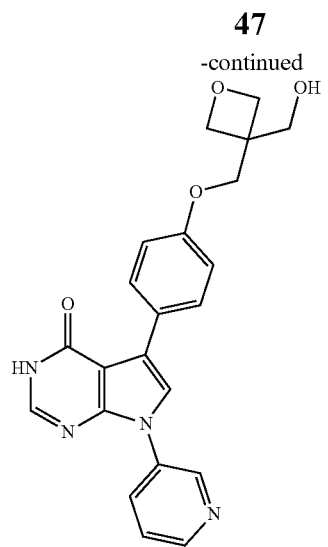
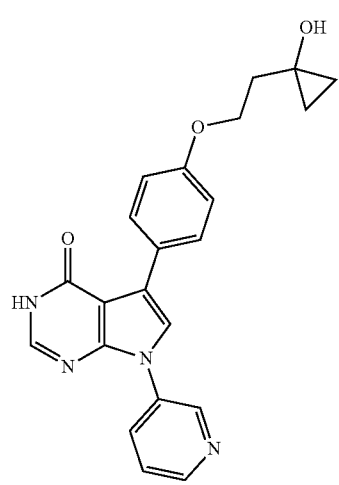
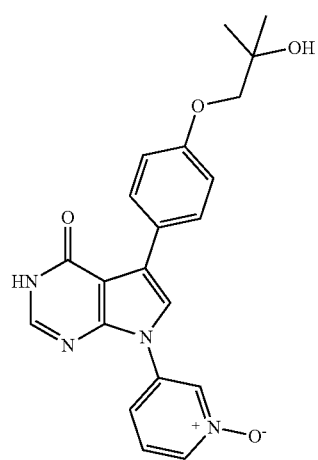
-continued
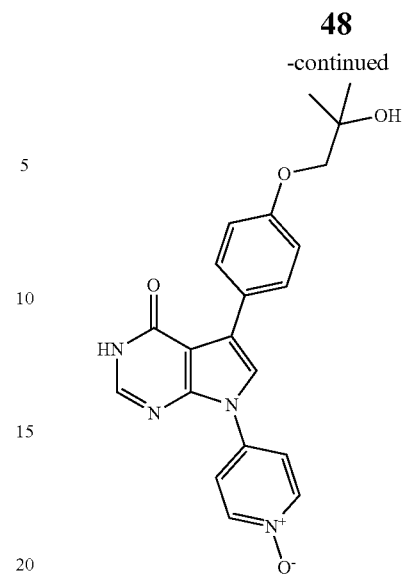
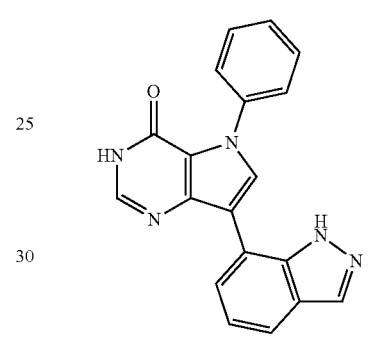
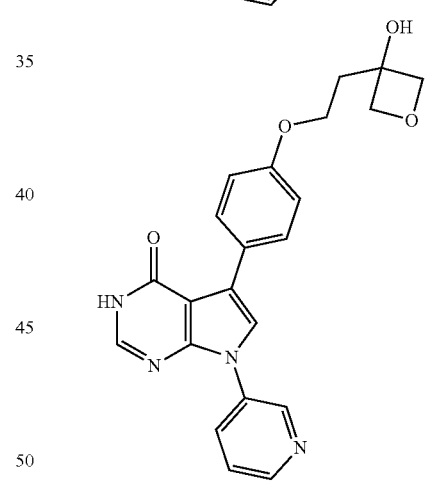
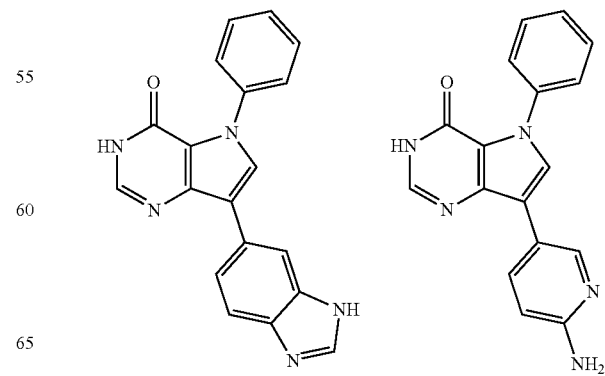

-continued
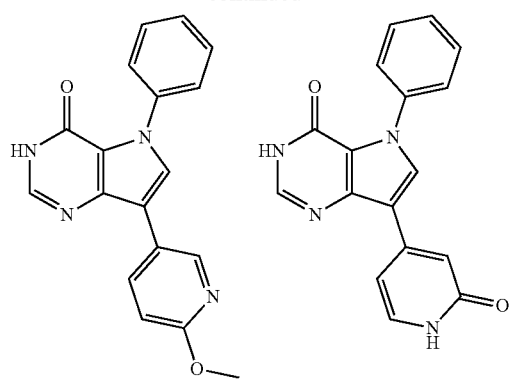
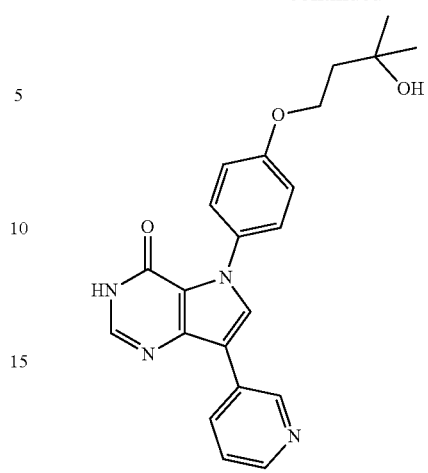
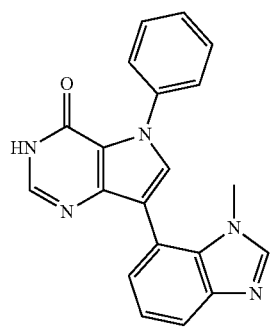
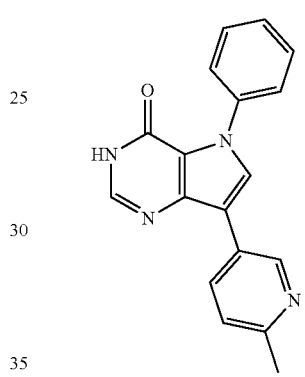
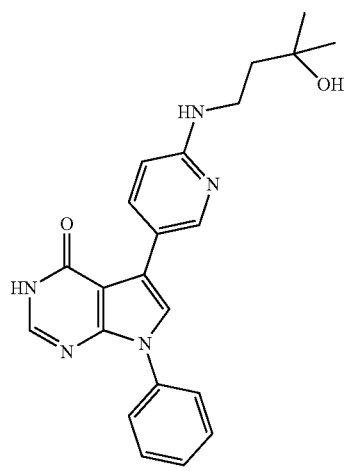
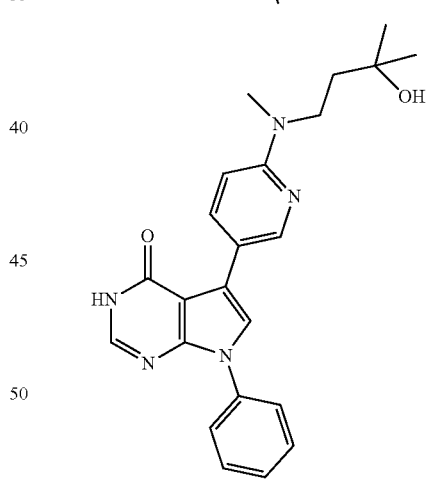
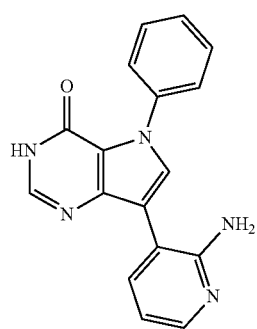
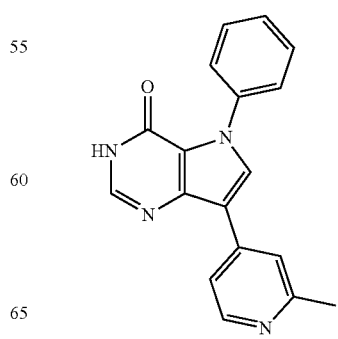

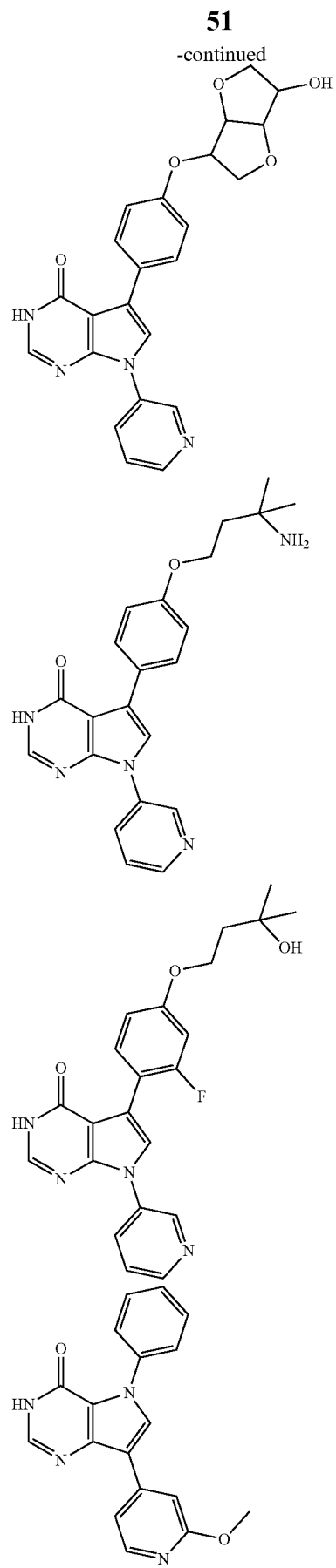
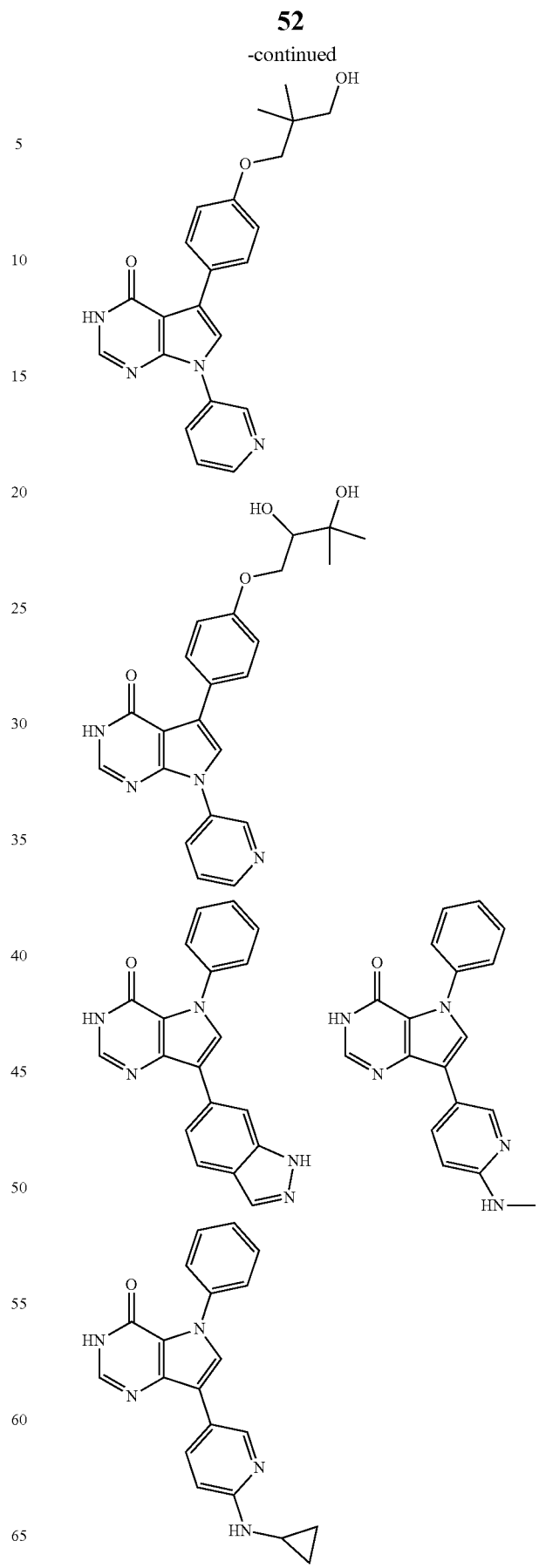

-continued
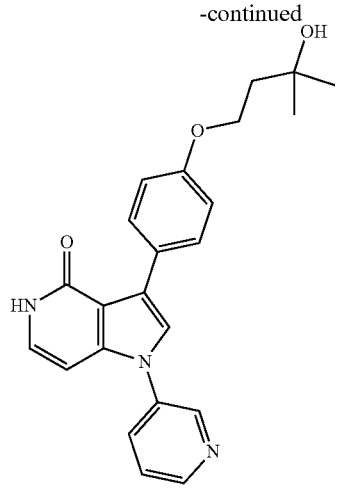
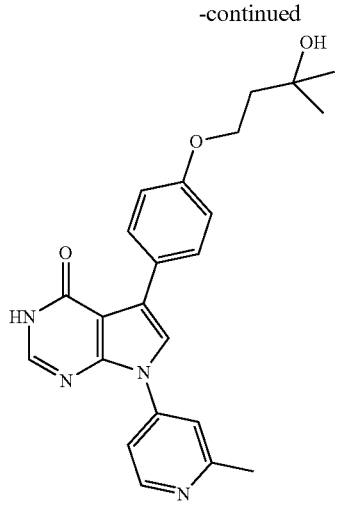
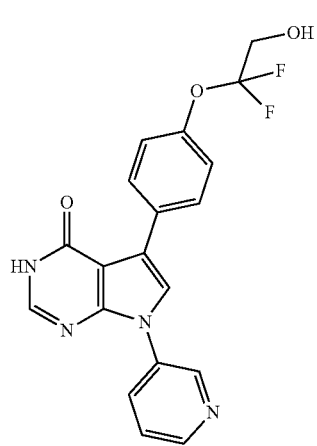
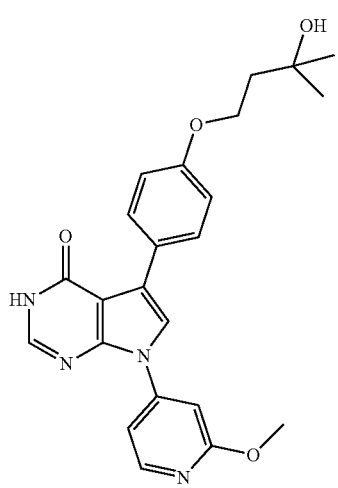
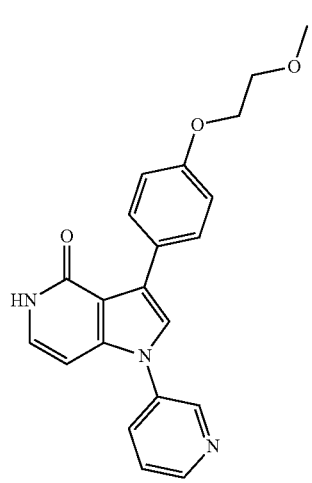
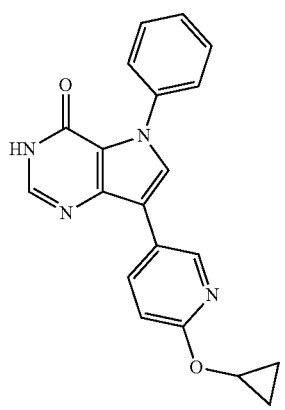

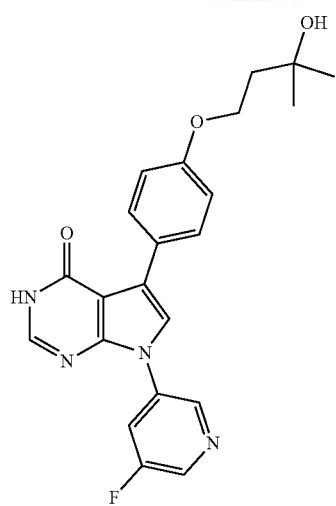
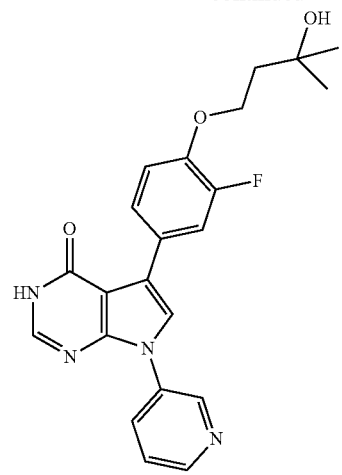
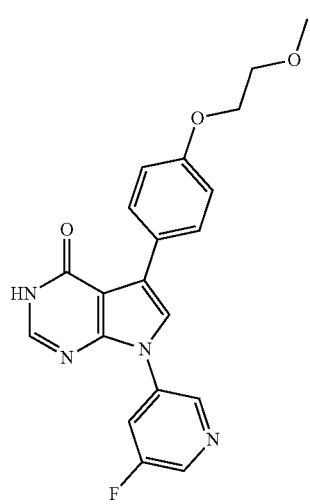
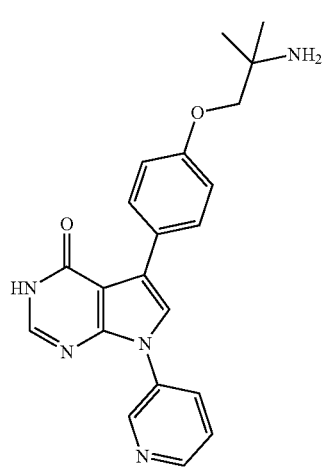
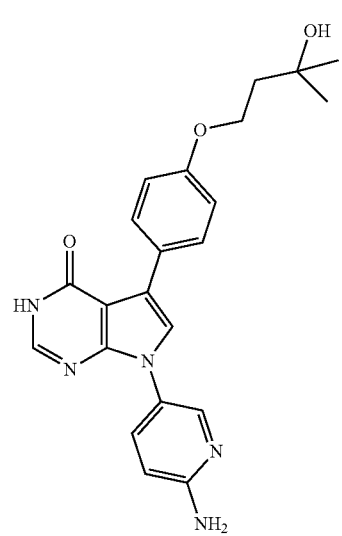

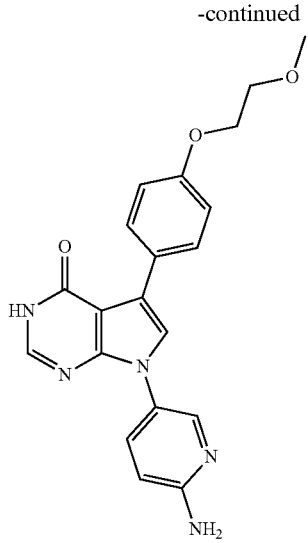

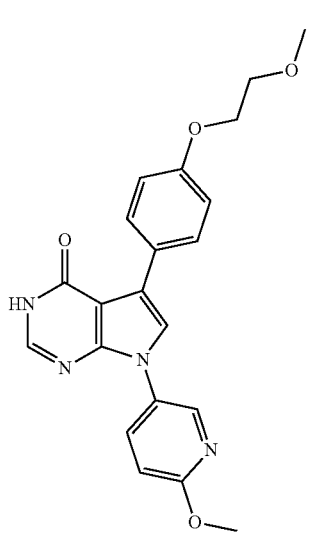

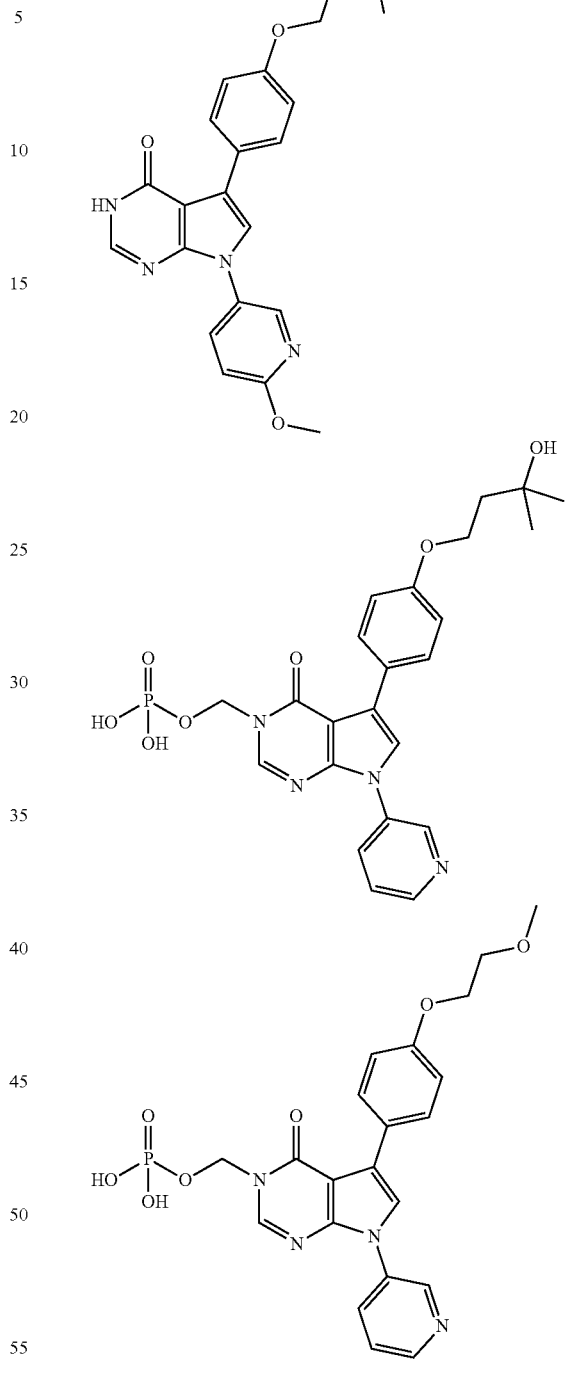

Any of the specific compounds in the preceding paragraph and the following paragraph may be a prodrug, wherein the prodrug is the compound with —CH$_2$OP(=O)(OH)$_2$ substituted on the NH (replacing the H) of the bicyclic core of the compounds. Alternatively, where the compound comprises a free OH or a OMe, the H or the Me could be replaced by —P(=O)(OH)$_2$. An example of potential prodrugs of the invention are demonstrated below. The prodrugs may for part of the present invention. The compounds disclosed herein as prodrugs may also have activity against MAP4K4. Accordingly, those compounds disclosed herein as being prodrugs may also be compounds of the present invention.

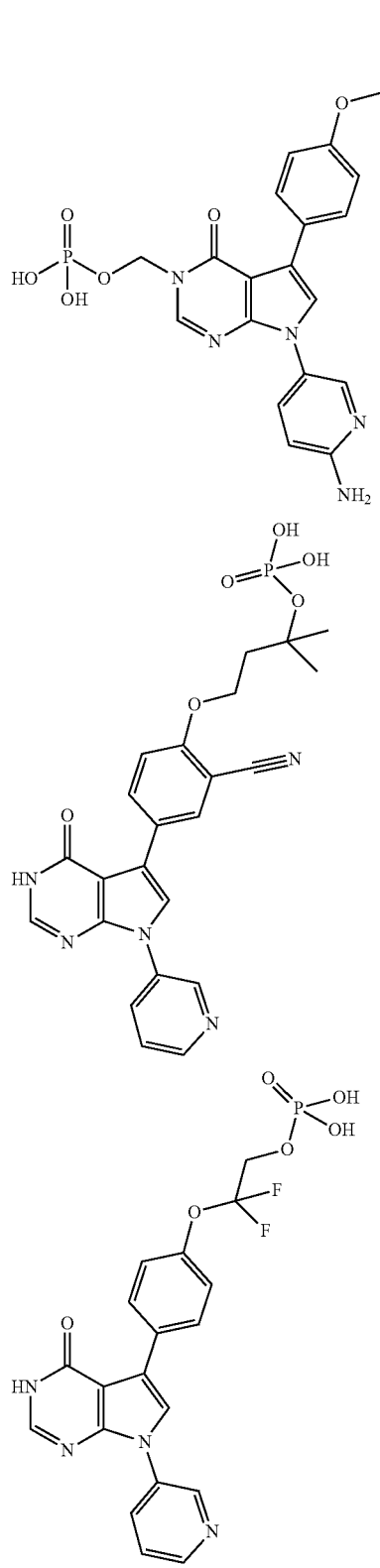

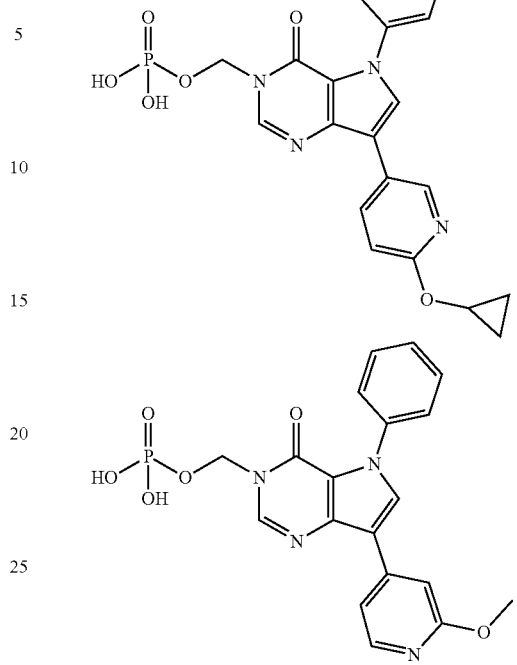

Therapeutic Uses and Applications

In accordance with another aspect, the present invention provides a compound of the invention, or a pharmaceutically acceptable salt thereof, for use as a medicament.

The present invention also provides the compounds of the present invention for use in the treatment of a disease mediated by MAP4K4. Thus, the invention contemplates a method of treating a disease mediated by MAP4K4, wherein the method comprises administering to a patient in need thereof a therapeutically effective amount of a compound of the invention.

The present invention also provides a MAP4K4 inhibitor for use in the treatment of myocardial infarction (colloquially, "heart attacks" due to atherosclerosis, coronary thrombosis, coronary artery anomalies, or other interference with blood flow or oxygen and nutrient delivery to the heart). This aspect of the invention may be a method of treating infarcts, wherein the method comprises the administration of a therapeutically effective amount of a MAP4K4 inhibitor. This aspect may also provide a MAP4K4 inhibitor for use in a method of treating infarcts as an adjunct to standard therapies that restore coronary blood flow (angioplasty, stent placement, thrombolysis) but may, paradoxically, be offset by reperfusion injury. The treatment of an infarct may constitute the complete reversal of an infarct or the reduction in size of an infarct. Reduction of infarct size is known to lessen subsequent progression to heart failure (Selker et al. 2017. Am Heart J 188:18-25).

In an embodiment the MAP4K4 inhibitor is a compound of the present invention, for use in the prevention or treatment of other forms of heart muscle cell injury. These include but are not limited to drug-induced cardiomyopathies (Varga et al. 2015 Am J Physiol Heart Circ Physiol. 2015 November; 309(9):H1453-67), e.g widely used anti-cancer drugs [anthracyclines (Doxorubicin/Adriamycin), cisplatin, trastuzumab (Herceptin), arsenic trioxide (Trisenox), mitoxantrone (Novantrone), imatinib (Gleevec), bevacizumab (Avastin), sunitinib (Sutent), and sorafenib (Nevaxar)], antiviral compound azidothymidine (AZT, Zidovudine), several oral antidiabetics [e.g., rosiglitazone (Avandia)], and illicit drugs such as alcohol, cocaine, methamphetamine, ecstasy, and synthetic cannabinoids (spice, K2).

In an embodiment the MAP4K4 inhibitor is a compound of the present invention, for use in the prevention or treatment of other forms of heart muscle cell injury, optionally due to cardiopulmonary bypass.

In an embodiment the MAP4K4 inhibitor is a compound of the present invention, for use in the prevention or treatment of chronic forms of heart muscle cell injury, such as hypertrophic, dilated, or mitochondrial cardiomyopathies. These include cardiomyopathies due to: genetic conditions; high blood pressure; heart tissue damage from a previous heart attack; chronic rapid heart rate; heart valve problems; metabolic disorders, such as obesity, thyroid disease or diabetes; nutritional deficiencies of essential vitamins or minerals, such as thiamine (vitamin B1); pregnancy complications; alcohol consumption; use of cocaine, amphetamines or anabolic steroids; radiotherapy to treat cancer; certain infections, which may injure the heart and trigger cardiomyopathy; hemochromatosis; sarcoidosis; amyloidosis; and connective tissue disorders.

In an embodiment the MAP4K4 inhibitor is a compound of the present invention, for use in the prevention or treatment of other forms of ischemic injury or ischemia-reperfusion injury, including ischemia stroke, renal artery occlusion, and global ischemia-reperfusion injury (cardiac arrest).

In an embodiment the MAP4K4 inhibitor is a compound of the present invention, for use in the prevention or treatment of cardiac muscle cell necrosis or cardiac muscle cell apoptosis.

In embodiments there is provided a compound of the present invention for use in a method of treatment of heart muscle cell injury, heart muscle cell injury due to cardiopulmonary bypass, chronic forms of heart muscle cell injury, hypertrophic cardiomyopathies, dilated cardiomyopathies, mitochondrial cardiomyopathies, cardiomyopathies due to genetic conditions; cardiomyopathies due to high blood pressure; cardiomyopathies due to heart tissue damage from a previous heart attack; cardiomyopathies due to chronic rapid heart rate; cardiomyopathies due to heart valve problems; cardiomyopathies due to metabolic disorders; cardiomyopathies due to nutritional deficiencies of essential vitamins or minerals; cardiomyopathies due to alcohol consumption; cardiomyopathies due to use of cocaine, amphetamines or anabolic steroids; cardiomyopathies due to radiotherapy to treat cancer; cardiomyopathies due to certain infections which may injure the heart and trigger cardiomyopathy; cardiomyopathies due to hemochromatosis; cardiomyopathies due to sarcoidosis; cardiomyopathies due to amyloidosis; cardiomyopathies due to connective tissue disorders; drug- or radiation-induced cardiomyopathies; idiopathic or cryptogenic cardiomyopathies; other forms of ischemic injury, including but not limited to ischemia-reperfusion injury, ischemia stroke, renal artery occlusion, and global ischemia-reperfusion injury (cardiac arrest); cardiac muscle cell necrosis; or cardiac muscle cell apoptosis.

In an aspect there is provided a method of using stem cell-derived cardiomyocytes for the identification of therapies for myocardial infarction, wherein the method comprising contacting stem cell derived cardiomyocytes with compounds in a cell culture model of cardiac muscle cell death. For example, as indicated in the examples of the present application.

In embodiments the method is conducted ex vivo. Thus, in embodiments the method is not a method of treatment or diagnosis.

In an embodiment the method of using stem cell-derived cardiomyocytes for the identification of therapies for myocardial infarction uses human stem cell derived cardiomyocytes.

In embodiments there is provided a method of using human stem cell-derived cardiomyocytes for the identification of therapies for myocardial infarction wherein the method comprises subjecting human stem cell-derived cardiomyocytes with candidate test compounds in a cell culture model of cardiac muscle cell death. Examples of relevant stressors, by which compounds may be tested, include: $H_2O_2$, menadione, and other compounds that confer oxidative stress; hypoxia; hypoxia/reoxygenation; glucose deprivation or compounds that interfere with metabolism; cardiotoxic drugs; proteins or genes that promote cell death; interference with the expression or function of proteins or genes that antagonise cell death. Cell death is taken to encompass apoptosis, necrosis, necroptosis, or autophagy, singly or in combination.

BRIEF DESCRIPTION OF THE DRAWINGS

Embodiments of the invention are further described hereinafter with reference to the accompanying drawings, in which:

FIG. 2 provides data where a simulated increase in MAP4K4 activity was simulated and a pro-apoptotic effect of MAP4K4 was demonstrated.

DETAILED DESCRIPTION

Figure 1A:
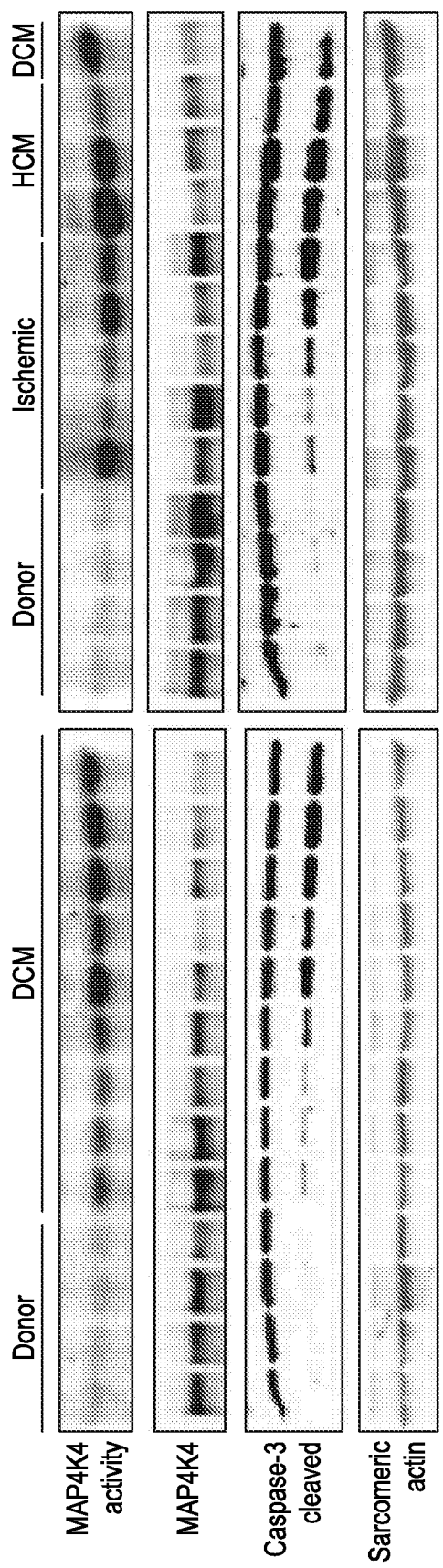
FIG. 1 provides data demonstrating the relationship between MAP4K4 and cardiac muscle cell death.

Unless otherwise stated, the following terms used in the specification and claims have the following meanings set out below.

It is to be appreciated that references to "treating" or "treatment" include prophylaxis as well as the alleviation of established symptoms or physical manifestations of a condition. "Treating" or "treatment" of a state, disorder or condition therefore includes: (1) preventing or delaying the appearance of clinical symptoms or physical manifestations of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the method of administration, the disease and its severity and the age, weight, etc., of the mammal to be treated.

The term "halo" or "halogen" refers to one of the halogens, group 17 of the periodic table. In particular the term refers to fluorine, chlorine, bromine and iodine. Preferably, the term refers to fluorine or chlorine.

The term $C_{m-n}$ refers to a group with m to n carbon atoms.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_{1-4}$ alkyl" similarly refers to such groups containing from 1 to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described in more detail below. Substituents for the alkyl group may be halogen, e.g. fluorine, chlorine, bromine and iodine, OH, $C_1$-$C_4$alkoxy. Other substituents for the alkyl group may alternatively be used.

The term "haloalkyl", e.g. "$C_{1-6}$ haloalkyl", refers to a hydrocarbon chain substituted with at least one halogen atom independently chosen at each occurrence, for example from fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{3-6}$ cycloalkyl" includes a saturated hydrocarbon ring system containing 3, 4, 5 or 6 carbon atoms. For example, the "$C_3$-$C_6$ cycloalkyl" may be cyclopropyl, cyclobutyl, cyclopentyl, cyclohexyl, bicyclo[2.1.1]hexane or bicyclo[1.1.1]pentane.

The term "heterocycloalkyl" includes a saturated monocyclic or fused, bridged, or spiro bicyclic heterocyclic ring system(s). The term "heterocycloalkyl" includes ring systems with from 1 to 5 (suitably 1, 2 or 3) heteroatoms selected from nitrogen, oxygen or sulfur in the ring. Unless otherwise indicated by a recital of the number of atoms within the heterocycloalkyl ring, monocyclic heterocycloalkyl rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 17 member atoms, suitably 7 to 12 member atoms, in the ring. Bicyclic heterocyclic(s) rings may be fused, spiro, or bridged ring systems. Examples of heterocycloalkyl groups include cyclic ethers such as oxiranyl, oxetanyl, tetrahydrofuranyl, dioxanyl, and substituted cyclic ethers. Heterocycloalkyl rings comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 3,8-diaza-bicyclo[3.2.1]octanyl, 8-aza-bicyclo[3.2.1]octanyl, 2,5-Diaza-bicyclo[2.2.1]heptanyl and the like. Typical sulfur containing heterocycloalkyl rings include tetrahydrothienyl, dihydro-1,3-dithiol, tetrahydro-2H-thiopyran, and hexahydrothiepine. Other heterocycloalkyl rings include dihydrooxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolanyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen.

The term "bridged ring systems" includes ring systems in which two rings share more than two atoms, see for example Advanced Organic Chemistry, by Jerry March, 4th Edition, Wiley Interscience, pages 131-133, 1992.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated TT system where all atoms contributing to the conjugated TT system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridyl N-oxide, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridyle N-oxide, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

A bond terminating in a "⌇" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

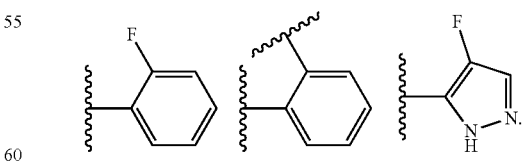

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

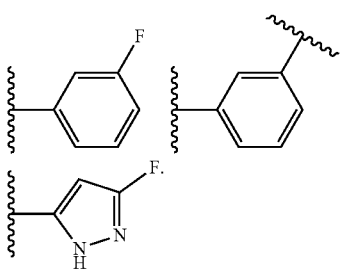

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

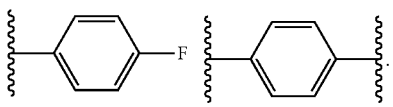

The term "acyl" includes an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, e.g. R is H or $C_{1-3}$ alkyl. In one embodiment acyl is alkyl-carbonyl. Examples of acyl groups include, but are not limited to, formyl, acetyl, propionyl and butyryl. A particular acyl group is acetyl (also represented as Ac).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:

(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%.

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2H$ (also written as "D" for deuterium), $^3H$ (also written as "T" for tritium), $^{11}C$, $^{13}C$, $^{14}C$, $^{15}O$, $^{17}O$, $^{18}O$, $^{18}F$ and the like. The radionuclide that is used will depend on the specific application of that radio-labelled derivative. For example, for in vitro competition assays, $^3H$ or $^{14}C$ are often useful. For radio-imaging applications, $^{11}C$ or $^{18}F$ are often useful. In some embodiments, the radionuclide is $^3H$. In some embodiments, the radionuclide is $^{14}C$. In some embodiments, the radionuclide is $^{11}C$. And in some embodiments, the radionuclide is $^{18}F$.

It is also to be understood that certain compounds of the invention may exist in solvated as well as unsolvated forms such as, for example, hydrated forms. It is to be understood that the invention encompasses all such solvated forms that possess MAP4K4 inhibitory activity.

It is also to be understood that certain compounds of the invention may exhibit polymorphism, and that the invention encompasses all such forms that possess MAP4K4 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

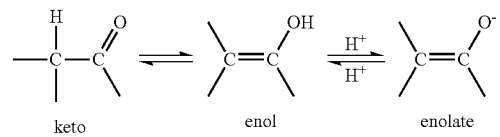

The in vivo effects of a compound of the invention may be exerted in part by one or more metabolites that are formed within the human or animal body after administration of a compound of the invention.

Equally a compound of the present invention may be responsible for in vivo effects but the compound may have been administered in a pro-drug form. Accordingly, the present invention contemplates pro-drugs of compounds of formula (I), whether with or without proviso.

Further information on the preparation of the compounds of the invention is provided in the Examples section. The general reaction schemes and specific methods described in the Examples form a further aspect of the invention.

The resultant compound of the invention from the processes defined above can be isolated and purified using techniques well known in the art.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The processes defined herein may further comprise the step of subjecting the compound of the invention to a salt exchange, particularly in situations where the compound of the invention is formed as a mixture of different salt forms. The salt exchange suitably comprises immobilising the compound of the invention on a suitable solid support or resin, and eluting the compounds with an appropriate acid to yield a single salt of the compound of the invention.

In a further aspect of the invention, there is provided a compound of the invention obtainable by any one of the processes defined herein.

Certain of the intermediates described in the reaction schemes above and in the Examples herein may be novel. Such novel intermediates, or a salt thereof, particularly a pharmaceutically acceptable salt thereof, form a further aspect of the invention.

Pharmaceutical Compositions

In accordance with another aspect, the present invention provides a pharmaceutical formulation comprising a compound of the invention, or a pharmaceutically acceptable salt thereof, and a pharmaceutically acceptable excipient.

Conventional procedures for the selection and preparation of suitable pharmaceutical formulations are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, intracoronary, subcutaneous, intramyocardial, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to achieve symptomatic relief in a warm-blooded animal, particularly a human of the symptoms of the condition, to mitigate the physical manifestations of the condition, or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the concentration of the compound required for effectiveness in isolated cells, the concentration of the compound required for effectiveness in experimental animals, the age and sex of the animal or patient and the route of administration, according to well known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Suitably the compound of the invention is adminstered orally, for example in the form of a tablet, or capsule dosage form. The daily dose administered orally may be, for example a total daily dose selected from 1 mg to 2000 mg, 5 mg to 2000 mg, 5 mg to 1500 mg, 10 mg to 750 mg or 25 mg to 500 mg. Typically, unit dosage forms will contain about 0.5 mg to 0.5 g of a compound of this invention.

EXPERIMENTAL

General Chemical Synthesis

All reagents were either purchased from commercial sources or synthesised in accordance with known literature procedures unless otherwise stated. Commercial reagents were used without further purification unless otherwise stated. Microwave reactions were conducted using a CEM Discover (200 W). Flash column chromatography was conducted using pre-packed silica Biotage® SNAP (KP-Sil/KP-C18-HS) cartridges. Ion exchange chromatography was performed using Isolute® SCX-2 and Isolute® NH2 cartridges. Palladium removal was conducted using SiliaPrep™ SPE Thiol cartridges referred to a Si-thiol in the experimental methods. On a number of occasion Biotage® phase separators were used to separate the organic from the aqeuous layer during aqueous work up. These are referred to as phase separators. All photochemical reactions were carried out using a Hepatochem photoredox duo fitted with 2 Evoluchem royal blue 18 W lights irradiating at 450-455 nM placed on a magnetic stirrer. Reactions were carried out in 28 mL vials fitted with solid lids sealed with parafilm.

Abbreviations Used

\* apparent
AcOH acetic acid
$Ac_2O$ acetic anhydride
aq. aqueous
br broad
Cpd # Compound number
$Cu(OAc)_2$ Copper(II) acetate monohydrate
CV column volume
d doublet
dd doublet of doublets
DCM dichloromethane
DIPEA N,N-diisopropylamine
DMF N,N-dimethylformamide
DMSO dimethyl sulfoxide
DMSO-d6 Dimethyl sulfoxide-d6
EDTA Ethylenediaminetetraacetic acid
ESI electrospray ionisation
$Et_2O$ diethyl ether
EtOAc ethyl acetate
EtOH ethanol
h hour(s)
HPLC high-performance liquid chromatography
HPLC-MS high-performance liquid chromatography-mass spectrometry
KOAc potassium acetate
KO$^t$Bu potassium tert-butoxide
LC-MS liquid chromatography-mass spectrometry
LiHMDS Lithium bis(trimethylsilyl)amide solution
m multiplet
MeCN acetonitrile
MeOH methanol
min minute(s)
m/z mass/charge ratio
NaOAc sodium acetate
$NEt_3$ triethylamine
NMR nuclear magnetic resonance
Pd(dppf)$Cl_2$.DCM [1,1'-bis(diphenylphosphino)ferrocene]dichloropalladium
Pd(PPh$_3$)$_4$ Tetrakis(triphenylphosphine)palladium(0)
PPh$_3$ triphenyl phosphine
PS polymer supported
q quartet
quant quantitative
quint quintet
RT room temperature
$R_t$ retention time
s singlet
satd. saturated
t triplet
tt triplet of triplets TBTU O-(benzotriazol-1-yl)-N,N,N',N'-tetramethyluronium tetrafluoroborate
TFA trifluoroacetic acid
THF tetrahydrofuran
WAX weak anion exchange Analytical Methods A number of compounds were purified by reversed phase preparative HPLC-MS: Mass-directed purification by preparative LC-MS using a preparative C-18 column (Phenomenex Luna C18 (2), 100×21.2 mm, 5 μm).

Analysis of products and intermediates was carried out using reversed phase analytical HPLC-MS using the parameters set out below.

HPLC Analytical Methods

AnalpH2_MeOH_4 min: Phenomenex Luna C18 (2) 3 μm, 50×4.6 mm; A=water+0.1% formic acid; B=MeOH; 45° C.; % B: 0 min 5%, 1 min 37.5%, 3 min 95%, 3.51 min 5%, 4.0 min 5%; 2.25 mL/min.

AnalpH2_MeOH_4 min(1): Phenomenex Luna C18 (2) 3 μm, 50×4.6 mm; A=water+0.1% formic acid; B=MeOH+0.1% formic acid; 45° C.; % B: 0 min 5%, 1 min 37.5%, 3 min 95%, 3.51 min 5%, 4.0 min 5%; 2.25 mL/min.

AnalpH2_MeCN_4 min: Phenomenex Luna C18 (2) 3 μm, 50×4.6 mm; A=water+0.1% formic acid; B=Acetonitrile; 45° C.; % B: 0 min 5%, 1 min 37.5%, 3 min 95%, 3.51 min 5%, 4.0 min 5%; 2.25 mL/min.

AnalpH2_MeCN_4 min(1): Acquity BEH C18 (2) 1.7 μm, 50×2.1 mm; A=water+0.1% formic acid; B=Acetonitrile+0.1% formic acid; 35° C.; % B: 0 min 3%, 0.4 min 3%, 2.5 min 98%, 3.4 min 98%, 3.5 min 3%, 4.0 min 3%; 0.6 mL/min.

AnalpH9_MeOH_4 min: Phenomenex Luna C18 (2) 3 μm, 50×4.6 mm; A=water pH9 (Ammonium Bicarbonate 10 mM); B=MeOH; 45° C.; % B: 0 min 5%, 1 min 37.5%, 3 min 95%, 3.51 min 5%, 4.0 min 5%; 2.25 mL/min.

AnalpH9_MeCN_4 min: Phenomenex Luna C18 (2) 3 μm, 50×4.6 mm; A=water pH9 (Ammonium Bicarbonate 10 mM); B=Acetonitrile; 45° C.; % B: 0 min 5%, 1 min 37.5%, 3 min 95%, 3.51 min 5%, 4.0 min 5%; 2.25 mL/min.

AnalpH2_MeOH_QC_V1: Phenomenex Gemini NX C18 5 μm, 150×4.6 mm; A=water+0.1% formic acid; B=MeOH; 40° C.; % B: 0 min 5%, 7.5 min 95%, 10 min 95%, 10.10 min 5%, 13.0 min 5%; 1.5 mL/min.

AnalpH2_MeOH_QC_V1 (1): Phenomenex Gemini NX C18 (2) 5 μm, 150×4.6 mm; A=water+0.1% formic acid; B=MeOH+0.1% formic acid; 40° C.; % B: 0 min 5%, 7.5 min 95%, 10 min 95%, 10.10 min 5%, 13.0 min 5%; 1.5 mL/min.

AnalpH2_MeCN_QC_V1: Phenomenex Gemini NX C18 5 μm, 150×4.6 mm; A=water+0.1% formic acid; B=Acetonitrile; 40° C.; % B: 0 min 5%, 7.5 min 95%, 10 min 95%, 10.10 min 5%, 13.0 min 5%; 1.5 mL/min.

AnalpH9_MeOH_QC_V1: Phenomenex Gemini NX C18 5 μm, 150×4.6 mm; A=water+pH9 (Ammonium Bicarbonate 10 mM); B=MeOH; 45° C.; % B: 0 min 5%, 7.5 min 95%, 10 min 95%, 10.10 min 5%, 13.0 min 5%; 1.5 mL/min.

AnalpH9_MeOH_QC_V1 (1): Phenomenex Gemini NX C18 5 μm, 150×4.6 mm; A=water+pH9 (Ammonium Bicarbonate 10 mM); B=MeOH; 40° C.; % B: 0 min 5%, 7.5 min 95%, 10 min 95%, 10.10 min 5%, 13.0 min 5%; 1.5 mL/min.

AnalpH9_MeCN_QC_V1: Phenomenex Gemini NX C18 5 μm, 150×4.6 mm; A=water+pH9 (Ammonium Bicarbonate 10 mM); B=Acetonitrile; 45° C.; % B: 0 min 5%, 7.5 min 95%, 10 min 95%, 10.10 min 5%, 13.0 min 5%; 1.5 mL/min.

Chemical Synthesis Examples

The synthesis of a number of the examples of formula (I) required the synthesis of boronic acid or esters that could not be readily purchased from commercial suppliers.

A number of these boronic acids/esters were prepared from the corresponding bromo compounds.

4-(4-Bromo-phenoxy)-2-methyl-butan-2-ol (A1)

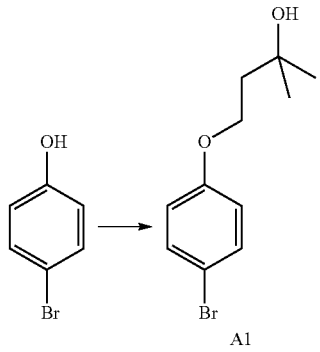

K$_2$CO$_3$ (29.9 g, 216 mmol) was added to a stirred solution of 4-bromophenol (12.5 g, 72.0 mmol) and 3-hydroxy-3-methylbutyl-4-methylbenzenesulfonate (20.4 g, 79.0 mmol) in DMF (125 mL). The mixture was stirred at 100° C. for 4 h before allowing to cool to RT. The reaction mixture was diluted with EtOAc (250 mL) and washed with water (250 mL). the aqueous layer was separated and twice extracted with EtOAc (2×200 mL). The combined organic layer was dried (anhydrous Na$_2$SO$_4$), filtered and concentrated in vacuo. The crude oil was pre-absorbed onto silica and purified by silica gel column chromatography eluting with 0-50% EtOAc/iso-hexane to afford 4-(4-bromo-phenoxy)-2-methyl-butan-2-ol (A1) as a colourless oil (12.55 g, 67%); LC-MS. R$_t$ 3.17 min, AnalpH2_MeOH_4 min(1); (ESI$^+$) m/z 241.2, 243.2 [M−H$_2$O+H]$^+$.

The following bromo compounds were prepared using analogous procedure to compound A1 with duration of heating varying between 6-66 h and heating between 80-140° C.:

TABLE 1

| Compound | Cpd # | Analytical Data | Mass, % Yield, State |
|---|---|---|---|
| 5-bromo-2-(3-hydroxy-3-methylbutoxy)benzonitrile | A2 | LC-MS. R$_t$ 2.94 min, AnalpH2_MeOH_4min(1); (ESI$^+$) m/z 266.2, 268.2 [M − H$_2$O + H]$^+$. | 1.28 g, 60%, white solid |
| 4-(4-bromo-3-fluorophenoxy)-2-methylbutan-2-ol | A3[a] | LC-MS. R$_t$ 3.21 min, AnalpH2_MeOH_4min(1); (ESI$^+$) m/z 299.2, 301.1 [M + Na]$^+$. | 1.45 g, qunatitative, yellow oil |
| 4-(4-bromo-2-fluorophenoxy)-2-methylbutan-2-ol | A4[a] | LC-MS. R$_t$ 3.17 min, AnalpH2_MeOH_4min(1); (ESI$^+$) m/z 299.1, 301.1 [M + Na]$^+$. | 1.70 g, 70%, orange oil |
| 3-(4-bromophenoxy)-2,2-dimethylpropan-1-ol | A5[a,b,c] | LC-MS. R$_t$ 3.25 min, AnalpH2_MeOH_4min(1); (ESI$^+$) m/z no ionization | 330 mg, 22%, light yellow oil |

TABLE 1-continued

| Compound | Cpd # | Analytical Data | Mass, % Yield, State |
|---|---|---|---|
| ![A6 structure: 4-bromophenoxy-methyl-oxetane with hydroxymethyl] | A6[b] | LC-MS. $R_t$ 2.92 min, AnalpH2_MeOH_4min(1); (ESI+) m/z 273.2, 275.2 [M + H]+. | 27.3 g, 86%, orange oil |
| ![A7 structure: 4-bromophenoxy-ethyl-oxetan-3-ol] | A7[d,##] | LC-MS. $R_t$ 17 min, AnalpH2_MeOH_4min(1); (ESI+) m/z 273.0, 275.0 [M + H]+. | 2.2 g, 63%, white solid |

[a]$Cs_2CO_3$ was used as the base.
[a]Bromide was used instead of the tosylate.
[c]2 eq. of KI was also used.
[d]Acetonitrile was used instead of DMF.
[##](A7) required the synthesis from the corresponding mesylate rather than tosylate.

The mesylate (A10) was synthesised in 3 steps by the following methods:

Step 1: Ethyl 2-(3-hydroxyoxetan-3-yl) acetate (A8)

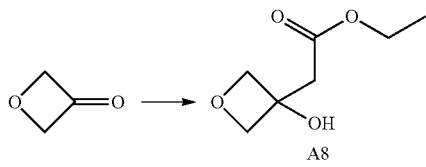

To a solution of EtOAc (36.68 g, 416 mmol) in THF (400 mL) was added LiHMDS (229 mL, 458 mmol, 2 M in THF) dropwise at −70° C. for 20 min. After addition, the reaction mixture was stirred at the same temperature for a further 1 h, and then oxetan-3-one (30 g, 416 mmol) in THF (50 mL) was added dropwise to the reaction mixture and stirred at −70° C. for 1 h. The reaction mixture was cooled to 0° C., quenched by addition of satd. aq. $NH_4Cl$ (200 mL) and allowed to stir at RT for 30 min. The crude mixture was diluted with $H_2O$ (200 mL) and extracted with EtOAc (3×400 mL). The combined organic layer was washed with water (2×100 mL), brine (1×200 mL), dried with $Na_2SO_4$, filtered and concentrated under reduced pressure. The crude residue was purified by silica gel column chromatography eluting with 20% EtOAc/hexane to afford ethyl 2-(3-hydroxyoxetan-3-yl)acetate (A8) as a yellow liquid (25 g, 37%).

Step 2: 3-(2-hydroxyethyl) oxetan-3-ol (A9)

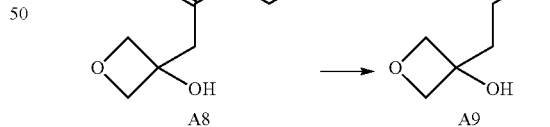

To a solution of ethyl 2-(3-hydroxyoxetan-3-yl) acetate (A8) (15 g, 93.8 mmol) in THF (400 mL) and EtOH (100 mL) was added sodium borohydride (7 g, 37.8 mmol) portionwise at 0° C. After addition, the reaction was stirred at ambient temperature for 16 h. The resulting suspension was acidified with Dowex 50WX8-100 (H+ form) to pH 6 at 0° C. The reaction mixture was stirred for 15 mins and then the resin was filtered and washed with EtOAc (100 mL). The filtrate was concentrated under reduced pressure to afford 3-(2-hydroxyethyl) oxetan-3-ol (A9) as a white solid (8 g, 72%).

Step 3: Synthesis of 2-(3-hydroxyoxetan-3-yl) ethyl methanesulfonate (A10)

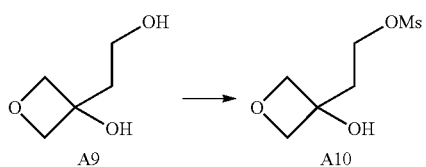

To a stirred solution of 3-(2-hydroxyethyl)oxetan-3-ol (A9) (8 g, 67.8 mmol) and NEt$_3$ (20.5 g, 203 mmol) in DCM (150 mL) was added mesyl chloride (11.59 g, 102 mmol) dropwise at 0° C. After addition, the reaction was stirred at 10° C. for 3 h. After completion, the reaction mixture was diluted with water (100 mL) and extracted with DCM (3×200 mL). The combined organic layer was washed with water (2×100 mL) and brine (1×200 mL), dried with Na$_2$SO$_4$, filtered and concentrated under reduced pressure to afford 2-(3-hydroxyoxetan-3-yl)ethyl methanesulfonate (A10) (5.5 g, 42%) as a yellow liquid.

The following bromo compound (A11) was prepared via reduction of ethyl 2-(4-bromophenoxy)-2,2-difluoroacetate (this ester was prepared in accordance to literature procedure as reported in *Org. Lett.*, 2016, 18, 18, 4570-4573):

2-(4-bromophenoxy)-2,2-difluoroethanol (A11)

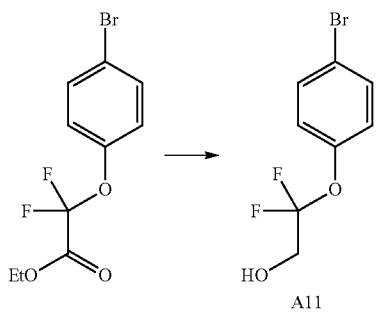

To a solution of sodium borohydride (2.7 g, 71.4 mmol) in EtOH (40 ml) was added ethyl 2-(4-bromophenoxy)-2,2-difluoroacetate (7 g, 23.8 mmol) portionwise at 0° C. The reaction mixture was slowly warmed to RT and stirred at this temperature for 2 h. After completion, the reaction was quenched with saturated ammonium chloride solution (30 mL), 1 M HCl solution (2 mL), and then extracted with EtOAc (2×300 mL). The combined organic layer dried over anhydrous Na$_2$SO$_4$, filtered and concentrated under reduced pressure to afford 2-(4-bromophenoxy)-2,2-difluoroethanol (A11) as a white solid (5 g, 59%).

Tert-butyl N-[3-(4-bromophenoxy)-1,1-dimethyl-propyl]carbamate (A12)

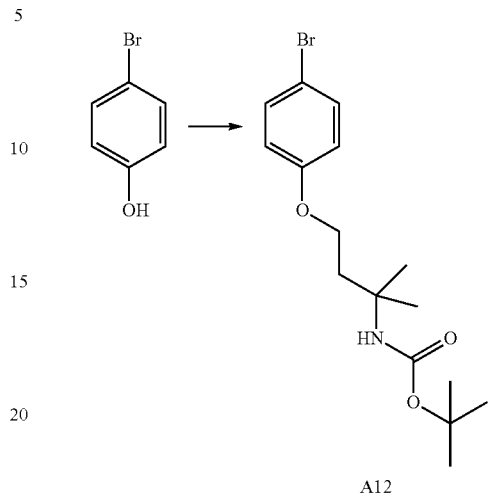

To a solution of 4-bromophenol (471 mg, 2.72 mmol), tert-butyl (4-hydroxy-2-methylbutan-2-yl)carbamate (1.38 g, 6.81 mmol) and triphenylphosphine (1.78 g, 6.81 mmol) in dry THF (9 mL) at RT was added dropwise a solution of 1,1'-(azodicarbonyl)dipiperidine (1.73 g, 6.81 mmol) in dry THF (9 mL). The resulting mixture was stirred at RT for 2 days and the mixture was filtered to remove a white precipitate. The filtrate was diluted with DCM and washed with aq NaOH (2 M) to remove the unreacted phenol starting material. The organic fraction was evaporated to dryness and was purified by silica gel chromatography eluting with 0-15% EtOAc/iso-hexane to afford the desired product (A12) as a white solid (464 mg, 48%).

1-(2-(4-bromophenoxy)ethyl)cyclopropan-1-ol (A13)

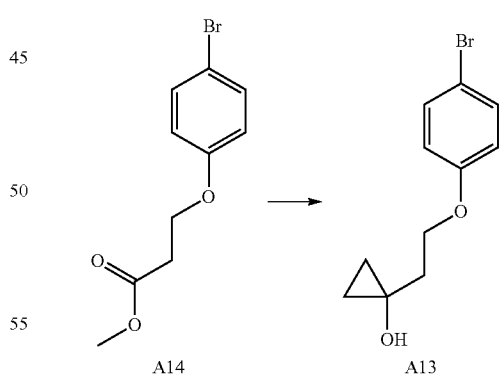

To a stirred solution of methyl 3-(4-bromophenoxy)propanoate (A14) (7.00 g, 27.0 mmol) in anhydrous THF (200 mL), was added titanium (IV) isopropoxide (3.13 mL, 10.8 mmol) and the mixture was cooled to 0° C. Ethylmagnesium bromide (3.0 M in Et$_2$O, 7 mL, 20.8 mmol) was then added dropwise over 15 mins and the resulting solution was stirred for a further 1 h at 0° C. The reaction was quenched with 1 M HCl solution and extracted with EtOAc (100 mL). The organic layer was dried (anhydrous Na$_2$SO$_4$), filtered and concentrated in vacuo. The crude residue was purified by silica gel chromatography, eluting with 37.5% EtOAc/hexane to afford 1-(2-(4-bromophenoxy)ethyl)cyclopropan-1-ol (A13) as an off-white solid (5.3 g, 75%); LC-MS. $R_t$ 1.97 min, AnalpH2_MeOH_4 min(1); (ESI$^+$) m/z 257.0, 259.0 [M+H]$^+$.

Compound (A13) required the ester (A14) which was prepared from the resulting acid:

Methyl 3-(4-bromophenoxy)propanoate (A14)

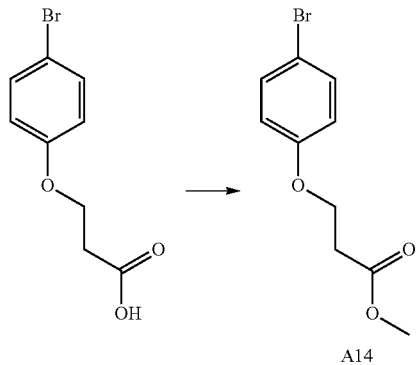

To a stirred suspension of 3-(4-bromophenoxy)propanoic acid (4.90 g, 20 mmol) in methanol (16 mL) was carefully added fuming sulfuric acid (98%, 20-30% SO$_3$, 4 drops). The reaction mixture was heated at 140° C. for 5 min in a microwave reactor and repeated once more on the same scale. The combined reaction mixtures were concentrated in vacuo and the resulting residue was partitioned between EtOAc (100 mL) and aq. 10% sodium hydroxide (100 mL). The organic layer was separated, and the aq. layer back-extracted with EtOAc (100 mL). The combined organic layer was then washed with brine (100 mL), dried over MgSO$_4$, filtered and concentrated in vacuo to afford the title compound (A14) as pale yellow solid (9.86 g, 95%). LC-MS. $R_t$ 3.10 min, AnalpH2_MeOH_4 min(1); (ESI$^+$) m/z 281.1, 283.1 [M+Na]$^+$.

The following bromo-isoglycoside A16 was prepared from the triflate intermediate A15 with 4-bromophenol:

(3S,3aS,6R,6aS)-6-(4-bromophenoxy)hexahydrofuro[3,2-b]furan-3-ol (A16)

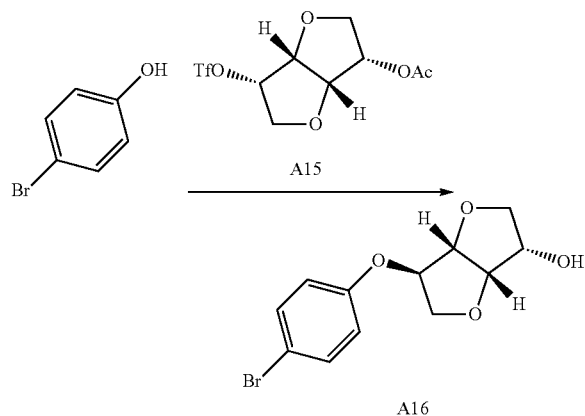

Sodium hydride (60% dispersion in oil, 109 mg, 2.86 mmol) was added to a solution of 4-bromophenol (461 mg, 2.7 mmol) in THF (10 mL) at 0° C., once bubbling had ceased the reaction was stirred for 30 mins at 0° C. Crude (3S,3aS,6S,6aR)-6-(((trifluoromethyl)sulfonyl)oxy)hexahydrofuro[3,2-b]furan-3-yl acetate (A15) (640 mg, 2.12 mmol) as a solution in THF (6 mL) was then added dropwise. Once addition was complete the reaction was stirred at 0° C. for 2 h then 30 mins at RT. Analysis by TLC showed consumption of triflate, and the reaction was concentrated under vacuum then redissolved in THF (12 mL), LiOH (890 mg, 21.2 mmol) as a solution in water (4 mL) was added and the reaction allowed to stir at 50° C. for 2 h, LiOH (800 mg, 19.0 mmol) was added and the reaction stirred at RT overnight. Reaction was shown to be complete by LCMS. The THF was removed under vacuum, EtOAc (50 mL) was added and the layers separated. The aqueous layer was extracted with EtOAc (3×50 mL), the organic layers combined then dried using a phase separator. The crude material was purified by silica gel column chromatography eluting with 5-65% EtOAc/iso-hexane to afford the title compound (A16) as a white solid (275 mg, 43%). $^1$H NMR (400 MHz, CDCl$_3$): δ 7.38 (d, J=8.7, 2H), 6.80 (d, J=8.7, 2H), 4.77 (d, 0=3.9, 1H), 4.68 (t, 0=4.8, 1H), 4.54 (d, 0=4.8, 1H), 4.31 (d, 0=6.9, 1H), 4.19-4.14 (m, 1H), 4.09 (dd, 0=3.9, 10.5 Hz, 1H), 3.90 (dd, 0=6.0, 9.6 Hz, 1H), 3.63 (dd, 0=5.5, 9.6 Hz, 1H), 2.58 (d, 0=6.9 Hz, 1H).

The following bromo compounds were prepared by displacement reactions of 2-fluoropyridines:

4-(5-Bromo-pyridin-2-yloxy)-2-methyl-butan-2-ol (A17)

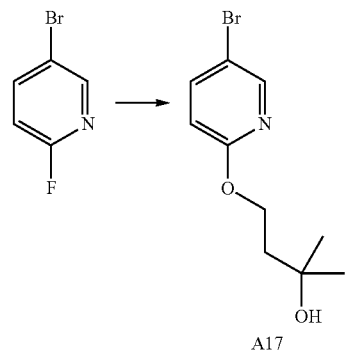

To a stirred solution of sodium hydride (568 mg, 14.2 mmol) in anhydrous DMF (7 mL), under a nitrogen atmosphere at 0° C., was added a solution of 3-methyl-1,3-butanediol (730 μL, 6.8 mmol) in anhydrous DMF (1 mL) over 5 min. The reaction mixture was allowed to warm to RT for 30 mins, then cooled to 0° C. and a solution of 5-bromo-2-fluoropyridine (0.58 mL, 5.7 mmol) in anhydrous DMF (1 mL) was added. The reaction was allowed to warm to RT and stirred for 18 h under a nitrogen atmosphere. The reaction mixture was poured into ice-water (100 mL) and the resulting mixture stirred for 10 min. The mixture was extracted with EtOAc (2×50 mL), the organics combined, washed with H$_2$O (50 mL), brine (50 mL), passed through a phase separator and the solvent removed in vacuo. The crude material was purified by silica gel chromatography, eluting with 0-25% EtOAc/iso-hexane, to afford 4-(5-bromo-pyridin-2-yloxy)-2-methyl-butan-2-ol (A17) as a colourless oil (1.52 g, 100%); LC-MS. $R_t$ 2.97 min, AnalpH2_MeOH_4 min(1); (ESI$^+$) m/z 260.1, 262.1 [M+H]$^+$.

4-[(5-bromo-2-pyridyl)amino]-2-methyl-butan-2-ol (A18)

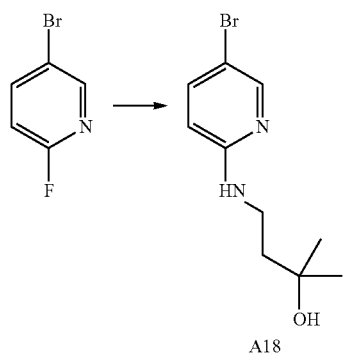

A suspension of 5-bromo-2-fluoropyridine (265 μL, 2.55 mmol), 4-amino-2-methyl-2-butanol (526 mg, 5.1 mmol) and K$_2$CO$_3$ (1.76 g, 12.76 mmol) in dry DMF (9 mL) was heated to 110° C. for 18 h. The reaction mixture was cooled to RT then poured into water and extracted with DCM (2×). The combined organic fractions were washed with water then dried by passing through a phase separator, evaporated and the residue purified by silica gel chromatography eluting with 25-45% EtOAc/iso-hexane to afford the product A18 as a white solid (584 mg, 88%). LC-MS $R_t$ 1.82 min, AnalpH2_MeOH_4 min(1); (ESI$^+$) m/z 259.1; 261.1 [M+H]$^+$.

The N-methyl compound was also prepared using analogues procedure to A18:

2-(5-Bromo-pyridin-2-ylamino)-ethanol (A20)

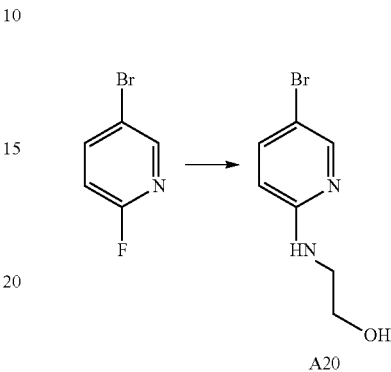

A solution of 5-bromo-2-fluoropyridine (1.00 g, 5.68 mmol) in ethanolamine (6 mL, 99.4 mmol) was heated at 120° C. for 3 days. The reaction mixture was diluted with water (75 mL) then extracted with EtOAc (×3). The combined organics were washed with water (×2) then brine (×1), dried (anhydrous MgSO$_4$), filtered and concentrated in vacuo. The crude material was purified by silica gel chromatography, eluting with 20-100% EtOAc/iso-hexane, to afford 2-(5-bromo-pyridin-2-ylamino)-ethanol (A20) as a waxy yellow solid (1.11 g, 90%). LC-MS. $R_t$ 1.12 min, AnalpH2_MeOH_4 min(1); (ESI$^+$) m/z 217.2, 219.2 [M+H]$^+$.

The following bromo derivative was prepared using analogous procedure to (A20):

TABLE 2

| Compound | Cpd # (Intermediate used*) | Analytical Data | Mass, % Yield, State |
|---|---|---|---|
| Br-pyridine-N(Me)-CH$_2$CH$_2$C(Me)$_2$OH | A19 | LCMS. $R_t$ 3.54 min, AnalpH2_MeOH_4min(1); (ESI$^+$) m/z 273.2; 275.2 [M + H]$^+$ | 714 mg, quant, pale yellow oil |

TABLE 3

| Compound | Cpd # (Intermediate used*) | Analytical Data | Mass, % Yield, State |
|---|---|---|---|
| Br-pyridine-N(Me)-CH$_2$CH$_2$OH | A21 | LC-MS. $R_t$ 1.66 min, AnalpH2_MeOH_4min(1); (ESI$^+$) m/z 231.2, 233.2 [M + H]$^+$ | 1.14 g, 87%, yellow oil |

The following bromo compounds were also prepared by displacement reactions of 2-chloropyridines:

5-Bromo-2-((R)-3-hydroxy-pyrrolidin-1-yl)-nicotinonitrile (A22)

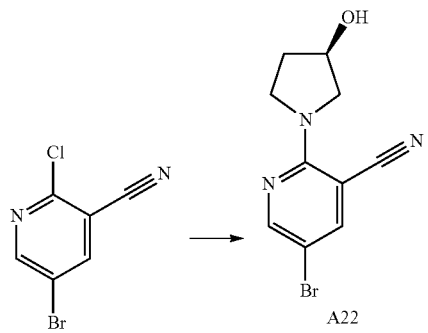

A mixture of 5-bromo-2-chloronicotinamide (300 mg, 1.38 mmol), (R)-3-pyrrolidinol (123 mg, 1.52 mmol), DIPEA (265 µL, 1.52 mmol) and MeCN (10 mL) was heated at 60° C. for 18 h. The reaction mixture was concentrated in vacuo, diluted with water (25 mL) and extracted with ethyl acetate (×2). The combined organics were washed with water (×2) then brine (×1), dried (anhydrous MgSO$_4$), filtered and concentrated in vacuo. The crude material was purified by silica gel chromatography, eluting with 0-100% EtOAc/iso-hexane, to afford 5-bromo-2-((R)-3-hydroxy-pyrrolidin-1-yl)-nicotinonitrile (A22) as a pale yellow solid (299 mg, 1.12 mmol, 81%); LC-MS. R$_t$ 2.69 min, AnalpH2_MeOH_4 min(1); (ESI$^+$) m/z 268.2, 270.2 [M+H]$^+$.

The bromo derivatives detailed in Table 4 were prepared using analogous procedure to A22:

TABLE 4

| Compound | Cpd # (Intermediate used") | Analytical Data | Mass, % Yield, State |
|---|---|---|---|
| (structure with OH pyrrolidine, CN, Br pyridine) | A23 | LC-MS. R$_t$ 2.69 min, AnalpH2_MeOH_4min(1); (ESI$^+$) m/z 268.1, 270.1 [M + H]$^+$ | 307 mg, 83%, pale yellow solid |
| (structure with N-methyl-ethanolamine, CN, Br pyridine) | A24 | LC-MS. R$_t$ 2.68 min, AnalpH2_MeOH_4min(1); (ESI$^+$) m/z 256.2, 258.2 [M + H]$^+$ | 265 mg, 73%, yellow oil |

The following alcohols were silyl-protected from the corresponding bromo compounds:

(5-bromo-pyridin-2-yl)-[2-(tert-butyl-dimethyl-silanyloxy)-ethyl]-amine (A25)

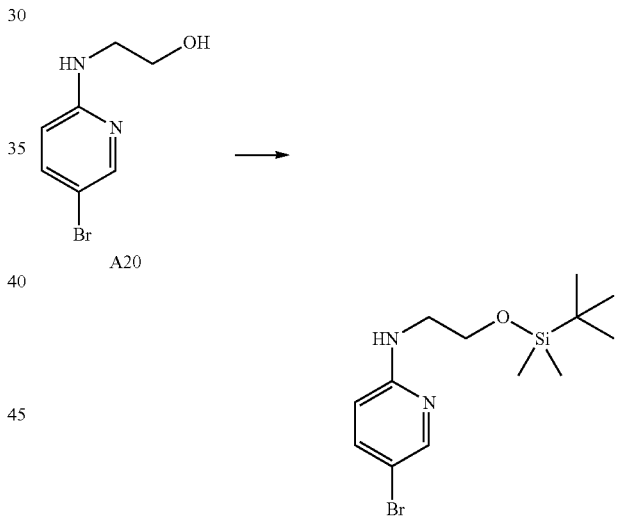

To a solution of 2-(5-bromo-pyridin-2-ylamino)-ethanol (A20) (1.11 g, 5.11 mmol) in dry DMF (under nitrogen atmosphere) was added imidazole (418 mg, 6.14 mmol) followed by tert-butyldimethylsilyl chloride (847 mg, 5.62 mmol). The reaction mixture was stirred at RT for 2 h. The reaction mixture was then diluted with water (50 mL) and extracted with EtOAc (×2). The combined organics were washed with water (×3) then brine (×1), dried (anhydrous MgSO$_4$), filtered and concentrated in vacuo. The crude material was purified by silica gel chromatography, eluting with 0-50% EtOAc/iso-hexane, to afford (5-bromo-pyridin-2-yl)-[2-(tert-butyl-dimethyl-silanyloxy)-ethyl]-amine as a pale yellow oil (1.52 g, 90%); LC-MS. R$_t$ 3.65 min, AnalpH2_MeOH_4 min(1); (ESI$^+$) m/z 331.2, 333.2 [M+H]$^+$.

The following bromo derivative was prepared using analogous procedure to A25:

TABLE 5

| Compound | Cpd # (Intermediate used*) | Analytical Data | Mass, % Yield, State |
|---|---|---|---|
| 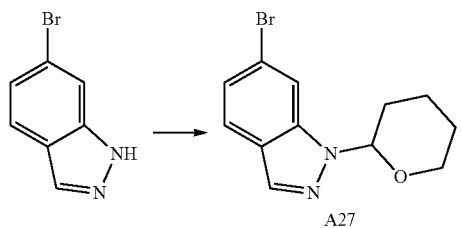 | A26 (A21) | LC-MS. $R_t$ 3.88 min, AnalpH2_MeOH_4min(1); (ESI$^+$) m/z 345.3, 347.3 [M + H]$^+$ | 1.34 g, 79%, pale yellow oil |

The following indazole intermediate was protected with tetrahydro-pyran-2-yl group:

6-Bromo-1-(tetrahydro-pyran-2-yl)-1H-indazole (A27)

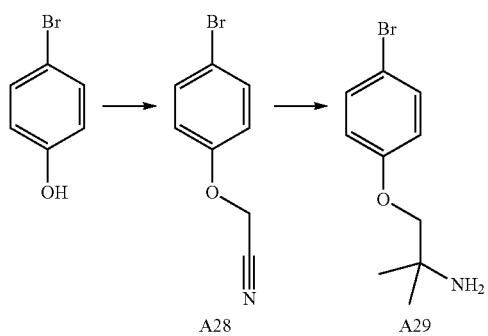

6-Bromo-1H-indazole (485 mg, 2.47 mmol) and p-toluenesulfonic acid (47 mg, 0.25 mmol) were dissolved in DCM (20 mL) and 3,4-dihydro-2H-pyran (674 µL, 7.41 mmol) was added. The reaction mixture stirred at RT for 18 h. The solution was partitioned with H$_2$O (20 mL) and extracted with DCM (3×15 mL) and combined organic fractions dried by phase separator. Material was dry loaded onto silica and purified by silica gel chromatography, eluting with 5-95% EtOAc/iso-hexane, to afford 6-bromo-1-(tetrahydro-pyran-2-yl)-1H-indazole (A27) as an orange solid (690 mg, quant); LC-MS. $R_t$ 3.22 min, AnalpH2_MeOH_4 min(1); (ESI$^+$) m/z 199.2, 201.2 [M-THP+H]$^+$.

1-(4-bromophenoxy)-2-methyl-propan-2-amine (A29)

Bromoacetonitrile (1.2 mL, 17.3 mmol) was added to a stirred suspension of 4-bromophenol (2.00 g, 11.6 mmol) and potassium carbonate (4.80 g, 34.8 mmol) in DMF (60 mL). Once addition was complete, the resulting mixture was heated at 50° C. overnight. The reaction mixture was cooled to RT, diluted with EtOAc (150 mL) and the organic layer was separated, washed with water (2×70 mL), brine (2×40 mL) then dried by passing through a phase separator. The organics were concentrated in vacuo and the crude compound was purified by silica gel chromatography eluting with 0-50% EtOAc/iso-hexane to afford 2-(4-bromophenoxy)acetonitrile (A28) (2.40 g). A portion of this material (1.00 g, 4.72 mmol) was dissolved in dry THF (20 mL) under N$_2$ and methylmagnesium bromide (3 M in Et$_2$O, 5.5 mL, 16.5 mmol) was added dropwise. The reaction mixture was heated to 60° C. for 1 h, then titanium (IV) isopropoxide (1.4 mL, 4.72 mmol) was added dropwise. The reaction mixture was stirred at 50° C. for 16 h. The reaction mixture was partitioned between DCM and brine. The mixture was filtered through celite and the filter cake washed with DCM. The organic fraction was separated, washed with brine again, followed by washing with aq 10% NaOH (aq) (2×) to remove the phenol starting material, dried by passing through a phase separator and evaporated to dryness to afford the desired product A29 as a brown oil (712 mg, 62%); LC-MS. $R_t$ 1.48 min, AnalpH2_MeCN_4 min(1); (ESI$^+$) m/z 244.0, 246.0 (M+H)$^+$.

Boc protection of the above bromo intermediate yielded A30:

Tert-butyl N-[2-(4-bromophenoxy)-1,1-dimethyl-ethyl]carbamate (A30)

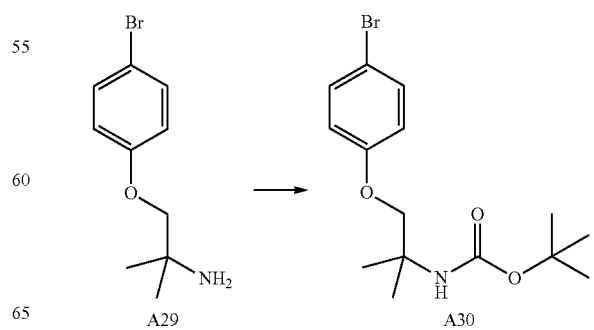

1-(4-bromophenoxy)-2-methylpropan-2-amine (A29) (712 mg, 2.92 mmol) was dissolved in DCM (5 mL). Di-tert-butyl dicarbonate (668 mg, 3.062 mmol) dissolved in DCM (4 mL) was added and the reaction mixture stirred at RT for 16 h. Water was added to the reaction mixture to quench unreacted di-tert-butyl dicarbonate and the mixture was stirred for a further 24 h. The reaction mixture was evaporated to dryness and purified by silica gel chromatography eluting with 0-15% EtOAc/iso-hexane to afford the product (A30) as a pale yellow solid (516 mg, 51%); LC-MS. $R_t$ 3.48 min, AnalpH2_MeCN_4 min(1); (ESI$^+$) m/z 365.9, 367.9 [M+Na]$^+$.

The following diol intermediate A32 was prepared in 2 steps from 4-bromophenol.

1-(4-bromophenoxy)-3-methylbutane-2,3-diol (A32)

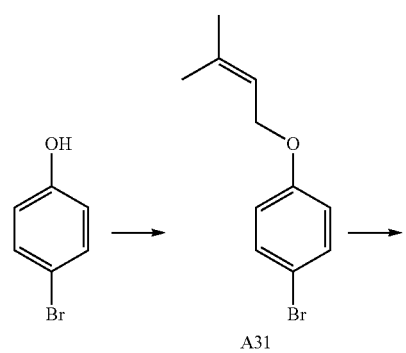

A31

A mixture of 4-bromophenol (1.00 g, 5.78 mmol) and sodium hydride (388 mg, 11.56 mmol, 60% dispersion in oil) were suspended in anhydrous THF (80 mL) at 0° C. and stirred for 30 min after which 1-bromo-3-methylbut-2-ene (1.29 g, 8.67 mmol) was added dropwise. Once addition was complete, the reaction was allowed to warm to RT and stirred for 18 h. The reaction mixture was diluted with water (70 mL), the aqueous layer was separated and washed with EtOAc (2×75 mL). The combined organics were passed through a phase separator and concentrated in vacuo. The crude compound was purified by silica gel chromatography eluting with 0-50% EtOAc/iso-hexane to afford 1-bromo-4-((3-methylbut-2-en-1-yl)oxy)benzene (A31) (1.35 g) as a colourless oil, which was used for further derivatization. Admixα (2.00 g) was added to a stirred biphasic solution of 1-bromo-4-((3-methylbut-2-en-1-yl)oxy)benzene (1.35 g, 5.6 mmol) in tert-butanol/water. A yellow biphasic solution formed and was allowed to stir for 16 h. A further portion of Admix-α (500 mg) was added and the reaction was allowed to stir for 18 h. A further portion of Admix-α (1.50 g) was added and reaction mixture was stirred for 18 h. The reaction mixture was quenched with sodium sulphite (5 g), and stirred for 1 h. The mixture was diluted with EtOAc (75 mL) and water (75 mL), layers were separated and the aqueous layer was extracted with EtOAc (3×50 mL), washed with brine (20 mL) and dried using a phase separator. The crude solid was purified by silica gel chromatography eluting with 0-75% EtOAc/iso-hexane to afford the title compound A32 as a yellow oil (1.13 g); LC-MS. $R_t$ 2.81 min, AnalpH2_MeOH_4 min(1); (ESI$^+$) m/z 297.1, 299.1 [M+Na]$^+$. The enantiomeric excess was not determined.

1-(4-Bromo-phenoxy)-3-morpholin-4-yl-propan-2-ol (A33)

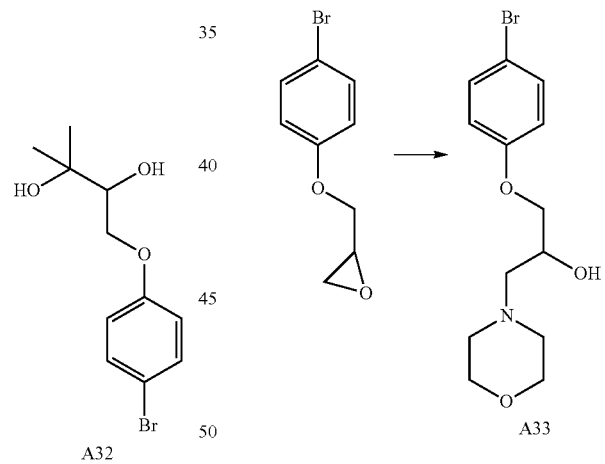

A33

A solution of 2-[(4-bromophenoxy)methyl]oxirane (500 mg, 2.18 mmol) and morpholine (267 μL, 3.05 mmol) in isopropanol (10 mL) was heated at 100° C. for 30 min in a microwave reactor (200 W). The reaction was repeated once more. The 2 reaction mixtures were combined and concentrated in vacuo. The crude solid was pre-absorbed onto silica and purified by silica gel chromatography eluting with 0-20% MeOH/DCM to afford 1-(4-bromo-phenoxy)-3-morpholin-4-yl-propan-2-ol (A33) as a colourless oil (1.21 g, 88%). LC-MS. $R_t$ 1.50 min, AnalpH2_MeOH_4 min(1); (ESI$^+$) m/z 316.2, 318.2 [M+H]$^+$.

The following methoxy compound was prepared via methylation of the corresponding alcohol:

4-[3-(4-Bromo-phenoxy)-2-methoxy-propyl]-morpholine (A34)

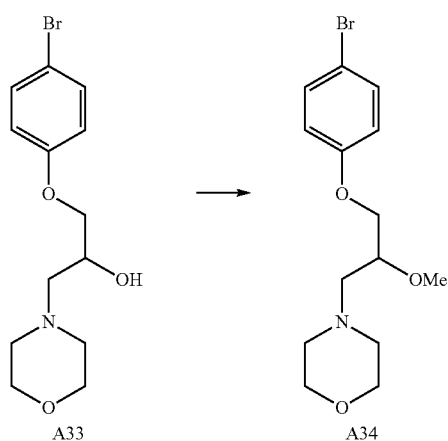

A solution of 1-(4-Bromo-phenoxy)-3-morpholin-4-yl-propan-2-ol (A33) (1.18 g, 3.7 mmol) was dissolved in THF (20 mL) and sodium hydride (60% dispersion in oil, 448 mg, 11.2 mmol) was added. After 10 min, iodomethane (279 µL, 4.5 mmol) was added and the mixture stirred at RT for 4 h. The reaction mixture was quenched with water at 0° C. and reduced to a residue by rotary evaporator. The residue was partitioned between water (100 mL) and EtOAc (100 mL). The organic layer was washed with brine (100 mL), dried (anhydrous $Na_2SO_4$), filtered and concentrated in vacuo. The crude solid was pre-absorbed onto silica and purified by silica gel chromatography eluting with 0-100% EtOAc/isohexane to afford 4-[3-(4-bromo-phenoxy)-2-methoxy-propyl]-morpholine (A34) as a colourless oil (993 mg, 81%); LC-MS. $R_t$ 1.72 min, AnalpH2_MeOH_4 min(1); (ESI$^+$) m/z 330.2, 332.2 [M+H]$^+$.

Bromo intermediates: A35 and A36 were synthesised in accordance with literature methods:

TABLE 6

| Bromo compound | Cpd # | Reference |
|---|---|---|
| ![Br-phenoxy-propyl-piperazine] | A35 | WO2013/267493 |

TABLE 6-continued

| Bromo compound | Cpd # | Reference |
|---|---|---|
| ![Br-pyridine-cyclopropoxy] | A36 | WO2015/65937 |

The bromo intermediates were used to synthesise the corresponding boronic esters or acids using bis(pinacalato) diboron. These reactions could be carried out using either traditional heating methods or in a microwave reactor.

2-[(tert-butoxycarbonyl)aminopyridin-4-yl]boronic acid (B1)

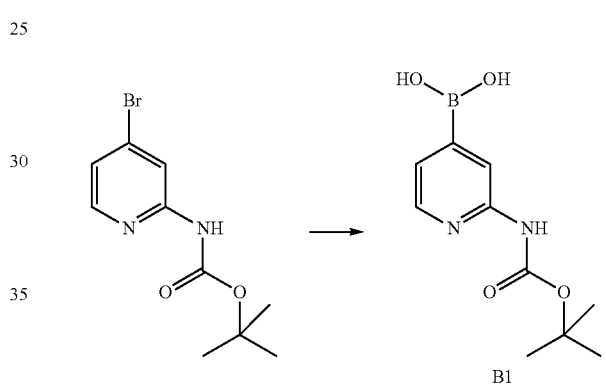

To (4-bromo-pyridin-2-yl)-carbamic acid tert-butyl ester (188 mg, 0.69 mmol), bis(pinacolato)diborane (526 mg, 2.07 mmol) and KOAc (203 mg, 2.07 mmol) was added DMSO (2.5 mL). The reaction mixture was flushed with nitrogen for 10 min. Pd(dppf)Cl$_2$.DCM (56 mg, 0.069 mmol) in DMSO (0.5 mL) was added and the system flushed with nitrogen for a further 5 min. The reaction was heated at 85° C., under N$_2$, for 1 h. The reaction mixture was diluted with EtOAc (10 mL) and washed with 0.1 M aq. HCl (10 mL). The organic phase was separated (phase separator) and evaporated to dryness. The residue was dissolved in the minimum amount of DMF and passed through a Si-thiol cartridge (2 g, pre-conditioned with DMF) and the cartridge washed with DMF (2×CV) and MeOH (2×CV) and the solvent removed in vacuo. The crude sample was triturated with/so-hexane. Product found to be mainly in filtrate, solid and filtrate re-combined and evaporated to dryness. Crude product re-dissolved in MeOH/CH$_2$Cl$_2$ and passed through a 2$^{nd}$ Si-thiol cartridge (1 g). The cartridge was washed with MeOH (2×CV), DCM (2×CV) and the solvent removed in vacuo. The crude compound was purified by silica gel column chromatography eluting with 0%-5% MeOH/DCM to afford 2-(tert-butoxycarbonylamino)pyridine-4-boronic acid (B1) as an off-white solid (50 mg, 30%); LC-MS. $R_t$ 1.93 min, AnalpH2_MeOH_4 min(1); (ESI$^-$) m/z 237.2 [M−H]$^-$

2-methyl-4-(4-(4,4,5,5-tetramethyl-1,3,2-dioxaborolan-2-yl)phenoxy)butan-2-ol (B2)

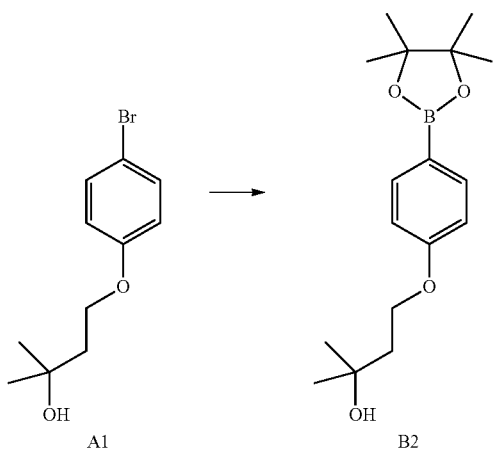

A mixture of 4-(4-bromophenoxy)-2-methylbutan-2-ol (A1) (12.5 g, 48.2 mmol), bis(pinacolato)diborane (15.3 g, 60.3 mmol), KOAc (11.8 g, 120 mmol) and Pd(dppf)Cl$_2$.DCM (1.97 g, 2.41 mmol) in dioxane (220 mL) was deoxygenated for 30 min then heated in the microwave at 100° C. for 4 h. The reaction mixture was filtered through a celite cartridge (10 g), the column washed with MeOH (6×CV) and the filtrate concentrated in vacuo. The crude compound was pre-absorbed onto silica then purified by silica gel column chromatography eluting with 0-50% EtOAc/iso-hexane to afford 2-methyl-4-(4-(4,4,5,5-tetramethyl-1,3,2-dioxaborolan-2-yl)phenoxy)butan-2-ol (B2) as an off-white solid (12.35 g, 84%); LC-MS. R$_t$ 3.29 min, AnalpH2_MeOH_4 min(1); (ESI$^+$) m/z 329.2 [M+Na]$^+$.

The following boronic esters were prepared using analogous procedures to compound B2 with duration of heating varying between 30 min and 18 h and heating between 100° C. and 130° C.:

TABLE 7

| Compound | Cpd # (Intermediate used*) | Analytical Data | Mass, % Yield, State |
|---|---|---|---|
| (structure) | B3 (A35) | LC-MS. R$_t$ 2.01 min, AnalpH2_MeOH_4min(1); (ESI$^+$) m/z 361.3 [M + H]$^+$ | 195 mg, 95%, brown solid |

TABLE 7-continued

| Compound | Cpd # (Intermediate used*) | Analytical Data | Mass, % Yield, State |
|---|---|---|---|
| [structure: pinacol boronate-phenyl-O-CH2-CH(OMe)-CH2-morpholine] | B4 (A34) | LC-MS. R$_t$ 2.06 min, AnalpH2_MeOH_4min(1); (ESI$^+$) m/z 378.3 [M + H]$^+$. | 168 mg, 73% yellow oil |
| [structure: pinacol boronate-pyridine-O-CH2CH2-C(CH3)2-OH] | B5 (A17) | LC-MS. R$_t$ 2.01 min, AnalpH2_MeOH_4min(1); (ESI$^+$) m/z 308.2 [M + H]$^+$ | 390 mg, 69%, brown oil |
| [structure: pinacol boronate-phenyl-O-CF2-CH2OH] | B6 (A11) | LC-MS. R$_t$ 3.14 min, AnalpH2_MeOH_4min (ESI$^+$) m/z 301.4 [M + H]$^+$ | 1.16 g, 44%, white solid |

TABLE 7-continued

| Compound | Cpd # (Intermediate used*) | Analytical Data | Mass, % Yield, State |
|---|---|---|---|
| (structure) | B7 (A13) | LC-MS. $R_t$ 3.27 min, AnalpH2_MeOH_4min (ESI$^+$) m/z 327.3 [M + Na]$^+$ | 1.25 g, 20%, white solid |
| (structure) | B8 (A7) | LC-MS. $R_t$ 3.04 min, AnalpH2_MeOH_4min (ESI$^+$) m/z 321.3 [M + H]$^+$ | 1.20 g, 40%, white solid |
| (structure) | B9 (A6) | LC-MS. $R_t$ 3.13 min, AnalpH2_MeOH_4min(1); (ESI$^+$) m/z 343.3 [M + Na]$^+$. | 174 mg, 99%, white solid |

TABLE 7-continued

| Compound | Cpd # (Intermediate used*) | Analytical Data | Mass, % Yield, State |
|---|---|---|---|
| (structure) | B10 (A5) | LC-MS. R$_t$ 3.03 min, AnalpH2_MeOH_4min(1); (ESI$^+$) m/z 307.2 [M + H]$^+$. | 361 mg, 93%, white solid |
| (structure) | B11 (A3) | LC-MS. R$_t$ 3.32 min, AnalpH2_MeOH_4min (ESI$^+$) m/z 347.3 [M + Na]$^+$ | 454 mg, 65%, pale yellow solid |
| (structure) | B12 (A30) | LC-MS. R$_t$ 3.55 min, AnalpH2_MeOH_4min (ESI$^+$) m/z 392.3 [M + Na]$^+$ | 574 mg, 98%, pale yellow solid |

TABLE 7-continued

| Compound | Cpd # (Intermediate used[a]) | Analytical Data | Mass, % Yield, State |
|---|---|---|---|
| (structure: pinacol boronate-phenyl-O-CH2CH2-C(CH3)2-NH-Boc) | B13[a] (A12) | LC-MS. $R_t$ 3.52 min, AnalpH2_MeOH_4min (ESI+) m/z 306.1 [M − Boc + H]+ | 305 mg, 58%, white solid |
| (structure: pinacol boronate-phenyl(3-F)-O-CH2CH2-C(CH3)2-OH) | B14 (A4) | LC-MS. $R_t$ 3.33 min, AnalpH2_MeOH_4min (ESI+) m/z 347.1 [M + Na]+ | 1.64 g, 83%, pale orange solid |
| (structure: pinacol boronate-phenyl(3-CN)-O-CH2CH2-C(CH3)2-OH) | B15 (A2) | LC-MS. $R_t$ 2.87 min, AnalpH2_MeOH_4min(1); (ESI+) m/z 332.2 [M + H]+. | 1.52 g, Quantitative, pale yellow oil |

TABLE 7-continued

| Compound | Cpd # (Intermediate used[a]) | Analytical Data | Mass, % Yield, State |
|---|---|---|---|
| (4-(3-methoxypropoxy)phenyl pinacol boronate structure) | B16 | LC-MS. R$_t$ 3.36 min, AnalpH2_MeOH_4min (ESI$^+$) m/z 315.2 [M + Na]$^+$ | 1.72 g, 72%, pale yellow oil |
| (hexahydrofurofuranyloxy phenyl pinacol boronate structure) | B17 (A16) | LC-MS R$_t$ 3.06 min, AnalpH2_MeOH_4min (ESI$^+$) m/z no ionization; $^1$HNMR (400 MHz, CDCl$_3$): δ 7.74 (d, J = 8.7 Hz, 2H), 6.89 (d, J = 8.7 Hz, 2H), 4.87 (d, J = 3.8 Hz, 1H), 4.69 (t, J = 4.6 Hz, 1H), 4.56 (d, J = 4.6 Hz, 1H), 4.32 (q, J = 5.5 Hz, 1H), 4.19 (d, J = 10.3 Hz, 1H), 4.10 (dd, J = 3.8, 10.3 Hz, 1H), 3.89 (dd, J = 5.5, 9.4 Hz, 1H), 3.64 (dd, J = 5.5, 9.4 Hz, 1H), 1.25 (s, 12H). | 305 mg, 98%, colourless oil |
| (diol propoxy phenyl pinacol boronate structure) | B18 (A32) | LC-MS. R$_t$ 3.04 min, AnalpH2_MeOH_4min(1); (ESI$^+$) m/z 345.3 [M + Na]$^+$. | 1.12 g, 99%, colourless oil |
| (N-methylbenzimidazol-4-yl pinacol boronate structure) | B19 | LC-MS. R$_t$ 2.18 min, AnalpH2_MeOH_4min(1); (ESI$^+$) m/z 259.3 [M + H]$^+$ | 254 mg, 69%, green oil |

[a]THF was used as solvent instead of 1,4-dioxane.

B20 was synthesised via ring opening of the corresponding epoxide:

1-Morpholin-4-yl-3-[4-(4,4,5,5-tetramethyl-[1,3,2]dioxaborolan-2-yl)-phenoxy]-propan-2-ol-(B20)

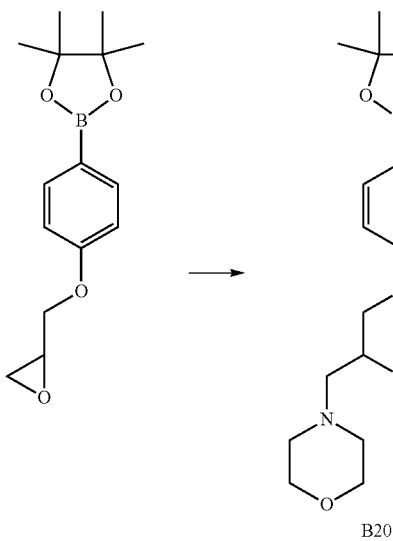

B20

A solution of 4-(oxiran-2-ylmethoxy)phenylboronic acid, pinacol ester (1.0 g, 3.62 mmol) and morpholine (443 µL, 5.07 mmol) in isopropanol (20 mL) was heated at 100° C. for 30 min in a microwave reactor (200 W). The reaction was repeated once more. The two reaction mixtures were combined and concentrated in vacuo. The crude solid was pre-absorbed onto silica and purified by silica gel chromatography eluting with 0-5% MeOH/DCM to afford 1-morpholin-4-yl-3-[4-(4,4,5,5-tetramethyl-[1,3,2]dioxaborolan-2-yl)-phenoxy]-propan-2-ol (B20) as a white solid (2.56 g, 97%); LC-MS. $R_t$ 1.90 min, AnalpH2_MeOH_4 min(1); (ESI$^+$) m/z 364.4 [M+H]$^+$.

The following boronic esters were prepared via alkylation of the corresponding pyrazoles:

[4-(4,4,5,5-Tetramethyl-[1,3]dioxaborolan-2-yl)-pyrazol-1-yl]-acetic Acid Methyl Ester (B21)

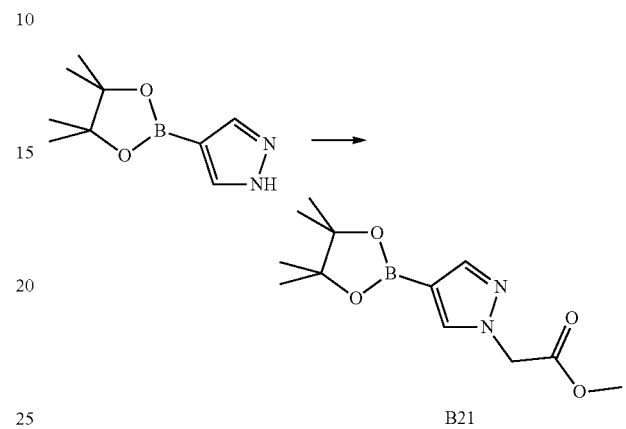

B21

4-(4,4,5,5-Tetramethyl-[1,3,2]dioxaborolan-2-yl)-1H-pyrazole (250 mg, 1.29 mmol), potassium carbonate (213 mg, 1.55 mmol) and bromo-acetic acid methyl ester (134 µL, 1.42 mmol) were suspended in DMF (5 mL) and stirred for 18 h at RT. Volatiles were removed by Genevac HT-4 and the residue re-suspended in DCM and filtered through a phase separator. The organics were concentrated in vacuo to afford the title compound (B21) as an orange oil (quantitative); LC-MS. $R_t$ 2.63 min, AnalpH2_MeOH_4 min(1); (ESI+) m/z 267.3 [M+H]$^+$.

The boronic esters detailed in Table 8 were prepared using analogous procedures to B21:

TABLE 8

| Compound | Cpd # (Intermediate used$^a$) | Analytical Data | Mass, % Yield, State |
|---|---|---|---|
| ![structure] | B22$^a$ | LC-MS. Rt 2.76 min, AnalpH2_MeOH_4min(1); (ESI+) m/z 253.3 [M + H]$^+$. | 293 mg, 75%, white solid |
| ![structure] | B23$^b$ | LC-MS. Rt 2.78 min, AnalpH2_MeOH_4min(1); (ESI+) m/z 281.3 [M + H]$^+$. | 598 mg, 83%, clear oil |

TABLE 8-continued

| Compound | Cpd # (Intermediate used[a]) | Analytical Data | Mass, % Yield, State |
|---|---|---|---|
| (structure) | B24[b] | LC-MS. Rt 2.89 min, AnalpH2_MeOH_4min91); (ESI+) m/z 267.3 [M + H]+. | 492 mg, 72%, orange oil |

[a] $Cs_2CO_3$ (1 eq) was also added.
[b] Stirred at RT the heated at 80° C..

The following compound was prepared via deprotection of the corresponding Boc-protected pyrazole intermediates:

1-Azetidin-3-yl-1H-pyrazole-4-boronic Acid Pinacol Ester (B25)

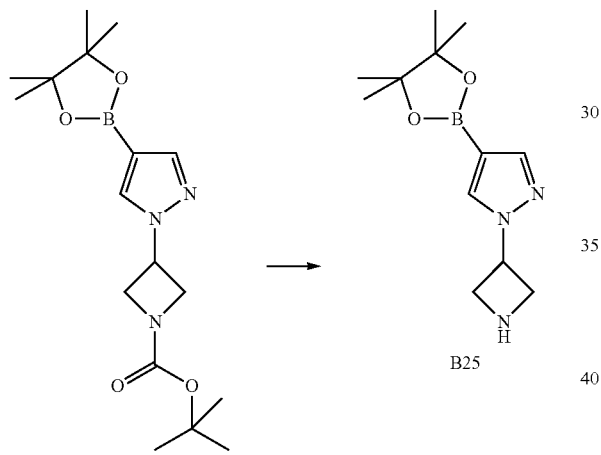

To t-butyl-3-(4-(4,4,5,5,-tetramethyl-1,3,2-dioxaborolan-2-yl)-1H-pyrazol-1-yl)-azetidine-1-carboxylate (1.03 g, 2.95 mmol) in DCM (20 mL) was added TFA (10 mL) and the reaction mixture stirred at RT for 1 h. The reaction mixture was evaporated to dryness, re-dissolved in MeOH and passed through a pre-conditioned SCX-2 cartridge (with MeOH, 25 g). The column was washed with MeOH (1×CV), DCM/MeOH 1:1 (1×CV) and DCM (1×CV). The product was eluted from the cartridge with 0.5 M $NH_3$/MeOH and the solvent removed in vacuo to afford 1-azetidin-3-yl-1H-pyrazole-4-boronic acid pinacol ester (B25) as a white sticky solid (614 mg, 84%) which was used in subsequent reactions without further purification; LC-MS. $R_t$ 1.41 min, AnalpH2_MeOH_4 min; (ESI+) m/z 250.4 [M+H]+.

The following boronic ester were prepared using analogous procedures to B25:

TABLE 9

| Compound | Cpd # (Intermediate used[a]) | Analytical Data | Mass, % Yield, State |
|---|---|---|---|
| (structure) | B26[##] | LC-MS. $R_t$ 1.75 min, AnalpH2_MeOH_4min(1); (ESI+) m/z 264.3 [M + H]+. | 164 mg, 89%, colourless glass |

[##] Intermediate (B26) required the synthesis of (B27)

Tert-butyl (3-(4-(4,4,5,5-tetramethyl-1,3,2-dioxaborolan-2-yl)-1H-pyrazol-1-yl)cyclobutyl)carbamate (B27)

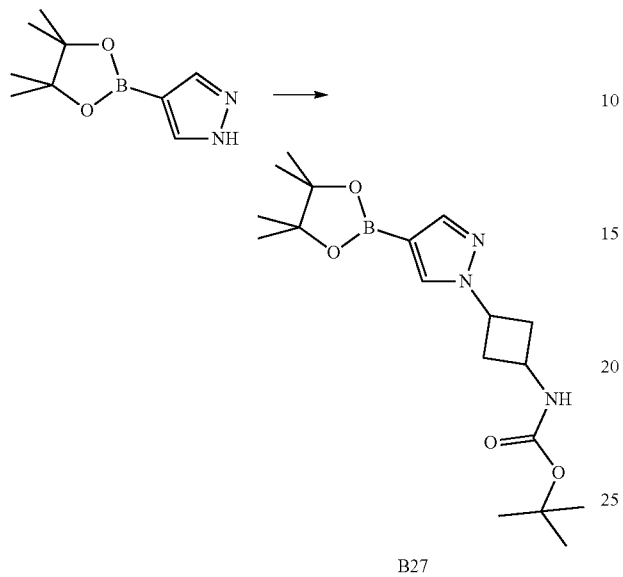

B27

To a stirred solution of 4-(4,4,5,5-Tetramethyl-[1,3,2]dioxaborolan-2-yl)-1H-pyrazole (576 mg, 2.97 mmol) in DMF (5 mL) at 0° C. was added sodium hydride (60% dispersion in oil, 213 mg, 1.55 mmol). The reaction mixture was stirred at this temperature for a further 1 h and then warmed to RT after which a solution of 3-((tert-butoxycarbonyl)amino)cyclobutyl 4-methylbenzenesulfonate (780 mg, 2.28 mmol) in DMF (4.5 mL) was added dropwise and the resulting mixture heated at 95° C. for 5 h. The reaction mixture was cooled to RT then quenched by pouring reaction mixture into ice-water and extracted with EtOAc (×2). The combined organic layer was passed through a phase separator and concentrated in vacuo. The crude compound was purified by reversed phase preparative HPLC-MS to afford tert-butyl (3-(4-(4,4,5,5-tetramethyl-1,3,2-dioxaborolan-2-yl)-1H-pyrazol-1-yl)cyclobutyl)carbamate (B25) as an colourless oil (255 mg, 31%). LC-MS. $R_t$ 3.24 min, AnalpH2_MeOH_4 min(1); (ESI+) m/z 386.3 [M+Na]$^+$.

The following boronic esters were prepared via acetylation of the corresponding pyrazole:

1-(1-Acetyl-azetidin-3-yl)-1H-pyrazole-4-boronic Acid Pinacol Ester (B28)

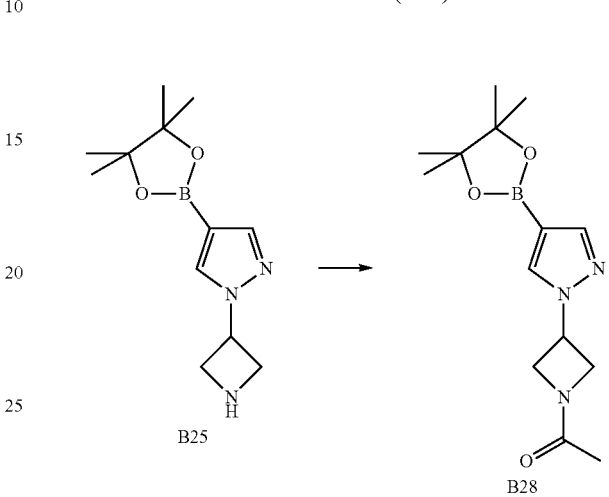

To 1-azetidin-3-yl-1H-pyrazole-4-boronic acid pinacol ester (B25) (614 mg, 2.46 mmol) in DCM was added DIPEA (860 μL, 4.93 mmol) and acetyl chloride (263 μL, 3.70 mmol) and the reaction mixture stirred at RT for 1 h. The reaction mixture was evaporated to dryness, re-suspended in DCM and washed with H$_2$O, passed through a phase separator and evaporated to dryness to afford 1-(1-acetyl-azetidin-3-yl)-1H-pyrazole-4-boronic acid pinacol ester (B28) as an orange oil (536 mg, 75%) which was used in the next step without further purification; LC-MS. $R_t$ 2.55 min, AnalpH2_MeOH_4 min(1); (ESI$^+$) m/z 292.4 [M+H]$^+$.

The following boronic esters were made using analogous procedures to B28:

TABLE 10

| Compound | Cpd # (Intermediate used*) | Analytical Data | Mass, % Yield, State |
|---|---|---|---|
| ![structure] | B29 (B25) | LC-MS. $R_t$ 2.76 min, AnalpH2_MeOH_4min(1); (ESI$^+$) m/z 318.3 [M + H]$^+$. | 299 mg, 73%, yellow oil |

TABLE 10-continued

| Compound | Cpd # (Intermediate used*) | Analytical Data | Mass, % Yield, State |
|---|---|---|---|
| 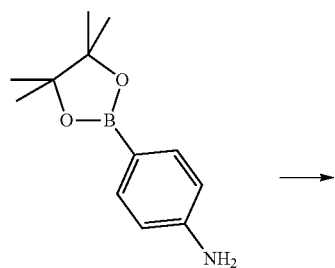 | B30 (B26) | LC-MS. R$_t$ 2.75 min, AnalpH2_MeOH_4min(1); (ESI$^+$) m/z 306.3 [M + H]$^+$. | 140 mg, 57%, dark red oil |

The boronic esters detailed below was synthesised from the corresponding anilino-substituted boronic ester using an amide coupling reaction:

Methyl-{2-[4-(4,4,5,5-tetramethyl-[1,3,2]dioxaborolan-2-yl)-phenylcarbamoyl]-ethyl}-carbamic Acid Tert-butyl Ester (B31)

To a mixture of 4-(4,4,5,5-tetramethyl-1,3,2-dioxaborolan-2-yl)aniline (500 mg, 2.28 mmol), 3-(tert-butoxycarbonyl-methyl-amino)-propionic acid (557 mg, 2.74 mmol), TBTU (880 mg, 2.74 mmol) in DMF (11 mL) was added DIPEA (1.2 mL, 6.85 mmol) and the reaction mixture was stirred at RT for 6 h. The solvent was removed in vacuo (Genevac) and the crude compound was dissolved in DCM and washed with sat. NaHCO$_3$ (aq). The aqueous layer was extracted with DCM, the layers separated by passing through a phase separator and the organic phase evaporated in vacuo. The crude compound was purified by silica gel column chromatography eluting with 0-30% EtOAc/isohexane to obtain methyl-{2-[4-(4,4,5,5-tetramethyl-[1,3,2]dioxaborolan-2-yl)-phenylcarbamoyl]-ethyl}-carbamic acid tert-butyl ester (B31) as a pale orange solid (841 mg, 91%); LC-MS. R$_t$ 3.24 min, AnalpH2_MeOH_4 min; (ESI$^+$) m/z 405.5 [M+H]$^+$.

The following boronic acids were prepared by displacement reactions of 2-chloropyrimidines:

(2-(3-hydroxyazetidin-1-yl)pyrimidin-5-yl)boronic Acid (B32)

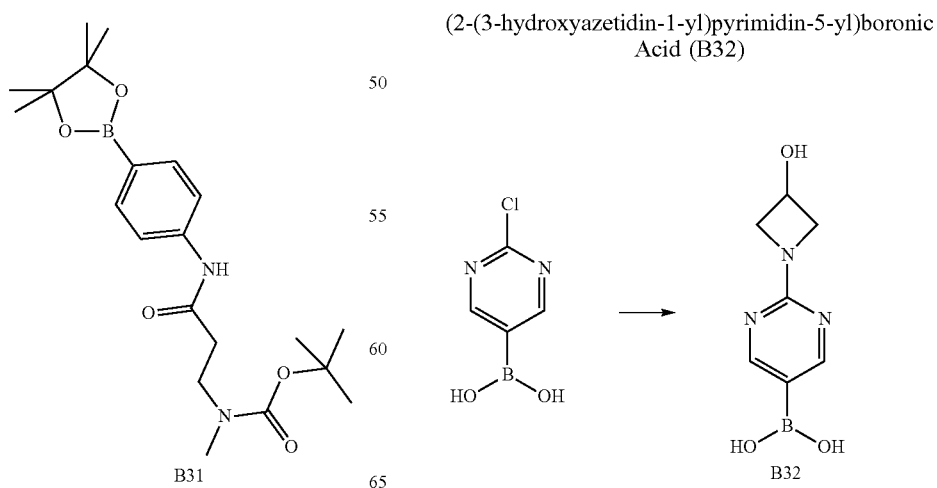

A solution of 2-chloro-5-(4,4,5,5-tetrmethyl)-1,3,2,-dioxaborolan-2-yl)pyrimidine (500 mg, 2.08 mmol), 3-hydroxyazetidine.hydrochloride (342 mg, 3.12 mmol), triethylamine (870 µL) and ethanol was heated to reflux for 90 min. The reaction mixture was concentrated in vacuo, redissolved in methanol and purified by SCX-2, eluting with methanol (2×CV) then 0.25M pyridine/MeOH (2×CV). The pyridine elution was concentrated in vacuo then triturated with Et$_2$O and dried under high vacuum to afford (2-(3-hydroxyazetidin-1-yl)pyrimidin-5-yl)boronic acid (B32) as an off-white solid (327 mg, 81%); LC-MS. R$_t$ 0.95 min, AnalpH2_MeOH_4 min(1); (ESI$^+$) m/z 196.3 [M+H]$^+$; $^1$H-NMR (400 MHz, DMSO-d$_6$): δ 8.58 (s, 2H), 8.07 (s, 2H), 5.71 (d, J=6.3 Hz, 1H), 4.59-4.51 (m, 1H), 4.23 (dd, J=10.4, 6.6 Hz, 2H), 3.77 (dd, J=10.4, 4.5 Hz, 2H).

The following boronic acids were prepared using analogous procedures to B32:

TABLE 11

| Compound | Cpd # (Intermediate used$^a$) | Analytical Data | Mass, % Yield, State |
|---|---|---|---|
| [structure: 2-(2-(hydroxymethyl)azetidin-1-yl)pyrimidin-5-yl boronic acid] | B33 | LC-MS. R$_t$ 1.10 min, AnalpH2_MeOH_4min(1); (ESI$^+$) m/z 210.3 [M + H]$^+$ | 321 mg, 53%, cream solid |
| [structure: 2-((2-hydroxyethyl)amino)pyrimidin-5-yl boronic acid] | B34 | LC-MS. R$_t$ 0.58 min, AnalpH2_MeOH_4min(1); (ESI$^+$) m/z 166.2 [M − H$_2$O + H]$^+$. | 164 mg, 36%, pale orange solide |

The boronic esters detailed below were synthesised in accordance with literature methods:

TABLE 12

| Boronic ester | Cpd # | Reference |
|---|---|---|
| (structure) | B35 | US2014/121200 |
| (structure) | B36 | ACS Med Chem Lett., 2016, 7, 714-718 |
| (structure) | B37 | WO2011/22473 |
| (structure) | B38 | WO2014/54841 |
| (structure) | B39 | WO2014/140076 |
| (structure) | B40 | WO2016/11390 |

A number of examples of formula (Ia) were synthesised according to the following route:

Route1: Scheme 1

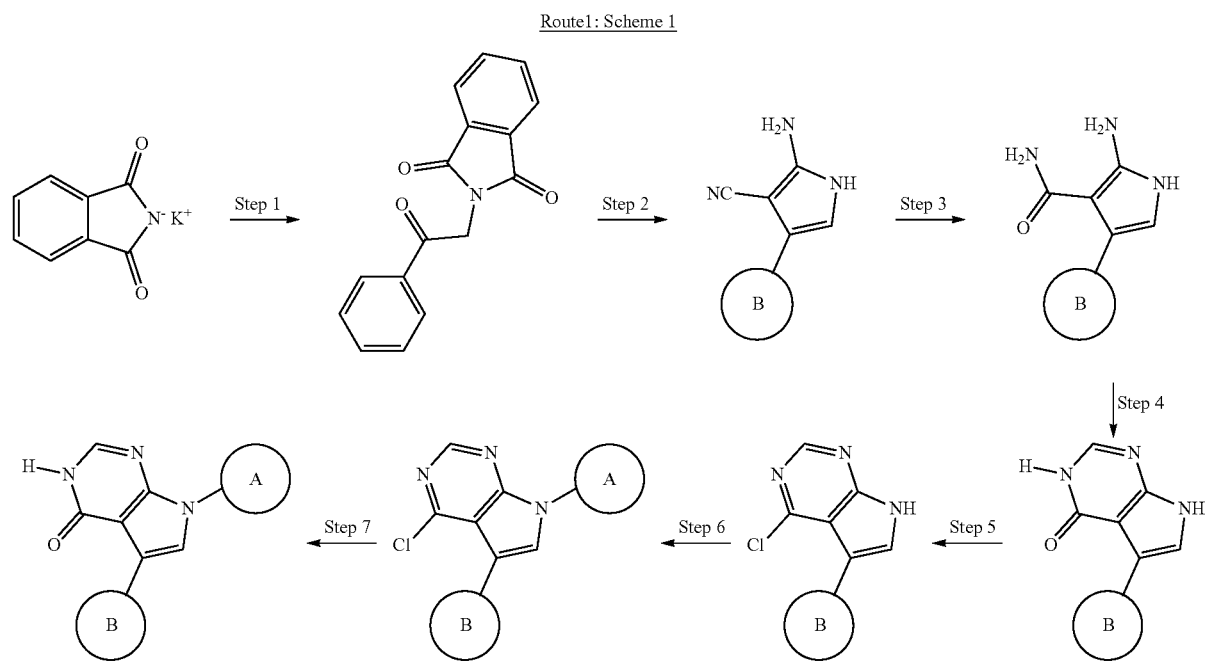

2-(2-Oxo-2-phenyl-ethyl)-isoindole-1,3-dione (A37)

2-amino-4-phenyl-1H-pyrrole-3-carbonitrile (A38)

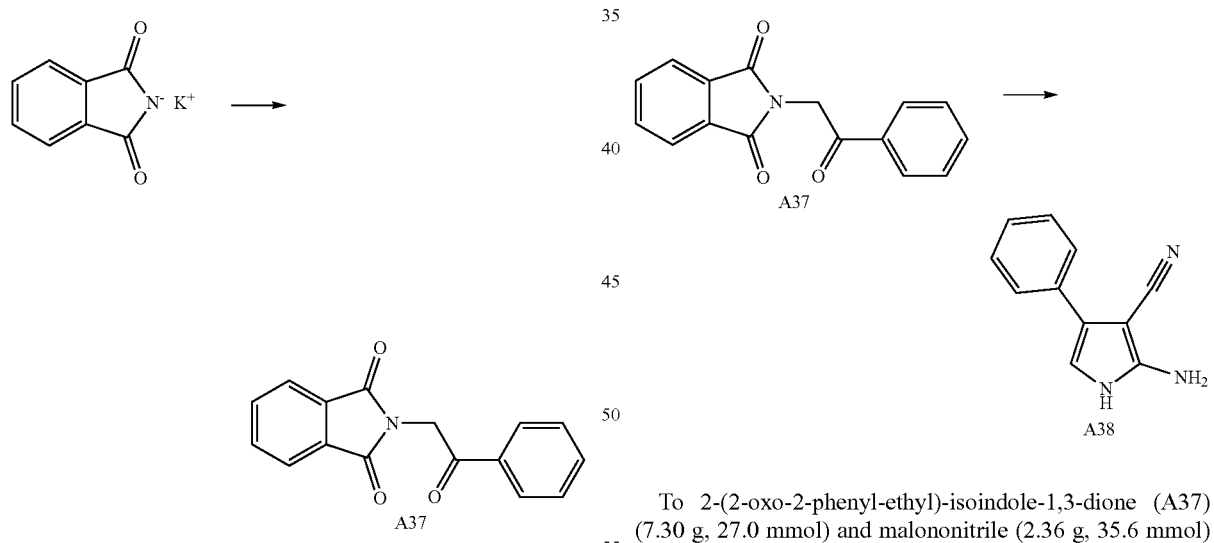

Potassium phthalimide (6.00 g, 32 mmol) and 2-bromo-acetophenone (6.44 g, 32 mmol) in anhydrous DMF (64 mL) was stirred at RT gently until the exothermic reaction ceased. The reaction mixture was heated at 150° C. for 30 min. The reaction mixture was cooled to RT and the resulting solid filtered. The filtrate was poured into $H_2O$ and the resulting solid filtered, washed with $H_2O$ and dried, under vacuum, overnight to afford 2-(2-oxo-2-phenyl-ethyl)-isoindole-1,3-dione (A37) as a pale yellow solid (7.30 g, 85%); LC-MS. $R_t$ 2.85 min, AnalpH2_MeOH_4 min; (ESI+) m/z 266.2 [M+H]+.

To 2-(2-oxo-2-phenyl-ethyl)-isoindole-1,3-dione (A37) (7.30 g, 27.0 mmol) and malononitrile (2.36 g, 35.6 mmol) in EtOH (55 mL) at 0° C. was added sodium ethoxide (3.75 g, 55.1 mmol) and the reaction was stirred at RT for 30 min and then at 60° C. for 1.5 h. The reaction mixture was cooled to RT and concentrated in vacuo. The residue was quenched with 1% AcOH (aq) (100 mL) to afford a brown precipitate which was filtered and washed with $H_2O$. The crude product was dissolved in MeOH (20 mL) and purified by SCX-2 (50 g) washing with MeOH (2×CV) and the compound eluted from the column with 0.5M $NH_3$/MeOH to afford 2-amino-4-phenyl-1H-pyrrole-3-carbonitrile (A38) as a dark red solid (3.30 g, 65%); LC-MS. $R_t$ 2.47 min, AnalpH2_MeOH_4 min; (ESI+) m/z 184.2 [M+H]+.

2-Amino-4-phenyl-1H-pyrrole-3-carboxylic Acid Amide (A39)

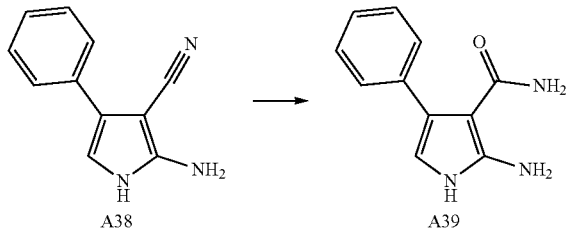

2-Amino-4-phenyl-1H-pyrrole-3-carbonitrile (A38) (670 mg, 3.65 mmol) was dissolved in conc. H₂SO₄ (6 mL) and the reaction mixture was heated at 100° C. for 45 min. The reaction mixture was cooled to 0° C. and quenched to pH 7-8 with 2M NaOH (100 mL). The compound was extracted with EtOAc (3×50 mL) and the combined organic layers washed with H₂O, dried over Na₂SO₄, filtered and the solvent removed in vacuo to afford 2-amino-4-phenyl-1H-pyrrole-3-carboxylic acid amide (A39) as a dark red solid (126 mg, 17%); LC-MS. R$_t$ 2.19 min, AnalpH9_MeOH_4 min; (ESI⁺) m/z 202.3 [M+H]⁺.

5-Phenyl-3,7-dihydro-pyrrolo[2,3-d]pyrimidin-4-one (A40)

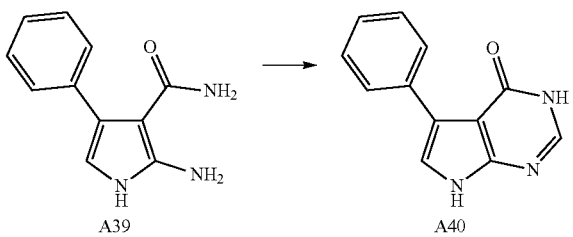

To a solution of 2-amino-4-phenyl-1H-pyrrole-3-carboxylic acid amide (A39) (1.46 g, 7.25 mmol) in DMF (18 mL) was added p-toluene sulfonic acid (41 mg, 0.22 mmol) and triethyl orthoformate (24 mL, 145 mmol) and the solution stirred at RT, under N₂ for 1 h. The reaction mixture was evaporated to dryness to afford 5-phenyl-3,7-dihydro-pyrrolo[2,3-d]pyrimidin-4-one (A40) as a dark red solid (1.8 g, quant.) which was used in the next step without further purification; LC-MS. R$_t$ 2.31 min, AnalpH2_MeOH_4 min (1); (ESI⁺) m/z 212.3 [M+H]⁺.

4-Chloro-5-phenyl-7H-pyrrolo[2,3-d]pyrimidine (A41)

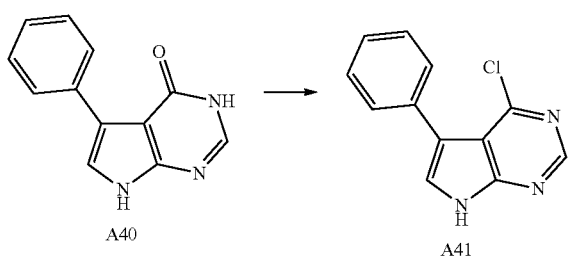

5-Phenyl-3,7-dihydro-pyrrolo[2,3-d]pyrimidin-4-one (A40) (1.53 g, 7.25 mmol) was dissolved in POCl₃ (36 mL, 7.2 mmol) and DMF (6.5 mL) and the reaction mixture was heated at 120° C. for 1 h. The reaction mixture was evaporated to obtain a viscous oil. Ice was added to the residue and the residue was placed in an ice-bath. NF₄OH (aq, 30% NH₃) was added with continuous stirring and the residue basified to pH10 then extracted with DCM (3×200 mL). The organic layer was passed through a phase-separation cartridge and evaporated to dryness. A precipitate was observed in both the aqueous layer and phase separation cartridge which was filtered and found to contain the desired product. This precipitate was combined with the evaporated filtrate. The crude compound was purified by silica gel column chromatography eluting with 15%-35% EtOAc/iso-hexane to obtain 4-chloro-5-phenyl-7H-pyrrolo[2,3-d]pyrimidine (A41) as an off-white solid (789 mg, 47%); LC-MS. R$_t$ 3.01 min, AnalpH2_MeOH_4 min(1); (ESI⁺) m/z 230.3, 232.3 [M+H]⁺; ¹H NMR (400 MHz, DMSO-d₆) δ 12.83-12.79 (brs, 1H), 8.63 (s, 1H), 7.79 (s, 1H), 7.55 (m, 2H), 7.44 (m, 2H), 7.36 (m, 1H).

4-Chloro-5-phenyl-7-pyridin-3-yl-7H-pyrrolo[2,3-d]pyrimidine (CP1)

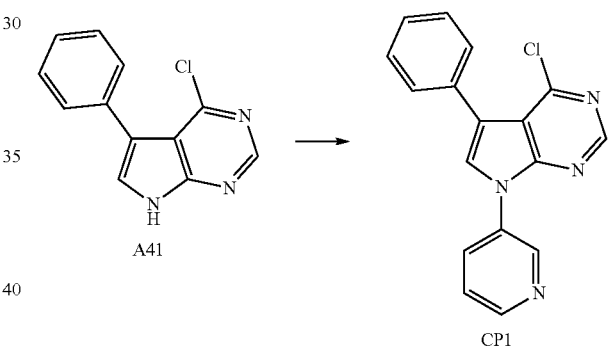

To 4-chloro-5-phenyl-7H-pyrrolo[2,3-d]pyrimidine (A41) (100 mg, 0.44 mmol), Cu(OAc)₂ (198 mg, 1.09 mmol), 3-pyridineboronic acid 1,3-propanediol ester (178 mg, 1.09 mmol), NEt₃ (303 µL, 2.18 mmol) and molecular sieves (4 Å, 1× small spatula) was added DMF (2.2 mL). The reaction vessel was capped and a needle inserted to allow O₂ into the reaction mixture. The reaction mixture was heated at 60° C. for 5 h. The reaction mixture was diluted with MeOH/DMF and passed through a Si-thiol cartridge (5 g). DMSO was added to aid filtration. The cartridge was washed with MeOH/DMF/DMSO and the filtrate evaporated to dryness (Genevac). The crude compound was purified by reverse phase preparative HPLC-MS to afford 4-chloro-5-phenyl-7-pyridin-3-yl-7H-pyrrolo[2,3-d]pyrimidine (CP1) as an off-white solid (36 mg, 27%); LC-MS. R$_t$ 3.20 min, AnalpH2_MeOH_4 min(1); (ESI⁺) m/z 307.2, 309.2 [M+H]⁺.

The following substituted 4-chloro-5-aryl pyrrolo[2,3-d] pyrimidine derivative was prepared using analogous procedures used for the synthesis of intermediate (CP1) with 1 h duration of reaction using a commercially available boronic acid:

TABLE 13

| Compound | Cpd # (Intermediate used*) | Analytical Data | Mass, % Yield, State |
|---|---|---|---|
| (4-chloro-5-phenyl-7-(pyridin-4-yl)-7H-pyrrolo[2,3-d]pyrimidine structure) | CP2 (A41) | LC-MS. R$_t$ 3.29 min, AnalpH2_MeOH_QC_V1(1); (ESI$^+$) m/z 307.1, 309.1 [M + H]$^+$. | 12 mg, 18%, brown solid |

5-Phenyl-7-pyridin-3-yl-3,7-dihydro-pyrrolo[2,3-d]pyrimidin-4-one (Ex-1)

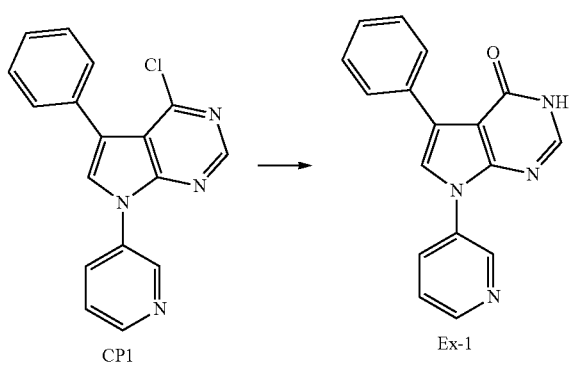

To 4-chloro-5-phenyl-7-pyridin-3-yl-7H-pyrrolo[2,3-d]pyrimidine (CP1) (36 mg, 0.12 mmol) was added sodium acetate (20 mg, 0.24 mmol) followed by AcOH (0.25 mL) and the reaction mixture heated at 100° C. for 18 h. The reaction mixture was allowed to cool to RT, diluted with DCM and evaporated in vacuo. The crude compound was purified by reversed phase preparative HPLC-MS to afford 5-phenyl-7-pyridin-3-yl-3,7-dihydro-pyrrolo[2,3-d]pyrimidin-4-one (Ex-1) as a white solid (23.1 mg, 66%); LC-MS. R$_t$ 6.95 min, AnalpH2_MeOH_QC_V1(1); (ESI$^+$) m/z 289.3 [M+H]$^+$; $^1$H NMR (400 MHz, DMSO-d$_6$) δ 12.27 (br s, 1H), 9.04 (d, J=3.03 Hz, 1H), 8.63 (dd, J=4.5, 1.3 Hz, 1H), 8.27-8.23 (m, 1H), 8.03 (s, 1H), 7.99 (dd, J=8.6, 1.3 Hz, 2H), 7.93 (s, 1H), 7.64-7.61 (m, 1H), 7.40 (t, J=7.3 Hz, 2H), 7.28 (tt, J=7.3, 1.3 Hz, 1H).

The following example was synthesised using analogous procedures to example (Ex-1) with 4 h reaction time:

TABLE 14

| Compound | Cpd # (Intermediate used*) | Analytical Data | Mass, % Yield, State |
|---|---|---|---|
| (5-phenyl-7-(pyridin-4-yl)-3,7-dihydro-4H-pyrrolo[2,3-d]pyrimidin-4-one structure) | Ex-2 (CP2) | LC-MS. R$_t$ 5.97 min, AnalpH2_MeOH_QC_V1(1); (ESI$^+$) m/z 289.2 [M + H]$^+$; $^1$H NMR (400 MHz, DMSO-d$_6$): δ 12.36 (br s, 1H), 8.73 (dd, J = 4.5, 1.5 Hz, 2H), 8.09 (s, 1H), 8.04 (dd, J = 4.5, 1.5 Hz, 2H), 8.03 (s, 1H), 7.98 (**dd, J = 7.1, 1.3 Hz, 2H), 7.40 (t, J = 7.3 Hz, 2H), 7.29 (tt, J = 7.3, 1.3 Hz, 1H) | 6 mg, 51%, off-white solid |

A number of examples of formula (Ia) were synthesised according to the following route:

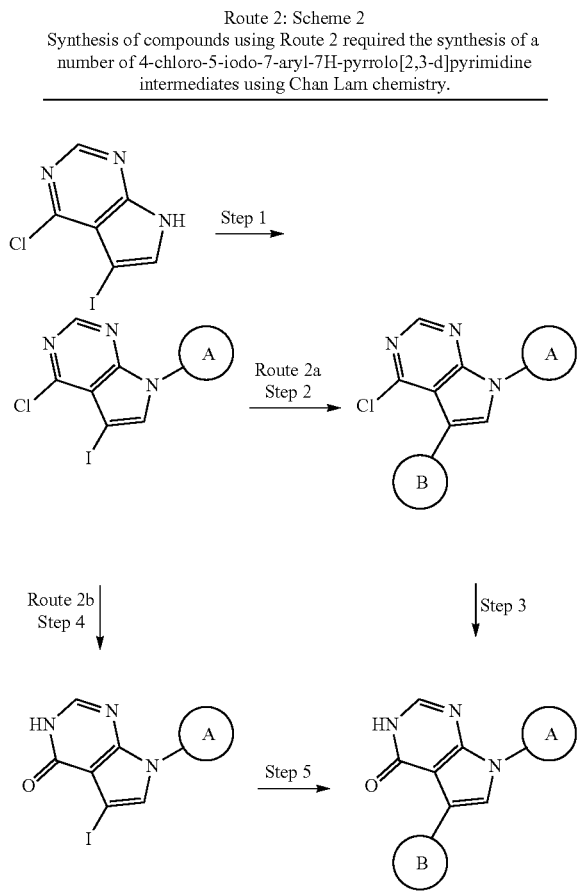

Route 2: Scheme 2
Synthesis of compounds using Route 2 required the synthesis of a number of 4-chloro-5-iodo-7-aryl-7H-pyrrolo[2,3-d]pyrimidine intermediates using Chan Lam chemistry.

4-Chloro-5-iodo-7-phenyl-7H-pyrrolo[2,3-d]pyrimidine (CH1)

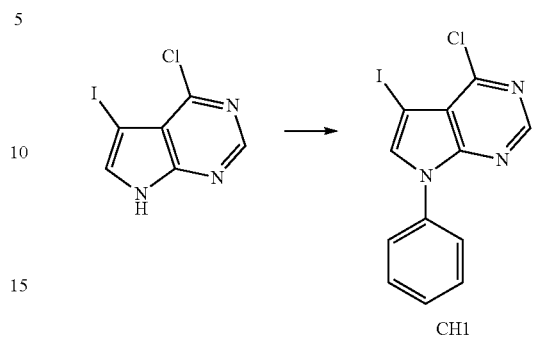

To a solution of 4-chloro-5-iodo-7H-pyrrolo[2,3-d]pyrimidine (15.0 g, 53.5 mmol) in DMF (100 mL) was added 2-phenyl-1,3,2-dioxoborinone (17.3 g, 107.0 mmol), Cu(OAc)$_2$ (21.35 g, 107.0 mmol) and activated molecular sieves (4 Å, 0.4 g), followed by addition of NEt$_3$ (22.3 mL, 160.4 mmol) and the resulting reaction mixture was stirred at 60° C. for 24 h. The reaction mixture was then cooled to RT and the solvent concentrated in vacuo. The crude residue was dissolved in DCM (300 mL) and quenched with saturated EDTA (aq) (100 mL). The separated aqueous layer was extracted with DCM (2×100 mL) and the combined organic layer was dried over anhydrous Na$_2$SO$_4$, filtered and concentrated in vacuo. The crude compound was purified by reversed phase preparative HPLC to afford 4-chloro-5-iodo-7-phenyl-7H-pyrrolo[2,3-d]pyrimidine (CH$_1$) as an off-white solid (6.2 g, 33%); LC-MS. R$_t$ 3.37 min, AnalpH2_MeOH_4 min(1); (ESI$^+$) m/z 356.1, 358.0 [M+H]$^+$; $^1$H NMR (400 MHz, DMSO-d$_6$): δ 8.70 (s, 1H), 8.39 (s, 1H), 7.81-7.77 (m, 2H), 7.61-7.56 (m, 2H), 7.47 (tt, J=7.8, 1.4 Hz, 1H).

The following intermediates were prepared using an analogous procedure to intermediate CH1 duration of heating varying between 4-18 h and heating between 45-60° C.:

TABLE 15

| Compound | Cpd # (Intermediate used") | Analytical Data | Mass, % Yield, State |
|---|---|---|---|
|  | CH2 | LC-MS. R$_t$ 3.47 min, AnalpH2_MeOH_4min; (ESI$^+$) m/z 374.0, 376.1 [M + H]$^+$. | 1.73 g, 65%, white solid |

TABLE 15-continued

| Compound | Cpd # (Intermediate used*) | Analytical Data | Mass, % Yield, State |
|---|---|---|---|
| 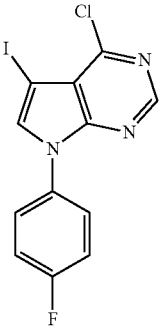 [SMILES: Fc1ccc(-n2cc(I)c3c(Cl)ncnc32)cc1] | CH3 | LC-MS. R$_t$ 3.40 min, AnalpH2_MeOH_4min(1); (ESI$^+$) m/z 374.1, 376.1 [M + H]$^+$. | 1.33 g, 25%, white solid |
| 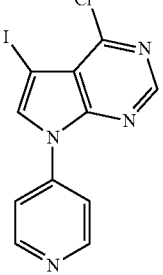 | CH4 | LC-MS. R$_t$ 3.12 min, AnalpH9_MeOH_4min(1); (ESI$^+$) m/z 357.1, 359.0 [M + H]$^+$. | 758 mg, 42%, brown solid |
| 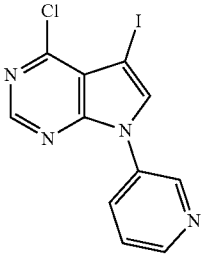 [SMILES: Clc1ncnc2c1c(I)cn2-c1cccnc1] | CH5 | LC-MS. R$_t$ 2.98 min, AnalpH2_MeOH_4min(1); (ESI$^+$) m/z 357.0, 359.0 [M + H]$^+$ | 1.17 g, 23%, off-white solid |
| 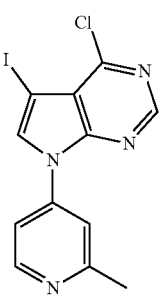 [SMILES: Cc1cc(-n2cc(I)c3c(Cl)ncnc32)ccn1] | CH6 | LC-MS. R$_t$ 2.53 min, AnalpH2_MeOH_4min(1); (ESI$^+$) m/z 371.0 [M + H]$^+$ | 304 mg, 6%, white solid |
| 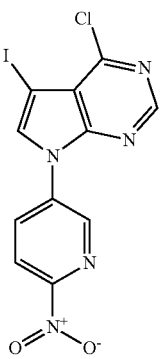 [SMILES: O=[N+]([O-])c1ccc(-n2cc(I)c3c(Cl)ncnc32)cn1] | CH7 | LC-MS. R$_t$ 2.95 min, AnalpH2_MeOH_4min(1); (ESI$^+$) m/z 402.0 [M + H]$^+$ | 320 mg, 8%, yellow solid |

127
4-chloro-7-(5-fluoropyridin-3-yl)-5-iodo-7H-pyrrolo[2,3-d]pyrimidine (CH8)

128
4-chloro-5-iodo-7-(6-methoxypyridin-3-yl)-7H-pyrrolo[2,3-d]pyrimidine (CH10)

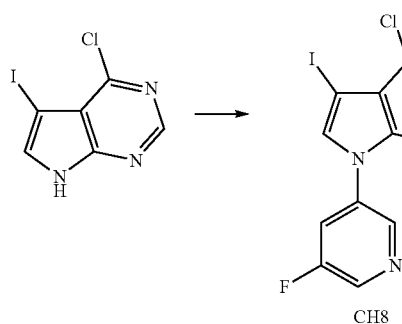

CH8

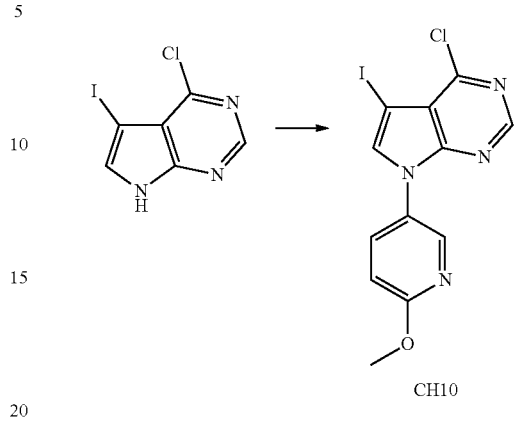

CH10

To an oven dried flask fitted with a $P_2O_5$ guard tube and purged with dry air was added to 4-chloro-5-iodo-7H-pyrrolo[2,3-d]pyrimidine (2.7 g, 9.8 mmol), 5-fluoropyridine-3-boronic acid (2.74 g, 19.6 mmol), 2,2'-bipyridyl (1.52 g, 9.8 mmol), anhydrous $NEt_3$ (20 mL, 147 mmol) and activated molecular sieves (4 Å, 3.0 g) followed by DMF (40 mL). The mixture was stirred until dissolved after which $Cu(OAc)_2$ (3.50 g, 19.6 mmol) was added and the resulting suspension was stirred at 50° C. for 24 h. Once the reaction was complete the reaction was filtered over a celite cartridge (10 g) washing with DMF and MeOH. The resulting blue solution was filtered over an SCX-2 column (45 g), product containing fractions were concentrated and loaded onto silica then purified by column chromatography eluting with EtOAc/iso-hexane to afford the title compound ($CH_8$) as a white solid (456 mg, 12%), AnalpH2_MeOH_4 min(1); (ESI$^+$) $R_t$ 3.10, m/z 375.0, 377.0 [M+H]$^+$.

The following intermediate was also prepared using an analogous procedure to intermediate ($CH_8$) with the reaction carried out at RT for 3 h:

$Cu(OAc)_2$ (16 mg, 10 mol %), was added to a 28 mL vial containing a stirred solution of (2-methoxypyridin-4-yl)boronic acid (204 mg, 1.3 mmol), 4-chloro-5-iodo-7H-pyrrolo[2,3-d]pyrimidine (250 mg, 0.89 mmol), 2,6 lutidine (156 µL, 0.98 mmol), myristic acid (40 mg, 20 mol %), and tris(2-phenylpyridinato)iridium$_{(III)}$ (6 mg, 1 mol %) in a mixture of DMF/Toluene (4 mL, 1:1). The reaction was then placed in a photoreactor and irradiated with blue light (450 nM) for 20 h. The resulting suspension was diluted with EtOAc and the resulting solid was filtered under vacuum and dried to afford the title compound (CH10) as a cream solid (235 mg, 68%). LC-MS. $R_t$ 3.36 min, AnalpH2_MeOH_4 min(x); (ESI$^+$) m/z 387.0, 389.0 [M+H]$^+$.

Route 2a, Step 2: Suzuki-Miyaura Coupling 5-(1-Benzyl-1H-pyrazol-4-yl)-4-chloro-7-phenyl-7H-pyrrolo[2,3-d]pyrimidine (CP3)

TABLE 16

| Compound | Cpd # (Intermediate used*) | Analytical Data | Mass, % Yield, State |
|---|---|---|---|
| (structure shown) | CH9 | LC-MS. $R_t$ 3.20 min, AnalpH2_MeOH_4min(1); (ESI$^+$) m/z 387.0, 389.0 [M + H]$^+$ | 900 mg, 24%, white solid |

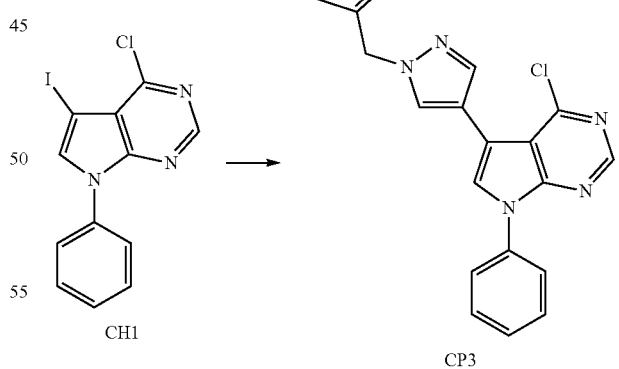

A mixture of 4-chloro-5-iodo-7-phenyl-7H-pyrrolo[2,3-d]pyrimidine (CH1) (25.0 mg, 0.070 mmmol), 1-benzylpyrazole-4-boronic acid pinacol ester (21.9 mg, 0.077 mmol), Pd(PPh$_3$)$_4$ (4.04 mg, 0.0035 mmol) and potassium carbonate (19.3 mg, 0.14 mmol) in dioxane:H$_2$O (0.5 mL, 4:1) was deoxygenated for 5 min then heated in the microwave at 100° C. for 20 min. The reaction was repeated once more. The reaction mixtures were filtered through Si-thiol cartridge and washed with methanol. The combined organics were concentrated in vacuo and the crude solid was purified by silica gel column chromatography eluting with 0-50% EtOAc/iso-hexane to afford 5-(1-benzyl-1H-pyrazol-4-yl)-4-chloro-7-phenyl-7H-pyrrolo[2,3-d]pyrimidine (CP3) as a white gummy oil (34.7 mg, 64%); LC-MS. $R_t$ 3.40 min, AnalpH2_MeOH_4 min(x); (ESI$^+$) m/z 386.3, 388.3 [M+H]$^+$.

1-{3-[4-(4-Chloro-7-pyridin-4-yl-7H-pyrrolo[2,3-d]pyrimidin-5-yl)-pyrazol-1-yl]-azetidin-1-yl}-ethanone (CP4)

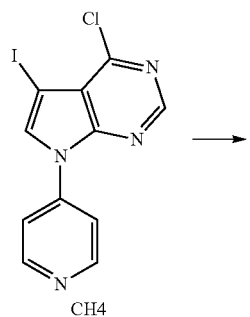

To 4-chloro-5-iodo-7-pyridin-4-yl-7H-pyrrolo[2,3-d]pyrimidine (CH4) (156 mg, 0.44 mmol), 1-(1-acetyl-azetidin-3-yl)-1H-pyrazole-4-boronic acid pinacol ester (B28) (140 mg, 0.48 mmol), Pd(dppf)Cl$_2$.DCM (36 mg, 0.04 mmol) and K$_2$CO$_3$ (121 mg, 0.87 mmol) was added dioxane/H$_2$O (4:1, 2.2 mL). The reaction mixture was deoxygenated with N$_2$ for 10 min and heated in the microwave at 90° C. for 30 min. The reaction mixture was passed through a Si-thiol cartridge (2 g), eluting with MeOH (2×CV) and CH$_2$Cl$_2$ (2×CV). The solvent was removed in vacuo, the residue was suspended in DCM and washed with H$_2$O. The organic phase was separated (phase separator) and evaporated to dryness. The material obtained was purified by further silica gel chromatography, eluting with 0-5% MeOH/DCM to afford 1-{3-[4-(4-chloro-7-pyridin-4-yl-7H-pyrrolo[2,3-d]pyrimidin-5-yl)-pyrazol-1-yl]-azetidin-1-yl}-ethanone (CP4) as a beige solid (78 mg, 45%); LC-MS. $R_t$ 2.15 min, AnalpH2_MeOH_4 min(1); (ESI$^+$) m/z 394.2, 396.2 [M+H]$^+$.

The following compounds were made using analogous procedures to CP4 (duration of heating varied between 15-90 min; temperature varied between 90-95° C.):

TABLE 17

| Compound | Cpd # (Intermediate used$^a$) | Analytical Data | Mass, % Yield, State |
|---|---|---|---|
| (structure: 4-chloro-5-(pyridin-3-yl)-7-phenyl-7H-pyrrolo[2,3-d]pyrimidine) | CP5 (CH1) | LC-MS. $R_t$ 2.39 min, AnalpH2_MeOH_4min; (ESI$^+$) m/z 309.3, 309.3 [M + H]$^+$. | 12 mg, 57%, yellow solid |

TABLE 17-continued

| Compound | Cpd # (Intermediate used) | Analytical Data | Mass, % Yield, State |
|---|---|---|---|
| (pyridin-3-yl substituted 4-chloro-7-phenyl-7H-pyrrolo[2,3-d]pyrimidine) | CP6 (CH1) | LC-MS. R$_t$ 2.83 min, AnalpH2_MeOH_4min(1); (ESI⁺) m/z 307.3, 309.3 [M + H]⁺. | 16 mg, 37%, off-white solid |
| (6-acetamidopyridin-3-yl substituted 4-chloro-7-phenyl-7H-pyrrolo[2,3-d]pyrimidine) | CP7 (CH1) | LC-MS. R$_t$ 3.04 min, AnalpH2_MeOH_4min(1); (ESI⁺) m/z 364.3, 366.3 [M + H]⁺. | 20 mg, 39%, white solid |
| (3,5-dimethylisoxazol-4-yl substituted 4-chloro-7-phenyl-7H-pyrrolo[2,3-d]pyrimidine) | CP8 (CH1) | LC-MS. R$_t$ 3.15 min, AnalpH2_MeOH_4min(1); (ESI⁺) m/z 325.3, 327.3 [M + H]⁺. | 26 mg, 31%, brown oil |
| (tert-butyl (pyridin-2-yl)carbamate substituted 4-chloro-7-phenyl-7H-pyrrolo[2,3-d]pyrimidine) | CP9 (CH1, B1) | LC-MS. R$_t$ 3.49 min, AnalpH2_MeOH_4min(1); (ESI⁺) m/z 422.3, 424.2 [M + H]⁺. | 74 mg, 93%, yellow oil |

TABLE 17-continued

| Compound | Cpd # (Intermediate used*) | Analytical Data | Mass, % Yield, State |
|---|---|---|---|
| (structure) | CP10 (CH1, B37) | LC-MS. R$_t$ 3.54 min, AnalpH2_MeOH_4min(1); (ESI⁺) m/z 422.2, 424.2 [M + H]⁺. | 57 mg, 71%, yellow oil |
| (structure) | CP11 (CH4, B31) | LC-MS. R$_t$ 3.16 min, AnalpH2_MeOH_4min(1); (ESI⁺) m/z 507.3, 509.3 [M + H]⁺. | 65 mg, 25%, yellow oil |
| (structure) | CP12 (CH2, B28) | LC-MS. R$_t$ 2.99 min, AnalpH2_MeOH_4min(1); (ESI⁺) m/z 411.2, 413.2 [M + H]⁺. | 79 mg, 39%, brown solid |

TABLE 17-continued

| Compound | Cpd # (Intermediate used*) | Analytical Data | Mass, % Yield, State |
|---|---|---|---|
| [structure] | CP13 (CH3, B28) | LC-MS. R_t 2.92 min, AnalpH2_MeOH_4min(1); (ESI+) m/z 411.2, 413.2 [M + H]+. | 17 mg, 9%, white solid |
| [structure] | CP14 (CH4) | LC-MS. R_t 2.97 min, AnalpH2_MeOH_4min(1); (ESI+) m/z 382.3, 384.3 [M + H]+. | 45 mg, 62%, off-white solid |
| [structure] | CP15 (CH4) | LC-MS. R_t 1.61 min, AnalpH2_MeOH_4min(1); (ESI+) m/z 381.2, 383.2 [M + H]+. | 42 mg, 58%, pale yellow solid |

TABLE 17-continued

| Compound | Cpd # (Intermediate used*) | Analytical Data | Mass, % Yield, State |
|---|---|---|---|
| | CP16 (CH2, B29) | LC-MS. R$_t$ 3.12 min, AnalpH2_MeOH_4min(1); (ESI$^+$) m/z 437.2, 439.1 [M + H]$^+$. | 89 mg, 42%, beige solid |
| | CP17 (CH1, B30) | LC-MS. R$_t$ 3.03 min, AnalpH2_MeOH_4min(1); (ESI$^+$) m/z 407.3, 409.3 [M + H]$^+$. | 41 mg, 24%, orange oil which solidified on standing |
| | CP18 (CH1) | LC-MS. R$_t$ 3.30 min, AnalpH2_MeOH_4min(1); (ESI$^+$) m/z 337.2, 339.2 [M + H]$^+$. | 18 mg, 25%, white solid |
| | CP19 (CH1) | LC-MS. R$_t$ 3.31 min, AnalpH2_MeOH_4min(1); (ESI$^+$) m/z 337.2, 339.2 [M + H]$^+$. | 36 mg, 49%, white solid |

TABLE 17-continued

| Compound | Cpd # (Intermediate used*) | Analytical Data | Mass, % Yield, State |
|---|---|---|---|
| (structure) | CP20 (CH5, B22) | LC-MS. R$_t$ 2.66 min, AnalpH2_MeOH_4min(1); (ESI$^+$) m/z 355.3, 357.3 [M + H]$^+$. | 64 mg, 65%, light brown solid |
| (structure) | CP21 (CH2, B22) | LC-MS. R$_t$ 3.19 min, AnalpH2_MeOH_4min(1); (ESI$^+$) m/z 372.3, 374.3 [M + H]$^+$. | 43 mg, 30%, beige solid |
| (structure) | CP22 (CH3, B38) | LC-MS. R$_t$ 2.89 min, AnalpH2_MeOH_4min(1); (ESI$^+$) m/z 358.3, 360.4 [M + H]$^+$. | 40 mg, 28%, off-white solid |

TABLE 17-continued

| Compound | Cpd # (Intermediate used) | Analytical Data | Mass, % Yield, State |
|---|---|---|---|
| (structure) | CP23 (CH1, B21) | LC-MS. R$_t$ 2.96 min, AnalpH2_MeOH_4min(1); (ESI$^+$) m/z 368.2, 370.2 [M + H]$^+$. | 64 mg, quant, brown solid |
| (structure) | CP24 (CH1, B23) | LC-MS. R$_t$ 3.08 min, AnalpH2_MeOH_4min(1); (ESI$^+$) m/z 382.2, 384.2 [M + H]$^+$. | 47 mg, 88%, yellow oil |
| (structure) | CP25 (CH2) | LC-MS. R$_t$ 3.40 min, AnalpH2_MeOH_4min(1); (ESI$^+$) m/z 399.2, 401.2 [M + H]$^+$. | 41 mg, 55%, orange solid |

TABLE 17-continued

| Compound | Cpd # (Intermediate used*) | Analytical Data | Mass, % Yield, State |
|---|---|---|---|
| (structure) | CP26 (CH4) | LC-MS. R$_t$ 3.00 min, AnalpH2_MeOH_4min(1); (ESI$^+$) m/z 381.2, 383.2 [M + H]$^+$. | 31 mg, 97%, pale yellow solid |
| (structure) | CP27 (CH5) | LC-MS. R$_t$ 1.99 min, AnalpH2_MeOH_4min(1); (ESI$^+$) m/z 408.2, 410.2 [M + H]$^+$. | 50 mg, 55%, yellow solid |
| (structure) | CP28 (CH5, B20) | LC-MS. R$_t$ 1.87 min, AnalpH2_MeOH_4min(1); (ESI$^+$) m/z 466.2, 468.3 [M + H]$^+$. | 70 mg, 49%, orange oil |

TABLE 17-continued
| Compound | Cpd # (Intermediate used") | Analytical Data | Mass, % Yield, State |
|---|---|---|---|
| 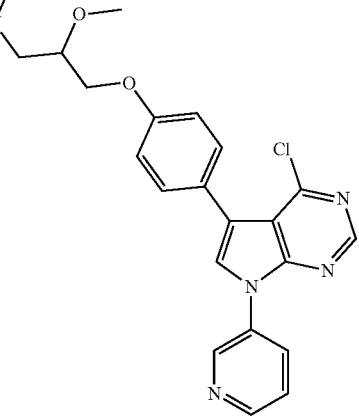 | CP29 (CH5, B4) | LC-MS. R, 1.96 min, AnalpH2_MeOH_4min(1); (ESI+) m/z 480.2, 482.2 [M + H]+. | 21 mg, 40%, orange oil |
| 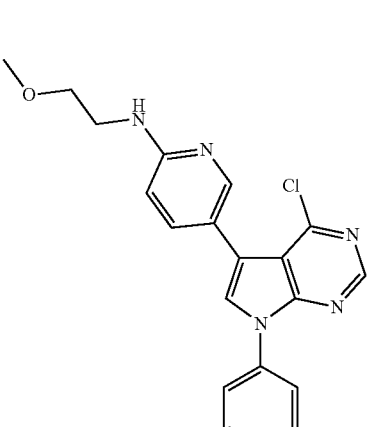 | CP30 (CH2) | LC-MS. R, 2.31 min, AnalpH2_MeOH_4min(1); (ESI+) m/z 398.2, 400.2 [M + H]+. | 23 mg, 31%, orange solid |
| 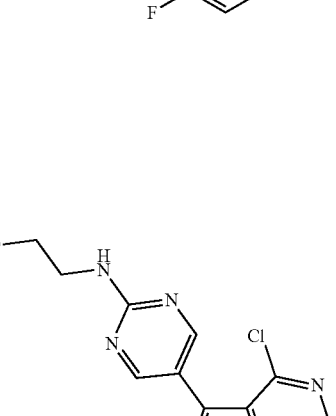 | CP31 (CH2) | LC-MS. R, 3.23 min, AnalpH2_MeOH_4min(1); (ESI+) m/z 399.2, 401.2 [M + H]+. | 33 mg, 76%, orange solid |

TABLE 17-continued

| Compound | Cpd # (Intermediate used) | Analytical Data | Mass, % Yield, State |
|---|---|---|---|
| | CP32 (CH4) | LC-MS. R$_t$ 2.57 min, AnalpH2_MeOH_4min(1); (ESI$^+$) m/z 382.2, 384.2 [M + H]$^+$. | 47 mg, 59%, orange solid |
| | CP33 (CH1) | LC-MS. R$_t$ 3.02 min, AnalpH2_MeOH_4min(1); (ESI$^+$) m/z 310.3, 312.3 [M + H]$^+$. | 8 mg, 12%, off-white solid |
| | CP34 (CH1, B38) | LC-MS. R$_t$ 2.86 min, AnalpH2_MeOH_4min(1); (ESI$^+$) m/z 340.2, 342.2 [M + H]$^+$. | 15 mg, 32%, off-white solid |
| | CP35 (CH1) | LC-MS. R$_t$ 2.99 min, AnalpH2_MeOH_4min(1); (ESI$^+$) m/z 352.2, 354.2 [M + H]$^+$. | 27 mg, 54%, off-white solid |

TABLE 17-continued

| Compound | Cpd # (Intermediate used) | Analytical Data | Mass, % Yield, State |
|---|---|---|---|
| | CP36 (CH1) | LC-MS. R$_t$ 3.04 min, AnalpH2_MeOH_4min(1); (ESI$^+$) m/z 310.2, 312.2 [M + H]$^+$. | 16 mg, 73%, off-white solid |
| | CP37 (CH5, B28) | LC-MS. R$_t$ 2.40 min, AnalpH2_MeOH_4min(1); (ESI$^+$) m/z 394.2, 396.2 [M + H]$^+$ | 55 mg, 67%, orange gum |
| | CP38 (CH5, B29) | LC-MS. R$_t$ 2.64 min, AnalpH2_MeOH_4min(1); (ESI$^+$) m/z 420.2, 422.2 [M + H]$^+$ | 101 mg, quantitative pale orange solid |

TABLE 17-continued

| Compound | Cpd # (Intermediate used*) | Analytical Data | Mass, % Yield, State |
|---|---|---|---|
| [structure: 4-chloro-5-(2-((2-hydroxyethyl)amino)pyrimidin-5-yl)-7-phenyl-7H-pyrrolo[2,3-d]pyrimidine] | CP39 (CH1, B34) | LC-MS. $R_t$ 2.88 min, AnalpH2_MeOH_4min(1); (ESI$^+$) m/z 367.2, 369.2 [M + H]$^+$ | 46 mg, 62%, pale orange solid |
| [structure: 4-chloro-5-(2-((2-hydroxyethyl)amino)pyrimidin-5-yl)-7-(pyridin-3-yl)-7H-pyrrolo[2,3-d]pyrimidine] | CP40 (CH5, B34) | LC-MS. $R_t$ 2.39 min, AnalpH2_MeOH_4min(1); (ESI$^+$) m/z 368.2, 370.2 [M + H]$^+$ | 41 mg, 53%, pale yellow solid |
| [structure: 1-(5-(4-chloro-7-(pyridin-3-yl)-7H-pyrrolo[2,3-d]pyrimidin-5-yl)pyrimidin-2-yl)azetidin-3-ol] | CP41 (CH5, B32) | LC-MS. $R_t$ 2.43 min, AnalpH2_MeOH_4min(1); (ESI$^+$) m/z 380.2, 382.2 [M + H]$^+$ | 46 mg, 58%, pale yellow solid |

TABLE 17-continued

| Compound | Cpd # (Intermediate used) | Analytical Data | Mass, % Yield, State |
|---|---|---|---|
| [structure: 4-chloro-5-(2-(3-hydroxyazetidin-1-yl)pyrimidin-5-yl)-7-phenyl-7H-pyrrolo[2,3-d]pyrimidine] | CP42 (CH1, B32) | LC-MS. R$_t$ 2.90 min, AnalpH2_MeOH_4min(1); (ESI$^+$) m/z 379.2, 381.2 [M + H]$^+$ | 39 mg, 30% |
| [structure: 4-chloro-5-(6-((2-methoxyethyl)amino)pyridin-3-yl)-7-phenyl-7H-pyrrolo[2,3-d]pyrimidine] | CP43 (CH1) | LC-MS. R$_t$ 2.17 min, AnalpH2_MeOH_4min(1); (ESI$^+$) m/z 380.3, 382.3 [M + H]$^+$ | 22 mg, 21%, yellow oil |
| [structure: 4-chloro-5-(6-((2-methoxyethyl)amino)pyridin-3-yl)-7-(pyridin-3-yl)-7H-pyrrolo[2,3-d]pyrimidine] | CP44 (CH5) | LC-MS. R$_t$ 1.80 min, AnalpH2_MeOH_4min(1); (ESI$^+$) m/z 381.3, 383.3 [M + H]$^+$ | 44 mg, 41% |

TABLE 17-continued
| Compound | Cpd # (Intermediate used*) | Analytical Data | Mass, % Yield, State |
|---|---|---|---|
| 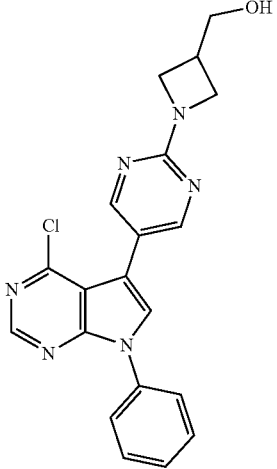 [SMILES: OCC1CN(c2ncc(-c3cn(-c4ccccc4)c4ncnc(Cl)c34)cn2)C1] | CP45 (CH1, B33) | LC-MS. R$_t$ 2.97 min, AnalpH2_MeOH_4min(1); (ESI$^+$) m/z 393.2, 395.2 [M + H]$^+$ | 58 mg, 35% |
| 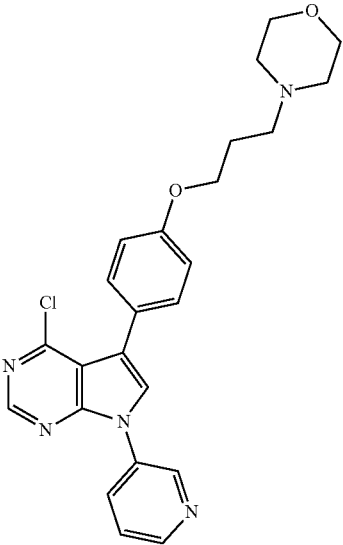 [SMILES: Clc1ncnc2c1c(-c1ccc(OCCCN3CCOCC3)cc1)cn2-c1cccnc1] | CP46 (CH5) | LC-MS. R$_t$ 1.92 min, AnalpH2_MeOH_4min(1); (ESI$^+$) m/z 450.2, 452.2 [M + H]$^+$ | 58 mg, 46%, pale brown solid |

TABLE 17-continued

| Compound | Cpd # (Intermediate used[a]) | Analytical Data | Mass, % Yield, State |
|---|---|---|---|
| 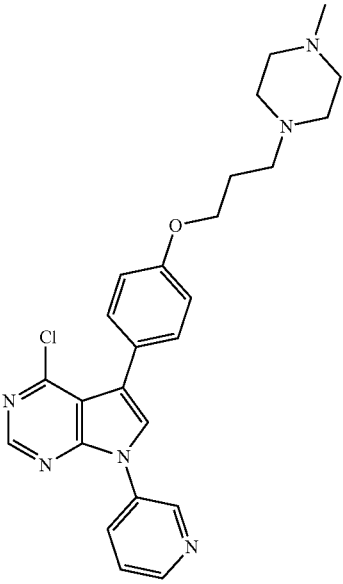 [SMILES: CN1CCN(CCCOc2ccc(-c3cn(-c4cccnc4)c4ncnc(Cl)c34)cc2)CC1] | CP47 (CH5, B3) | LC-MS. R$_t$ 1.96 min, AnalpH2_MeOH_4min(1); (ESI$^+$) m/z 463.3, 465.3 [M + H]$^+$ | 56 mg, 44%, brown solid |
| 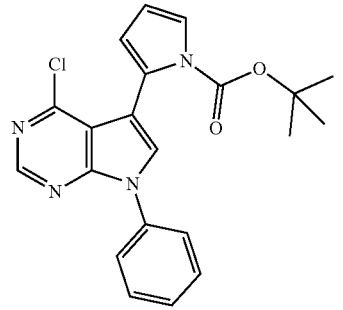 [SMILES: CC(C)(C)OC(=O)n1cccc1-c1cn(-c2ccccc2)c2ncnc(Cl)c12] | CP48 (CH1) | LC-MS. R$_t$ 3.49 min, AnalpH2_MeOH_4min(1); (ESI$^+$) m/z 395.1, 397.1 [M + H]$^+$ | 57 mg, 69%, colourless oil |
| 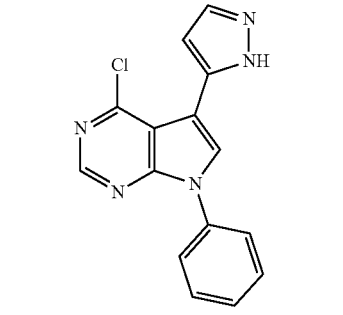 [SMILES: Clc1ncnc2c1c(-c1ccn[nH]1)cn2-c1ccccc1] | CP49 (CH1)[a] | LC-MS. R$_t$ 2.88 min, AnalpH2_MeOH_4min(1); (ESI$^+$) m/z 296.1, 298.1 [M + H]$^+$ | 9 mg, 14%, yellow oil |
| 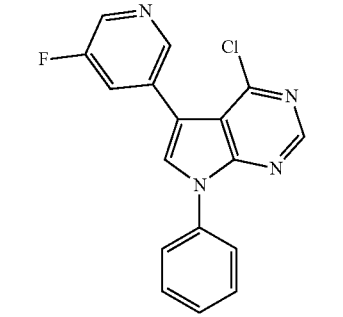 [SMILES: Fc1cncc(-c2cn(-c3ccccc3)c3ncnc(Cl)c23)c1] | CP50 (CH1) | LC-MS. R$_t$ 3.23 min, AnalpH2_MeOH_4min(1); (ESI$^+$) m/z 325.1, 327.1 [M + H]$^+$. | 72 mg, 100%, orange oil |

TABLE 17-continued

| Compound | Cpd # (Intermediate used[a]) | Analytical Data | Mass, % Yield, State |
|---|---|---|---|
| 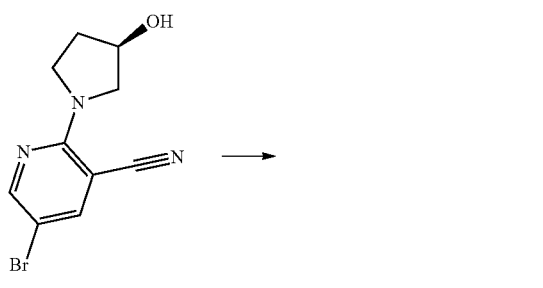 | CP51 (CH1, B36) | LC-MS. R$_t$ 3.23 min, AnalpH2_MeOH_4min(1); (ESI$^+$) m/z 395.3, 397.3 [M + H]$^+$ | 68 mg, 49%, yellow oil |

[a] Boc group was also removed during the reaction conditions.

The following chloropyrimidine compounds were made in one pot directly from the bromo compound without isolation of the corresponding boronic acid or ester.

5-(4-Chloro-7-phenyl-7H-pyrrolo[2,3-d]pyrimidin-5-yl)-2-((R)-3-hydroxy-pyrrolidin-1-yl)-nicotinonitrile (CP52)

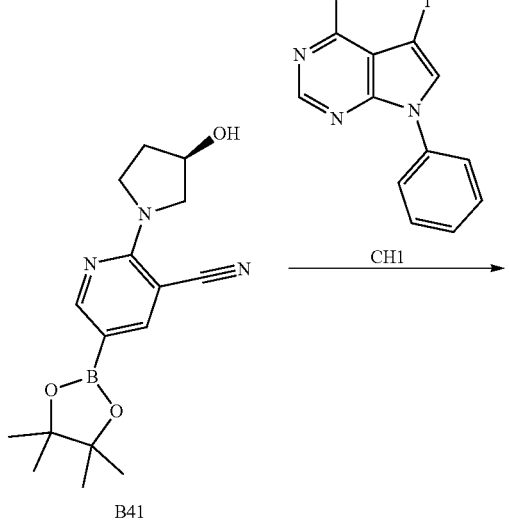

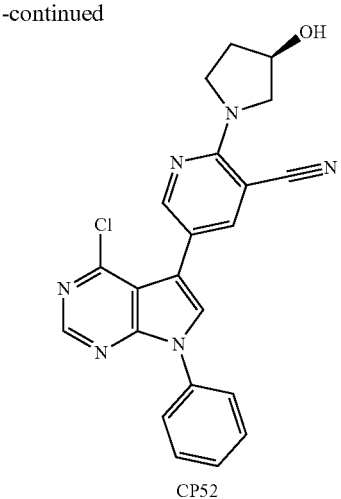

A mixture of 5-bromo-2-((R)-3-hydroxy-pyrrolidin-1-yl)-nicotinonitrile (A22) (299 mg, 1.12 mmol), bis(pinacolato)diborane (427 mg, 1.68 mmol), Pd(dppf)Cl$_2$.DCM (90 mg, 0.11 mmol), KOAc (330 mg, 3.36 mmol) and dioxane (10 mL) was deoxygenated with nitrogen for 10 min then heated in the microwave at 130° C. for 1 h to provide the crude boronic ester (B41). To the mixture was then added 4-chloro-5-iodo-7-phenyl-7H-pyrrolo[2,3-d]pyrimidine (CH$_1$) (319 mg, 0.90 mmol), Pd(dppf)Cl$_2$.DCM (46 mg, 0.056 mmol), dioxane (10 ml) and H$_2$O (5 mL). The resulting suspension was de-gassed with nitrogen for 10 min then heated in the microwave at 90° C. for 30 min. The mixture was filtered through celite, with further methanol washing then concentrated in vacuo. The crude material was partitioned between DCM and water, passed through a phase separator, concentrated in vacuo then purified by silica gel chromatography, eluting with 0-5% MeOH/DCM. The material obtained was purified by further silica gel chromatography, eluting with 20-100% EtOAc/iso-hexane to afford 5-(4-chloro-7-phenyl-7H-pyrrolo[2,3-d]pyrimidin-5-yl)-2-((R)-3-hydroxy-pyrrolidin-1-yl)-nicotinonitrile (CP52) as a yellow solid (156 mg, 0.37 mmol, 33%). LC-MS. R$_t$ 3.11 min, AnalpH2_MeOH_4 min(1); (ESI$^+$) m/z 417.2, 419.2 [M+H]$^+$ The following (CP52) derivatives were prepared using analogous procedures.

TABLE 18

| Compound | Cpd # (Intermediate used*) | Analytical Data | Mass, % Yield, State |
|---|---|---|---|
| (structure) | CP53 (CH1, A23) | LC-MS. $R_t$ 3.11 min, AnalpH2_MeOH_4min(1); (ESI$^+$) m/z 417.2, 419.2 [M + H]$^+$ | 201 mg, 42%, yellow solid |
| (structure) | CP54 (CH1, A24) | LC-MS. $R_t$ 3.13 min, AnalpH2_MeOH_4min(1); (ESI$^+$) m/z 405.1, 407.1 [M + H]$^+$ | 139 mg, 33%, yellow solid |

The following chloropyrimidine compounds were synthesized directly from the corresponding bromo TBDMS protected alcohol without isolation of the boronic acid/ester.

2-[5-(4-Chloro-7-phenyl-7H-pyrrolo[2,3-d]pyrimidin-5-yl)-pyridin-2-ylamino]-ethanol (CP55)

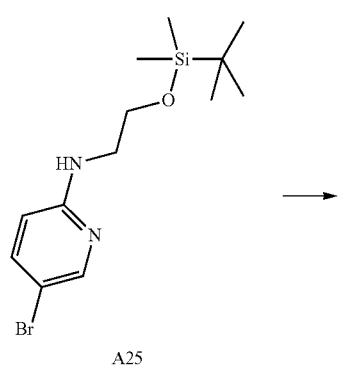

A25

-continued

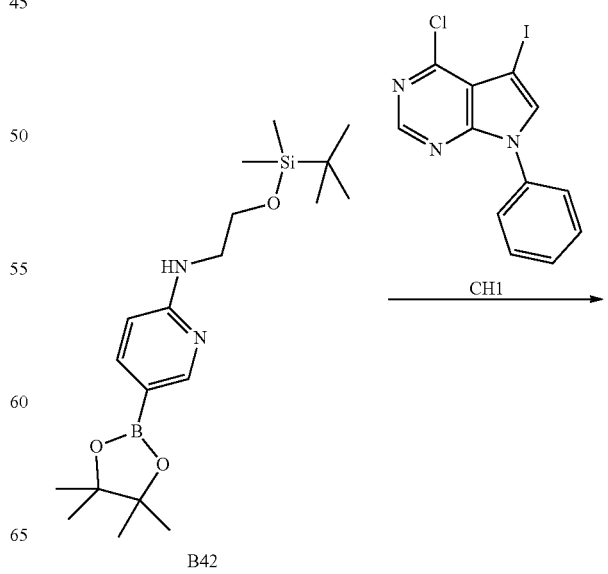

B42

-continued

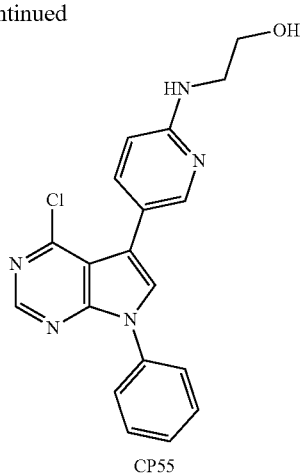

CP55

A mixture of (5-bromo-pyridin-2-yl)-[2-(tert-butyl-dimethyl-silanyloxy)-ethyl]-amine (A25) (135 mg, 0.41 mmol), bis(pinacolato)diborane (115 mg, 0.45 mmol), X-Phos (39 mg, 0.082 mmol), Pd$_2$(dba)$_3$ (19 mg, 0.021 mmol), KOAc (121 mg, 1.23 mmol) and dioxane (4 mL) was deoxygenated with nitrogen for 5 min then heated (under nitrogen balloon) at 100° C. for 2 h. The reaction mixture was filtered through celite and concentrated in vacuo to afford the crude boronic ester B42. To this material was added 4-chloro-5-iodo-7-phenyl-7H-pyrrolo[2,3-d]pyrimidine (CH1) (131 mg, 0.37 mmol), Pd(dppf)Cl$_2$.DCM (17 mg, 0.021 mmol), sodium carbonate (130 mg, 1.23 mmol), dioxane (4 mL) and water (1 mL) The mixture was deoxygenated with nitrogen for 5 min then heated (under N$_2$ balloon) at 100° C. for 2 h. The reaction mixture was filtered through celite, with further MeOH washing then concentrated in vacuo. The crude material was partitioned between DCM and water, passed through a phase separator, concentrated in vacuo then purified by silica gel chromatography, eluting with 0-5% MeOH/DCM. The material obtained was purified further by silica gel chromatography, eluting with 1-2% MeOH/DCM. The material obtained was purified further by SCX-2, eluting with methanol (2×CV) then 2M NH$_3$/MeOH (3×CV). The material obtained was further purified by silica gel chromatography, eluting with 2-5% methanol in DCM to afford 2-[5-(4-Chloro-7-phenyl-7H-pyrrolo[2,3-d]pyrimidin-5-yl)-pyridin-2-ylamino]-ethanol (CP55) as a yellow solid (24 mg, 16%). LC-MS. R$_t$ 1.97 min, AnalpH2_MeOH_4 min(1); (ESI$^+$) m/z 366.3, 368.3 [M+H].

The following (CP55) derivatives were prepared using analogous procedures.

TABLE 19

| Compound | Cpd # (Intermediate used*) | Analytical Data | Mass, % Yield, State |
|---|---|---|---|
| (structure) | CP56 (CH1, A26) | LC-MS. R$_t$ 2.12 min, AnalpH2_MeOH_4min(1); (ESI$^+$) m/z 380.3, 382.3 [M + H]$^+$ | 57 mg, 36%, yellow solid |

Route 2a, Step 3: Final Compounds Via Acidic Hydrolysis

5-[1-(1-Acetyl-azetidin-3-yl)-1H-pyrazol-4-yl]-7-(4-fluoro-phenyl)-3,7-dihydro-pyrrolo[2,3-d]pyrimidin-4-one (Ex-3)

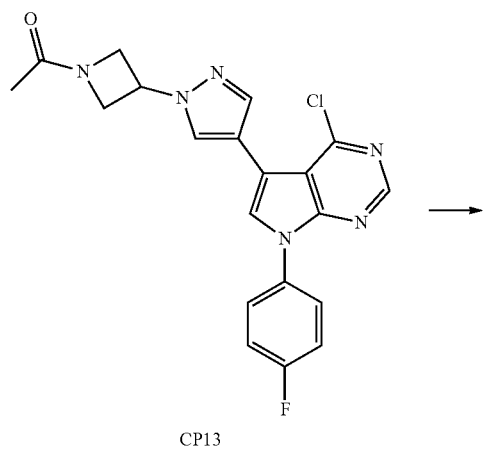

CP13

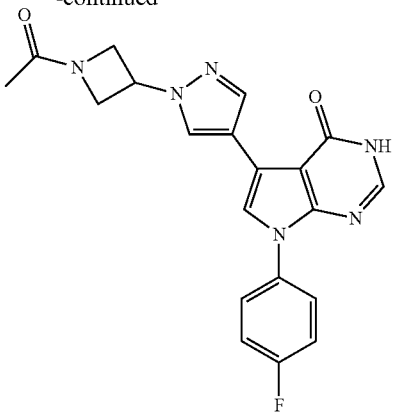

Ex-3

To 1-(3-{4-[4-Chloro-7-(4-fluoro-phenyl)-7H-pyrrolo[2,3-d]pyrimidin-5-yl]-pyrazol-1-yl}-azetidin-1-yl)-ethanone (CP13) (17 mg, 0.04 mmol) was added sodium acetate (7 mg, 0.08 mmol) and AcOH (0.2 mL) and the reaction mixture was heated at 100° C. for 1.75 h. The reaction mixture was evaporated to dryness, re-dissolved in DMSO and purified by reverse phase preparative HPLC-MS. The fractions were evaporated and lyophilised from MeCN:H$_2$O (1:1) to afford 5-[1-(1-acetyl-azetidin-3-yl)-1H-pyrazol-4-yl]-7-(4-fluoro-phenyl)-3,7-dihydro-pyrrolo[2,3-d]pyrimidin-4-one (Ex-3) as a white solid (15 mg, 91%); LC-MS. R$_t$ 6.90 min, AnalpH2_MeOH_QC_V1(1); (ESI$^+$) m/z 393.5 [M+H]$^+$; $^1$H NMR (400 MHz, DMSO-d$_6$): δ 12.15 (brs, 1H), 8.58 (s, 1H), 8.18 (s, 1H), 7.95 (s, 1H), 7.84 (s, 1H), 7.79 (m, 2H), 7.41 (t, 0=9.1 Hz, 2H), 5.35-5.27 (m, 1H), 4.59 (t, J=8.3 Hz, 1H), 4.43-4.39 (m, 1H), 4.31 (t, 0=9.3 Hz, 1H), 4.14-4.10 (m, 1H), 1.84 (s, 3H).

The following compounds were made using analogous procedures to (Ex-3) with reaction time varying between 1.5-24 h:

TABLE 20

| Compound | Ex. # (Intermediate used) | Analytical Data | Mass, % Yield, State |
|---|---|---|---|
| (structure) | Ex-4 (CP5) | LC-MS. R$_t$ 4.52 min, AnalpH2_MeOH_QC_V1(1); (ESI$^+$) m/z 289.3 [M + H]$^+$. | 6 mg, 66%, white solid |

TABLE 20-continued

| Compound | Ex. # (Intermediate used) | Analytical Data | Mass, % Yield, State |
|---|---|---|---|
| (pyridin-3-yl pyrrolopyrimidinone, N-phenyl) | Ex-5 (CP6) | LC-MS. R$_t$ 4.97 min, AnalpH2_MeOH_QC_V1(1); (ESI$^+$) m/z 289.3 [M + H]$^+$. | 2 mg, 14%, white solid |
| (acetamido-pyridinyl pyrrolopyrimidinone, N-phenyl) | Ex-6 (CP7) | LC-MS. R$_t$ 6.59 min, AnalpH2_MeOH_QC_V1(1); (ESI$^+$) m/z 346.3 [M + H]$^+$. | 5 mg, 26%, white solid |
| (3,5-dimethylisoxazol-4-yl pyrrolopyrimidinone, N-phenyl) | Ex-7 (CP8) | LC-MS. R$_t$ 7.10 min, AnalpH2_MeOH_QC_V1(1); (ESI$^+$) m/z 307.3 [M + H]$^+$; $^1$H NMR (400 MHz, DMSO-d$_6$): δ 12.17 (br s, 1H), 7.99 (s, 1H), 7.76 (**dd, J = 7.6, 1.0 Hz, 2H), 7.62 (s, 1H), 7.57 (t, J = 7.3 Hz, 2H), 7.43 (tt, J = 7.3, 1.3 Hz, 1H), 2.38 (s, 3H), 2.22 (s, 3H) | 16 mg, 64%, white solid |
| (2-aminopyridin-4-yl pyrrolopyrimidinone, N-phenyl) | Ex-8 (CP9)$^a$ | LC-MS. R$_t$ 4.69 min, AnalpH2_MeOH_QC_V1(1); (ESI$^+$) m/z 304.2 [M + Na]$^+$. | 7 mg, 13%, white solid |

TABLE 20-continued

| Compound | Ex. # (Intermediate used) | Analytical Data | Mass, % Yield, State |
| --- | --- | --- | --- |
| (structure) | Ex-9 (CP10)[a] | LC-MS. R$_t$ 4.64 min, AnalpH2_MeOH_QC_V1(1); (ESI$^+$) m/z 304.2 [M + H]$^+$. | 4 mg, 9%, white solid |
| (structure) | Ex-10 (CP11) | LC-MS. R$_t$ 3.50 min, AnalpH2_MeOH_QC_V1(1); (ESI$^+$) m/z 389.3 [M + H]$^+$. | 7 mg, 13%, off-white solid |
| (structure) | Ex-11 (CP12) | LC-MS. R$_t$ 6.90 min, AnalpH2_MeOH_QC_V1(1); (ESI$^+$) m/z 393.5 [M + H]$^+$; $^1$H NMR (400 MHz, DMSO-d$_6$): δ 12.20 (br s, 1H), 8.59 (s, 1H), 8.20 (s, 1H), 8.00 (s, 1H), 7.95 (s, 1H), 7.75 (dt, J = 10.6, 2.0 Hz, 1H), 7.68 (m, 1H), 7.60 (m, 1H), 7.26 (m, 1H), 5.35-5.28 (m, 1H), 4.59 (t, J = 8.6 Hz, 1H), 4.43-4.40 (m, 1H), 4.32 (t, J = 9.1 Hz, 1H), 4.13 (m, 1H), 1.84 (s, 3H) | 28 mg, 37%, white solid |

TABLE 20-continued

| Compound | Ex. # (Intermediate used) | Analytical Data | Mass, % Yield, State |
|---|---|---|---|
| (structure) | Ex-12 (CP4) | LC-MS. R$_t$ 4.65 min, AnalpH2_MeOH_QC_V1(1); (ESI$^+$) m/z 376.3 [M + H]$^+$; $^1$H NMR (400 MHz, DMSO-d$_6$): δ 12.37 (br s, 1H), 8.73-8.71 (m, 2H), 8.60 (s, 1H), 8.21 (s, 1H), 8.11 (s, 1H), 8.06 (s, 1H), 8.02-8.01 (m, 2H), 5.36-5.29 (m, 1H), 4.59 (t, J = 8.6 Hz, 1H), 4.34-4.40 (m, 1H), 4.32 (t, J = 9.3 Hz, 1H), 4.14-4.11 (m, 1H), 1.84 (s, 3H) | 22 mg, 29%, white solid |
| (structure) | Ex-13 (CP14) | LC-MS. R$_t$ 5.54 min, AnalpH2_MeOH_QC_V1(1); (ESI$^+$) m/z 364.2 [M + H]$^+$. | 32 mg, 73%, off-white solid |
| (structure) | Ex-14 (CP15) | LC-MS. R$_t$ 3.67 min, AnalpH2_MeOH_QC_V1(1); (ESI$^+$) m/z 363.3 [M + H]$^+$; $^1$H NMR (400 MHz, DMSO-d$_6$): δ 12.33 (br d, J = 3.5 Hz, 1H), 8.71 (dd, J = 4.8, 1.8 Hz, 2H), 8.58 (d, J = 2.5 Hz, 1H), 8.07 (d, J = 3.8 Hz, 1H), 8.02 (dd, J = 4.8, 1.8 Hz, 2H), 7.94 (dd, J = 8.6, 2.5 Hz, 1H), 7.91 (s, 1H), 6.63-6.62 (m, 1H), 6.55 (d, J = 8.6 Hz, 1H), 3.51-3.43 (m, 4H), 3.29 (s, 3H) | 22 mg, 55%, off-white solid |

TABLE 20-continued

| Compound | Ex. # (Intermediate used) | Analytical Data | Mass, % Yield, State |
|---|---|---|---|
| 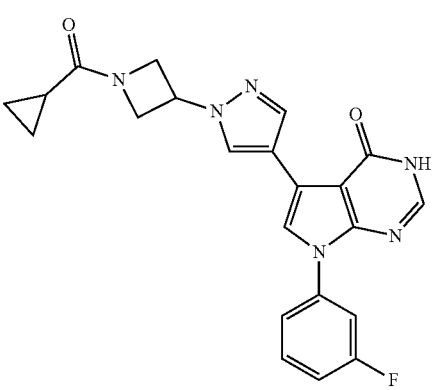 [SMILES: O=C(C1CC1)N1CC(n2cc(-c3cn(-c4cccc(F)c4)c4nc[nH]c(=O)c34)cn2)C1] | Ex-15 (CP16) | LC-MS. R$_t$ 7.22 min, AnalpH2_MeOH_QC_V1(1); (ESI$^+$) m/z 419.2 [M + H]$^+$. | 53 mg, 63%, white solid |
| 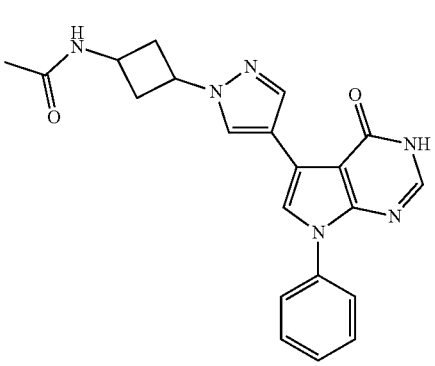 [SMILES: CC(=O)NC1CC(n2cc(-c3cn(-c4ccccc4)c4nc[nH]c(=O)c34)cn2)C1] | Ex-16 (CP17) | LC-MS. R$_t$ 6.98 min, AnalpH2_MeOH_QC_V1(1); (ESI$^+$) m/z 389.2 [M + H]$^+$. | 12 mg, 32%, off-white solid |
| 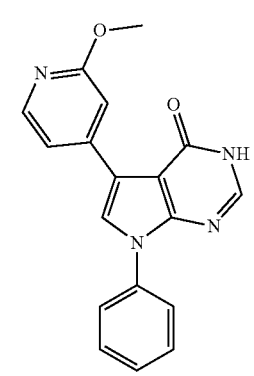 [SMILES: COc1cc(-c2cn(-c3ccccc3)c3nc[nH]c(=O)c23)ccn1] | Ex-17 (CP18) | LC-MS. R$_t$ 6.84 min, AnalpH2_MeOH_QC_V1(1); (ESI$^+$) m/z 319.2 [M + H]$^+$. | 12 mg, 74%, white solid |
| 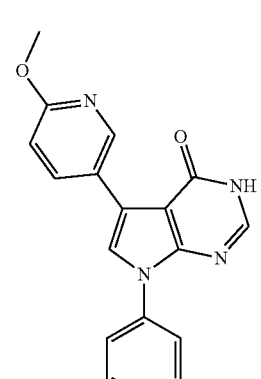 | Ex-18 (CP19) | LC-MS. R$_t$ 7.40 min, AnalpH2_MeOH_QC_V1(1); (ESI$^+$) m/z 319.2 [M + H]$^+$; $^1$H NMR (400 MHz, DMSO-d$_6$): δ 12.58-11.92 (br s, 1H), 8.79 (d, J = 2.5 Hz, 1H), 8.30 (dd, J = 8.6, 2.5 Hz, 1H), 7.99 (s, 1H), 7.85 (s, 1H), 7.78 (d, J = 7.6 Hz, 2H), 7.57 (t, J = 7.6 Hz, 2H), 7.43 (t, J = 7.3 Hz, 1H), 6.86 (d, J = 8.6 Hz, 1H), 8.39 (s, 3H) | 23 mg, 66%, white solid |

TABLE 20-continued

| Compound | Ex. # (Intermediate used) | Analytical Data | Mass, % Yield, State |
|---|---|---|---|
| (structure) | Ex-19 (CP20) | LC-MS. R$_t$ 5.97 min, AnalpH2_MeOH_QC_V1(1); (ESI$^+$) m/z 337.4 [M + H]$^+$. | 39 mg, 64%, white solid |
| (structure) | Ex-20 (CP21) | LC-MS. R$_t$ 7.14 min, AnalpH2_MeOH_QC_V1(1); (ESI$^+$) m/z 354.3 [M + H]$^+$; $^1$H NMR (400 MHz, DMSO-d$_6$): δ 12.19 (br s, 1H), 9.01 (d, J = 2.8 Hz, 1H), 8.61 (dd, J = 5.1, 1.5 Hz, 1H), 8.4 (s, 1H), 8.24-8.21 (m, 1H), 8.05 (d, J = 0.5 Hz, 1H), 7.99 (s, 1H), 7.93 (s, 1H), 7.63-7.60 (m, 1H), 4.28 (t, J = 5.1 Hz, 2H), 3.70 (t, J = 5.3 Hz, 2H), 3.25 (s, 3H) | 18 mg, 43%, white solid |
| (structure) | Ex-21 (CP23) | LC-MS. R$_t$ 6.74 min, AnalpH2_MeOH_QC_V1(1); (ESI$^+$) m/z 350.2 [M + H]$^+$; $^1$H NMR (400 MHz, DMSO-d$_6$): δ 12.13 (br s, 1H), 8.51 (s, 1H), 8.09 (s, 1H), 7.94 (s, 1H), 7.87 (s, 1H), 7.75 (dd, J = 1.2, 8.6 Hz, 2H), 7.56 (t, J = 7.6 Hz, 2H), 7.42 (tt, J = 7.6, 1.2 Hz, 1H), 5.14 (s, 2H), 3.70 (s, 3H), | 9 mg, 13%, white solid |

TABLE 20-continued

| Compound | Ex. # (Intermediate used) | Analytical Data | Mass, % Yield, State |
|---|---|---|---|
| | Ex-22 (CP24) | LC-MS. R$_t$ 7.13 min, AnalpH2_MeOH_QC_V1(1); (ESI$^+$) m/z 364.3 [M + H]$^+$. | 48 mg, 90%, off-white solid |
| | Ex-23 (CP3) | LC-MS. R$_t$ 7.87 min, AnalpH2_MeOH_QC_V1(1); (ESI$^+$) m/z 368.3 [M + H]$^+$. | 21 mg, 63%, off-white solid |
| | Ex-24 (CP33) | LC-MS. R$_t$ 7.00 min, AnalpH2_MeOH_QC_V1(1); (ESI$^+$) m/z 292.2 [M + H]$^+$; | 9 mg, 96%, white solid |
| | Ex-25 (CP36) | LC-MS. R$_t$ 6.86 min, AnalpH2_MeOH_QC_V1(1); (ESI$^+$) m/z 292.2 [M + H]$^+$; | 9 mg, 59%, white solid |

TABLE 20-continued

| Compound | Ex. # (Intermediate used) | Analytical Data | Mass, % Yield, State |
|---|---|---|---|
| (structure) | Ex-26 (CP35) | LC-MS. R$_t$ 6.95 min, AnalpH2_MeOH_QC_V1(1); (ESI$^+$) m/z 334.2 [M + H]$^+$; | 9 mg, 65%, white solid |
| (structure) | Ex-27 (CP34) | LC-MS. R$_t$ 6.63 min, AnalpH2_MeOH_QC_V1(1); (ESI$^+$) m/z 322.2 [M + H]$^+$; | 9 mg, 65%, white solid |
| (structure) | Ex-28 (CP26) | LC-MS. R$_t$ 5.84 min, AnalpH2_MeOH_QC_V1(1); (ESI$^+$) m/z 363.2 [M + H]$^+$; | 14 mg, 48%, white solid |
| (structure) | Ex-29 (CP25) | LC-MS. R$_t$ 7.54 min, AnalpH2_MeOH_QC_V1(1); (ESI$^+$) m/z 381.2 [M + H]$^+$; | 26 mg, 66%, white solid |

TABLE 20-continued

| Compound | Ex. # (Intermediate used) | Analytical Data | Mass, % Yield, State |
|---|---|---|---|
| | Ex-30 (CP30) | LC-MS. R$_t$ 5.18 min, AnalpH2_MeOH_QC_V1(1); (ESI$^+$) m/z 380.3 [M + H]$^+$; | 15 mg, 68%, white solid |
| | Ex-31 (CP31) | LC-MS. R$_t$ 7.10 min, AnalpH2_MeOH_QC_V1(1); (ESI$^+$) m/z 381.2 [M + H]$^+$. | 14 mg, 44%, white solid |
| | Ex-32 (CP32) | LC-MS. R$_t$ 4.98 min, AnalpH2_MeOH_QC_V1(1); (ESI$^+$) m/z 364.3 [M + H]; | 3 mg, 6%, white solid |

TABLE 20-continued

| Compound | Ex. # (Intermediate used) | Analytical Data | Mass, % Yield, State |
|---|---|---|---|
| | Ex-33 (CP27) | LC-MS. R$_t$ 4.52 min, AnalpH2_MeOH_QC_V1(1); (ESI$^+$) m/z 390.3 [M + H]$^+$; | 37 mg, 79%, white solid |
| | Ex-34 (CP29) | LC-MS. R$_t$ 4.71 min, AnalpH2_MeOH_QC_V1(1); (ESI$^+$) m/z 462.2 [M + H]$^+$; | 10 mg, 52%, white solid |
| | Ex-35 (CP37) | LC-MS. R$_t$ 5.72 min, AnalpH2_MeOH_QC_V1(1); (ESI$^+$) m/z 376.2 [M + H]$^+$ | 19 mg, 37%, white solid |

TABLE 20-continued

| Compound | Ex. # (Intermediate used) | Analytical Data | Mass, % Yield, State |
|---|---|---|---|
| | Ex-36 (CP38) | LC-MS. $R_t$ 6.22 min, AnalpH2_MeOH_QC_V1(1); (ESI$^+$) m/z 402.2 [M + H]$^+$ | 29 mg, 31%, white solid |
| | Ex-37 (CP41) | LC-MS. $R_t$ 5.58 min, AnalpH2_MeOH_QC_V1(1); (ESI$^+$) m/z 362.2 [M + H]$^+$ | 2 mg, 4%, white solid |
| | Ex-38 (CP43) | LC-MS. $R_t$ 5.02 min, AnalpH2_MeOH_QC_V1(1); (ESI$^+$) m/z 362.3 [M + H]$^+$; $^1$H-NMR (400 MHz, DMSO-d$_6$): δ 12.13 (d, J = 3.5 Hz, 1H), 8.58 (br s, 1H), 7.97-7.93 (m, 2H), 7.75 (d, J = 8.3 Hz, 2H), 7.69 (s, 1H), 7.55 (t, J = 7.8 Hz, 2H), 7.41 (t, J = 7.5 Hz, 1H), 6.57-6.53 (m, 2H), 3.50-3.43 (m, 4H), 3.27 (s, 3H). | 9 mg, 42%, white solid |

TABLE 20-continued

| Compound | Ex. # (Intermediate used) | Analytical Data | Mass, % Yield, State |
|---|---|---|---|
| (structure) | Ex-39 (CP44) | LC-MS. R$_t$ 4.30 min, AnalpH2_MeOH_QC_V1(1); (ESI$^+$) m/z 363.2 [M + H]$^+$; $^1$H-NMR (400 MHz, DMSO-d$_6$): δ 12.21 (d, J = 3.5 Hz, 1H), 9.01 (d, J = 2.5 Hz, 1H), 8.62-8.58 (m, 2H), 8.22 (ddd, J = 8.3, 2.5, 1.5 Hz, 1H), 7.99 (d, J = 3.8 Hz, 1H), 7.95 (dd, J = 8.7, 2.1 Hz, 1H), 7.80 (s, 1H), 7.61 (dd, J = 8.1, 4.8 Hz, 1H), 6.61 (br s, 1H), 6.56 (d, J = 8.3 Hz, 1H), 3.50-3.43 (m, 4H), 3.28 (s, 3H). | 15 mg, 37%, white solid |
| (structure) | Ex-40 (CP52) | LC-MS. R$_t$ 7.20 min, AnalpH2_MeOH_QC_V1(1); (ESI$^+$) m/z 399.3 [M + H]$^+$ | 20 mg, 13%, off-white solid |
| (structure) | Ex-41 (CP53) | LC-MS. R$_t$ 7.20 min, AnalpH2_MeOH_QC_V1(1); (ESI$^+$) m/z 399.3 [M + H]$^+$ | 32 mg, 17%, off-white solid |

TABLE 20-continued

| Compound | Ex. # (Intermediate used) | Analytical Data | Mass, % Yield, State |
|---|---|---|---|
| (structure) | Ex-42 (CP46) | LC-MS. R$_t$ 4.48 min, AnalpH2_MeOH_QC_V1(1); (ESI$^+$) m/z 432.2 [M + H]$^+$ | 23 mg, 40%, white solid |
| (structure) | Ex-43 (CP47) | LC-MS. R$_t$ 4.31 min, AnalpH2_MeOH_QC_V1(1); (ESI$^+$) m/z 445.3 [M + H]$^+$ | 8 mg, 14%, white solid |
| (structure) | Ex-44 (CP50) | LC-MS. R$_t$ 7.23 min, AnalpH2_MeOH_QC_V1(1); (ESI$^+$) m/z 307.2 [M + H]$^+$. | 12 mg, 18%, white solid |

TABLE 20-continued

| Compound | Ex. # (Intermediate used) | Analytical Data | Mass, % Yield, State |
|---|---|---|---|
| (structure) | Ex-45 (CP40) | LC-MS. R$_t$ 5.30 min, AnalpH2_MeOH_QC_V1(1); (ESI⁺) m/z 350.2 [M + H]⁺. | 3 mg, 8%, white solid |
| (structure) | Ex-46 (CP51) | LC-MS. R$_t$ 7.78 min, AnalpH2_MeOH_QC_V1(1); (ESI⁺) m/z 377.4 [M + H]⁺. | 6 mg, 9%, white solid |

$^a$Boc group was also removed under the reaction conditions.

2-(4-(7-(4-fluorophenyl)-4-oxo-4,7-dihydro-3H-pyrrolo[2,3-d]pyrimidin-5-yl)-1H-pyrazol-1-yl)ethyl Acetate (Ex-47)

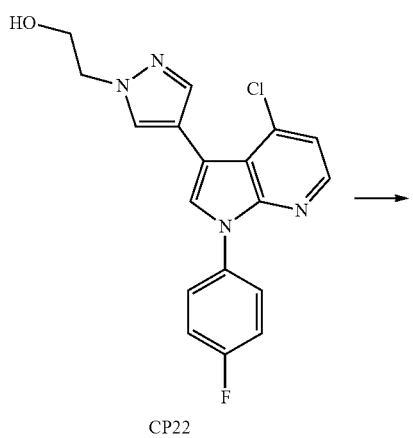

CP22

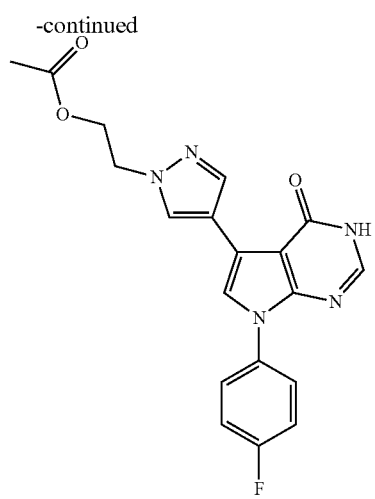

Ex-47

To a stirred suspension of 2-(4-(4-chloro-1-(4-fluorophenyl)-1H-pyrrolo[2,3-b]pyridin-3-yl)-1H-pyrazol-1-yl)ethan-1-ol (CP22) (10 mg, 0.03 mmol) in acetic acid (1 mL) was added sodium acetate (5 mg, 0.06 mmol) and the reaction mixture was heated at 100° C. for 15 h. The reaction mixture was dissolved in DCM and evaporated to dryness, re-dissolved in DMSO and purified by reverse phase preparative HPLC-MS. The fractions were evaporated and lyophilised from MeCN:H$_2$O (1:1) to afford acetic acid 2-{4-[7-(4-fluoro-phenyl)-4-oxo-4,7-dihydro-3H-pyrrolo[2,3-d]pyrimidin-5-yl]-pyrazol-1-yl}-ethyl ester (Ex-47) as a white solid (4 mg, 50%); LC-MS. R$_t$ 7.02 min, AnalpH2_MeOH_QC_V1 (1); (ESI$^+$) m/z 382.3 [M+H]$^+$.

Route 2a, Step 3: Final Compounds Via Acidic Hydrolysis Followed by LiOH Ester Hydrolysis

5-[6-(2-Hydroxy-ethylamino)-pyridin-3-yl]-7-phenyl-3,7-dihydro-pyrrolo[2,3-d]pyrimidin-4-one (Ex-48)

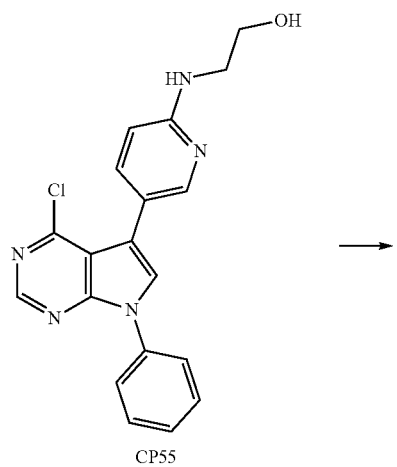

CP55

→

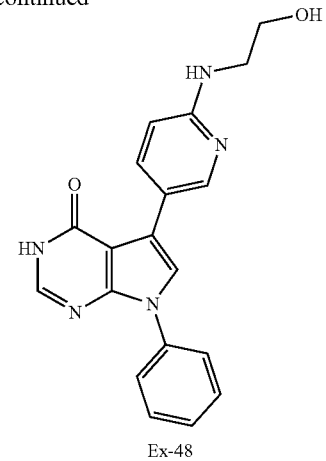

Ex-48

A solution of 2-[5-(4-chloro-7-phenyl-7H-pyrrolo[2,3-d]pyrimidin-5-yl)-pyridin-2-ylamino]-ethanol (CP55) (24.1 mg, 0.066 mmol), sodium acetate (0.198 mmol) and AcOH (1 mL) was heated at 100° C. for 2 h. The mixture was concentrated in vacuo, re-dissolved in methanol then purified by SCX-2, eluting with methanol (2×CV) then 2M NH$_3$/MeOH (2×CV). The NH$_3$ elution was concentrated in vacuo. The material obtained was re-dissolved in a mixture of THF (2 mL) and water (2 mL). Lithium hydroxide monohydrate (13.9 mg, 0.33 mmol) was added and the mixture stirred at room temperature for 50 min. The mixture was concentrated in vacuo then purified by reversed phase preparative HPLC-MS. The material obtained was re-dissolved in a mixture of acetonitrile (1 mL) and water (1 mL) then freeze dried to afford 5-[6-(2-hydroxy-ethylamino)-pyridin-3-yl]-7-phenyl-3,7-dihydro-pyrrolo[2,3-d]pyrimidin-4-one (Ex-48) as a white solid (5.2 mg, 23%); LC-MS. R$_t$ 4.69 min, AnalpH2_MeOH_QC_V1(1); (ESI$^+$) m/z 348.2 [M+H]$^+$.

The following (Ex-48) derivatives were prepared using analogous procedures with reaction time varying between 1-4.5 h.

TABLE 21

| Compound | Ex. # (Intermediate used) | Analytical Data | Mass, % Yield, State |
|---|---|---|---|
| 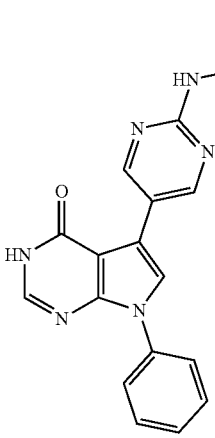 | Ex-49 (CP39) | LC-MS. R$_t$ 6.39 min, AnalpH2_MeOH_QC_V1(1); (ESI$^+$) m/z 349.2 [M + H]$^+$ | 4 mg, 10%, light yellow solid |

TABLE 21-continued

| Compound | Ex. # (Intermediate used) | Analytical Data | Mass, % Yield, State |
|---|---|---|---|
| (structure) | Ex-50 (CP42) | LC-MS. R$_t$ 6.60 min, AnalpH2_MeOH_QC_V1(1); (ESI$^+$) m/z 361.2 [M + H]$^+$ | 12 mg, 31%, white solid |
| (structure) | Ex-51 (CP45) | LC-MS. R$_t$ 6.70 min, AnalpH2_MeOH_QC-V1(1); (ESI$^+$) m/z 375.2 [M + H]$^+$ $^1$H-NMR (400 MHz, DMSO-d$_6$): δ 11.90 (br s, 1H), 8.88 (s, 2H), 7.99 (s, 1H), 7.82 (s, 1H), 7.75 (d, J = 7.3 Hz, 2H), 7.56 (t, J = 7.8 Hz, 2H), 7.43 (t, J = 7.5 Hz, 1H), 4.82 (t, J = 5.4 Hz, 1H), 4.07 (t, J = 8.3 Hz, 2H), 3.80 (dd, J = 8.6, 5.6 Hz, 2H), 3.59 (t, J = 5.7 Hz, 2H), 2.83-2.73 (m, 1H). | 15 mg, 31%, white solid |
| (structure) | Ex-52 (CP56) | LC-MS. R$_t$ 4.72 min, AnalpH2_MeOH_QC_V1(1); (ESI$^+$) m/z 362.2 [M + H]$^+$ $^1$H-NMR (400 MHz, DMSO-d$_6$): δ 12.06 (br s, 1H), 8.67 (d, J = 2.5 Hz, 1H), 8.08 (dd, J = 8.8, 2.5 Hz, 1H), 7.95 (s, 1H), 7.78-7.74 (m, 2H), 7.71 (s, 1H), 7.55 (dd, J = 8.3, 7.6, 2H), 7.41 (t, J = 7.5 Hz, 1H), 6.65 (d, J = 8.8 Hz, 1H), 4.72 (br s, 1H), 3.63-3.55 (m, 4H), 3.07 (s, 3H). | 12 mg, 22%, off-white solid |

TABLE 21-continued

| Compound | Ex. # (Intermediate used) | Analytical Data | Mass, % Yield, State |
|---|---|---|---|
| | Ex-53 (CP54) | LC-MS. $R_t$ 7.28 min, AnalpH2_MeOH_QC_V1(1); (ESI+) m/z 387.2 [M + H]+ | 6 mg, 5%, white solid |
| | Ex-54 (CP28) | LC-MS. $R_t$ 4.39 min, AnalpH2_MeOH_QC_V1(1); (ESI+) m/z 448.2 [M + H]+ | 18 mg, 30%, white solid |

Route 2a, Step 3: Final Compounds Via Basic Hydrolysis 7-(4-fluorophenyl)-5-(1-(2-hydroxyethyl)-1H-pyrazol-4-yl)-3,7-dihydro-4H-pyrrolo[2,3-d]pyrimidin-4-one (Ex-55)

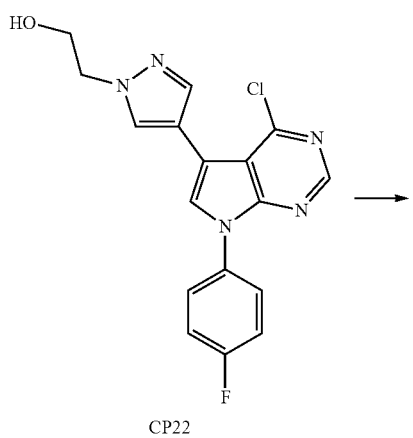

CP22

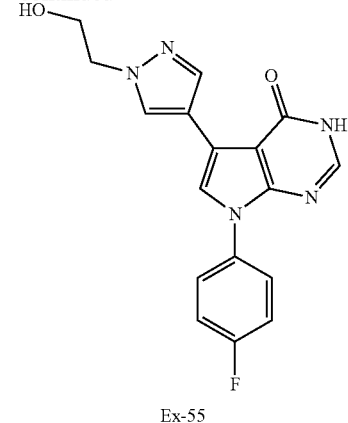

Ex-55

A solution of 2-(4-(4-chloro-7-(4-fluorophenyl)-7H-pyrrolo[2,3-d]pyrimidin-5-yl)-1H-pyrazol-1-yl)ethan-1-ol (CP22) (40 mg, 0.11 mmol), 2 M NaOH (aq) (0.3 mL, 0.55 mmol) and dioxane (1.1 mL) was heated at 100° C. for 3 h. The reaction mixture was cooled to RT then acidified to pH 3-4 by adding formic acid (10 drops). The solution was dissolved in DCM and water and layers were separated using a phase separator then combined and concentrated in vacuo. The crude material was purified by reversed phase preparative HPLC-MS to afford 7-(4-fluorophenyl)-5-(1-(2-hydroxyethyl)-1H-pyrazol-4-yl)-3,7-dihydro-4H-pyrrolo[2,3-d]pyrimidin-4-one (Ex-55) as a white solid (8 mg, 18%); LC-MS. $R_t$ 6.60 min, AnalpH2_MeOH_QC_V1(1); (ESI$^+$) m/z 340.3 [M+H]$^+$.

7-Phenyl-5-(1H-pyrrol-2-yl)-3,7-dihydro-pyrrolo[2,3-d]pyrimidin-4-one (Ex-56)

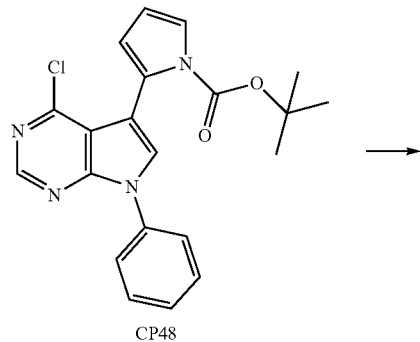

CP48

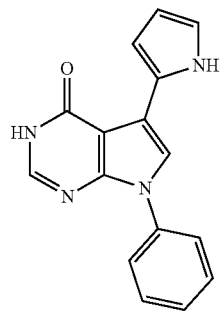

Ex-56

A solution of 2-(4-chloro-7-phenyl-7H-pyrrolo[2,3-d]pyrimidin-5-yl)-pyrrole-1-carboxylic acid tert-butyl ester (CP48) (57.4 mg. 0.15 mmol), 2 M NaOH (aq) (1 mL, 2 mmol) and dioxane (1 mL) was heated at 100° C. for 90 min. The mixture was purified by reversed phase preparative HPLC-MS. to afford 7-phenyl-5-(1H-pyrrol-2-yl)-3,7-dihydro-pyrrolo[2,3-d]pyrimidin-4-one (Ex-56) as a grey solid (8 mg, 20%); LC-MS. $R_t$ 7.91 min, AnalpH2_MeOH_QC_V1(1); (ESI$^+$) m/z 277.2 [M+H]$^+$; $^1$H-NMR (400 MHz, DMSO-d$_6$): δ 12.45 (brs, 1H), 12.09 (brs, 1H), 7.99 (s, 1H), 7.85 (s, 1H), 7.72 (d, J=8.2 Hz, 2H), 7.53 (dd, J=8.2, 7.3 Hz, 2H), 7.39 (t, J=7.3 Hz, 1H), 6.81-6.79 (m, 1H), 6.57-6.55 (m, 1H), 6.07-6.05 (m, 1H).

The following compound was prepared using analogous procedures to (Ex-56):

TABLE 22

| Compound | Ex. # (Intermediate used) | Analytical Data | Mass, % Yield, State |
|---|---|---|---|
|  | Ex-57 (CP49) | LC-MS. $R_t$ 7.22 min, AnalpH2_MeOH_QC_V1(1); (ESI$^+$) m/z 278.2 [M + H]$^+$ | 6 mg, 18%, white solid |

Route 2b Step 4: Acidic Hydrolysis

5-Iodo-7-phenyl-3,7-dihydro-pyrrolo[2,3-d]pyrimidin-4-one (CH11)

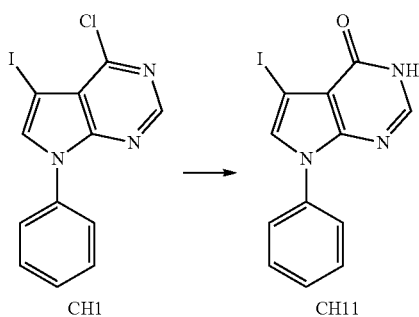

A suspension of 4-chloro-5-iodo-7-phenyl-7H-pyrrolo[2,3-d]pyrimidine (CH$_1$) (4.00 g, 11.25 mmol) and sodium acetate (1.85 g, 22.5 mmol) in AcOH (25 mL) was heated at 100° C. for 15 h. The reaction mixture was concentrated in vacuo. The crude solid was diluted with water and the resulting solid was filtered and dried under vacuum to afford 5-Iodo-7-phenyl-3,7-dihydro-pyrrolo[2,3-d]pyrimidin-4-one (CH$_{11}$) as a yellow solid (3.68 g, 97%); LC-MS. R$_t$ 2.79 min, AnalpH2_MeOH_4 min(1); (ESI$^+$) m/z 338.1 [M+H]$^+$.
$^1$H NMR (400 MHz, DMSO-d$_6$): δ 12.16 (brs, 1H), 7.95 (s, 1H), 7.70-7.66 (m, 2H), 7.68 (s, 1H), 7.56-7.51 (m, 2H), 7.41 (tt, J=7.3 1.4 Hz, 1H).

The following substituted 7 substituted-5-iodo-3,7-dihydropyrrolo[2,3-d]pyrimidin-4-one derivatives were prepared using analogous procedures to CH11 with duration of heating varying between 3-18 h and heating between 100-110° C.:

TABLE 23

| Compound | Ex. # (Intermediate used) | Analytical data | Mass, % Yield, State |
|---|---|---|---|
| CH12 structure | CH12 (CH5) | LC-MS. R$_t$ 2.09 min, AnalpH2_MeOH_QC_V1(1); (ESI$^+$) m/z 339.1 [M + H]$^+$. | 2.09 g, 93%, brown solid |
| CH13 structure | CH13 (CH4) | LC-MS. R$_t$ 1.68 min, AnalpH2_MeOH_4min(1); (ESI$^+$) m/z 339.0 [M + H]$^+$. | 308 mg, 89%, brown solid |
| CH14 structure | CH14 (CH2) | LC-MS. R$_t$ 2.85 min, AnalpH2_MeOH_4min(1); (ESI$^+$) m/z 356.0 [M + H]$^+$. | 3.66 g, 96%, off-white solid |

TABLE 23-continued

| Compound | Ex. # (Intermediate used) | Analytical data | Mass, % Yield, State |
|---|---|---|---|
| (5-iodo-7-(2-methylpyridin-4-yl)-7H-pyrrolo[2,3-d]pyrimidin-4(3H)-one) | CH15 (CH6) | LC-MS. R$_t$ 1.51 min, AnalpH2_MeOH_4min(1); (ESI$^+$) m/z 353.1 [M + H]$^+$. | 306 mg, 100%, white solide |
| (5-iodo-7-(6-nitropyridin-3-yl)-7H-pyrrolo[2,3-d]pyrimidin-4(3H)-one) | CH16 (CH7) | LC-MS. R$_t$ 2.27 min, AnalpH2_MeOH_4min(1); (ESI$^+$) m/z 384.1 [M + H]$^+$. | 245 mg, 80%, yellow solid |
| (7-(5-fluoropyridin-3-yl)-5-iodo-7H-pyrrolo[2,3-d]pyrimidin-4(3H)-one) | CH17 (CH8) | LC-MS. R$_t$ 2.40 min, AnalpH2_MeOH_4min(1); (ESI$^+$) m/z 356.8 [M + H]$^+$. | 320 mg, 75%, white solid |
| (5-iodo-7-(2-methoxypyridin-4-yl)-7H-pyrrolo[2,3-d]pyrimidin-4(3H)-one) | CH18$^a$ (CH9) | LC-MS. R$_t$ 2.67 min, AnalpH2_MeOH_4min(1); (ESI$^+$) m/z 369.2 [M + H]$^+$. | 371 mg, 43%, beige solid |

TABLE 23-continued

| Compound | Ex. # (Intermediate used) | Analytical data | Mass, % Yield, State |
|---|---|---|---|
| ![CH19 structure] | CH19 (CH10) | LC-MS. R$_t$ 2.69 min, AnalpH2_MeOH_4min(1); (ESI$^+$) m/z 369.2 [M + H]$^+$. | 184 mg, 82%, beige solid |

$^a$Crude compound was purified by silica gel chromatography using DCM/MeOH

Route 2b, Step 5: Final Compounds Via Suzuki Coupling Using Potassium Carbonate

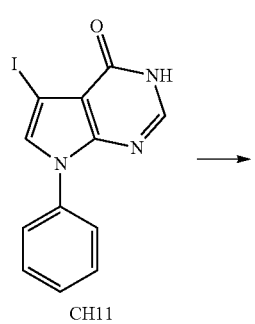

Tert-butyl methyl(2-(4-(4-oxo-7-phenyl-4,7-dihydro-3H-pyrrolo[2,3-d]pyrimidin-5-yl)-1H-pyrazol-1-yl)ethyl)carbamate (Ex-58)

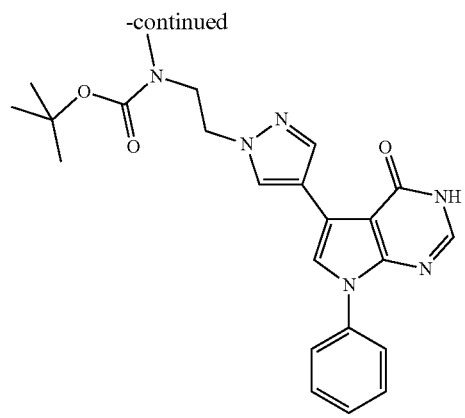

Ex-58

A mixture of 5-Iodo-7-phenyl-3,7-dihydropyrrolo[2,3-d]pyrimidin-4-one (CH11) (67 mg, 0.198 mmol), 1-[2-(tert-butoxycarbonyl-methyl-amino)-ethyl]-1H-pyrazole-4-boronic acid pinacol ester (B39) (58 mg, 0.165 mmol), Pd(dppf)Cl$_2$.DCM (13 mg, 0.017 mmol) and potassium carbonate (46 mg, 0.33 mmol) in 1,4-dioxane:H$_2$O (900 µL, 4:1) was de-oxygenated for 10 min then heated in a microwave reactor at 120° C. for 1 h. The reaction mixture was filtered through Si-thiol cartridge and washed with MeOH (2×CV) and DCM (2×CV). The combined organics were concentrated in vacuo. The crude solid was diluted with DCM (25 mL) and H$_2$O (25 mL) and the layers separated via a phase separator cartridge. The combined organics were concentrated in vacuo to afford methyl-{2-[4-(4-oxo-7-phenyl-4,7-dihydro-3H-pyrrolo[2,3-d]pyrimidin-5-yl)-pyrazol-1-yl]-ethyl}-carbamic acid tert-butyl ester (Ex-58) as a brown solid (87 mg, quant.) LC-MS. R$_t$ 3.12 min, AnalpH2_MeOH_4 min(1); (ESI$^+$) m/z 435.3 [M+H]$^+$.

The following derivatives of formula x are prepared using analogous procedures with reaction time varying between 1-2 h:

TABLE 24

| Compound | Ex. # (Intermediate used) | Analytical Data | Mass, % Yield, State |
|---|---|---|---|
| (structure) | Ex-59 (CH14, B38) | LC-MS. R$_t$ 6.75 min, AnalpH2_MeOH_QC_V1(1); (ESI$^+$) m/z 340.3 [M + H]$^+$. | 3 mg, 3%, white solid |
| (structure) | Ex-60 (CH11, B28) | LC-MS. R$_t$ 6.71 min, AnalpH2_MeOH_QC_V1(1); (ESI$^+$) m/z 375.2 [M + H]$^+$. | 9 mg, 11%, white solid |
| (structure) | Ex-61 (CH11) | LC-MS. R$_t$ 7.08 min, AnalpH2_MeOH_QC-V1(1); (ESI$^+$) m/z 307.2 [M + H]$^+$. | 1 mg, 6%, off-white solid |
| (structure) | Ex-62 (CH11, B22) | LC-MS. R$_t$ 7.00 min, AnalpH2_MeOH_QC-V1(1); (ESI$^+$) m/z 336.3 [M + H]$^+$. | 4 mg, 13%, pink solid |

TABLE 24-continued

| Compound | Ex. # (Intermediate used) | Analytical Data | Mass, % Yield, State |
|---|---|---|---|
| | Ex-63 (CH13, B22) | LC-MS. R$_t$ 4.74 min, AnalpH2_MeOH_QC-V1(1): (ESI$^+$) m/z 337.3 [M + H]$^+$. | 14 mg, 28%, white solid |
| | Ex-64 (CH11, B24) | LC-MS. R$_t$ 7.25 min, AnalpH2_MeOH_QC_V1(1); (ESI$^+$) m/z 350.3 [M + H]$^+$. | 4 mg, 6%, Off white solid |
| | Ex-65 (CH11) | LC-MS. R$_t$ 7.87 min, AnalpH2_MeOH_QC_V1(1); (ESI$^+$) m/z 433.2 [M + H]$^+$. | 3 mg, 4%, white solid; |

Route 2b, Step 5: Final Compounds Via Suzuki Coupling Using PdXPhosG3 with K$_3$PO$_4$ as Base 5-(4-(2-hydroxy-2-methylpropoxy)phenyl)-7-(pyridin-3-yl)-3,7-dihydro-4H-pyrrolo[2,3-d]pyrimidin-4-one (Ex-66)

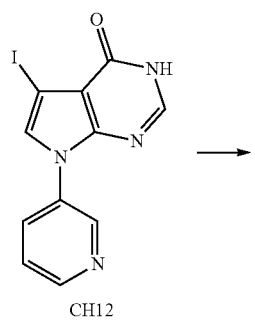

CH12

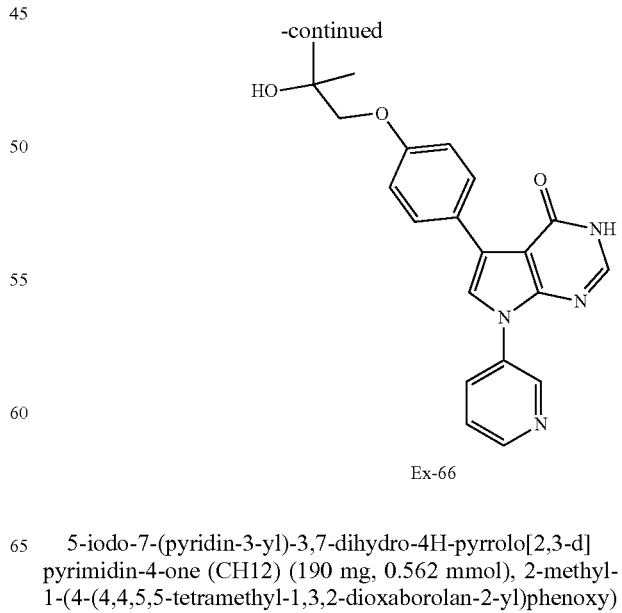

Ex-66

5-iodo-7-(pyridin-3-yl)-3,7-dihydro-4H-pyrrolo[2,3-d]pyrimidin-4-one (CH12) (190 mg, 0.562 mmol), 2-methyl-1-(4-(4,4,5,5-tetramethyl-1,3,2-dioxaborolan-2-yl)phenoxy)

propan-2-ol (B35) (246 mg, 0.843 mmol), K₃PO₄ (238 mg, 1.12 mmol), PdXPhosG3 (23.7 mg, 0.028 mmol) in 1,4-dioxane:water (5 mL, 4:1) was de-oxygenated with N₂ for 5 min and then heated in a microwave reactor at 90° C. for 1 h. The reaction mixture was filtered through a Si-thiol cartridge (2 g) and washed with MeOH (3×CV) followed by DCM (3×CV). The filtrate was evaporated to dryness and the crude compound was purified by reversed phase preparative HPLC-MS to afford 5-(4-(2-hydroxy-2-methyl-propoxy)phenyl)-7-(pyridin-3-yl)-3,7-dihydro-4H-pyrrolo[2,3-d]pyrimidin-4-one (Ex-66) as a white solid (108 mg, 51%); LC-MS. R$_t$ 7.18 min, AnalpH2_MeOH_QC_V1(1); (ESI⁺) m/z 377.3 [M+H]⁺; ¹H-NMR (400 MHz, DMSO-d₆) δ 12.19 (s, 1H), 9.03 (d, J=2.7 Hz, 1H), 8.61 (dd, J=4.6, 1.4 Hz, 1H), 8.23 (m, 1H), 8.00 (s, 1H), 7.93 (d, J=9.2 Hz, 2H), 7.83 (s, 1H), 7.65-7.56 (m, 1H), 6.95 (d, J=11.9 Hz, 2H), 4.64 (s, 1H), 3.75 (s, 2H), 1.22 (s, 6H).

The following compounds of formula (Ia) were made using analogous procedures to compound (Ex-66) with duration of heating between 1-10.5 h and heating between 90-100° C.:

TABLE 25

| Compound | Ex. # (Intermediate used) | Analytical Data | Mass, % Yield, State |
|---|---|---|---|
|  | Ex-67 (CH12) | LC-MS. R$_t$ 6.94 min, AnalpH2_MeOH_QC_V1(1); (ESI⁺) m/z 363.2 [M + H]⁺. | 351 mg, 41% white solid |
|  | Ex-68 (CH13, B35) | LC-MS. R$_t$ 6.47 min, AnalpH2_MeOH_QC_V1(1); (ESI⁺) m/z 377.3 [M + H]⁺. | 132 mg, 78%, white solid |
|  | Ex-69$^a$ (CH13, B2) | LC-MS. R$_t$ 6.68 min, AnalpH2_MeOH_QC_V1(1); (ESI⁺) m/z 391.3 [M + H]⁺. | 90 mg, 52%, white solid |

TABLE 25-continued
| Compound | Ex. # (Intermediate used) | Analytical Data | Mass, % Yield, State |
|---|---|---|---|
| 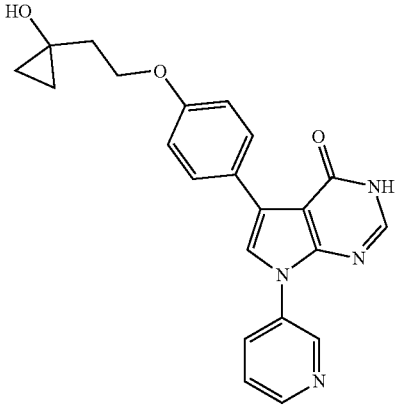 [SMILES: O=c1[nH]cnc2c1c(-c1ccc(OCCC3(O)CC3)cc1)cn2-c1cccnc1] | Ex-70 (CH12, B7) | LC-MS. $R_t$ 7.24 min, AnalpH2_MeOH_QC_V1(1); (ESI$^+$) m/z 389.2 [M + H]$^+$. | 56 mg, 16%, white solid |
| 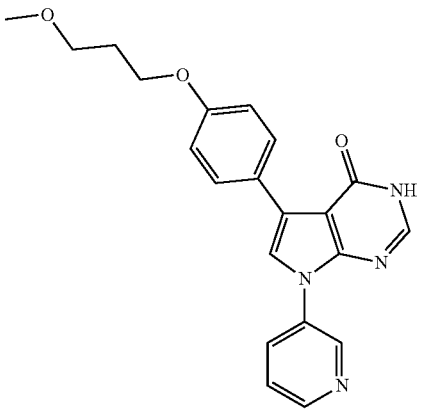 [SMILES: COCCCOc1ccc(-c2cn(-c3cccnc3)c3nc[nH]c(=O)c23)cc1] | Ex-71 (CH12, B16) | LC-MS. $R_t$ 7.35 min, AnalpH2_MeOH_QC_V1(1); (ESI$^+$) m/z 377.3 [M + H]$^+$. | 77 mg, 46%, white solid |
| 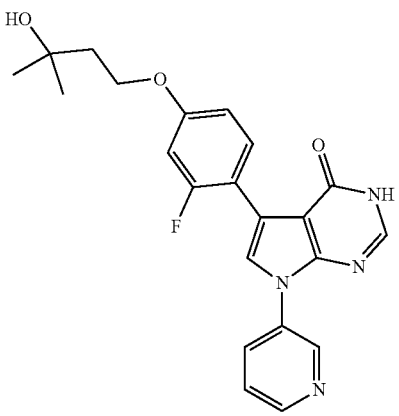 [SMILES: CC(C)(O)CCOc1ccc(-c2cn(-c3cccnc3)c3nc[nH]c(=O)c23)c(F)c1] | Ex-72 (CH12, B11) | LC-MS. $R_t$ 7.47 min, AnalpH2_MeOH_QC_V1(1); (ESI$^+$) m/z 409.3 [M + H]$^+$. | 48 mg, 27%, white solid |

TABLE 25-continued

| Compound | Ex. # (Intermediate used) | Analytical Data | Mass, % Yield, State |
|---|---|---|---|
| (structure) | Ex-73 (CH12, B14) | LC-MS. R$_t$ 7.33 min, AnalpH2_MeOH_QC_V1(1); (ESI$^+$) m/z 409.3 [M + H]$^+$. | 75 mg, 41%, white solid |
| (structure) | Ex-74 (CH12, B12) | LC-MS. R$_t$ 3.15 min, AnalpH2_MeOH_QC_V1(1); (ESI$^+$) m/z 476.3 [M + H]$^+$. | 116 mg, 62%, white solid |
| (structure) | Ex-75$^a$ (CH11, B5) | LC-MS. R$_t$ 7.88 min, AnalpH2_MeOH_QC_V1(1); (ESI$^+$) m/z 391.2 [M + H]$^+$; $^1$H-NMR (400 MHz, DMSO-d$_6$): δ 12.17 (s, 1H), 8.72 (d, J = 1.8 Hz, 1H), 8.23 (dd, J = 8.7, 2.7 Hz, 1H), 7.95 (s, 1H), 7.81 (s, 1H), 7.78-7.67 (m, 2H), 7.60-7.46 (m, 2H), 7.45-7.32 (m, 1H), 6.77 (d, J = 9.2 Hz, 1H), 4.42-4.27 (m, 3H), 1.82 (t, J = 7.3 Hz, 2H), 1.14 (s, 6H) | 32 mg, 17%, white solid; |

TABLE 25-continued

| Compound | Ex. # (Intermediate used) | Analytical Data | Mass, % Yield, State |
|---|---|---|---|
| 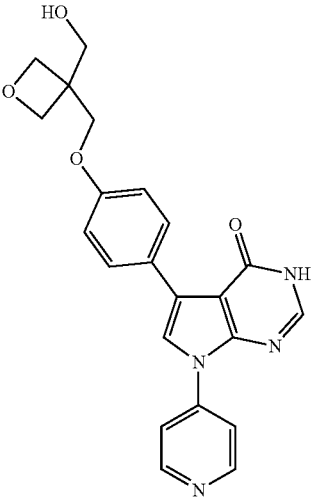 [SMILES: O=c1[nH]cnc2c1c(-c1ccc(OCC3(CO)COC3)cc1)cn2-c1ccncc1] | Ex-76[a,f] (CH13, B9) | LC-MS. $R_t$ 5.65 min, AnalpH2_MeOH_QC_V1(1); (ESI+) m/z 405.2 [M + H]+. | 14 mg, 12%, pale yellow solid |
| 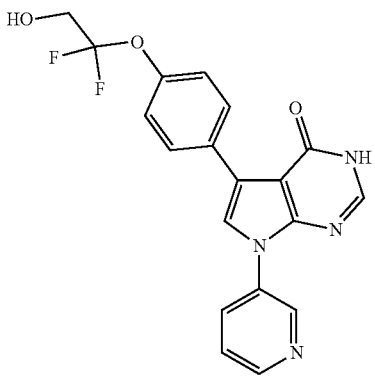 [SMILES: O=c1[nH]cnc2c1c(-c1ccc(OC(F)(F)CO)cc1)cn2-c1cccnc1] | Ex-77[a,f] (CH12, B6) | LC-MS. $R_t$ 6.82 min, AnalpH2_MeOH_QC_V1(1); (ESI+) m/z 385.2 [M + H]+. | 36 mg, 28%, white solid |
| 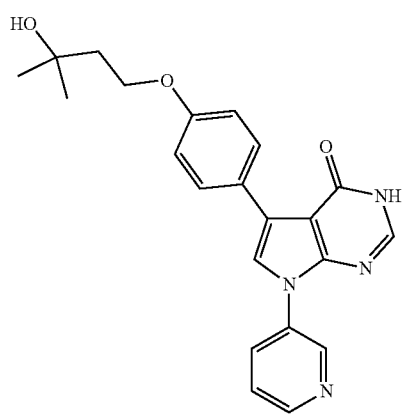 [SMILES: CC(C)(O)CCOc1ccc(-c2cn(-c3cccnc3)c3nc[nH]c(=O)c23)cc1] | Ex-78[b] (CH12, B2) | LC-MS. $R_t$ 7.29 min, AnalpH2_MeOH_QC_V1(1); (ESI+) m/z 391.2 [M + H]+; $^1$H-NMR (400 MHz, DMSO-$d_6$): δ 12.15 (s, 1H), 8.99 (d, J = 2.7 Hz, 1H), 8.57 (dd, J = 4.8, 1.6 Hz, 1H), 8.23-8.17 (m, 1H), 7.96 (s, 1H), 7.88 (d, J = 8.9 Hz, 2H), 7.79 (s, 1H), 7.57 (dd, J = 8.2, 5.5 Hz, 1H), 6.91 (d, J = 8.9 Hz, 2H), 4.35 (s, 1H), 4.08 (t, J = 7.1 Hz, 2H), 1.82 (t, J = 7.3 Hz, 2H), 1.14 (s, 6H). | 267 mg, 46%, white solid |

TABLE 25-continued

| Compound | Ex. # (Intermediate used) | Analytical Data | Mass, % Yield, State |
|---|---|---|---|
| (structure) | Ex-79[b] (CH12, B9) | LC-MS. $R_t$ 6.60 min, AnalpH2_MeOH_QC_V1(1); (ESI$^+$) m/z 405.3 [M + H]$^+$; $^1$H-NMR (400 MHz, DMSO-d$_6$): δ 12.15 (s, 1H), 8.99 (d, J = 2.3 Hz, 1H), 8.57 (dd, J = 4.6, 1.4 Hz, 1H), 8.23-8.16 (m, 1H), 7.96 (s, 1H), 7.92 (d, J = 9.2 Hz, 2H), 7.81 (s, 1H), 7.57 (q, J = 4.3 Hz, 1H), 7.26 (dd, J = 8.7, 7.3 Hz, 1H), 7.00-6.87 (m, 4H), 4.98 (s, 1H), 4.44-4.32 (m, 4H), 4.14 (s, 2H), 4.09 (s, 1H), 3.68 (dd, J = 9.8, 5.3 Hz, 2H) | 32 mg, 27%, white solid |
| (structure) | Ex-80[b] (CH12, B17) | LC-MS. $R_t$ 6.56 min, AnalpH2_MeOH_QC_V1(1); (ESI$^+$) m/z 433.2 [M + H]$^+$; $^1$H-NMR (400 MHz, DMSO-d$_6$): δ 12.20 (br s, 1H), 8.98 (d, J = 2.7 Hz, 1H), 8.57 (dd, J = 4.3, 1.4 Hz, 1H), 8.19 (ddd, J = 8.2, 2.7, 1.4 Hz, 1H), 7.96 (s, 1H), 7.91 (d, J = 8.7 Hz, 2H), 7.82 (s, 1H), 7.58 (dd, J = 8.2, 4.3 Hz, 1H), 6.95 (d, J = 8.7 Hz, 2H), 4.94 (d, J = 6.4 Hz, 1H), 4.84 (d, J = 2.7 Hz, 1H), 4.47 (d, J = 12.8 Hz, 2H), 4.16-4.07 (m, 1H), 4.03 (dd, J = 10.3, 3.9 Hz, 1H), 3.92 (d, J = 10.5 Hz, 1H), 3.74 (dd, J = 8.7, 6.4 Hz, 1H), 3.40 (t, J = 8.0 Hz, 1H) | 40 mg, 21%, white solid |
| (structure) | Ex-81[b] (CH12, B18) | LC-MS. $R_t$ 6.61 min, AnalpH2_MeOH_QC_V1(1); (ESI$^+$) m/z 407.2 [M + H]$^+$; $^1$H-NMR (400 MHz, DMSO-d$_6$): δ 12.16 (s, 1H), 8.98 (d, J = 2.3 Hz, 1H), 8.57 (dd, J = 4.8, 1.1 Hz, 1H), 8.23-8.14 (m, 1H), 7.95 (s, 1H), 7.88 (d, J = 8.7 Hz, 2H), 7.79 (s, 1H), 7.57 (dd, J = 8.2, 5.0 Hz, 1H), 6.92 (d, J = 8.7 Hz, 2H), 4.98 (d, J = 5.0 Hz, 1H), 4.39 (s, 1H), 4.22 (dd, J = 10.1, 2.3 Hz, 1H), 3.79 (dd, J = 10.1, 8.2 Hz, 1H), 3.52 (s, 1H), 1.12 (s, 3H), 1.05 (s, 3H) | 12 mg, 6%, white solid |

TABLE 25-continued

| Compound | Ex. # (Intermediate used) | Analytical Data | Mass, % Yield, State |
|---|---|---|---|
| (structure) | Ex-82[b] (CH15, B2) | LC-MS. R$_t$ 6.05 min, AnalpH2_MeOH_QC_V1(1); (ESI$^+$) m/z 405.3 [M + H]$^+$; $^1$H-NMR (400 MHz, DMSO-d$_6$): δ 12.26 (s, 1H), 8.52 (d, J = 5.5 Hz, 1H), 8.02 (s, 1H), 7.93-7.75 (m, 5H), 6.91 (d, J = 8.7 Hz, 2H), 4.37 (s, 1H), 4.07 (t, J = 7.1 Hz, 2H), 2.52 (s, 3H), 1.81 (t, J = 7.1 Hz, 2H), 1.13 (s, 6H) | 13 mg, 6%, white solid |
| (structure) | Ex-83[b] (CH18, B2) | LC-MS. R$^t$ 7.93 min, AnalpH2_MeOH_QC_V1(1); (ESI$^+$) m/z 421.3 [M + H]$^+$; $^1$H-NMR (400 MHz, DMSO-d$_6$): δ 12.09 (br s, 1H), 8.48 (d, J = 2.7 Hz, 1H), 8.05 (dd, J = 8.7, 2.7 Hz, 1H), 7.91 (s, 1H), 7.86 (d, J = 8.7 Hz, 2H), 7.66 (s, 1H), 6.97 (d, J = 8.7 Hz, 1H), 6.90 (d, J = 8.7 Hz, 2H), 4.36 (s, 1H), 4.07 (t, J = 7.1 Hz, 2H), 3.88 (s, 3H), 1.82 (t, J = 7.1 Hz, 2H), 1.14 (s, 6H) | 32 mg, 16%, white solid |
| (structure) | Ex-84[b] (CH17, B2) | LC-MS. R$_t$ 7.68 min, AnalpH2_MeOH_QC_V1(1); (ESI$^+$) m/z 409.2 [M + H]$^+$; $^1$H-NMR (400 MHz, DMSO-d$_6$): δ 12.22 (br s, 1H), 8.99 (s, 1H), 8.61 (d, J = 2.7 Hz, 1H), 8.31 (dt, J = 10.5, 2.3 Hz, 1H), 8.01 (s, 1H), 7.85-7.89 (m, 3H), 6.92 (d, J = 8.7 Hz, 2H), 4.36 (s, 1H), 4.08 (t, J = 7.3 Hz, 2H), 3.27 (s, 3H), 1.82 (t, J = 7.3 Hz, 2H). | 56 mg, 27%, white solid |

TABLE 25-continued

| Compound | Ex. # (Intermediate used) | Analytical Data | Mass, % Yield, State |
|---|---|---|---|
| | Ex-85[b] (CH17) | LC-MS. $R_t$ 7.35 min, AnalpH2_MeOH_QC_V1(1); (ESI+) m/z 381.2 [M + H]+; $^1$H-NMR (400 MHz, DMSO-$d_6$): δ 12.18 (s, 1H), 8.93 (d, J = 1.8 Hz, 1H), 8.54 (d, J = 2.3 Hz, 1H), 8.24 (dt, J = 10.5, 2.3 Hz, 1H), 7.95 (s, 1H), 7.87-7.87 (m, 3H), 6.87 (d, J = 9.2 Hz, 2H), 4.05-4.00 (m, 2H), 3.61-3.54 (m, 2H), 3.22 (s, 3H). | 61 mg, 38%, white solid |
| | Ex-86[b] (CH19, B2) | LC-MS. $R_t$ 8.01 min, AnalpH2_MeOH_QC_V1(1); (ESI+) m/z 421.3 [M + H]+; $^1$H-NMR (400 MHz, DMSO-$d_6$): δ 12.26 (s, 1H), 8.25 (d, J = 6.0 Hz, 1H), 8.02 (s, 1H), 7.90-7.81 (m, 3H), 7.63 (dd, J = 5.5, 1.8 Hz, 1H), 7.46 (d, J = 1.8 Hz, 1H), 6.91 (d, J = 8.7 Hz, 2H), 4.36 (s, 1H), 4.08 (t, J = 7.2 Hz, 2H), 3.88 (s, 3H), 1.82 (t, J = 7.2 Hz, 2H), 1.14 (s, 6H) | 34 mg, 37%, white solid |
| | Ex-87[b] (CH12, B15) | LC-MS. $R_t$ 7.15 min, AnalpH2_MeOH_QC_V1(1); (ESI+) m/z 416.2 [M + H]+. | 53 mg, 29%, white solid |

TABLE 25-continued

| Compound | Ex. # (Intermediate used) | Analytical Data | Mass, % Yield, State |
|---|---|---|---|
| (structure) | Ex-88[b] (CH19) | LC-MS. R$_t$ 2.71 min, AnalpH2_MeOH_QC_V1(1); (ESI$^+$) m/z 408.2 [M + H]$^+$; $^1$H-NMR (400 MHz, DMSO-d$_6$): δ 12.27 (s, 1H), 8.25 (d, J = 5.5 Hz, 1H), 8.02 (s, 1H), 7.93-7.85 (m, 3H), 7.63 (dd, J = 5.5, 1.6 Hz, 1H), 7.46 (d, J = 1.6 Hz, 1H), 6.93 (d, J = 8.7 Hz, 2H), 4.12-4.06 (m, 2H), 3.91-3.84 (m, 3H), 3.67-3.58 (m, 2H). | 44 mg, 52%, white solid |
| (structure) | Ex-89[b] (CH16) | LC-MS. R$_t$ 2.71 min, AnalpH2_MeOH_4min(1); (ESI$^+$) m/z 408.2 | 90 mg (crude) |
| (structure) | Ex-90[b] (CH16, B2) | LC-MS. R$_t$ 2.86 min, AnalpH2_MeOH_4min(1); (ESI$^+$) m/z 418.2. | 120 mg (crude) |

TABLE 25-continued

| Compound | Ex. # (Intermediate used) | Analytical Data | Mass, % Yield, State |
|---|---|---|---|
| | Ex-91[b] (CH12, B8) | LC-MS: $R_t$ 6.66 min, AnalpH2_MeOH_QC_V1(1); (ESI+) m/z 405.2 [M + H]+. $^1$H NMR (400 MHz, DMSO-$d_6$): δ 12.13 (br s, 1H), 9.04 (d, J = 2.3 Hz, 1H), 8.62 (d, J = 4.1 Hz, 1H), 8.24 (d, J = 7.8 Hz, 1H), 8.00 (s, 1H), 7.94 (d, J = 8.7 Hz, 2H), 7.84 (s, 1H), 7.62 (dd, J = 7.8, 4.1 Hz, 1H), 6.96 (d, J = 8.7 Hz, 2H), 5.80 (s, 1H), 4.53 (d, J = 6.4 Hz, 2H), 4.48 (d, J = 6.4 Hz, 2H), 4.16 (t, J = 6.4 Hz, 2H), 2.20 (t, J = 6.4 Hz, 2H). | 64 mg, 43%, white solid |
| | Ex-92[b] (CH12, B10) | LC-MS: $R_t$ 7.57 min, AnalpH2_MeOH_QC_V1(1); (ESI+) m/z 391.3 [M + H]+; $^1$H NMR (400 MHz, DMSO-$d_6$): δ 12.20 (br s, 1H), 9.04 (d, J = 2.8 Hz, 1H), 8.62 (dd, J = 4.6, 1.4 Hz, 1H), 8.25 (ddd, J = 8.2, 2.8, 1.4 Hz, 1H), 8.00 (s, 1H), 7.93 (d, J = 8.7 Hz, 2H), 7.84 (s, 1H), 7.62 (ddd, J = 8.2, 4.6, 1.4 Hz, 1H), 6.95 (d, J = 8.7 Hz, 2H), 4.63 (t, J = 5.5 Hz, 1H), 3.75 (s, 2H), 3.31 (d, J = 5.5 Hz, 2H), 0.95 (s, 6H). | 38 mg, 25%, white solid |
| | Ex-93[b] (CH12, B13) | LC-MS: $R_t$ 2.64 min, AnalpH2_MeCN; (ESI+) m/z 490.1 [M + H]+. | 112 mg, 62%, white solid |

[a] Aqueous work-up carried out with DCM and $H_2O$;
[b] $K_3PO_4$ added as a solution in water.
[f] Isolated as a formic acid salt.

A number of compounds have been synthesised starting from the bromo intermediate, without the isolation of the boronic ester or acid:

5-[6-[(3-hydroxy-3-methyl-butyl)amino]-3-pyridyl]-7-phenyl-3H-pyrrolo[2,3-d]pyrimidin-4-one (Ex-94)

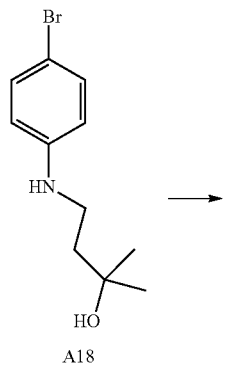

A18

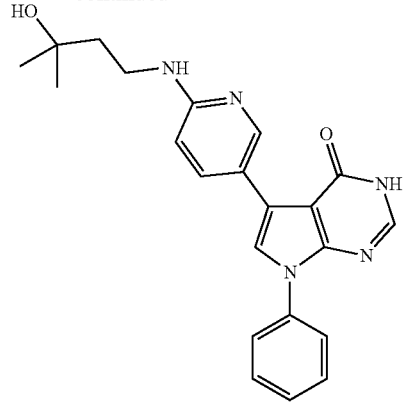

Ex-94

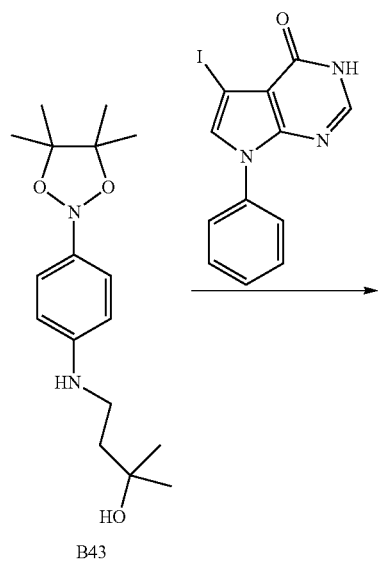

B43

4-((4-bromophenyl)amino)-2-methylbutan-2-ol (A18) (100 mg, 0.386 mmol), bis(pinacolato)diboron (147 mg, 0.579 mmol), Pd(dppf)Cl$_2$.DCM (32 mg, 0.04 mmol) and KOAc (114 mg, 1.16 mmol) in anhydrous 1,4-dioxane (3 mL) was de-oxygenated with N$_2$ for 5 min then heated at 100° C. for 18 h to provide the crude boronic acid/ester (B43), which was cooled to RT and used directly in the next step. 5-iodo-7-phenyl-3,7-dihydro-4H-pyrrolo[2,3-d]pyrimidin-4-one (130 mg, 0.386 mmol), PdXPhosG3 (32 mg, 0.04 mmol) and aq. K$_3$PO$_4$ (1.5 M, 0.5 mL, 0.75 mmol) were added to the crude boronic acid/ester (B43) and the resulting reaction mixture was de-oxygenated with N$_2$ for 5 min then heated to 100° C. for 18 h. The reaction mixture was cooled to RT, filtered through a Si-thiol column (2 g) and the column was washed with MeOH (3×CV), 1,4-dioxane (3×CV) then with MeOH (3×CV). The solvents were removed in vacuo and the residue was purified by reversed phase preparative HPLC-MS. In order to remove residual formic acid from the sample, the solid was dissolved in DCM and washed with sat. aq. Na$_2$CO$_3$. The organic fraction was dried by passing it through a phase separator cartridge (Biotage), evaporated and lyophilised to afford the desired product (Ex-94) as a white solid (16 mg, 11%). LC-MS. R$_t$ 5.40 min, AnalpH2_MeOH_QC_V1(1); (ESI$^+$) m/z 390.3 [M+H]$^+$; $^1$H NMR (400 MHz, DMSO-d$_6$): δ 12.10 (brs, 1H), 8.59 (d, J=2.3 Hz, 1H), 7.97 (dd, J=8.7, 2.3 Hz, 1H), 7.95 (s, 1H), 7.78 (d, J=7.8 Hz, 2H), 7.66 (s, 1H), 7.56 (t, J=7.8 Hz, 2H), 7.41 (**t, J=7.8 Hz, 1H), 6.46 (d, J=8.7 Hz, 1H), 6.38 (t, J=5.5 Hz, 1H), 4.36 (br s, 1H), 3.32-3.29 (m, 2H), 1.71-1.64 (m, 2H), 1.16 (s, 6H).

The following compound was prepared using analogous procedures to compound (Ex-94):

TABLE 26

| Compound | Ex. # (Intermediate used) | Analytical Data | Mass, % Yield, State |
|---|---|---|---|
| 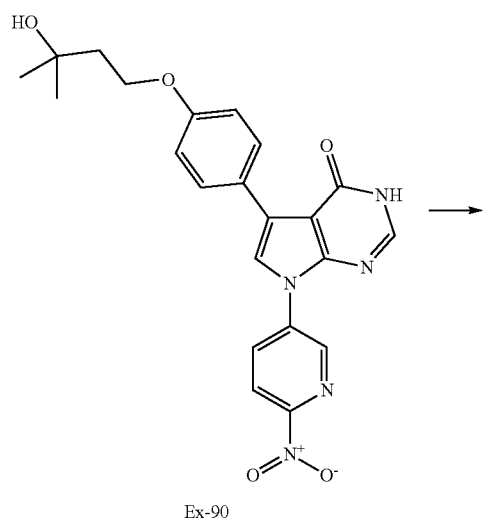 | Ex-95[a] (CH11, A19) | LC-MS. $R_t$ 5.53 min, AnalpH2_MeOH_QC_V1(1); (ESI+) m/z 404.3 [M + H]+; $^1$H NMR (400 MHz, DMSO-$d_6$): δ 12.16 (br s, 1H), 8.68 (d, J = 2.3 Hz, 1H), 8.09 (dd, J = 8.7, 2.3 Hz, 1H), 7.96 (s, 1H), 7.77 (d, J = 7.3 Hz, 2H), 7.72 (s, 1H), 7.56 (t, J = 7.3 Hz, 2H), 7.42 (**t, J = 7.3 Hz, 1H), 6.63 (d, J = 8.7 Hz, 1H), 4.39 (s, 1H), 3.65-3.56 (m, 2H), 3.02 (s, 3H), 1.67-1.59 (m, 2H), 1.16 (s, 6H). | 29 mg, 20%, white solid |

[a]Aqueous work-up carried out with EtOAc and H$_2$O then organics passed through SCX-2; title compound was eluted with NH$_3$ in MeOH.

Synthesis of Final Compounds Via Reduction of Nitro Compounds 7-(6-aminopyridin-3-yl)-5-(4-(3-hydroxy-3-methylbutoxy)phenyl)-3,7-dihydro-4H-pyrrolo[2,3-d]pyrimidin-4-one (Ex-96)

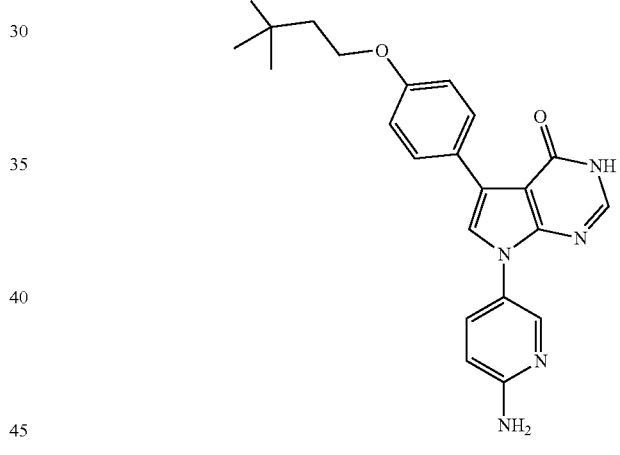

10% Palladium/Carbon (25 mg) was added to a solution of the 5-(4-(3-hydroxy-3-methylbutoxy)phenyl)-7-(6-nitropyridin-3-yl)-3,7-dihydro-4H-pyrrolo[2,3-d]pyrimidin-4-one (Ex-90) (120 mg, 0.298 mmol) in EtOH/DMF (50:50, 30 mL). The reaction flask was evacuated under vacuum and backfilled with hydrogen (×3). The reaction mixture was allowed to stir under hydrogen at RT for 18 h and the catalyst was removed by filtration over celite cartridge (2.5 g). LC-MS analysis revealed the reaction was incomplete so the crude material was re-dissolved in DMF/AcOH (10 mL; 9:1), 10% Palladium/Carbon (25 mg) was added, the flask was evacuated under vacuum and backfilled with hydrogen (×3). The reaction mixture was stirred under a hydrogen atmosphere for 18 h at RT. Reaction mixture was then filtered through a pad of celite, washed with MeOH and the organics were concentrated in vacuo. The crude compound was purified by reversed phase preparative HPLC and the product was lyophilised from 1:1 MeCN/H$_2$O to afford the title compound (Ex-96) as a white solid (33 mg, 27%).

LC-MS. R$_t$ 5.48 min, AnalpH9_MeOH_QC_V1 (1): (ESI$^+$) m/z 406.3 [M+H]$^+$; $^1$H NMR (400 MHz, DMSO-d$_6$): δ 11.99 (s, 1H), 8.19-8.10 (m, 1H), 7.86 (d, J=8.7 Hz, 3H), 7.63 (dd, J=8.7, 2.3 Hz, 1H), 7.56-7.49 (1H), 6.88 (d, J=8.7 Hz, 2H), 6.52 (d, J=8.7 Hz, 1H), 6.18 (s, 2H), 4.36 (s, 1H), 4.07 (t, J=7.1 Hz, 2H), 1.81 (t, J=7.1 Hz, 2H), 1.14 (s, 6H).

The following example was synthesised using an analogous procedure to (Ex-96):

TABLE 27

| Compound | Ex. # (Intermediate used) | Analytical Data | Mass, % Yield, State |
|---|---|---|---|
|  | Ex-97 (Ex-89) | LC-MS. R$_t$ 7.75 min, AnalpH2_MeOH_QC_V1(1); (ESI$^+$) m/z 378.1 [M + H]$^+$; $^1$H NMR (400 MHz, DMSO-d$_6$): δ 8.13 (d, J = 2.7 Hz, 1H), 7.90-7.84 (m, 3H), 7.63 (dd, J = 8.7, 2.7 Hz, 1H), 7.54 (s, 1H), 6.90 (d, J = 8.7 Hz, 2H), 6.52 (d, J = 8.7 Hz, 1H), 6.18 (s, 2H), 4.10-4.04 (m, 2H), 3.66-3.59 (m, 2H) 3.28 (s, 3H) | 17 mg, 15%, white solid |

Synthesis of N-Oxides 4-(5-(4-(2-hydroxy-2-methylpropoxy)phenyl-4-oxo-3,4-dihydro-7H-pyrrolo[2,3-d]pyrimidin-7-yl_pyridine-1-oxide (Ex-98)

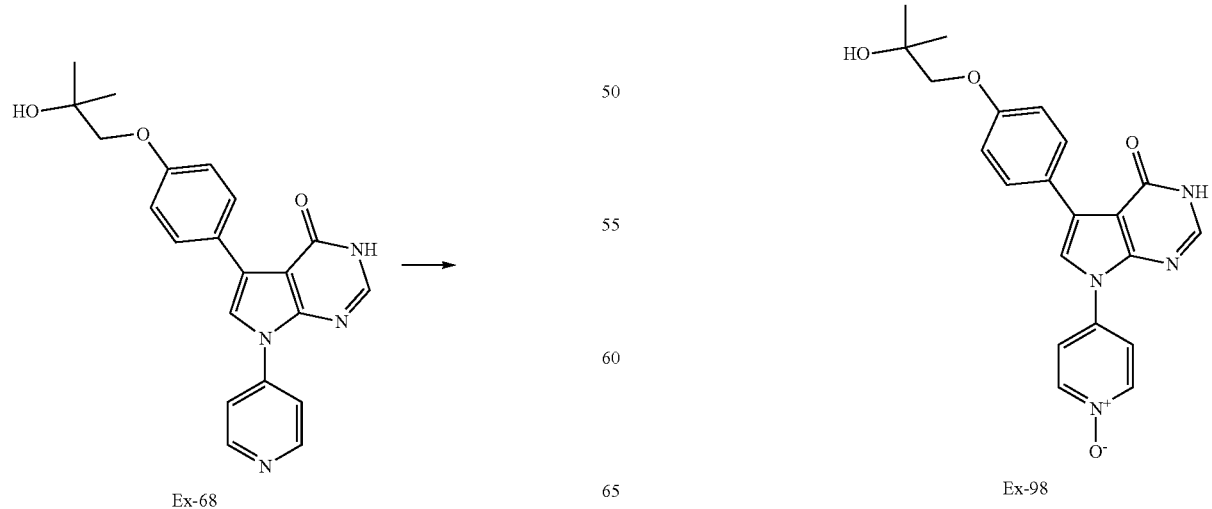

To a solution of 5-(4-(2-hydroxy-2methylpropoxy)phenyl)-7-(pyridine-4-yl)-3,7-dihydro-4H-pyrrolo[2,3-d]pyrimidin-4-one (19.5 mg, 0.052 mmol) in DCM (1 mL) was added meta-chloroperoxybenzoic acid (Ex-68) and the resulting mixture was stirred at RT for 30 min. DMSO (1 mL) was added and the mixture concentrated in vacuo. The crude compound was purified by reversed phase preparative HPLC-MS to afford 4-(5-(4-(2-hydroxy-2-methylpropoxy)phenyl-4-oxo-3,4-dihydro-7H-pyrrolo[2,3-d]pyrimidin-7-yl_pyridine-1-oxide (Ex-98) as an off-white solid (2 mg, 8%); LC-MS. $R_t$ 6.40 min, AnalpH9_MeOH_QC_V1(1); (ESI$^+$) m/z 393.3 [M+H]$^+$; $^1$H-NMR (400 MHz, DMSO-d$_6$): δ 12.40-12.24 (brs, 1H), 8.38 (d, J=7.8 Hz, 2H), 8.07-8.05 (m, 2H), 8.04 (s, 1H), 7.93 (s, 1H), 7.91-7.89 (m, 2H), 6.96 (d, J=8.7 Hz, 2H), 4.65 (s, 1H), 3.75 (s, 2H), 1.22 (s, 6H).

The following example was synthesised using an analogous procedure to Ex-98 with aqueous work-up carried out with DCM and NaHCO$_3$ and the crude compound purified by silica gel chromatography followed by reversed phase preparative HPLC-MS

TABLE 28

| Compound | Ex. # (Intermediate used) | Analytical Data | Mass, % Yield, State |
|---|---|---|---|
|  | Ex-99 (Ex-66) | LC-MS. $R_t$ 6.47 min, AnalpH2_MeOH_QC_V1(1); (ESI$^+$) m/z 393.2 [M + H]$^+$. | 1 mg, 3%, off-white solid |

Synthesis of Phosphate Pro-Drugs

A number of phosphate pro-drugs examples were synthesised according to the following route:

Route 3: Scheme 3

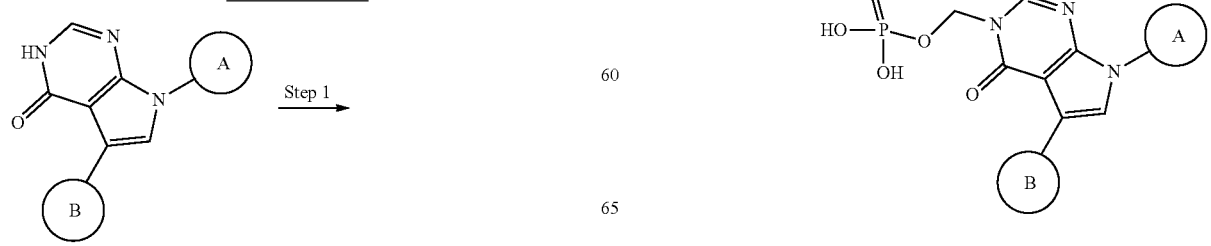

Route 3; Step 1

Phosphoric acid di-tert-butyl ester 5-[4-(2-methoxy-ethoxy)-phenyl]-4-oxo-7-phenyl-4,7-dihydro-pyrrolo[2,3-d]pyrimidin-3-ylmethyl Ester (Ex-100)

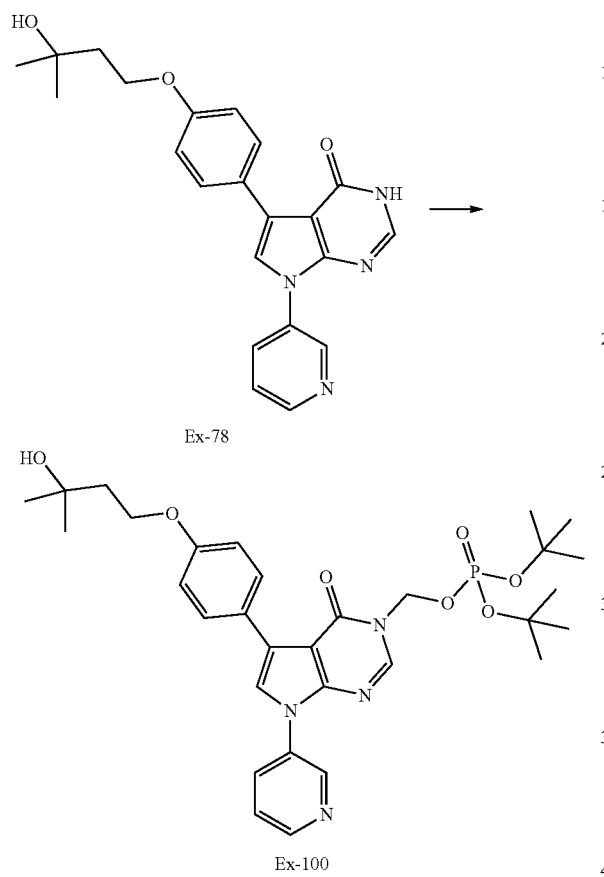

A mixture of 5-(4-(3-hydroxy-3-methylbutoxy)phenyl)-7-(pyridin-3-yl)-3,7-dihydro-4H-pyrrolo[2,3-d]pyrimidin-4-one (Ex-78) (150 mg, 0.38 mmol), di-tert-butyl(chloromethyl)phosphate (108 μL, 0.45 mmol), $CS_2CO_3$ (138 mg, 0.41 mmol) and DMF (12 mL) were stirred at RT under $N_2$ for 4 h then for a further 18 h at 30° C. The reaction mixture was diluted with $H_2O$ (20 mL), extracted with EtOAc (2×20 mL), washed with $H_2O$ (2×20 mL), brine (20 mL) and dried over $MgSO_4$. The crude compound was purified by reversed phase chromatography by eluting with 5-95% MeOH/0.1% formic acid in water to afford tert-tert-butyl ((5-(4-(3-hydroxy-3-methylbutoxy)phenyl)-4-oxo-7-(pyridin-3-yl)-4,7-dihydro-3H-pyrrolo[2,3-d]pyrimidin-3-yl)methyl) phosphate (Ex-100) as a yellow solid (192 mg, 81%); LC-MS. $R_t$ 3.34 min, AnalpH2_MeOH_4 min(1); (ESI$^+$) m/z 613.1 [M+H]$^+$.

The following example was synthesised using an analogous procedure to (Ex-100) and stirred at RT for 24 h:

TABLE 29

| Compound | Ex. # (Intermediate used) | Analytical Data | Mass, % Yield, State |
|---|---|---|---|
|  | Ex-101[a,b] (Ex-67) | LC-MS. $R_t$ 3.16 min, AnalpH2_MeOH_4min(1); (ESI$^+$) m/z 585.3 [M + H]$^+$ | 205 mg, 80%, pale yellow oil |

[a]Mixture of N and O-alkylated compounds (4:1 by LC-MS) not separated and used directly in the next step Route 3; Step 2

5-(4-(3-hydroxy-3-methylbutoxy)phenyl)-4-oxo-7-(pyridin-3-yl)-4,7-dihydro-3H-pyrrolo[2,3-d]pyrimidin-3-yl)methyl Dihydrogen Phosphate (Ex-102)

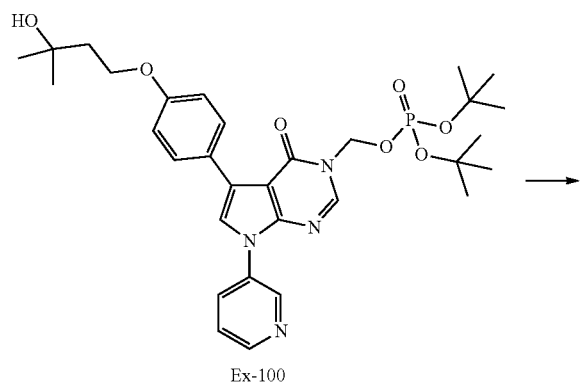

Ex-100

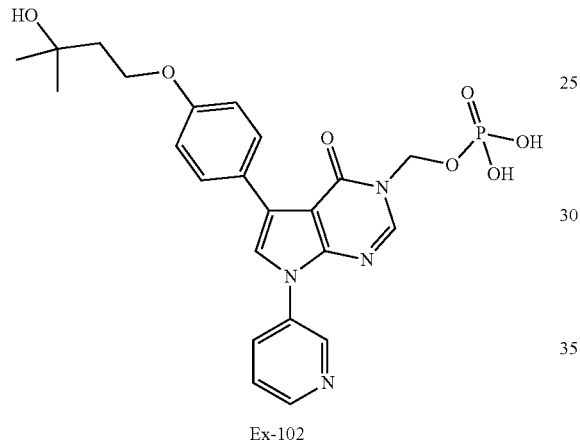

Ex-102

A mixture of di-tert-butyl ((5-(4-(3-hydroxy-3-methylbutoxy)phenyl)-4-oxo-7-(pyridin-3-yl)-4,7-dihydro-3H-pyrrolo[2,3-d]pyrimidin-3-yl)methyl) phosphate (Ex-100) (192 mg, 0.314 mmol) and AcOH:$H_2O$ (4:1, 10 mL) was heated at 65° C. for 2 h. The reaction mixture was evaporated to dryness and the crude compound was purified by reversed phase preparative HPLC-MS to afford (5-(4-(3-hydroxy-3-methylbutoxy)phenyl)-4-oxo-7-(pyridin-3-yl)-4,7-dihydro-3H-pyrrolo[2,3-d]pyrimidin-3-yl)methyl dihydrogen phosphate (Ex-102) as the bis ammonium salt, white solid (132 mg, 79%); LC-MS. $R_t$ 6.09 min, AnalpH9_MeOH_QC_V1 (1); (ESI$^+$) m/z 501.3 [M+H]$^+$; $^1$H-NMR (400 MHz, DMSO-$d_6$): δ 9.00 (d, J=1.8 Hz, 1H), 8.60 (dd, J=4.8, 1.6 Hz, 1H), 8.45 (s, 1H), 8.24-8.20 (m, 1H), 7.87 (d, J=2.7 Hz, 2H), 7.78 (s, 1H), 7.59 (dd, J=8.2, 4.2 Hz, 1H), 7.30-7.10 (br s, 2H), 6.92 (d, J=9.2 Hz, 2H), 5.56 (d, J=11 Hz, 2H), 4.11 (t, J=7.4 Hz, 2H), 1.86 (t, J=7.4 Hz, 2H), 1.18 (s, 6H).

The following example was synthesised using an analogous procedure to (Ex-102) with a reaction time of 1 h:

TABLE 30

| Compound | Ex. # (Intermediate used) | Analytical Data | Mass, % Yield, State |
|---|---|---|---|
| (structure shown) | Ex-103 (Ex-101) | LC-MS. $R_t$ 5.65 min, AnalpH2_MeOH_QC_V1(1); (ESI$^+$) m/z 473.1 [M + H]$^+$ | 68 mg, 38%, yellow solid |

A number of examples of formula (Ia) were synthesised according to the following route:

Route 4: Scheme 4

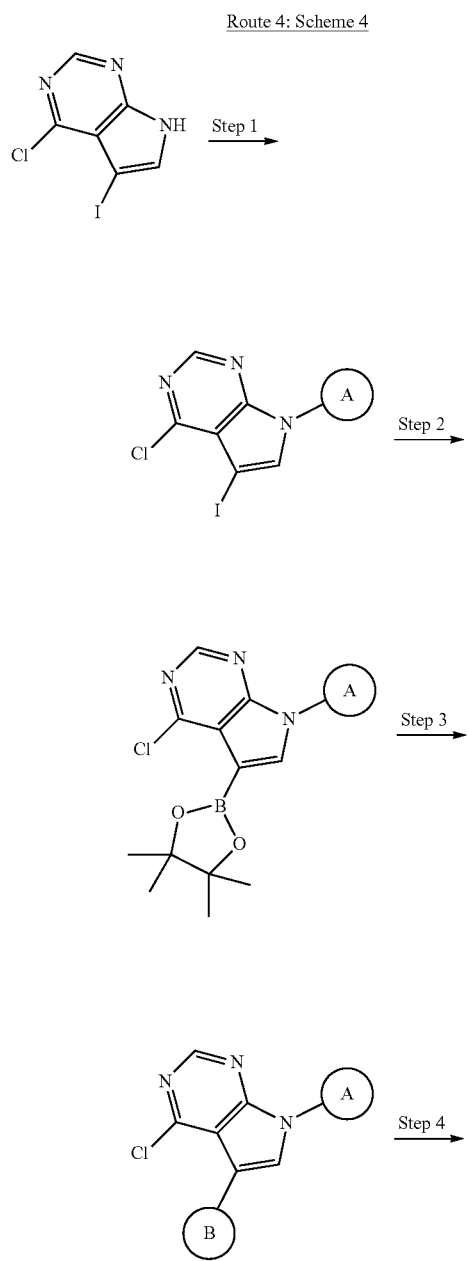

Route 4, Step 2:

4-Chloro-7-phenyl-5-(4,4,5,5-tetramethyl-[1,3,2] dioxaborolan-2-yl)-7H-pyrrolo[2,3-d]pyrimidine (CP57)

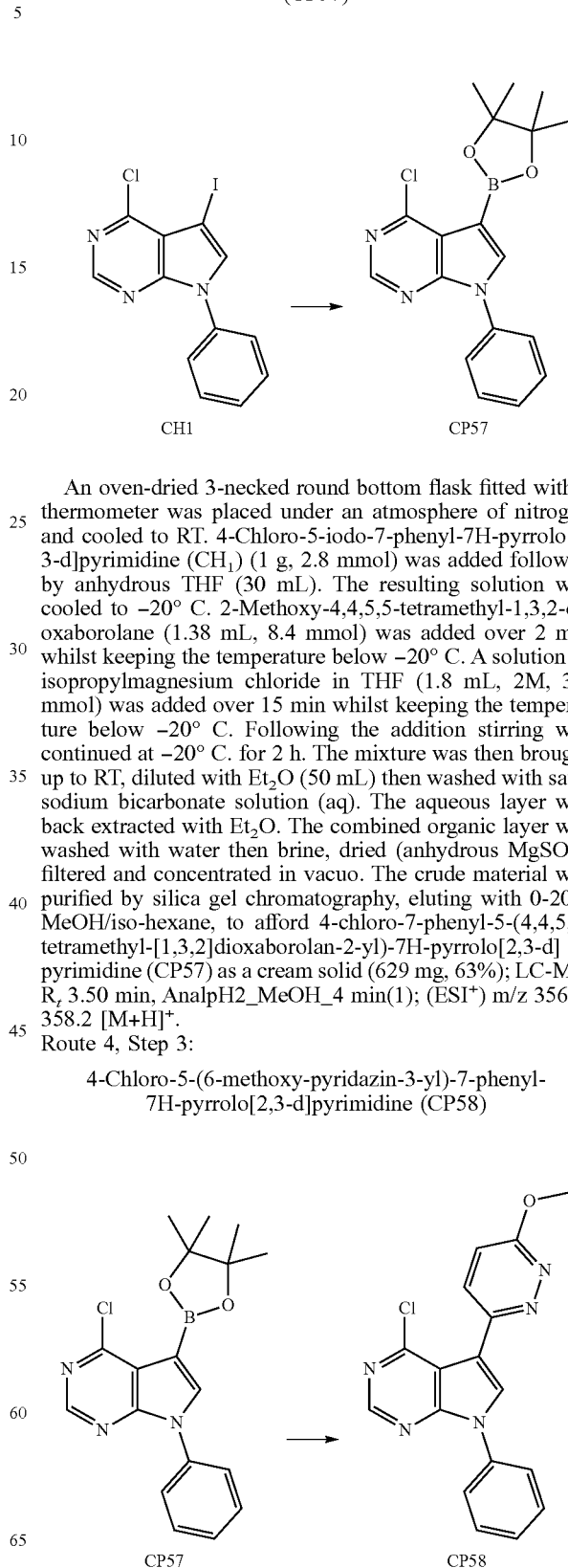

An oven-dried 3-necked round bottom flask fitted with a thermometer was placed under an atmosphere of nitrogen and cooled to RT. 4-Chloro-5-iodo-7-phenyl-7H-pyrrolo[2,3-d]pyrimidine (CH$_1$) (1 g, 2.8 mmol) was added followed by anhydrous THF (30 mL). The resulting solution was cooled to −20° C. 2-Methoxy-4,4,5,5-tetramethyl-1,3,2-dioxaborolane (1.38 mL, 8.4 mmol) was added over 2 min whilst keeping the temperature below −20° C. A solution of isopropylmagnesium chloride in THF (1.8 mL, 2M, 3.6 mmol) was added over 15 min whilst keeping the temperature below −20° C. Following the addition stirring was continued at −20° C. for 2 h. The mixture was then brought up to RT, diluted with Et$_2$O (50 mL) then washed with satd. sodium bicarbonate solution (aq). The aqueous layer was back extracted with Et$_2$O. The combined organic layer was washed with water then brine, dried (anhydrous MgSO$_4$), filtered and concentrated in vacuo. The crude material was purified by silica gel chromatography, eluting with 0-20% MeOH/iso-hexane, to afford 4-chloro-7-phenyl-5-(4,4,5,5-tetramethyl-[1,3,2]dioxaborolan-2-yl)-7H-pyrrolo[2,3-d]pyrimidine (CP57) as a cream solid (629 mg, 63%); LC-MS. R$_t$ 3.50 min, AnalpH2_MeOH_4 min(1); (ESI$^+$) m/z 356.2, 358.2 [M+H]$^+$.

Route 4, Step 3:

4-Chloro-5-(6-methoxy-pyridazin-3-yl)-7-phenyl-7H-pyrrolo[2,3-d]pyrimidine (CP58)

A mixture of 4-chloro-7-phenyl-5-(4,4,5,5-tetramethyl-[1,3,2]dioxaborolan-2-yl)-7H-pyrrolo[2,3-d]pyrimidine (CP57) (75 mg, 0.21 mmol), 3-bromo-6-methoxypyridazine (40 mg, 0.21 mmol), potassium phosphate tribasic (134 mg, 0.63 mmol), THF (1.6 ml) and water (0.4 ml) was deoxygenated with nitrogen for 10 min. Pd(PPh$_3$)$_4$ (12.1 mg, 0.0105 mmol) was added then the mixture heated in the microwave at 90° C. for 30 min. The mixture was filtered through celite with further methanol washing, then concentrated in vacuo. The crude material was partitioned between DCM and water, passed through a phase separator, concentrated in vacuo then purified by silica gel chromatography, eluting with 0-100% EtOAc/iso-hexane to afford 4-chloro-5-(6-methoxy-pyridazin-3-yl)-7-phenyl-7H-pyrrolo[2,3-d]pyrimidine (CP58) (27.0 mg, 38%); LC-MS. R$_t$ 3.02 min, AnalpH2_MeOH_4 min(1); (ESI$^+$) m/z 338.1, 340.1 [M+H]$^+$.

The following compounds were made using analogous procedures to (CP58) (duration of heating varied between 15-90 min; temperature varied between 90-120° C.):

TABLE 31

| Compound | Cpd # (Intermediate used*) | Analytical Data | Mass, % Yield, State |
|---|---|---|---|
| | CP59 (CP57) | LC-MS. R$_t$ 2.99 min, AnalpH2_MeOH_4min(1); (ESI$^+$) m/z 337.2, 339.2 [M + H]$^+$ | Used directly in next reaction quantitative |
| | CP60 (CP57) | LC-MS. R$_t$ 2.73 min, AnalpH2_MeOH_4min(1); (ESI$^+$) m/z 307.2, 309.2 [M + H]$^+$ | Used directly in next reaction quantitative |
| | CP61 (CP57) | LC-MS. R$_t$ 3.32 min, AnalpH2_MeOH_4min(1); (ESI$^+$) m/z 338.1, 340.1 [M + H]$^+$ | 27.3 mg, 38% |

Route 4, Step 4: Final Compounds Via Acidic Hydrolysis 5-(6-Methoxy-pyridazin-3-yl)-7-phenyl-3,7-dihydro-pyrrolo[2,3-d]pyrimidin-4-one (Ex-104)

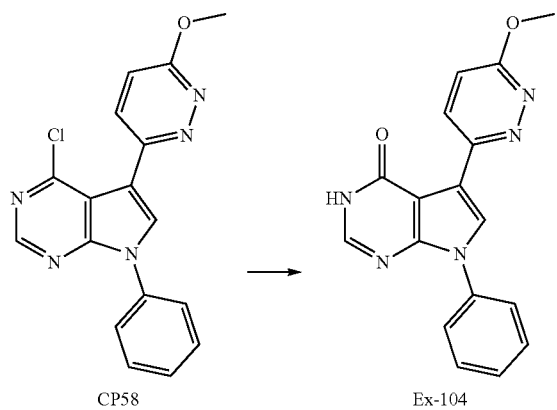

A solution of 4-chloro-5-(6-methoxy-pyridazin-3-yl)-7-phenyl-7H-pyrrolo[2,3-d]pyrimidine (CP58) (27.0 mg, 0.08 mmol), sodium acetate (20.0 mg, 0.24 mmol) and AcOH (1 mL) was heated to 100° C. for 3 h. The mixture was purified by reversed phase preparative HPLC-MS. The material obtained was lyopilised to afford 5-(6-methoxy-pyridazin-3-yl)-7-phenyl-3,7-dihydro-pyrrolo[2,3-d]pyrimidin-4-one (Ex-104) as a white solid (2.5 mg, 6%); LC-MS. $R_t$ 5.54 min, AnalpH2_MeOH_QC_V1 (1); (ESI$^+$) m/z 320.2 [M+H]$^+$.

The following compounds of formula (1a) were prepared using analogous procedures to compound Ex-104 with reaction time varying between 1-3 h:

TABLE 32

| Compound | Ex. # (Intermediate used$^a$) | Analytical Data | Mass, % Yield, State |
|---|---|---|---|
| ![structure] | Ex-105 (CP59) | LC-MS. $R_t$ 4.67 min, AnalpH2_MeOH_QC_V1(1); (ESI$^+$) m/z 319.2 [M + H]$^+$ | 6 mg, 24%, white solid |
| ![structure] | Ex-106 (CP60) | LC-MS. $R_t$ 4.27 min, AnalpH2_MeOH_QC_V1(1); (ESI$^+$) m/z 289.2 [M + H]$^+$ | 9 mg, 14%, white solid |

TABLE 32-continued

| Compound | Ex. # (Intermediate used) | Analytical Data | Mass, % Yield, State |
|---|---|---|---|
| 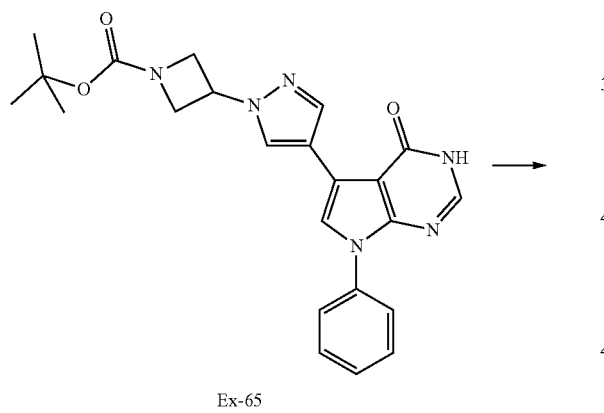 | Ex-107 (CP61) | LC-MS. $R_t$ 7.98 min, AnalpH2_MeOH_QC_V1(1); (ESI$^+$) m/z 320.2 [M + H]$^+$ | 14 mg, 56%, yellow solid |

Final Compounds Via Further Functionalisation after Hydrolysis //Suzuki

Ex-108 was prepared from Ex-65 using Boc-deprotection conditions:

5-(1-Azetidin-3-yl-1H-pyrazol-4-yl)-7-phenyl-3,7-dihydro-pyrrolo[2,3-d]pyrimidin-4-one (Ex-108)

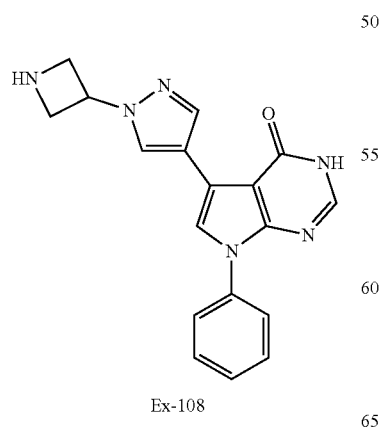

Ex-65

To a solution of 3-[4-(4-oxo-7-phenyl-4,7-dihydro-3H-pyrrolo[2,3-d]pyrimidin-5-yl)-pyrazol-1-yl]-azetidine-1-carboxylic acid tert-butyl ester (Ex-65) (16.1 mg, 0.037 mmol) in DCM (500 µL) was added TFA (250 µL) dropwise. The resulting mixture was stirred at RT for 90 min. The reaction mixture was concentrated in vacuo, azeotroped with toluene. The crude compound was purified by reversed phase chromatography to afford the title compound which was passed through SCX-2 cartridge eluting with 0.5% MeOH/DCM then purified by reverse phase chromatography to afford 5-(1-Azetidin-3-yl-1H-pyrazol-4-yl)-7-phenyl-3,7-dihydro-pyrrolo[2,3-d]pyrimidin-4-one (Ex-108) as a white solid (0.91 mg, 7%); LC-MS. $R_t$ 4.80 min, AnalpH2_MeOH_QC_V1(1); (ESI$^+$) m/z 333.3 [M+H]$^+$.

Ex-108

The following examples were made using analogous procedures to (Ex-108) with reaction time varying between 30 min-2 h.

TABLE 33

| Compound | Ex. # (Intermediate used*) | Analytical Data | Mass, % Yield, State |
|---|---|---|---|
| (structure) | Ex-109 (Ex-58) | LC-MS. R$_t$ 4.66 min, AnalpH2_MeOH_QC_V1(1); (ESI$^+$) m/z 335.3 | 6 mg, 9%, white solid |
| (structure) | Ex-110 (Ex-74) | LC-MS. R$_t$ 4.93 min, AnalpH2_MeOH_QC_V1(1); (ESI$^+$) m/z 376.3 [M + H]$^+$. | 44 mg, 48%, white solid |
| (structure) | Ex-111 (Ex-93) | LC-MS. R$_t$ 5.09 min, AnalpH2_MeOH_QC_V1(1); (ESI$^+$) m/z 390.3 [M + H]$^+$; $^1$H-NMR (400 MHz, DMSO-d$_6$): δ 9.04 (d, J = 2.8 Hz, 1H), 8.62 (dd, J = 4.6, 1.4 Hz, 1H), 8.25 (ddd, J = 8.2, 2.8, 1.4 Hz, 1H), 8.01 (s, 1H), 7.93 (d, J = 8.7 Hz, 2H), 7.84 (s, 1H), 7.62 (ddd, J = 8.2, 4.6, 1.4 Hz, 1H), 6.96 (d, J = 8.7 Hz, 2H), 4.13 (t, J = 7.3 Hz, 2H), 1.79 (t, J = 7.3 Hz, 2H), 1.11 (s, 6H). | 44 mg, 31% over 2 steps (including Suzuki coupling), white solid |

Ex-112 was prepared from Ex-23 using hydrogenation conditions:

7-Phenyl-5-(1H-pyrazol-4-yl)-3,7-dihydro-pyrrolo[2,3-d]pyrimidin-4-one (Ex-112)

(Ex-113) was synthesised from (Ex-22) using reduction of the corresponding ester:

5-[1-(3-Hydroxy-propyl)-1H-pyrazol-4-yl]-7-phenyl-3,7-dihydro-pyrrolo[2,3-d]pyrimidin-4-one (Ex-113)

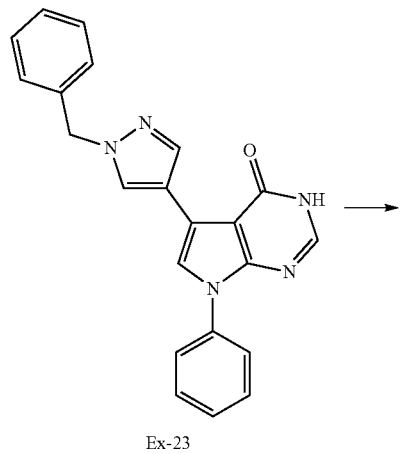
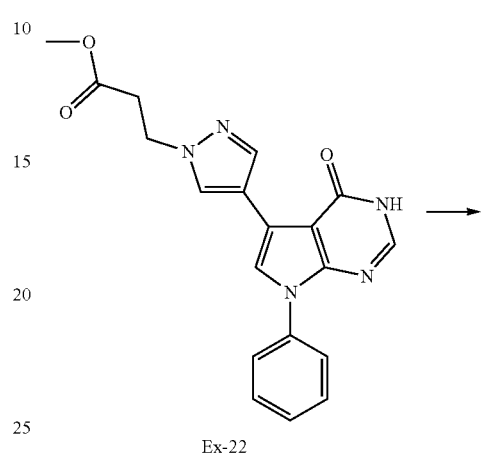
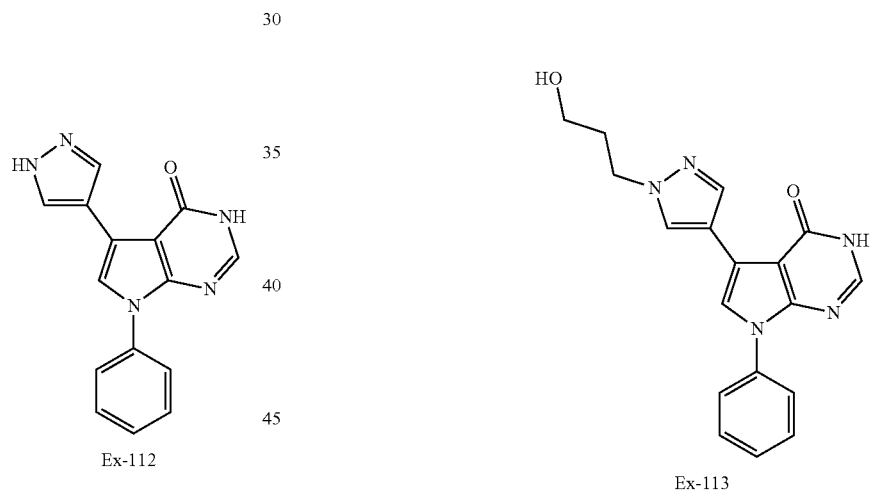

A mixture of 10% palladium/carbon (1.53 mg, 10% wt by weight) and (5-(1-benzyl-1H-pyrazol-4-yl)-4-chloro-7-phenyl-7H-pyrrolo[2,3-d]pyrimidine (Ex-23) (15.3 mg, 0.042 mmol) in EtOH (2 mL) was heated at 70° C. for 3 h under a hydrogen atmosphere. The reaction mixture was then filtered through a pad of celite and washed with MeOH. The organics were concentrated in vacuo and the crude compound was then purified by reversed phase chromatography to afford 7-phenyl-5-(1H-pyrazol-4-yl)-3,7-dihydro-pyrrolo[2,3-d]pyrimidin-4-one (Ex-112) as a white solid (5.02 mg, 43%); LC-MS. $R_t$ 6.68 min, AnalpH2_MeOH_QC_V1(1); (ESI$^+$) m/z 278.2 [M+H]$^+$.

3-[4-(4-Oxo-7-phenyl-4,7-dihydro-3H-pyrrolo[2,3-d]pyrimidin-5-yl)-pyrazol-1-yl]-propionic acid methyl ester (Ex-22) (48 mg, 0.13 mmol) was dissolved in anhydrous THF (5 mL) and cooled to 0° C. under an nitrogen atmosphere. Lithium aluminium hydride (1 M in THF, 160 μL, 0.16 mmol) was added dropwise over 2 min and the reaction allowed to reach RT over 4 h whilst stirring. EtOAc was added to the reaction mixture and the solution stirred for 30 min. Volatiles were removed by rotary evaporator and the residue partitioned between EtOAc and H$_2$O. The organic layer was separated and dried by passing through a phase separator and the organics were concentrated in vacuo. The product was purified by reversed phase chromatography to afford 5-[1-(3-hydroxy-propyl)-1H-pyrazol-4-yl]-7-phenyl-3,7-dihydro-pyrrolo[2,3-d]pyrimidin-4-one (Ex-113) as a white solid (6 mg, 14%; LC-MS. $R_t$ 6.75 min, AnalpH2_MEOH_QC_V1(1); (ESI$^+$) m/z 336.3 [M+H]+.

A number of examples of formula (1b) were synthesised according to route 5
Route 5: Scheme 5

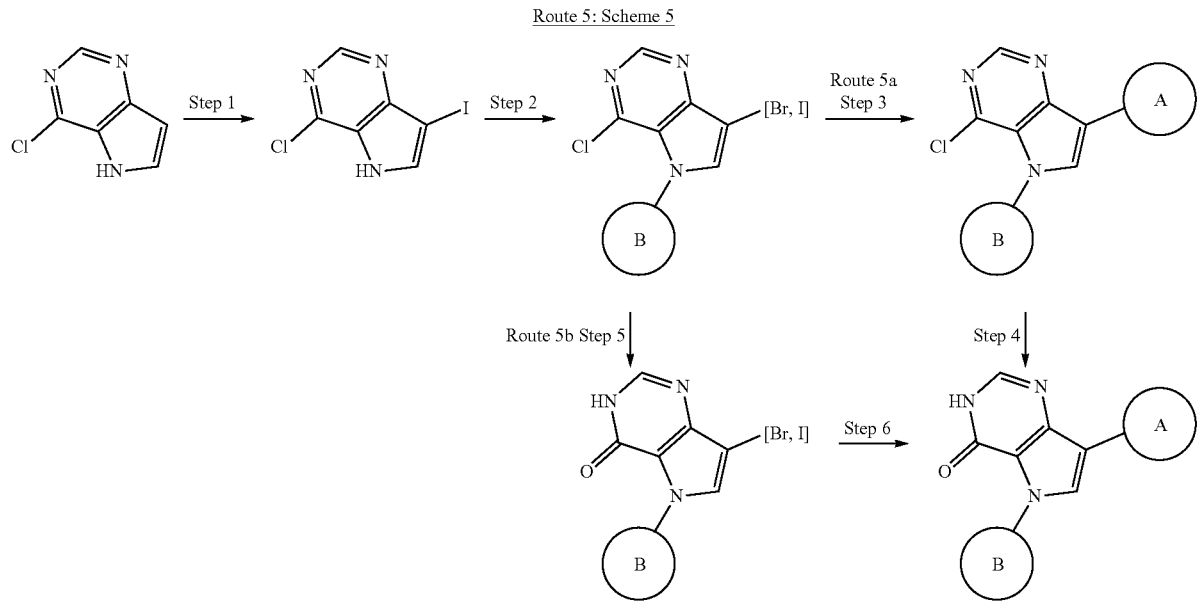

Route 5, Step 1: Iodination

4-Chloro-7-iodo-5H-pyrrolo[3,2-d]pyrimidine (CH20)

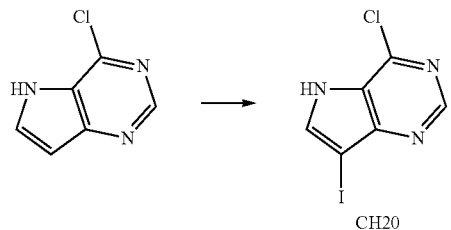

To a solution of 4-chloro-5H-pyrrolo[3,2-d]pyrimidine (25.0 g, 162.8 mmol) in THF (700 mL) was added N-iodosuccinamide (40.1 g, 179 mmol) at the resulting mixture was stirred for 4 h at RT and then was concentrated in vacuo. The residue triturated in Et$_2$O, the resulting solid was collected by filtration and washed with Et$_2$O. The crude compound was purified by silica gel column chromatography eluting with 20-30% EtOAc/petroleum ether to afford 4-chloro-7-iodo-5H-pyrrolo[3,2-d]pyrimidine (CH2O) as a yellow solid (32.0 g, 70%); LC-MS. R$_t$ 2.29 min, AnalpH2_MeOH_4 min(1); (ESI$^+$) m/z 280.0, 282.0 [M+H]$^+$.

Route 5, Step 2: Chan-Lam

4-Chloro-7-iodo-5-phenyl-5H-pyrrolo[3,2-d]pyrimidine (CH21)

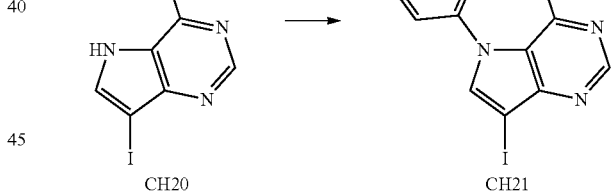

To a solution of 4-chloro-7-iodo-5H-pyrrolo[3,2-d]pyrimidine (CH6) (40.42 g, 249.55 mmol) in DMF (250 mL) was added Cu(OAc)$_2$ (49.82 g, 249.55 mmol) and activated molecular sieves (1.00 g) followed by addition of NEt$_3$ (52.07 mL, 374.31 mmol) and the resulting reaction mixture was heated at 60° C. for 24 h. The reaction mixture was cooled to RT and the solvent concentrated in vacuo. The crude solid was dissolved in DCM (600 mL) and quenched with saturated aqueous solution of EDTA (200 mL). The separated aqueous layer was dried (anhydrous Na$_2$SO$_4$), filtered and concentrated in vacuo to afford a crude solid. The crude compound was purified by silica gel column chromatography eluting with 0-5% EtOAc/petroleum ether to afford 4-chloro-7-iodo-5-phenyl-5H-pyrrolo[3,2-d]pyrimidine (CH$_8$) as an off-white solid (5.2 g, 12%); LC-MS. R$_t$ 3.08 min, AnalpH2_MeOH_4 min(1); (ESI$^+$) m/z 356.1, 358.1 [M+H]$^+$; $^1$H NMR (400 MHz, DMSO-d$_6$): δ 8.80 (s, 1H), 8.39 (s, 1H), 7.64-7.54 (m, 5H).

The following intermediates were synthesised using an analogous procedure to CH$_{21}$ from CH20:

TABLE 34

| Compound | Cpd # (Intermediate used[a]) | Analytical Data | Mass, % Yield, State |
|---|---|---|---|
| (structure shown) | CH22[a] | LC-MS. R$_t$ 3.11 min, AnalpH2_MeOH_4min; (ESI$^+$) m/z 308.2, 310.2 [M + H]$^+$ | 844 mg, 21%, off-white solid |
| (structure shown) | CH23[b] (CH21, B2) | LC-MS. R$_t$ 3.16 min, AnalpH2_MeOH_4min; (ESI$^+$) m/z 457.9, 459.9 [M + H]$^+$ | 792 mg, 17%, pale beige solid |

[a]Work-up carrried out with 20% aq. NH$_4$OH;
[b]Work-up carried out with EDTA solution.

Route 5a, Step 3: Suzuki-Miyaura Coupling

7-[6-(3-Dimethylamino-propoxy)-pyridin-3-yl]-5-phenyl-3,5-dihydro-pyrrolo[3,2-d]pyrimidin-4-one (CP62)

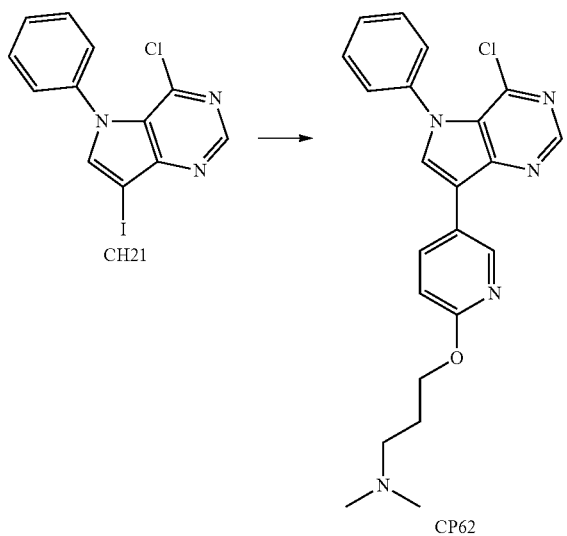

A mixture of 4-chloro-7-iodo-5-phenyl-5H-pyrrolo[3,2-d]pyrimidine (CH$_{21}$) (100 mg, 0.281 mmol), N,N-dimethyl-3-((5-(4,4,5,5-tetramethyl-1,3,2-dioxaborolan-2-yl)pyridine-2-yl)oxypropan-1-amine (103 mg, 0.337 mmol), (commercial source), Pd(dppf)Cl$_2$.DCM (22.9 mg, 0.028 mmol) and potassium carbonate (77.7 mg, 0.56 mmol) in 1,4-dioxane:H$_2$O (1.5 mL, 9:1) was deoxygenated with N$_2$ for 5 mins and then heated in the microwave at 90° C. for 1 h. The reaction mixture was filtered through a Si-thiol cartridge (1 g) and washed with MeOH (3×CV) followed by DCM (3×CV). The organics were concentrated in vacuo. The crude solid was purified by reversed phase preparative HPLC-MS to afford 7-[6-(3-dimethylamino-propoxy)-pyridin-3-yl]-5-phenyl-3,5-dihydro-pyrrolo[3,2-d]pyrimidin-4-one formic acid salt (CP62) as an orange oil (75 mg, 59%). LC-MS. R$_t$ 2.20 min, AnalpH2_MeOH_4 min(1); (ESI$^+$) m/z 408.2, 410.2 [M+H]$^+$.

The following compounds were made using analogous procedures to (CP62) (duration of heating varied between 15-90 min; temperature varied between 90-95° C.):

TABLE 35

| Compound | Cpd # (Intermediate used*) | Analytical Data | Mass, % Yield, State |
|---|---|---|---|
| (structure) | CP63 (CH21) | LC-MS. R$_t$ 2.98 min, AnalpH2_MeOH_4min(1); (ESI$^+$) m/z 308.2, 310.2 [M + H]$^+$. | 32.8 mg, 54%, orange oil |
| (structure) | CP64 (CH21) | LC-MS. R$_t$ 2.82 min, AnalpH2_MeOH_4min(1); (ESI$^+$) m/z 308.3, 310.3 [M + H]$^+$. | 32.1 mg, 49%, orange oil |
| (structure) | CP65 (CH21) | LC-MS. R$_t$ 2.31 min, AnalpH2_MeOH_4min(1); (ESI$^+$) m/z 346.2, 348.2 [M + H]$^+$. | 144 mg, quant, brown oil |
| (structure) | CP66 (CH21) | LC-MS. R$_t$ 3.39 min, AnalpH2_MeOH_4min; (ESI$^+$) m/z 346.1, 348.1 [M + H]$^+$. | 151 mg, quant, yellow oil |

Route 5a, Step 4: Final Compounds Via Acidic Hydrolysis

7-[6-(3-Dimethylamino-propoxy)-pyridin-3-yl]-5-phenyl-3,5-dihydro-pyrrolo[3,2-d]pyrimidin-4-one (Ex-114)

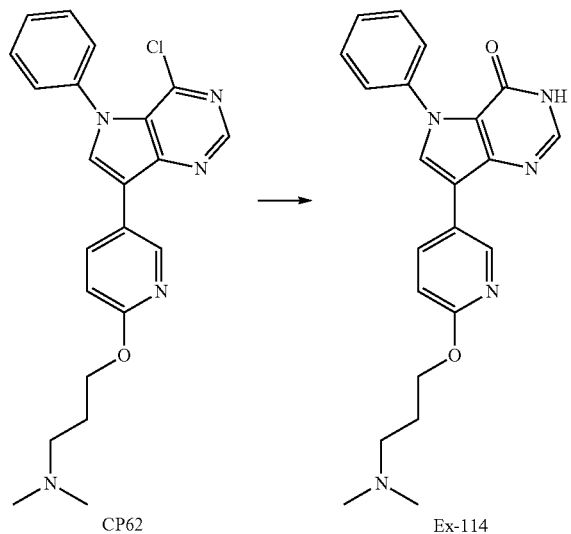

A mixture of {3-[5-(4-chloro-5-phenyl-5H-pyrrolo[3,2-d]pyrimidin-7-yl)-pyridin-2-yloxy]-propyl}dimethylamine formic acid salt (CP62) (73.9 mg, 0.163 mmol) and sodium acetate (26.7 mg, 0.326 mmol) in AcOH (326 µL) was heated at 100° C. for 5 h. The reaction mixture was concentrated in vacuo. The crude residue was purified by reversed phase preparative HPLC-MS and isolated as a free base after passing through SCX-2 (2 g) to afford {3-[5-(4-chloro-5-phenyl-5H-pyrrolo[3,2-d]pyrimidin-7-yl)-pyridin-2-yloxy]-propyl}-dimethyl-amine (Ex-114) as a white solid (55 mg, 87%). LC-MS. $R_t$ 5.16 min, AnalpH2_MeOH_QC_V1(1); (ESI$^+$) m/z 390.2 [M+H]$^+$; $^1$H-NMR (400 MHz, DMSO-d$_6$): δ 12.17 (s, 1H), 8.86 (d, 0=2.3 Hz, 1H), 8.41 (dd, J=8.5, 2.5 Hz, 1H), 8.16 (s, 1H), 8.00 (s, 1H), 7.59-7.55 (m, 2H), 7.50 (**t, J=7.6 Hz, 2H), 7.45-7.40 (m, 1H), 6.87 (d, J=8.7 Hz, 1H), 4.30 (t, J=6.6 Hz, 2H), 2.35 (t, J=7.3 Hz, 2H), 2.14 (s, 6H), 1.86 (quint, J=8.7 Hz, 2H).

The following examples were synthesised using an analogous procedure to Ex-114 with reaction time varying between 3-16 h:

TABLE 36

| Compound | Ex. # (Intermediate used) | Analytical Data | Mass, % Yield, State |
|---|---|---|---|
|  | Ex-115 (CP63) | LC-MS. $R_t$ 6.43 min, AnalpH2_MeOH_QC_V1(1); (ESI$^+$) m/z 290.2 [M + H]$^+$. | 18 mg, 58%, white solid |
|  | Ex-116 (CP64) | LC-MS. $R_t$ 6.00 min, AnalpH2_MeOH_QC_V1(1); (ESI$^+$) m/z 290.2 [M + H]$^+$ | 10 mg, 34%, white solid |

| Compound | Ex. # (Intermediate used) | Analytical Data | Mass, % Yield, State |
|---|---|---|---|
| (structure) | Ex-117 (CP65) | LC-MS. $R_t$ 7.92 min, AnalpH2_MeOH_QC_V1(1); (ESI$^+$) m/z 328.2 [M + H]$^+$; $^1$H-NMR (400 MHz, DMSO-$d_6$): δ 12.31 (br s, 1H), 8.29 (s, 1H), 8.17 (s, 1H), 8.12 (s, 1H), 8.08 (d, J = 6.9 Hz, 1H), 7.72 (d, J = 8.2 Hz, 1H), 7.69 (d, J = 7.4 Hz, 2H), 7.53 (t, J = 7.4 Hz, 2H), 7.44 (tt, J = 7.4, 1.3 Hz, 1H), 7.21 (t, J = 7.33 Hz, 1H). | 14 mg, 10%, white solid |
| (structure) | Ex-118 (CP66) | LC-MS. $R_t$ 5.13 min, AnalpH2_MeOH_QC_V1(1); (ESI$^+$) m/z 328.2 [M + H]$^+$ | 25 mg, 18%, off-white solid |

A number of examples of formula (1b) were synthesised according to Route 5b, Step 5

7-Bromo-5-phenyl-3,5-dihydro-pyrrolo[3,2-d]pyrimidin-4-one (CH24)

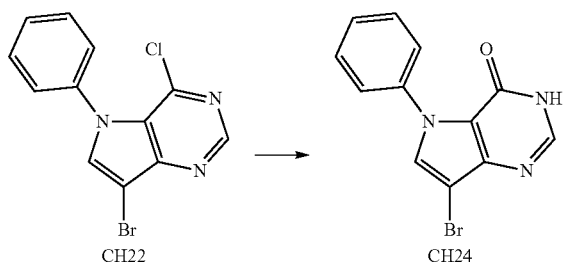

To a solution of 7-bromo-4-chloro-5-phenyl-5H-pyrrolo[3,2-d]pyrimidine (CH22) (840 mg, 2.72 mmol) in AcOH (13.6 mL) was added sodium acetate (447 mg, 5.44 mmol) and the reaction mixture heated at 100° C. for 18 h. The reaction mixture was cooled to RT, diluted with H$_2$O and DCM. The layers were separated (phase separator) and the organic phase evaporated in vacuo. The crude compound was purified by silica gel column chromatography eluting with 0-10% MeOH/DCM to obtain 7-bromo-5-phenyl-3,5-dihydro-pyrrolo[3,2-d]pyrimidin-4-one (CH$_{24}$) as an off-white solid (341 mg, 43%); LC-MS. $R_t$ 2.72 min, AnalpH2_MeOH_4 min(1); (ESI$^+$) m/z 290.2, 292.2 [M+H]$^+$.

The following examples were synthesised using an analogous procedure to CH$_{24}$ with reaction time varying between 4-16 h:

TABLE 37

| Compound | Cpd # (Intermediate used[a]) | Analytical Data | Mass, % Yield, State |
|---|---|---|---|
| 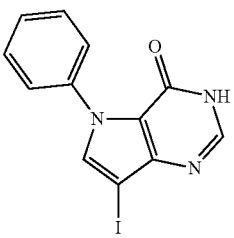 [SMILES: O=c1[nH]cnc2c(I)cn(-c3ccccc3)c12] | CH25[a] (CH21) | LC-MS. $R_t$ 2.74 min, AnalpH2_MeOH_4min; (ESI$^+$) m/z 338.1 [M + H]$^+$. | 2.85 g, quant., off-white solid |
| 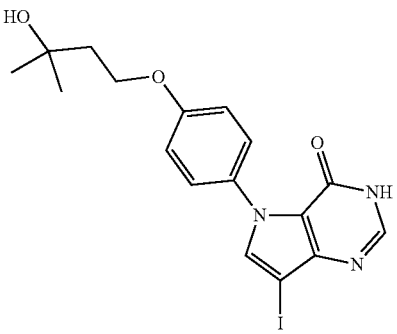 [SMILES: CC(C)(O)CCOc1ccc(-n2cc(I)c3nc[nH]c(=O)c32)cc1] | CH26[a] (CH23) | LC-MS. $R_t$ 2.94 min, AnalpH2_MeOH_4min; (ESI$^+$) m/z 440.1 [M + H]$^+$. | 71 mg, 81%, pale brown solid |

[a]Compound was isolated by trituration with water.

Route 5b, Step 6—Suzuki-Miyaura Coupling

5-Phenyl-7-pyridin-4-yl-3,5-dihydro-pyrrolo[3,2-d]pyrimidin-4-one (Ex-119)

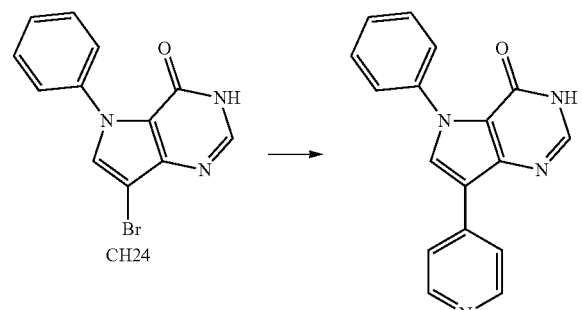

A mixture of 7-bromo-5-phenyl-3,5-dihydro-pyrrolo[3,2-d]pyrimidin-4-one (CH24) (46.8 mg, 0.161 mmol), 4-pyridineboronic acid pinacol ester (33.0 mg, 0.161 mmol), Pd(dppf)Cl$_2$.DCM (13.1 mg, 0.016 mmol) and potassium carbonate (44.5 mg, 0.322 mmol) in dioxane:water (1.5 mL, 9:1) was degassed for 5 min and then heated in the microwave at 120° C. for 1 h. The reaction mixture was filtered through Si-thiol cartridge (1 g) and washed with MeOH. The organics were concentrated in vacuo. The crude solid was purified by reverse phase preparative HPLC-MS to afford 5-phenyl-7-pyridin-4-yl-3,5-dihydro-pyrrolo[3,2-d]pyrimidin-4-one (Ex-119) as an off-white solid (13.4 mg, 29%); LC-MS. $R_t$ 4.28 min, AnalpH2_MeOH_QC_V1(1); (ESI$^+$) m/z 289.2 [M+H]$^+$.

The following examples were synthesised using an analogous procedure to (Ex-119) with reaction time varying between 1-2 h:

TABLE 38

| Compound | Ex. # (Intermediate used) | Analytical Data | Mass, % Yield, State |
|---|---|---|---|
| *structure* | Ex-120 (CH25) | LC-MS. R$_t$ 6.73 min, AnalpH2_MeOH_QC_V1(1); (ESI$^+$) m/z 292.3 [M + H]$^+$. | 10 mg, 38%, off-white solid |
| *structure* | Ex-121 (CH25) | LC-MS. R$_t$ 6.73 min, AnalpH2_MeOH_QC_V1(1); (ESI$^+$) m/z 307.2 [M + H]$^+$. | 2 mg, 12%, off-white solid |
| *structure* | Ex-122 (CH25) | LC-MS. R$_t$ 6.57 min, AnalpH2_MeOH_QC_V1(1); (ESI$^+$) m/z 292.2 [M + H]$^+$. | 20 mg, 43%, white solid |
| *structure* | Ex-123 (CH25, B38) | LC-MS. R$_t$ 6.22 min, AnalpH2_MeOH_QC_V1(1); (ESI$^+$) m/z 322.2 [M + H]$^+$; $^1$H NMR (400 MHz, DMSO-d$_6$): δ 12.11 (br s, 1H), 8.23 (s, 1H), 7.98-7.97 (m, 3H), 7.55-7.47 (m, 4H), 7.40 (tt, J = 1.5, 7.1 Hz, 1H), 4.93 (t, J = 5.3 Hz, 1H), 4.18 (t, J = 5.8 Hz, 2H), 3.75 (q, J = 5.8 Hz, 2H). | 14 mg, 29%, off-white solid |

TABLE 38-continued

| Compound | Ex. # (Intermediate used) | Analytical Data | Mass, % Yield, State |
|---|---|---|---|
| | Ex-124 (CH25) | LC-MS. R$_t$ 4.75 min, AnalpH2_MeOH_QC_V1(1); (ESI$^+$) m/z 289.3 [M + H]$^+$. | 15 mg, 35%, off-white solid |

Route 5a, Step 6: Final Compounds Via Suzuki Coupling Using PdXPhosG3 with K$_3$PO$_4$ as Base 5-(4-(3-hydroxy-3-methylbutoxy)phenyl)-7-(pyridin-3-yl)-3,5-dihydro-4H-pyrrolo[3,2-d]pyrimidin-4-one (Ex-125)

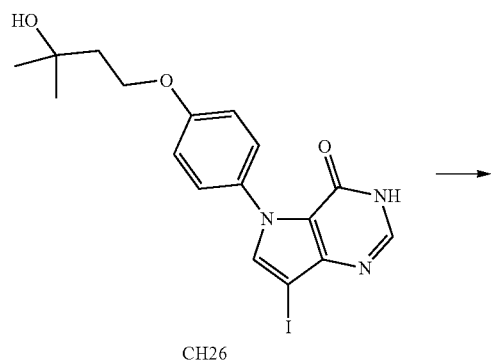

CH26

5-(4-(3-hydroxy-3-methylbutoxy)phenyl)-7-iodo-3,5-dihydro-4H-pyrrolo[3,2-d]pyrimidin-4-one (CH26) (68.4 mg, 0.156 mmol), pyridine-3-boronic acid (28.8 mg, 0.234 mmol), K$_3$PO$_4$ (66.2 mg, 0.312 mmol), PdXPhosG3 (6.6 mg, 0.0078 mmol) in 1,4-dioxane:water (1.5 mL, 4:1) was deoxygenated with N$_2$ for 5 min and then heated in a microwave reactor at 90° C. for 1 h. The reaction mixture was filtered through a Si-thiol cartridge (1 g) and washed with MeOH (3×CV) followed by DCM (3×CV). The filtrate was evaporated to dryness and the crude compound was purified by reversed phase preparative HPLC-MS twice to afford 5-(4-(3-hydroxy-3-methylbutoxy)phenyl)-7-(pyridin-3-yl)-3,5-dihydro-4H-pyrrolo[3,2-d]pyrimidin-4-one (Ex-125) as a white solid (32 mg, 37%); LC-MS. R$_t$ 5.91 min, AnalpH2_MeOH_QC_V1(1); (ESI$^+$) m/z 391.2 [M+H]$^+$; $^1$H-NMR (400 MHz, DMSO-d$_6$): δ 12.20 (s, 1H), 9.32-9.30 (m, 1H), 8.50 (dt, J=8.1, 1.9 Hz, 1H), 8.44 (dd, J=4.6, 1.8 Hz, 1H), 8.22 (s, 1H), 8.01 (s, 1H), 7.47 (d, J=9.2 Hz, 2H), 7.45-7.41 (m, 1H), 7.03 (d, J=9.2 Hz, 2H), 4.43 (s, 1H), 4.15 (t, J=7.3 Hz, 2H), 1.88 (t, 0=7.1 Hz, 2H).

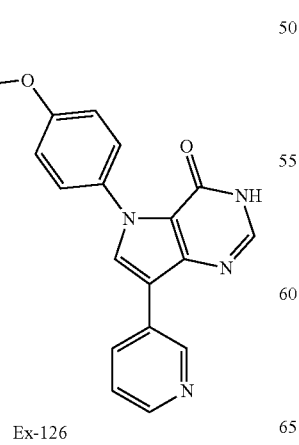

Ex-126

The following compounds of formula 0 were made using analogous procedures to compound (Ex-125) with reaction time varying between 1-1.5 h:

TABLE 39

| Compound | Ex. # (Intermediate used) | Analytical Data | Mass, % Yield, State |
|---|---|---|---|
| (structure) | Ex-126 (CH25) | LC-MS. R$_t$ 4.2 min, AnalpH2_MeOH_QC_V1(1); (ESI$^+$) m/z 304.2 [M + H]$^+$. | 12 mg, 13%, white solid |
| (structure) | Ex-127 (CH25) | LC-MS. R$_t$ 7.25 min, AnalpH2_MeOH_QC_V1(1); (ESI$^+$) m/z 319.2 [M + H]$^+$. | 18 mg, 19%, white solid |
| (structure) | Ex-128$^a$ (CH25) | LC-MS. R$_t$ 6.23 min, AnalpH2_MeOH_QC_V1(1); (ESI$^+$) m/z 305.2 [M + H]$^+$. | 2 mg, 2%, white solid |
| (structure) | Ex-129$^a$ (CH25, B19) | LC-MS. R$_t$ 5.10 min, AnalpH2_MeOH_QC_V1(1); (ESI$^+$) m/z 342.3 [M + H]$^+$. | 26 mg, 17%, white solid |

TABLE 39-continued

| Compound | Ex. # (Intermediate used) | Analytical Data | Mass, % Yield, State |
|---|---|---|---|
| | Ex-130[a] (CH25) | LC-MS. R$_t$ 4.53 min, AnalpH2_MeOH_QC_V1(1); (ESI$^+$) m/z 303.5. | 8 mg, 9%, White solid |
| | Ex-131[a] (CH25) | LC-MS. R$_t$ 4.74 min, AnalpH2_MeOH_QC_V1(1); (ESI$^+$) m/z 303.2. | 10 mg, 10%, white solid |
| | Ex-132[a] (CH25) | LC-MS. R$_t$ 7.66 min, AnalpH2_MeOH_QC_V1(1); (ESI$^+$) m/z 319.2 | 18 mg, 20%, pink solid |
| | Ex-133[a] (CH25, B37) | LC-MS. R$_t$ 3.13 min, AnalpH2_MeOH_4min; (ESI$^+$) m/z 404.2 [M + H]$^+$. | Assume quant. |

TABLE 39-continued

| Compound | Ex. # (Intermediate used) | Analytical Data | Mass, % Yield, State |
|---|---|---|---|
| 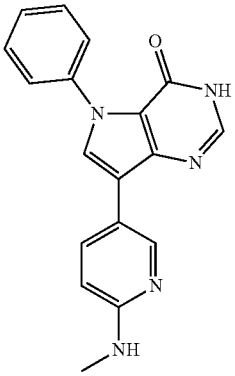 [SMILES: COc1ccc(-c2cn(-c3ccccc3)c3c(=O)[nH]cnc23)cn1] | Ex-134[a] (CH25) | LC-MS. R$_t$ 4.87 min, AnalpH2_MeOH_QC_V1(1); (ESI$^+$) m/z 318.2 [M + H]$^+$; $^1$H-NMR (400 MHz, DMSO-d$_6$): δ 12.13 (br s, 1H), 8.73 (d, J = 1.8 Hz, 1H), 8.10 (dd, J = 8.7, 2.3 Hz, 1H), 8.01 (s, 1H), 7.97 (s, 1H), 7.59-7.53 (m, 2H), 7.50 (t, J = 7.3 Hz, 2H), 7.41 (t, J = 7.3 Hz, 1H), 6.54-6.45 (m, 2H), 2.80 (d, J = 4.6 Hz, 3H). | 16 mg, 17%, white solid |
| 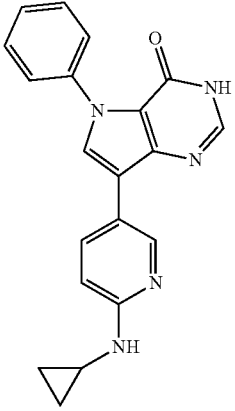 [SMILES: O=c1[nH]cnc2c(-c3ccc(NC4CC4)nc3)cn(-c3ccccc3)c12] | Ex-135[a] (CH25) | LC-MS. R$_t$ 5.24 min, AnalpH2_MeOH_QC_V1(1); (ESI$^+$) m/z 344.2 [M + H]$^+$; $^1$H-NMR (400 MHz, DMSO-d$_6$): δ 12.15 (br s, 1H), 8.75 (d, J = 1.8 Hz, 1H), 8.16 (dd, J = 8.7, 2.3 Hz, 1H), 8.03 (s, 1H), 7.98 (s, 1H), 7.59-7.54 (m, 2H), 7.50 (t, J = 7.3 Hz, 2H), 7.41 (t, J = 7.3 Hz, 1H), 6.81 (d, J = 1.8 Hz, 1H), 6.67 (d, J = 8.7 Hz, 1H), 2.56-2.52 (m, 1H), 0.75-0.67 (m, 2H), 0.47-0.40 (m, 2H). | 34 mg, 34%, white solid |
| 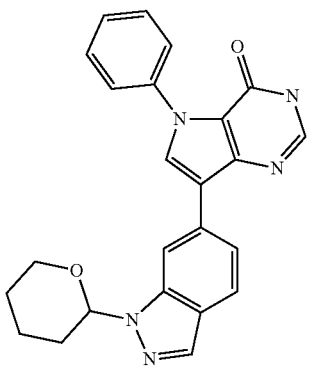 [SMILES: O=c1[nH]cnc2c(-c3ccc4cnn(C5CCCCO5)c4c3)cn(-c3ccccc3)c12] | Ex-136[a] (CH25, B40) | LC-MS. R$_t$ 3.25 min, AnalpH2_MeOH_4min; (ESI$^+$) m/z 412.1 [M + H]$^+$. | 72 mg, 41%, yellow solid |

[a]K$_3$PO$_4$ added as a solution of water

The following compound was synthesised from the bromo intermediate, without the isolation of the boronic ester or acid:

7-(6-cyclopropoxypyridin-3-yl)-5-phenyl-3,5-dihydro-4H-pyrrolo[3,2-d]pyrimidin-4-one (Ex-137)

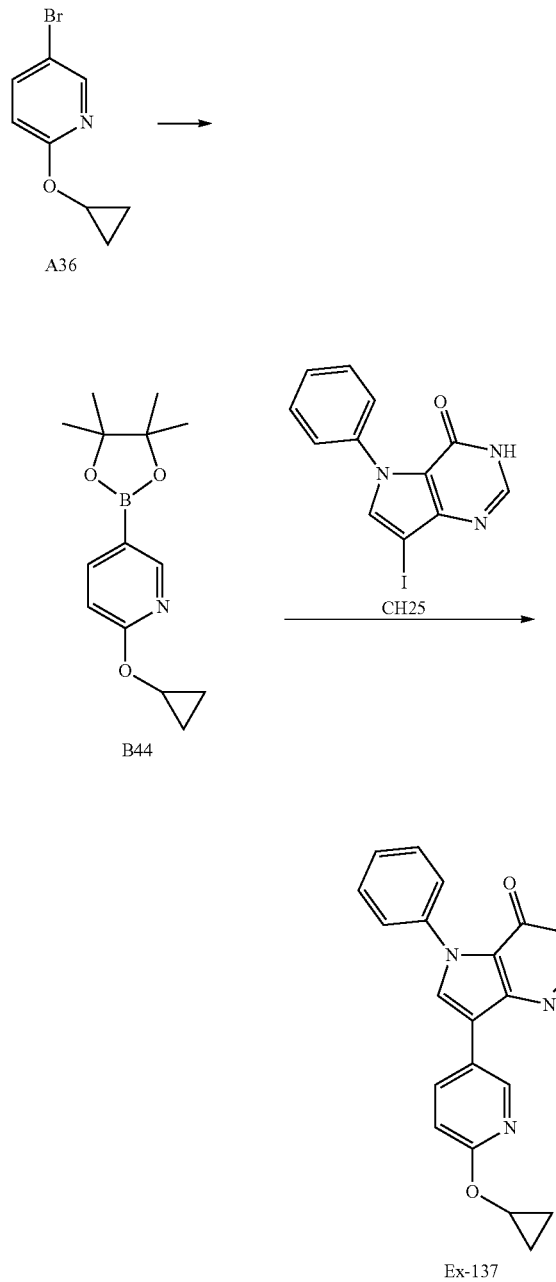

5-bromo-2-cyclopropoxypyridine (A36) (500 mg, 2.34 mmol), bis(pinacolato)diboron (890 mg, 3.50 mmol), Pd(dppf)Cl$_2$.DCM (191 mg, 0.234 mmol) and KOAc (689 mg, 7.20 mmol) in anhydrous 1,4-dioxane (18 mL) was deoxygenated with N$_2$ for 5 min then heated at 100° C. for 18 h. The reaction mixture was cooled to RT then filtered through a celite cartridge (2.5 g) and the filter cake was washed several times with MeOH. The filtrate was evaporated to dryness to afford the crude boron acid/ester (B44) which was re-dissolved in anhydrous 1,4-dioxane (13.2 mL) to afford a 0.18 M stock solution. 7-Iodo-5-phenyl-3,5-dihydro-4H-pyrrolo[3,2-d]pyrimidin-4-one (CH25) (100 mg, 0.296 mmol), PdXPhosG3 (25 mg, 0.03 mmol) and aqueous K$_3$PO$_4$ (1.5 M, 0.5 mL, 0.75 mmol) were then added to the prepared crude boronic acid/ester stock solution (0.18 M, 2.5 mL, 0.444 mmol). The resulting reaction mixture was deoxygenated with N$_2$ for 5 min then heated to 90° C. for 1 h in the microwave. The reaction mixture was cooled to RT, filtered through a Si-thiol column (2 g) and the column was washed with MeOH (2×CV), 1,4-dioxane (2×CV) then with MeOH (3×CV). The solvents were removed in vacuo and the residue was purified by purified by silica gel column chromatography eluting with 0-10% MeOH/DCM followed by reversed phase preparative HPLC to afford 7-(6-cyclopropoxypyridin-3-yl)-5-phenyl-3,5-dihydro-4H-pyrrolo[3,2-d]pyrimidin-4-one (Ex-137) as a white solid (10 mg, 9%). LC-MS. R$_t$ 7.82 min, AnalpH2_MeOH_QC_V1(1); (ESI$^+$) m/z 345.1 [M+H]$^+$; $^1$H-NMR (400 MHz, DMSO-d$_6$): δ 12.30 (brs, 1H), 8.91 (d, J=1.8 Hz, 1H), 8.44 (dd, J=8.7, 2.3 Hz, 1H), 8.19 (s, 1H), 8.02 (s, 1H), 7.61-7.55 (m, 2H), 7.54-7.48 (t, J=7.3 Hz, 2H); 7.46-7.40 (t, J=7.3 Hz, 1H), 6.95 (d, J=8.7 Hz, 1H), 4.27-4.19 (m, 1H), 0.83-0.65 (m, 4H).

Final Compounds Via Further Functionalisation after Hydrolysis (Ex-138) was prepared from (Ex-133) using Boc-deprotection conditions:

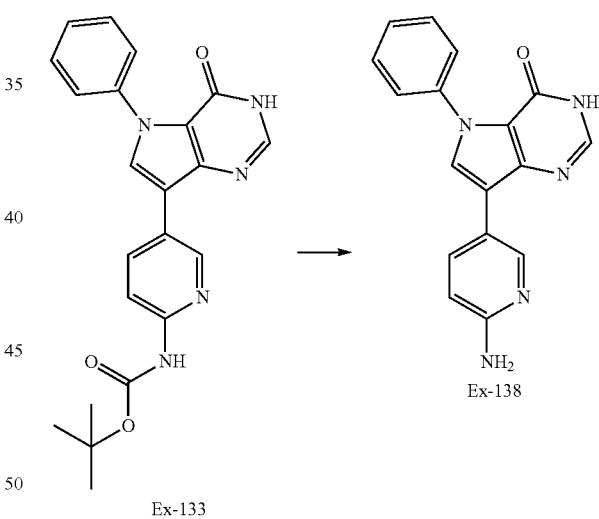

To a solution of tert-butyl (5-(4-oxo-5-phenyl-4,5-dihydro-3H-pyrrolo[3,2-d]pyrimidin-7-yl)pyridin-2-yl)carbamate (Ex-133) (assumed 120 mg, 0.298 mmol) in DCM (15 mL) was added TFA (2 mL) dropwise. The resulting mixture was stirred at RT for 18 h. The reaction mixture was concentrated in vacuo. The crude compound was purified by reversed phased chromatography to afford 7-(6-aminopyridin-3-yl)-5-phenyl-3,5-dihydro-4H-pyrrolo[3,2-d]pyrimidin-4-one (Ex-138) as a white solid (24 mg, 24% over 2 steps); LC-MS. R$_t$ 5.76 min, AnalpH2_MeOH_QC_V1(1); (ESI$^+$) m/z 304.2 [M+H]$^+$; $^1$H NMR (400 MHz, DMSO-d$_6$): δ 12.21 (bs, 1H), 8.67 (d, J=1.8 Hz, 1H), 8.32 (bs, 1H), 8.17-8.04 (m, 2H), 7.97 (d, J=3.7 Hz, 1H), 7.57-7.31 (m, 6H).

(Ex-139) was synthesised from (Ex-136) using THP-deprotection conditions:

7-(1H-Indazol-6-yl)-5-phenyl-3,5-dihydro-pyrrolo[3,2-d]pyrimidin-4-one (Ex-139)

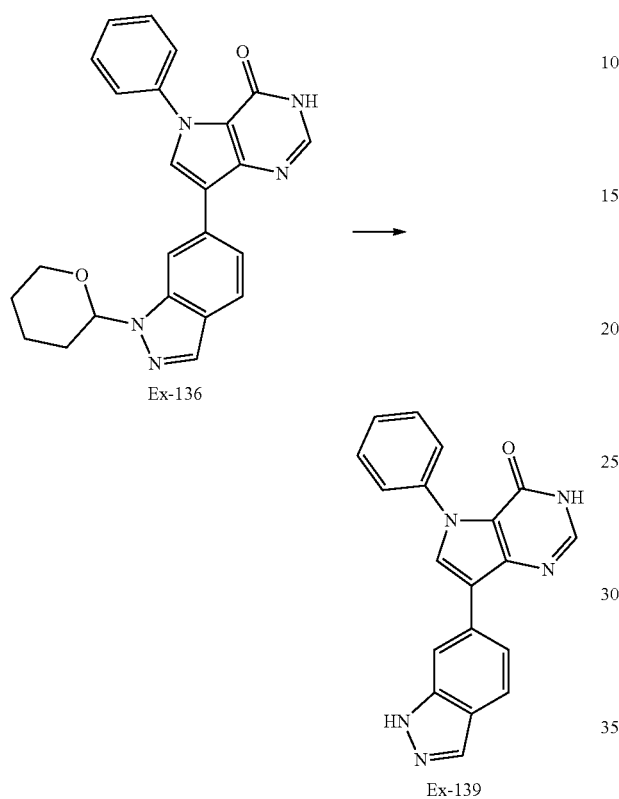

5-Phenyl-7-[1-(tetrahydro-pyran-2-yl)-1H-indazol-6-yl]-3,5-dihydro-pyrrolo[3,2-d]pyrimidin-4-one (Ex-136) (72 mg, 0.18 mmol) was dissolved in a solution of HCl in MeOH (1.25 M, 15 mL) and the reaction mixture stirred at RT for 18 h. Volatiles were removed by rotary evaporator and the crude solid was purified by reversed phase preparative HPLC-MS to afford 7-(1H-Indazol-6-yl)-5-phenyl-3,5-dihydro-pyrrolo[3,2-d]pyrimidin-4-one (Ex-139) as a white solid (23 mg, 40%); LC-MS. $R_t$ 7.52 min, AnalpH2_MeOH_QC_V1 (1); (ESI$^+$) m/z 328.2 [M+H]$^+$; $^1$H-NMR (400 MHz, DMSO-d$_6$): δ 12.24 (br s, 1H), 8.57 (d, J=1.2 Hz, 1H), 8.27 (s, 1H), 8.07 (s, 1H), 8.03 (s, 1H), 7.78 (dd, J=8.2, 1.4 Hz, 1H), 7.74 (d, J=8.7 Hz, 1H), 7.60 (dd, J=8.2, 1.2 Hz, 2H), 7.51 (**t, J=7.3 Hz, 2H), 7.42 (tt, J=7.3, 1.2 Hz, 1H).

A number of examples of formula (Ia) were synthesised according to the following route:

Route 6: Scheme 6

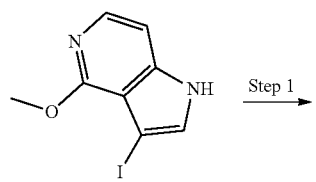

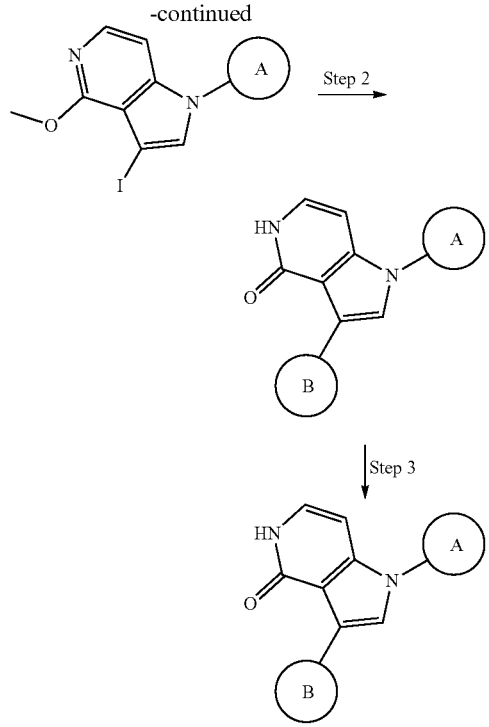

3-Iodo-4-methoxy-1-pyridin-3-yl-1H-pyrrolo[3,2-c]pyridine (CH27)

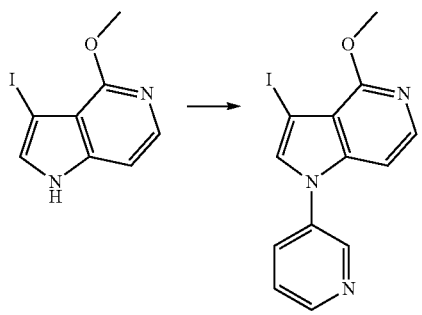

To a solution of 3-Iodo-4-methoxy-1H-pyrrolo[3,2-c]pyridine (1.00 g, 3.6 mmol), 3-pyridyl boronic acid (718 mg, 5.8 mmol), 2,2'-bipyridyl (1.14 g, 7.3 mmol), NEt$_3$ (7.6 mL, 55 mmol) and molecular sieves (4 Å, 1 g) in DCM (18 mL) was added Cu(OAc)$_2$ (1.33 g, 7.3 mmol). The flask was evacuated and flushed with dried air (×2). The flask was sealed and a P$_2$O$_5$ filled syringe was placed in the suba seal and the reaction was stirred at RT overnight. The reaction mixture was passed through a celite cartridge (10 g) and the cartridge washed with MeOH (2×CV) and DCM (2×CV) and the filtrate evaporated to dryness. The residue was dissolved in MeOH and passed through a SCX-2 cartridge (25 g), washing with MeOH (2×CV) and DCM (2×CV). The compound was eluted from the column with 0.7 M NH$_3$/MeOH and the solvent removed in vacuo. The crude compound was purified by silica gel column chromatography eluting with 15-60% EtOAc/iso-hex to obtain 3-Iodo-4-methoxy-1-pyridin-3-yl-1H-pyrrolo[3,2-c]pyridine (CH$_{27}$)

as a beige solid (542 mg, 43%); LC-MS. R$_t$ 2.94 min, AnalpH2_MeOH_4 min(1); (ESI$^+$) m/z 352.1 [M+H]$^+$.

3-Iodo-1-pyridin-3-yl-1,5-dihydro-pyrrolo[3,2-c]pyridin-4-one (CH28)

To a solution of 3-iodo-4-methoxy-1-pyridin-3-yl-1H-pyrrolo[3,2-c]pyridine (CH27) (542 mg, 1.54 mmol) and sodium iodide (630 mg, 4.2 mmol) in MeCN (13.5 mL) was added chlorotrimethylsilane (2.1 mL, 16.2 mmol) dropwise and the reaction mixture heated at 50° C. for 16 h. The resulting reaction mixture was cooled to RT then quenched by adding to an aq. sat. solution of NaHCO$_3$ (50 mL). The mixture was extracted with EtOAc (2×50 mL), and the organic layer was separated, washed with brine (100 mL), passed through a phase separator and the solvents removed in vacuo. The crude compound was purified by silica gel column chromatography eluting with DCM 0-8% MeOH/DCM to obtain 3-Iodo-1-pyridin-3-yl-1,5-dihydro-pyrrolo[3,2-c]pyridin-4-one (CH28) as a pale yellow solid (228 mg, 44%); LC-MS. R$_t$ 2.17 min, AnalpH2_MeOH_4 min; (ESI$^+$) m/z 338.0 [M+H]$^+$.

3-[4-(2-Methoxy-ethoxy)-phenyl]-1-pyridin-3-yl-1,5-dihydro-pyrrolo[3,2-c]pyridin-4-one (Ex-140)

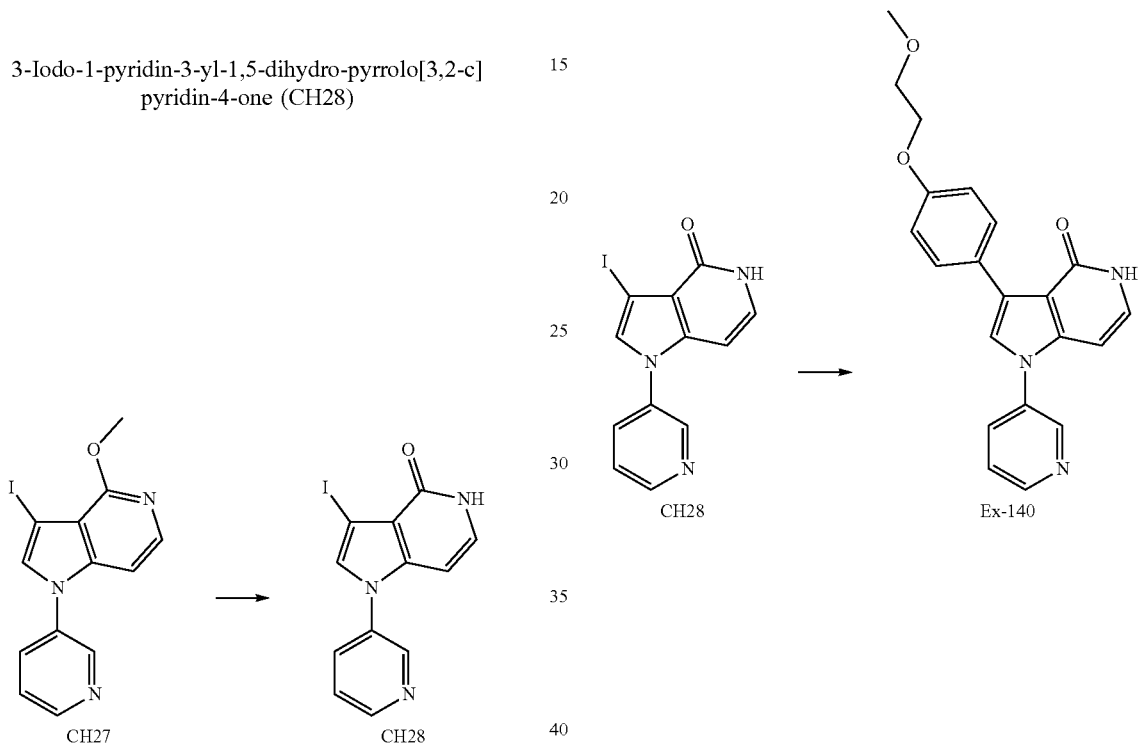

3-Iodo-1-pyridin-3-yl-1,5-dihydro-pyrrolo[3,2-c]pyridin-4-one (CH$_{28}$) (100 mg, 0.30 mmol), 2-(4-(2-methoxy-ethoxy)phenyl-4,4,5,5-tetramethyl-1,3,2-dioxaboralane (116 mg, 0.42 mmol), potassium phosphate tribasic (126 mg, 0.59 mmol), PdXPhosG3 (25 mg, 0.03 mmol) in 1,4-dioxane:water (1.5 mL, 4:1) was de-oxygenated with N$_2$ for 5 min then heated in a microwave reactor at 90° C. for 1 h. The reaction mixture was filtered through a Si-thiol cartridge (1 g) and washed with DCM (2×CV) followed by MeOH (2×CV). The filtrate was evaporated to dryness, suspended in DCM (25 mL) and washed with H$_2$O (25 mL). The organic phase was separated using a phase separator and concentrated in vacuo. The crude compound was purified by reversed phase preparative HPLC-MS to afford 3-[4-(2-methoxy-ethoxy)-phenyl]-1-pyridin-3-yl-1,5-dihydro-pyrrolo[3,2-c]pyridin-4-one (Ex-140) as a pale yellow solid (35 mg, 29%); LC-MS. R$_t$ 6.93 min, AnalpH2_MeOH_QC_V1 (1); (ESI$^+$) m/z 362.2 [M+H]$^+$; $^1$H-NMR (400 MHz, DMSO-d$_6$): δ 11.02 (d, J=6.0 Hz, 1H), 8.84 (d, J=2.3 Hz, 1H), 8.67 (dd, J=5.0, 1.4 Hz, 1H), 8.09-8.03 (m, 1H), 7.85-7.79 (m, 2H), 7.67-7.59 (m, 2H), 7.11 (t, J=6.6 Hz, 1H), 6.96-6.90 (m, 2H), 6.39 (d, J=7.3 Hz, 1H), 4.15-4.08 (m, 2H), 3.70-3.62 (m, 2H), 3.31 (s, 3H).

The following example was synthesised in an analogous procedure to (Ex-140):

TABLE 40

| Compound | Ex. # (Intermediate used) | Analytical Data | Mass, % Yield, State |
|---|---|---|---|
| 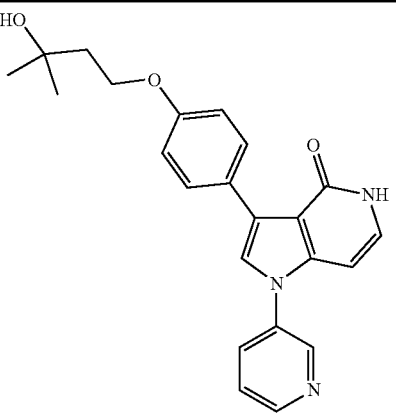 | Ex-141 (CH28, B2) | LC-MS. $R_t$ 7.28 min, AnalpH2_MeOH_QC_V1(1); (ESI$^+$) m/z 390.2 [M + H]$^+$. | 60 mg, 44%, white solid |

Figure 1B:
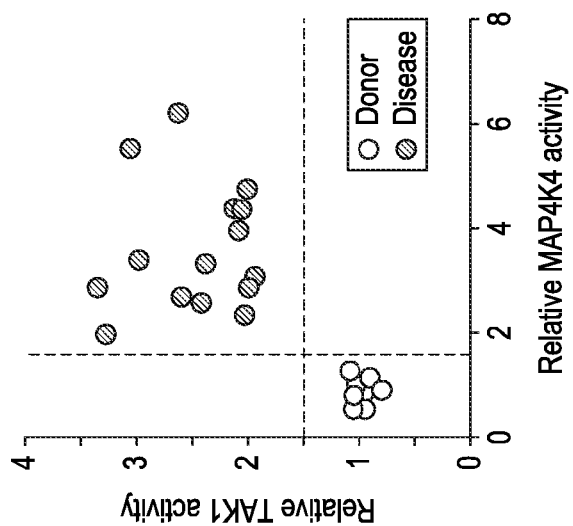
Figures 1C, 1D:
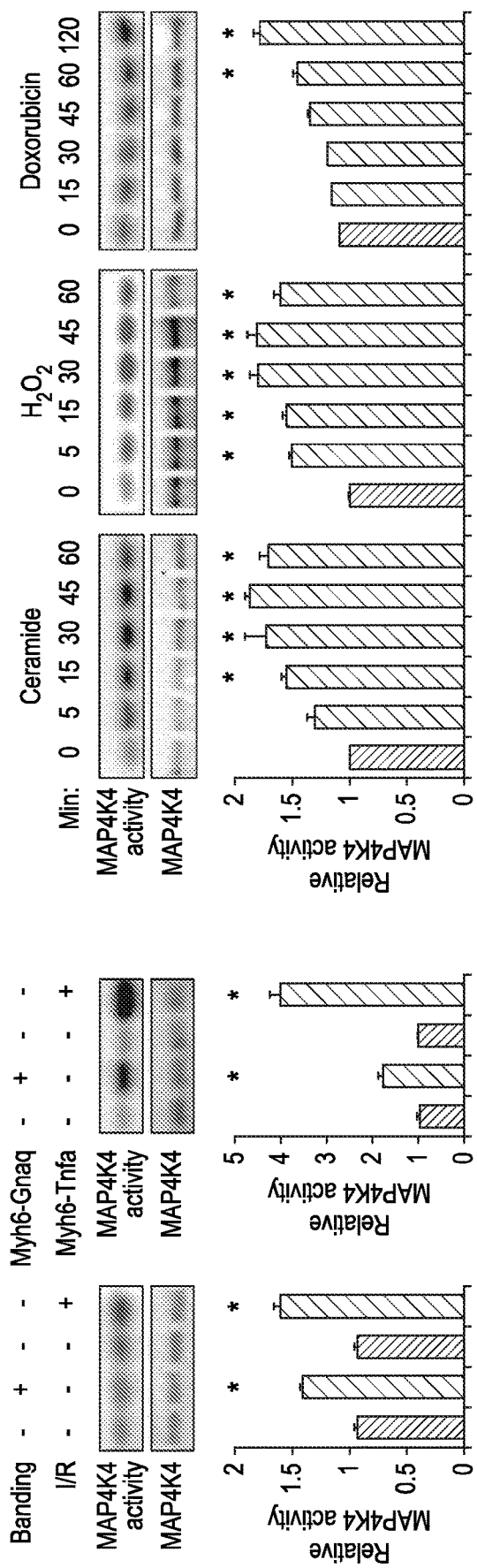
Figure 3A:
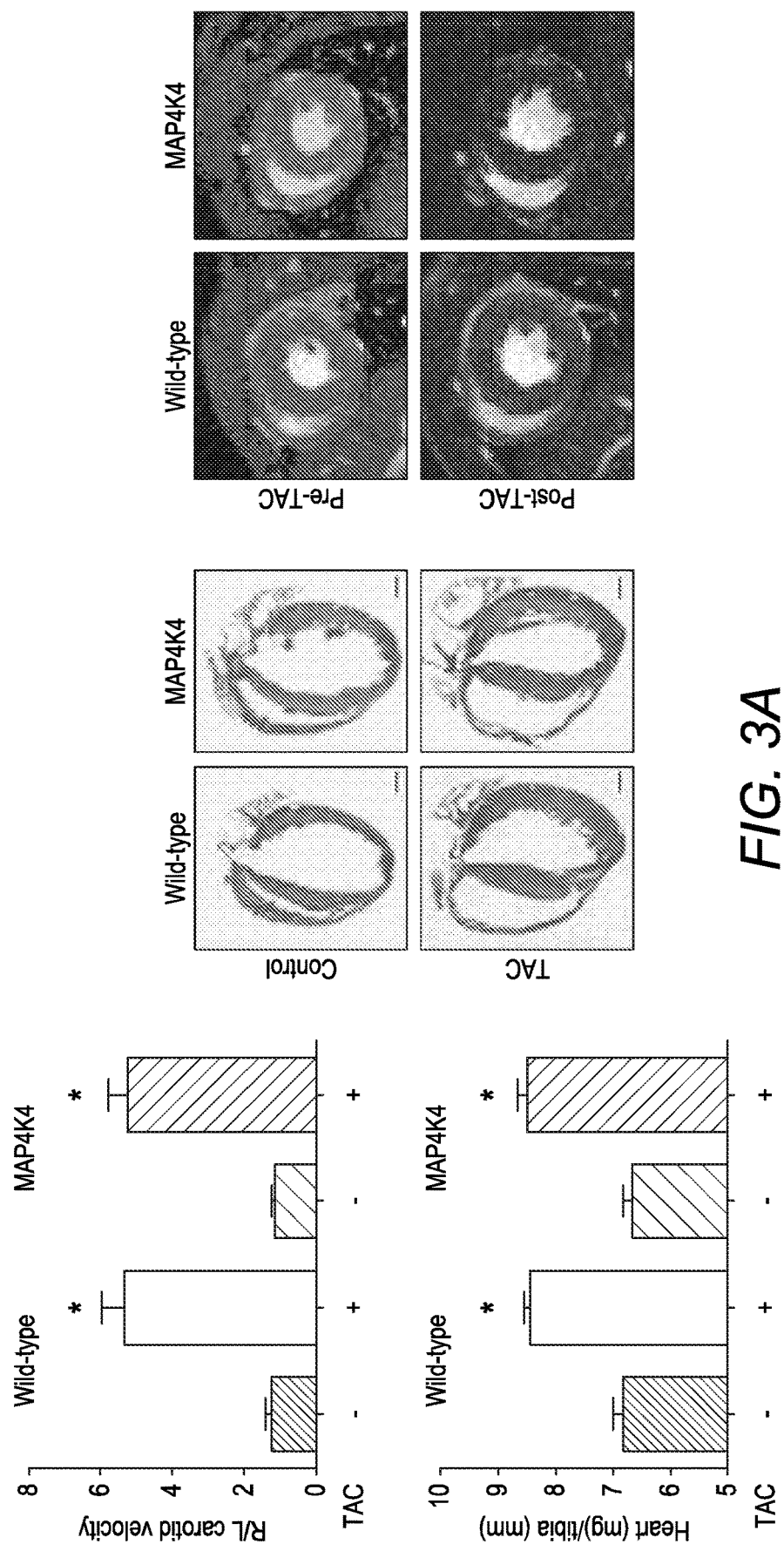
FIG. 3 provides demonstrating that cardiomyocyte-restricted MAP4K4 sensitized the myocardium to otherwise sub-lethal death signals potentiating myocyte loss, fibrosis, and dysfunction.
Figure 3B:
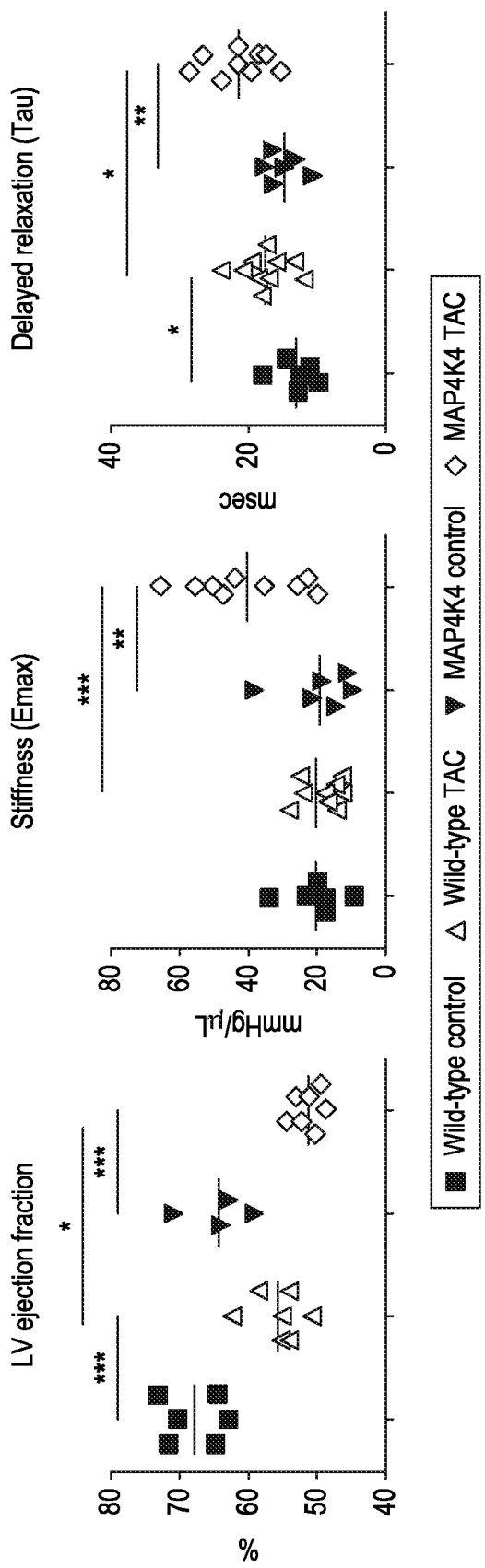
Figure 3C:
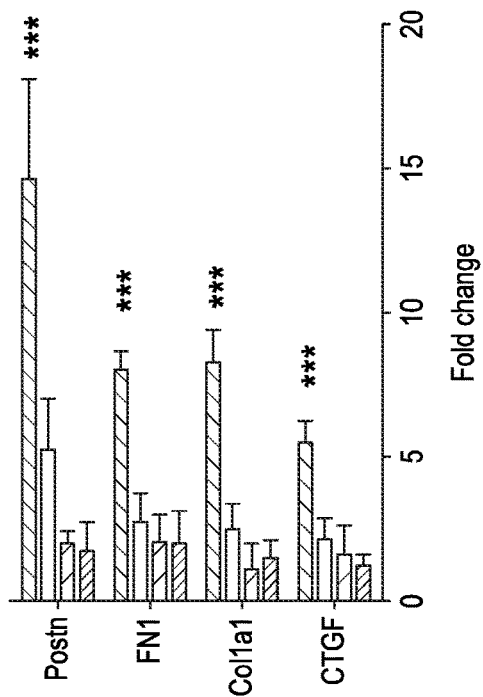
Figure 3C:
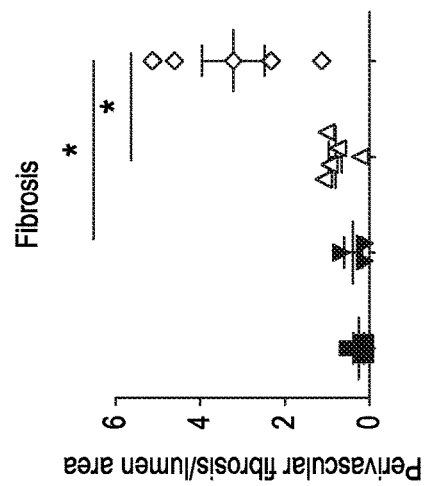
Figure 3C:
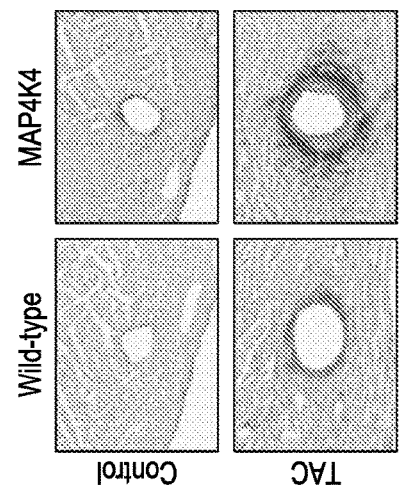
Figure 3D:
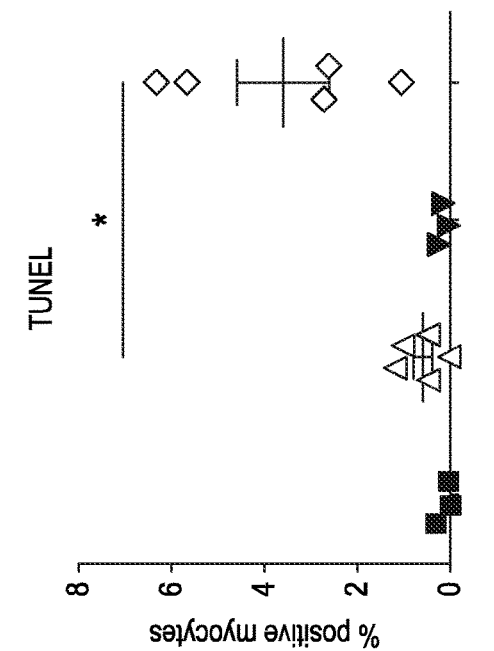
Figure 3D:
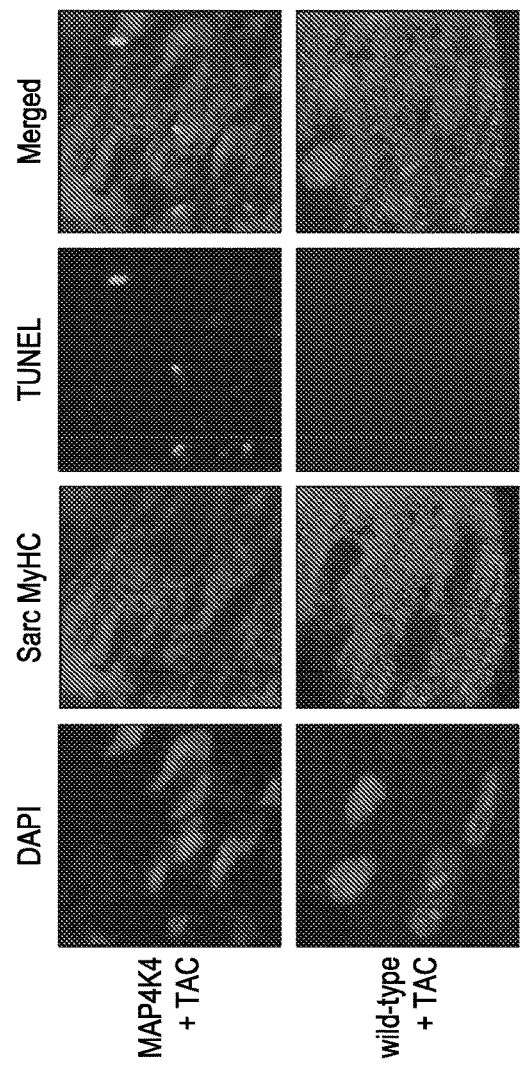
Figure 3G:
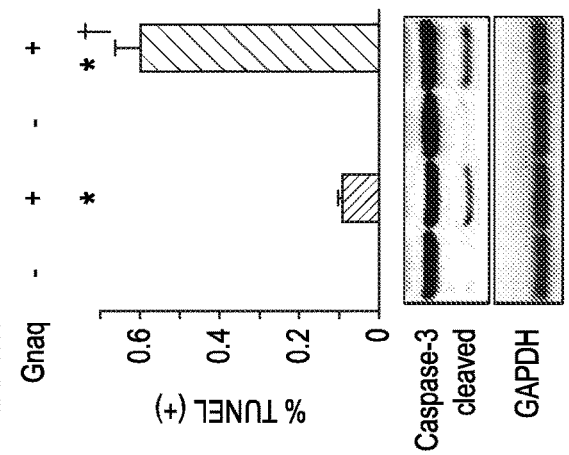
Figure 3F:
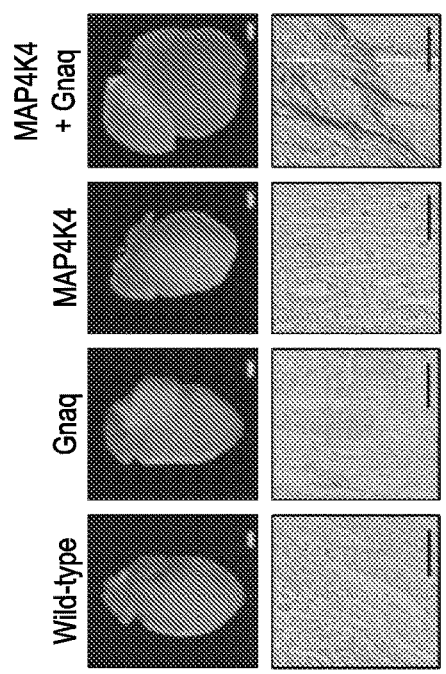
Figure 3E:
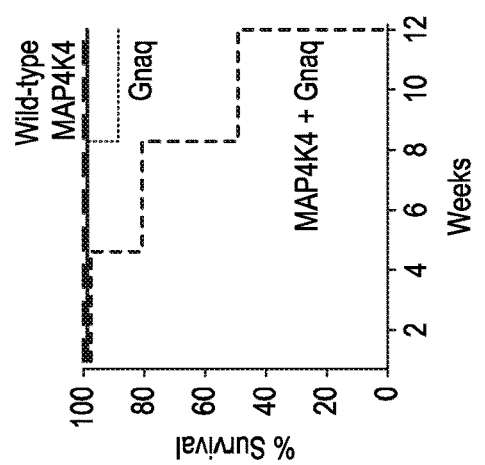
Figure 3H:
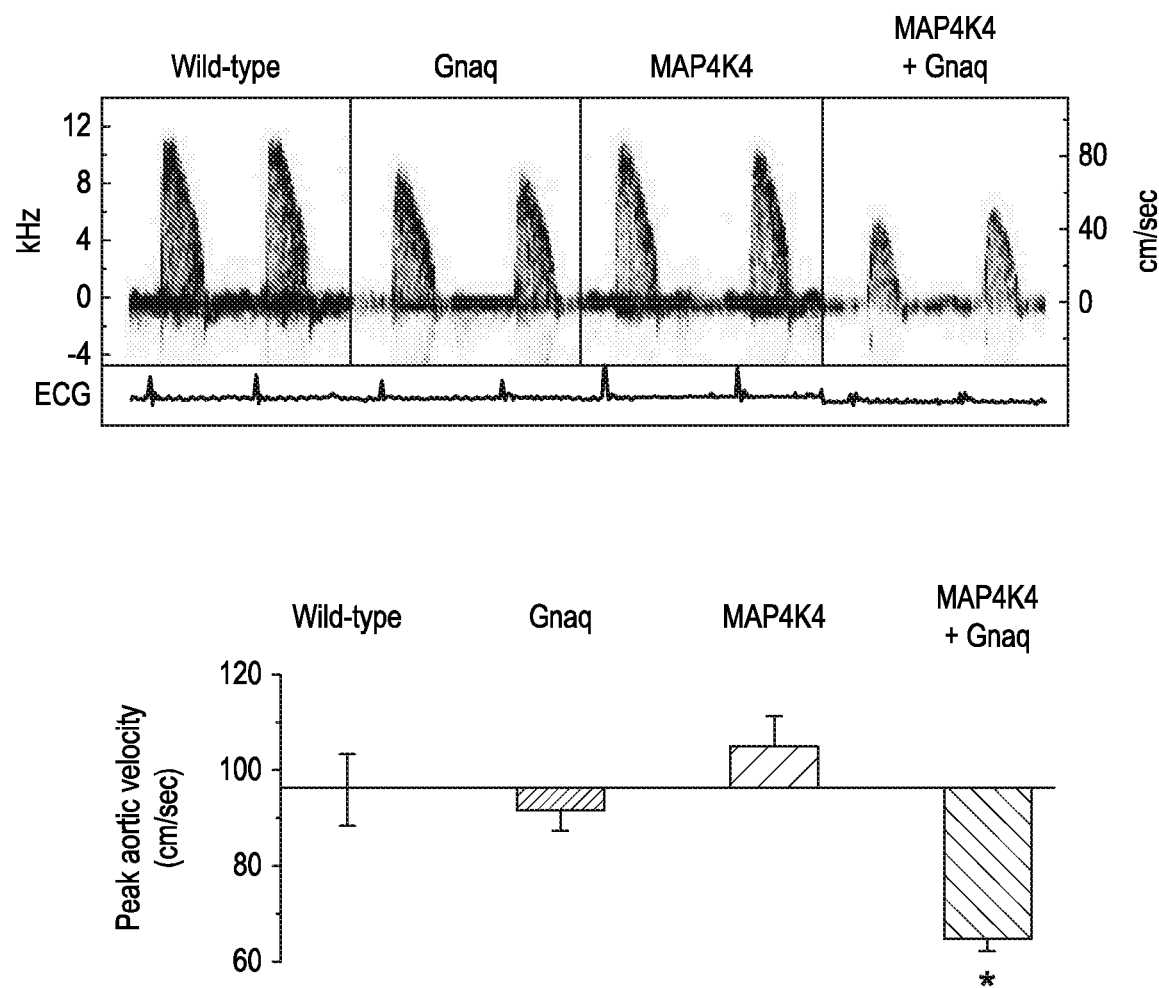

MAP4K4 is Activated by Cardiac Death Signals and Promotes Cardiac Muscle Cell Death To ascertain the scientific case for inhibiting MAP4K4 in cardiac cell death, three biological settings first were explored: diseased human heart tissue, mouse models, and rat cardiomyocytes (FIGS. 1-4). Activation of human cardiac MAP4K4 was prevalent in chronic heart failure from diverse etiologies (N=26), relative to healthy donor hearts (N=10; FIG. 1). MAP4K4 activation was associated uniformly with active (cleaved) caspase-3, a mediator of apoptosis (FIG. 1A), and activation of its MAP3K intermediary, TAK1 (FIG. 1B), which itself can drive cardiac cell death (Zhang et al., 2000). In adult mouse myocardium, MAP4K4 was activated by ischemia/reperfusion injury, biomechanical load (transverse aortic constriction, TAC), and cardiomyocyte-restricted expression of tumour necrosis factor-α or the G-protein Gαq all of which promote cardiac muscle cell death, FIG. 1C. Likewise, in cultured rat cardiomyocytes, MAP4K4 was activated by defined death signals: the cardiotoxic drug, doxorubicin; ceramide, a mediator of apoptotic signals including ischemia/reperfusion and TNFα (Suematsu et al., 2003); and $H_2O_2$, a surrogate for oxidative stress (Brown and Griendling, 2015) (FIG. 1D). Thus, it was shown that MAP4K4 activation accompanies cardiac muscle cell death, both in vitro and in vivo.

Figure 4A:
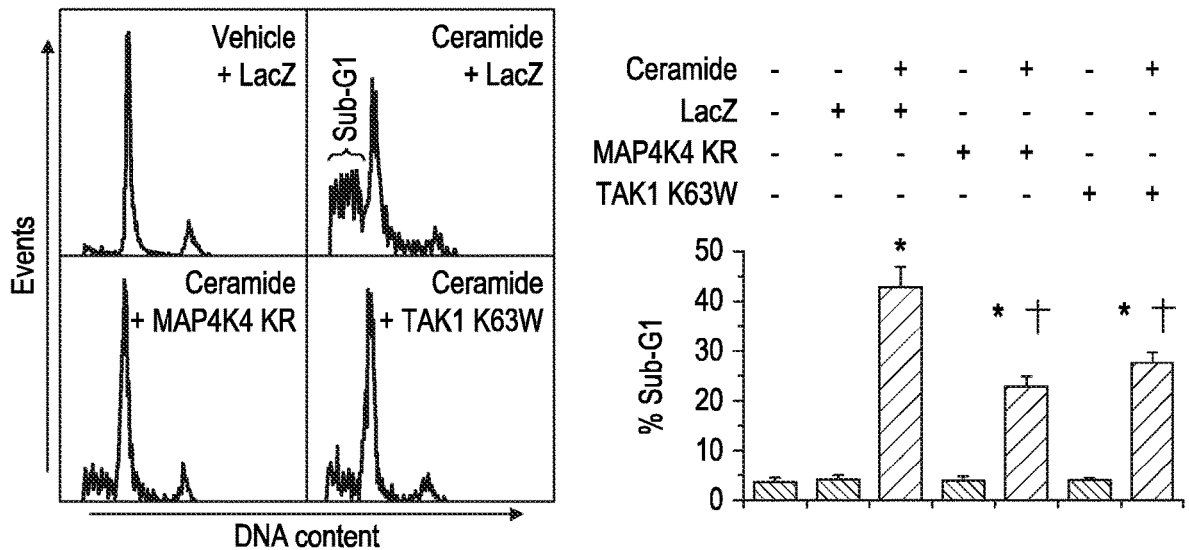
FIG. 4 provides data suggest a pivotal role for MAP4K4 in cardiac muscle cell death.
Figure 4B:
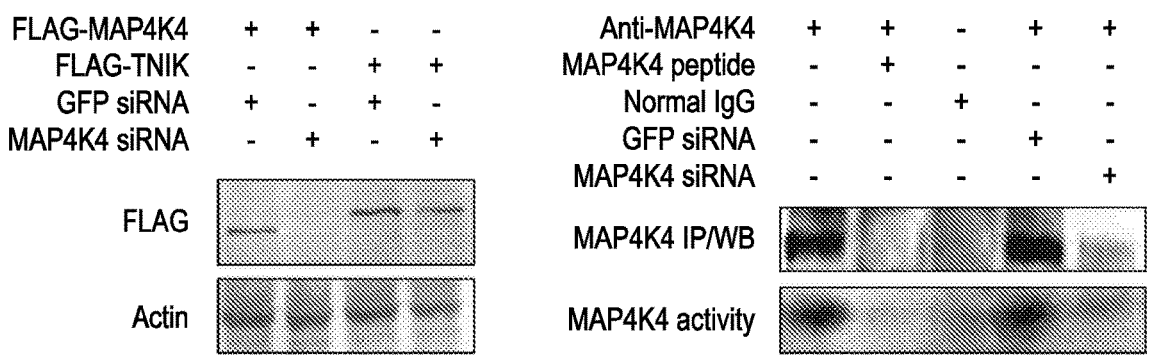
Figure 4C:
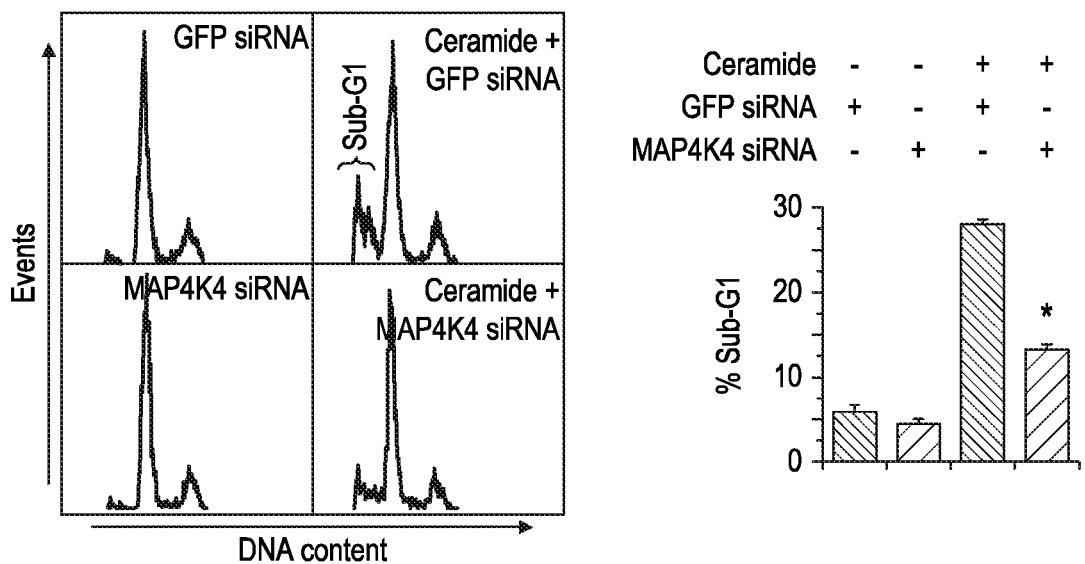
Figure 4D:
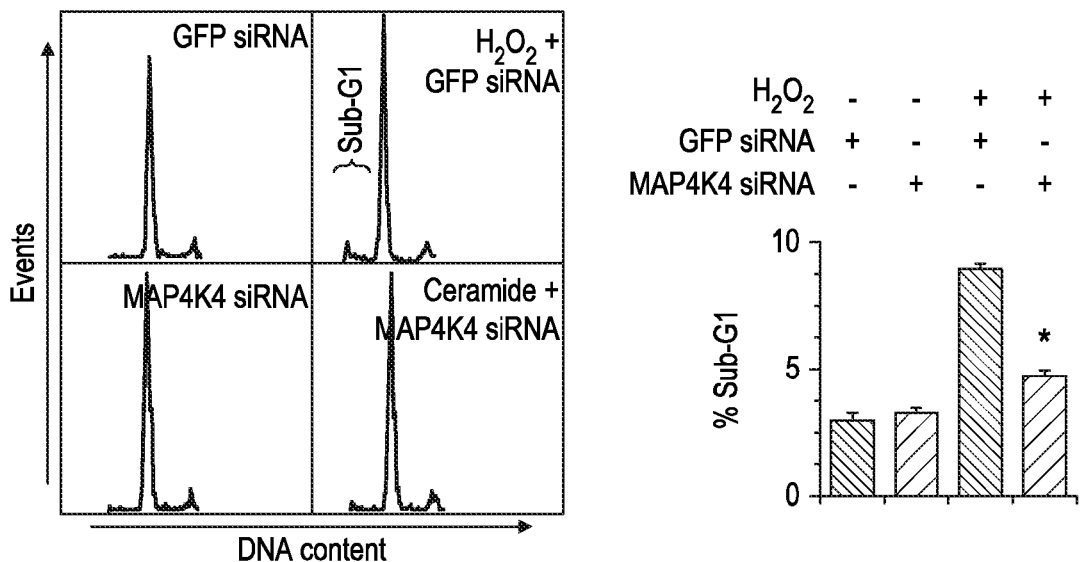
Figure 4E:
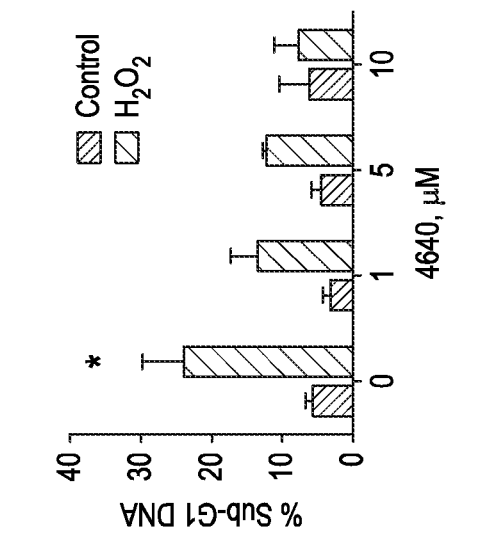
Figure 4E:
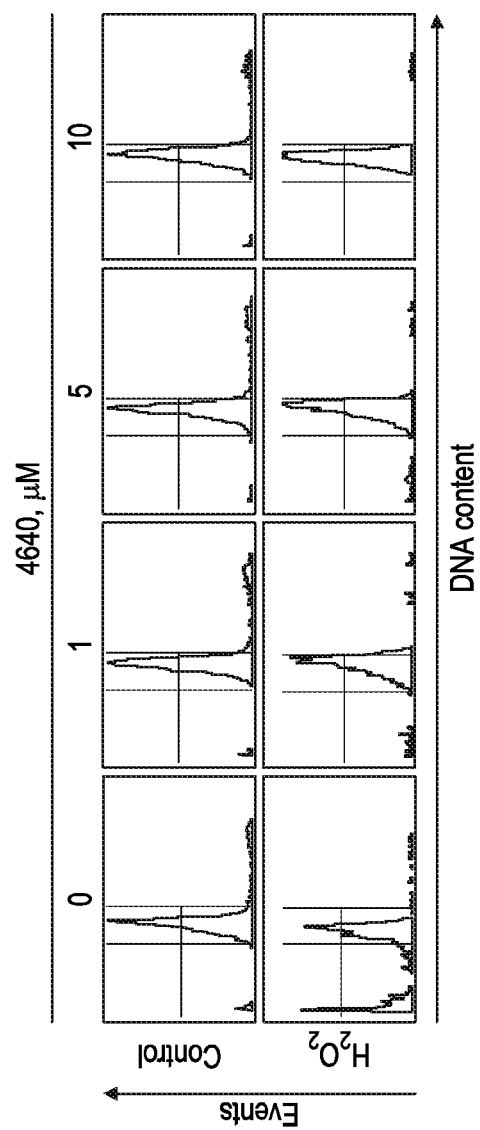

Next, an increase in MAP4K4 activity was simulated by viral gene transfer in rat cardiomyocytes (FIG. 2A), with the caveat that kinase activity, not expression, increases in the settings above. A pro-apoptotic effect of exogenous MAP4K4 was confirmed (FIG. 2B), potentially involving TAK1 (FIG. 2C), JNK (FIG. 2D, E), and the mitochondrial death pathway (FIG. 2E, F). In adult mice, cardiomyocyte-restricted MAP4K4 sensitized the myocardium to otherwise sub-lethal death signals—TAC and low copy number Myh6-Gnaq—potentiating myocyte loss, fibrosis, and dysfunction (FIG. 3). In clear contrast to the pro-apoptotic effect of wild-type MAP4K4, cultured rat cardiomyocytes were protected at least 50% not only by dominant-interfering mutations (FIG. 4A), but also by MAP4K4 shRNA (FIG. 4B-D). Together, these gain-of-function, dominant-negative, and loss-of-function studies suggest a pivotal role for MAP4K4 in cardiac muscle cell death, albeit with the limitations inherent to non-human models.

MAP4K4 Target Validation in Human Stem Cell-Derived Cardiomyocytes

To establish whether an equivalent requirement for MAP4K4 also exists in human cardiac muscle cells, the role of MAP4K4 in cardiomyocytes derived from human induced pluripotent stem cells was investigated. Human stem cell-derived cardiomyocytes (hiPSC-CMs) are envisioned as a highly auspicious tool for cardiac drug discovery. MAP4K4 function was tested in well-characterized, purified, commercially available hiPSC-CMs that have already gained acceptance by industry and regulatory authorities as a human platform (Blinova et al., 2017; Rana et al., 2012; Sirenko et al., 2013), and initiated our studies using iCell cardiomyocytes (Ma et al., 2011).

Figure 5A:
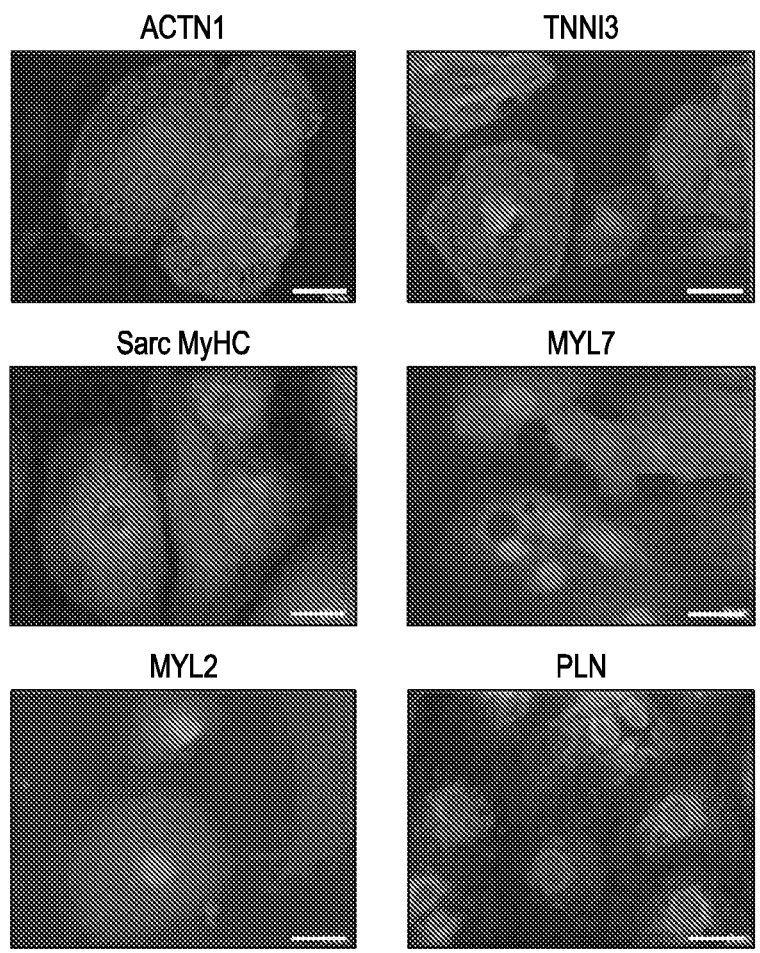
FIG. 5 provides data for the role of MAP4K4 in cardiomyocytes derived from human induced pluripotent stem cells.
Figure 5B:
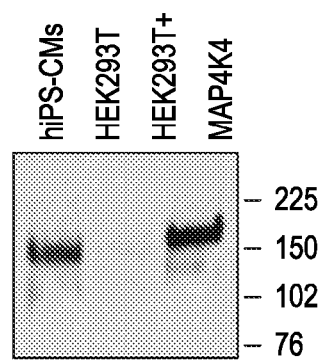
Figure 5C:
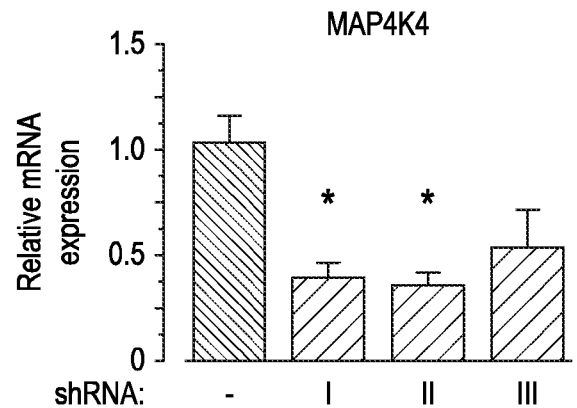
Figure 5C:
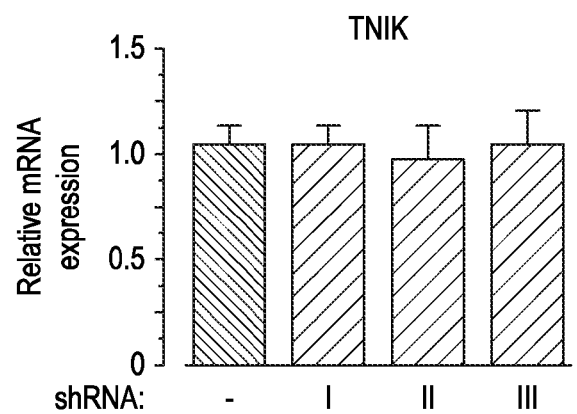
Figure 5C:
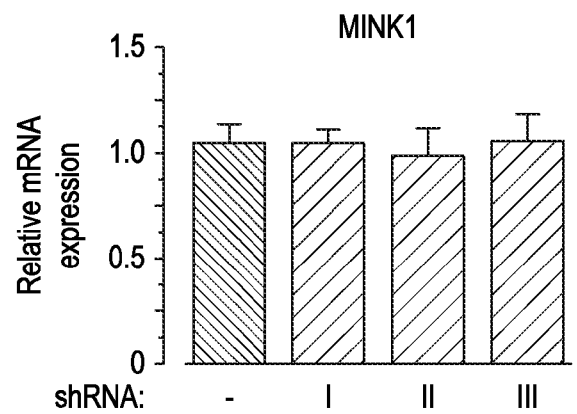
Figure 5E:
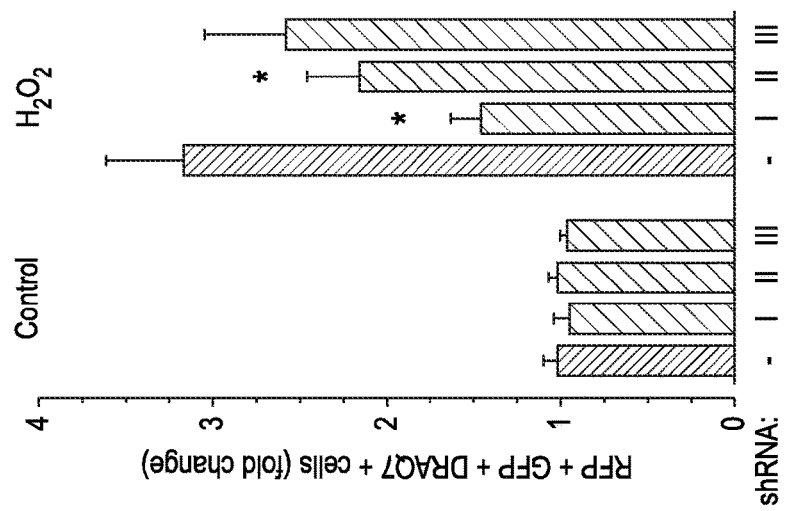
Figure 5D:
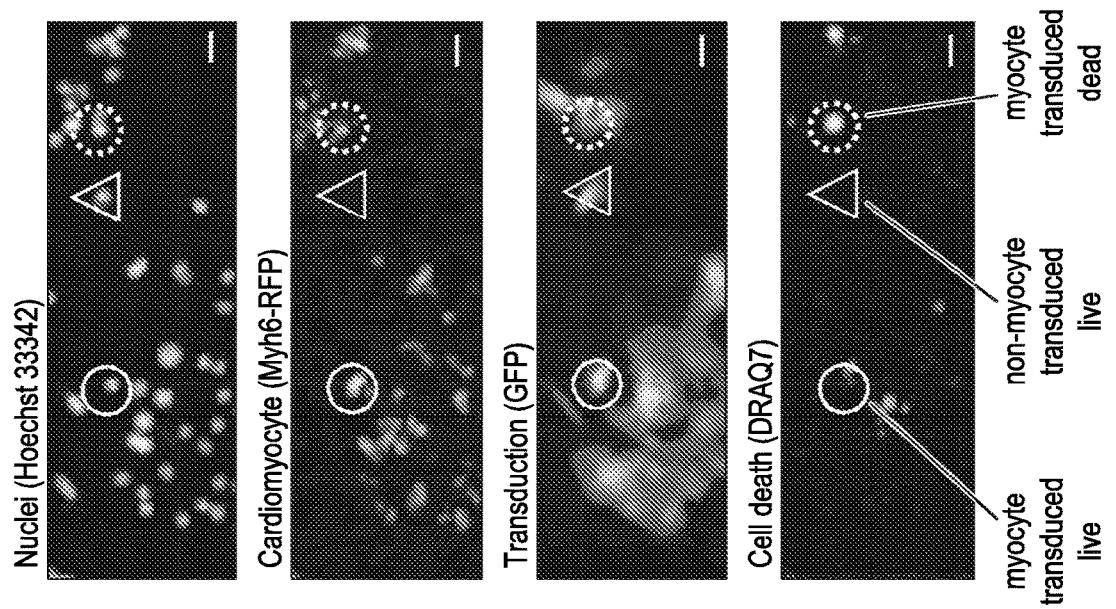

First, the expression of cardiomyocyte-specific markers and of MAP4K4 protein was validated (FIG. 5A, B). Two of three shRNAs directed against human MAP4K4 reduced expression>60%, with no extraneous effect on MINK/MAP4K6 and TNIK/MAP4K7, the most closely related genes (FIG. 5C). Cell death was quantified by high-content analysis (FIG. 5D) as the loss of membrane integrity (DRAQ7 uptake) in successfully transduced (GFP$^+$) hiPSC-CMs (Myh6-RFP$^+$). Each of the two potent shRNAs conferred protection against $H_2O_2$: myocyte loss was reduced up to 50% (FIG. 5E). By contrast, shRNA with little effect on MAP4K4 did not confer protection. Thus, the results of gene silencing strongly suggest a requirement for endogenous MAP4K4 in human cardiac muscle cell death.

Novel Inhibitors of MAP4K4

Small molecule inhibitors of MAP4K4 were identified with sufficient potency and selectivity. One such compound was the known compound F1386-0303 (5,7-diphenyl-7H-pyrrolo[2,3-d]pyrimidin-4-ol).

Compounds of the present invention were screened for their inhibitory activity against MAP4K4, versus selected off-target hits found with early members of this chemical series. MAP4K4 kinase activity was monitored using the CisBio HTRF Transcreener ADP assay, a competitive immunoassay with a reproducible Z'>0.6. In the detection step, endogenous ADP and d2-labeled ADP compete for binding an anti-ADP monoclonal antibody labelled with $Eu^{3+}$ cryptate. A ratiometric fluorescent read-out is used at 665 and 620 nm. Reactions were performed in the presence of 1% DMSO with ATP added at $K_m$ (10 µM), 0.5 nM human MAP4K4 kinase domain (Invitrogen), 1 µM biotin-myelin basic protein as substrate (Invitrogen), and extension of reaction time to 2 h. Assays were run in Greiner low volume plates with a final reaction volume of 10 µl. The MAP4K4 inhibition data are provided in Table 41 below for selected compounds of the present invention. The data has been categorised based on the $IC_{50}$ value of the compound as "A", "B" or "C". $IC_{50}$: A≤100 nM; 100 nM<B≤1 µM; 1 µM<C; nd=not determined.

TABLE 41

| Ex. No. | MAP4K4 (nM) |
| --- | --- |
| 1 | B |
| 2 | B |
| 3 | B |
| 4 | A |
| 5 | A |
| 6 | A |
| 7 | C |
| 8 | A |
| 9 | A |
| 10 | B |
| 11 | A |
| 12 | B |
| 13 | A |
| 14 | A |
| 15 | A |
| 16 | A |
| 17 | A |
| 18 | A |
| 19 | B |
| 20 | A |
| 21 | A |
| 23 | A |
| 24 | A |
| 25 | C |
| 26 | A |
| 27 | A |
| 28 | A |
| 29 | A |
| 30 | A |
| 31 | A |
| 32 | B |
| 33 | A |
| 34 | A |
| 35 | B |
| 36 | B |
| 37 | C |
| 38 | A |
| 39 | B |
| 40 | A |
| 41 | A |
| 42 | A |
| 43 | A |
| 44 | A |
| 45 | B |
| 46 | A |
| 47 | B |
| 48 | A |
| 49 | A |
| 50 | B |
| 51 | B |
| 52 | A |
| 53 | A |
| 54 | A |
| 55 | B |
| 56 | A |
| 57 | B |
| 59 | A |
| 60 | A |
| 61 | B |
| 62 | A |
| 63 | B |
| 64 | A |
| 65 | A |
| 66 | A |
| 67 | A |
| 68 | A |
| 69 | A |
| 70 | A |
| 71 | A |
| 72 | A |
| 73 | A |
| 75 | A |
| 76 | A |
| 77 | A |
| 78 | A |
| 79 | A |
| 80 | A |
| 81 | A |
| 82 | B |
| 83 | B |
| 84 | B |
| 85 | A |
| 86 | A |
| 87 | A |
| 88 | A |
| 91 | A |
| 92 | A |
| 94 | A |
| 95 | A |
| 96 | A |
| 97 | A |
| 98 | B |
| 99 | B |
| 102 | C |
| 103 | C |
| 104 | C |
| 105 | B |
| 106 | C |
| 107 | B |
| 108 | B |
| 109 | B |
| 110 | B |
| 111 | B |
| 112 | A |
| 113 | A |
| 114 | B |
| 115 | C |
| 116 | B |
| 117 | B |
| 118 | B |
| 119 | B |
| 120 | B |
| 121 | C |
| 122 | C |
| 123 | B |
| 124 | B |
| 125 | A |
| 126 | C |
| 127 | B |
| 128 | B |
| 129 | C |
| 130 | B |
| 131 | C |
| 132 | B |
| 134 | C |
| 135 | C |
| 137 | B |
| 138 | A |
| 139 | B |
| 140 | A |
| 141 | B |

MAP4K4 inhibitory data and comparative data for 10 other protein kinases are provided in Table 42. The data in Table 42 also provides the fold selectivity of the two compounds in favour of MAP4K4 over the tested kinase. The fold selectivity is indicated in parenthesis.

TABLE 42

| Target | Ex-78 pIC50 (fold selectivity) | Ex-67 pIC50 (fold selectivity) | Ex-54 pIC50 (fold selectivity) | Ex-28 pIC50 (fold selectivity) |
|---|---|---|---|---|
| MAP4K4 | 7.5 | 7.6 | 7.5 | 7.9 |
| MINK1/MAP4K6 | 7.2 | | 7.5 | 7.5 |
| TNIK/MAP4K7 | 6.9 | 6.7 | 7.3 | 7.3 |
| GCK/MAP4K2 | 6 (32) | 5.7 (79) | 6.8 (5) | 6 (79) |
| GLK/MAP4K3 | 5.8 (50) | 4.6 (1000) | 5.8 (50) | |
| KHS/MAP4K5 | 6.5 (10) | 5.8 (63) | 6.7 (6) | 6.1 (63) |
| ABL1 | 5.1 (251) | 4.5 (>1000) | 5.4 (126) | 5.2 (501) |
| Aurora B | 4.5 (1000) | | | 5.2 (501) |
| MLK1/MAP3K9 | 6.9 (4) | | 5.5 (100) | 5.3 (398) |
| MLK3/MAP3K11 | 6.6 (8) | 5.8 (63) | 6.4 (13) | 6 (79) |
| NUAK1 | 6.3 (16) | 5.9 (50) | 6.9 (4) | 5.5 (251) |

| Target | Ex-29 pIC50 (fold selectivity) | Ex-26 pIC50 (fold selectivity) | Ex-27 pIC50 (fold selectivity) |
|---|---|---|---|
| MAP4K4 | 7.7 | 7.5 | 7.8 |
| MINK1/MAP4K6 | 7.9 | 7.2 | 8 |
| TNIK/MAP4K7 | 7.5 | 6.5 | 7.7 |
| GCK/MAP4K2 | 6 (50) | 6.3 (16) | 6.3 (31) |
| GLK/MAP4K3 | 4.5 (>1000) | | |
| KHS/MAP4K5 | 6 (50) | | |
| ABL1 | | | |
| Aurora B | 4.5 (>1000) | | |
| MLK1/MAP3K9 | 6.4 (20) | 6.9 (8) | 7.1 (5) |
| MLK3/MAP3K11 | 6.3 (25) | 7.5 (1) | 7.1 (5) |
| NUAK1 | 6.5 (16) | 7 (3) | 6.7 (13) |

MAP4K4 Inhibition Reduces Infarct Size in Mice

Figure 6:
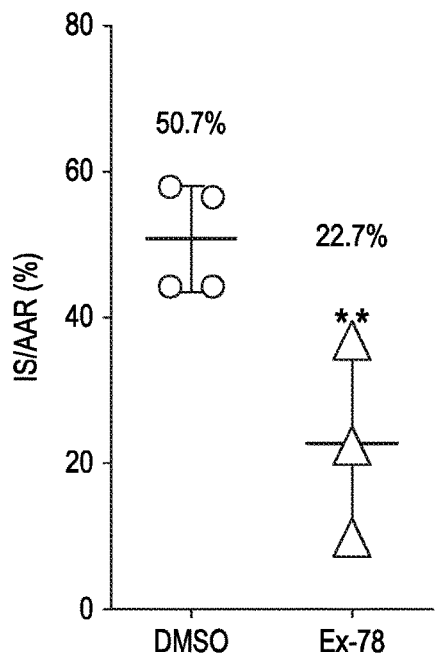
FIG. 6 provides data demonstrating that MAP4K4 inhibition reduces infarct size in mice.

To test if target validation and compound development in hiPSC-CMs might predict success in a whole-animal context, mice undergoing experimental myocardial infarction were treated with Ex-78 or the vehicle control (DMSO) (FIG. 6). The suppression of cardiac muscle cell death achieved roughly a 55% reduction in infarct size as a proportion of the area at ischemic risk compared to control.

Prodrugs

It is envisaged that compounds of the invention may be delivered as a prodrug, wherein an active substance is generated in vivo by hydrolysis of said prodrug. It is envisaged that the prodrug may be a compound with —CH$_2$OP(=O)(OH)$_2$ substituted on the NH (replacing the H) of the bicyclic core of the compounds. Alternatively, the prodrug may be a compound in which a free OH is replaced by —OP(=O)(OH)$_2$.

Figure 7:
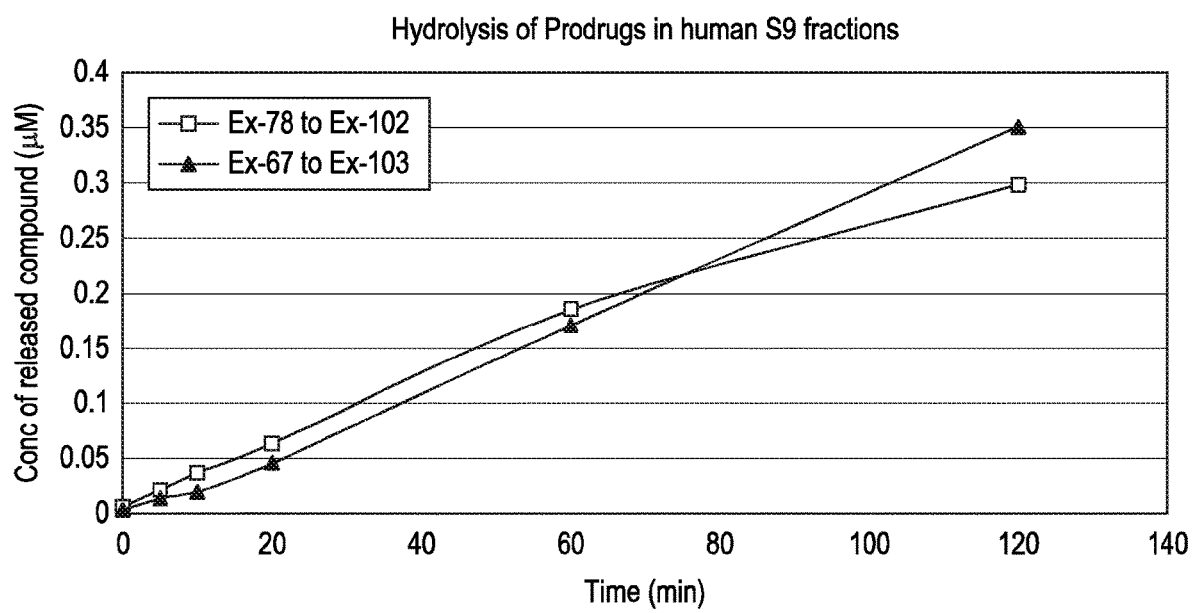
FIG. 7 shows the rate of hydrolysis of prodrugs into the corresponding compounds in human S9 liver fraction.

Examples of compounds that can act as prodrugs and the compounds that are generated from the said prodrugs are shown in Table 43 below Various in vitro systems have been used to study the metabolism of compounds in humans such as microsomes, hepatocytes and the liver S9 fraction. The S9 fraction consists of both microsomes and cytosol and contains most of the metabolic enzymes present in a human liver. 1 µM of the prodrugs described in Table 43 were incubated with human S9 liver fraction for 120 min and the release of the corresponding MAP4K4 inhibitor was quantified by mass spectrometry relative to a 1 µM standard of said compound. This experiment demonstrates that prodrugs of the type described herein can be hydrolysed in humans to give the corresponding MAP4K4 inhibitor. FIG. 7 shows the rate of hydrolysis of prodrugs into the corresponding compounds.

TABLE 43

| Pro-drug | | Compound generated | |
|---|---|---|---|
| Structure | Cpd # | Structure | Cpd # |
| [Structure: HO-C(CH₃)₂-CH₂CH₂-O-phenyl-pyrrolopyrimidinone with N-CH₂-O-P(=O)(OH)₂ and N-pyridin-3-yl] | Ex-102 | [Structure: HO-C(CH₃)₂-CH₂CH₂-O-phenyl-pyrrolopyrimidinone (NH) with N-pyridin-3-yl] | Ex-78 |
| [Structure: CH₃O-CH₂CH₂-O-phenyl-pyrrolopyrimidinone with N-CH₂-O-P(=O)(OH)₂ and N-pyridin-3-yl] | Ex-103 | [Structure: CH₃O-CH₂CH₂-O-phenyl-pyrrolopyrimidinone (NH) with N-pyridin-3-yl] | Ex-67 |

REFERENCES

Beilin, M., Marchetto, M. C., Gage, F. H., and Mummery, C. L. (2012). Induced pluripotent stem cells: the new patient? Nat Rev Mol Cell Biol 13, 713-726.

Birket, M. J., Ribeiro, M. C., Kosmidis, G., Ward, D., Leitoguinho, A. R., van de Pol, V., Dambrot, C., Devalla, H. D., Davis, R. P., Mastroberardino, P. G., et al. (2015). Contractile defect caused by mutation in MYBPC3 revealed under conditions optimized for human PSC-cardiomyocytefunction. Cell Rep 13, 733-745.

Breckwoldt, K., Letuffe-Breniere, D., Mannhardt, I., Schulze, T., Ulmer, B., Werner, T., Benzin, A., Klampe, B., Reinsch, M. C., Laufer, S., et al. (2017). Differentiation of cardiomyocytes and generation of human engineered heart tissue. Nat Protoc 12, 1177-1197.

Brown, D. I., and Griendling, K. K. (2015). Regulation of signal transduction by reactive oxygen species in the cardiovascular system. Circ Res 116, 531-549.

Burridge, P. W., Li, Y. F., Matsa, E., Wu, H., Ong, S. G., Sharma, A., Holmstrom, A., Chang, A. C., Coronado, M. J., Ebert, A. D., et al. (2016). Human induced pluripotent stem cell-derived cardiomyocytes recapitulate the predilection of breast cancer patients to doxorubicin-induced cardiotoxicity. Nat Med 22, 547-556.

Cameron, B. J., Gerry, A. B., Dukes, J., Harper, J. V., Kannan, V., Bianchi, F. C., Grand, F., Brewer, J. E., Gupta, M., Plesa, G., et al. (2013). Identification of a Titin-derived HLA-A1-presented peptide as a cross-reactive target for engineered MAGE A3-directed T cells. Sci Transl Med 5, 197ra103.

Chapman, J. O., Li, H., and Lundquist, E. A. (2008). The MIG-15 NIK kinase acts cell-autonomously in neuroblast polarization and migration in C. elegans. Dev Biol 324, 245-257.

Cheeseright, T. J., Mackey, M. D., and Scoffin, R. A. (2011). High content pharmacophores from molecular fields: a biologically relevant method for comparing and understanding ligands. Curr Comput Aided Drug Des 7, 190-205.

Chen, S., Li, X., Lu, D., Xu, Y., Mou, W., Wang, L., Chen, Y., Liu, Y., Li, X., Li, L. Y., et al. (2014). SOX2 regulates apoptosis through MAP4K4-survivin signaling pathway in human lung cancer cells. Carcinogenesis 35, 613-623.

Dan, I., Watanabe, N. M., and Kusumi, A. (2001). The Ste20 group kinases as regulators of MAP kinase cascades. Trends Cell Biol 11, 220-230.

Devalla, H. D., Schwach, V., Ford, J. W., Milnes, J. T., El-Haou, S., Jackson, C., Gkatzis, K., Elliott, D. A., Chuva de Sousa Lopes, S. M., Mummery, C. L., et al. (2015). Atrial-like cardiomyocytes from human pluripotent stem cells are a robust preclinical model for assessing atrial-selective pharmacology. EMBO Mol Med 7, 394-410.

Dorn, G. W., 2nd (2009). Novel pharmacotherapies to abrogate postinfarction ventricular remodeling. Nat Rev Cardiol 6, 283-291.

Fiedler, L. R., Maifoshie, E., and Schneider, M. D. (2014). Mouse models of heart failure: cell signaling and cell survival. Curr Top Dev Biol 109, 171-247.

Gao, X. M., Xu, Q., Kiriazis, H., Dart, A. M., and Du, X. J. (2005). Mouse model of post-infarct ventricular rupture: time course, strain- and gender-dependency, tensile strength, and histopathology. Cardiovasc Res 65, 469-477.

Gintant, G., Fermini, B., Stockbridge, N., and Strauss, D. (2017). The evolving roles of human iPSC-derived cardiomyocytes in drug safety and discovery. Cell Stem Cell 22, 14-17.

Gintant, G., Sager, P. T., and Stockbridge, N. (2016). Evolution of strategies to improve preclinical cardiac safety testing. Nat Rev Drug Discov 15, 457-471.

Guimaraes, C. R., Rai, B. K., Munchhof, M. J., Liu, S., Wang, J., Bhattacharya, S. K., and Buckbinder, L. (2011). Understanding the impact of the P-loop conformation on kinase selectivity. J Chem Inf Model 51, 1199-1204.

Hausenloy, D. J., and Yellon, D. M. (2015). Targeting myocardial reperfusion Injury—the search continues. N Engl J Med 373, 1073-1075.

Heusch, G. (2013). Cardioprotection: chances and challenges of its translation to the clinic. Lancet 381, 166-175.

Hinson, J. T., Chopra, A., Nafissi, N., Polacheck, W. J., Benson, C. C., Swist, S., Gorham, J., Yang, L., Schafer, S., Sheng, C. C., et al. (2015). Titin mutations in iPS cells define sarcomere insufficiency as a cause of dilated cardiomyopathy. Science 349, 982-986.

Jacquet, S., Nishino, Y., Kumphune, S., Sicard, P., Clark, J. E., Kobayashi, K. S., Flavell, R. A., Eickhoff, J., Cotten, M., and Marber, M. S. (2008). The role of RIP2 in p38 MAPK activation in the stressed heart. J Biol Chem 283, 11964-11971.

Lee, S. H., Cunha, D., Piermarocchi, C., Paternostro, G., Pinkerton, A., Ladriere, L., Marchetti, P., Eizirik, D. L., Cnop, M., and Levine, F. (2017a). High-throughput screening and bioinformatic analysis to ascertain compounds that prevent saturated fatty acid-induced beta-cell apoptosis. Biochem Pharmacol 138, 140-149.

Lee, Y. K., Lau, Y. M., Cai, Z. J., Lai, W. H., Wong, L. Y., Tse, H. F., Ng, K. M., and Siu, C. W. (2017b). Modeling treatment response for Lamin A/C related dilated cardiomyopathy in human induced pluripotent stem cells. J Am Heart Assoc 6.

Liang, P., Lan, F., Lee, A. S., Gong, T., Sanchez-Freire, V., Wang, Y., Diecke, S., Sallam, K., Knowles, J. W., Wang, P. J., et al. (2013). Drug screening using a library of human induced pluripotent stem cell-derived cardiomyocytes reveals disease-specific patterns of cardiotoxicity. Circulation 127, 1677-1691.

Lincoff, A. M., Roe, M., Aylward, P., Galla, J., Rynkiewicz, A., Guetta, V., Zelizko, M., Kleiman, N., White, H., McErlean, E., et al. (2014). Inhibition of delta-protein kinase C by delcasertib as an adjunct to primary percutaneous coronary intervention for acute anterior ST-segment elevation myocardial infarction: results of the PROTECTION AMI Randomized Controlled Trial. Eur Heart J. 35, 2516-23.

Loh S H, Francescut L, Lingor P, Bahr M, Nicotera P (2008). Identification of new kinase clusters required for neurite outgrowth and retraction by a loss-of-function RNA interference screen. Cell Death Differ 15, 283-298.

Ma, J., Guo, L., Fiene, S. J., Anson, B. D., Thomson, J. A., Kamp, T. J., Kolaja, K. L., Swanson, B. J., and January, C. T. (2011). High purity human-induced pluripotent stem cell-derived cardiomyocytes: electrophysiological properties of action potentials and ionic currents. Am J Physiol Heart Circ Physiol 301, H2006-2017.

Matsa, E., Burridge, P. W., and Wu, J. C. (2014). Human stem cells for modeling heart disease and for drug discovery. Sci Transl Med 6, 239ps236.

Michael, L. H., Entman, M. L., Hartley, C. J., Youker, K. A., Zhu, J., Hall, S. R., Hawkins, H. K., Bernes, K., and Ballantyne, C. M. (1995). Myocardial ischemia and reperfusion: a murine model. Am J Physiol 269, H2147-H2154.

Miled, C., Pontoglio, M., Garbay, S., Yaniv, M., and Weitzman, J. B. (2005). A genomic map of p53 binding sites identifies novel p53 targets involved in an apoptotic network. Cancer Res 65, 5096-5104.

Moran, A. E., Forouzanfar, M. H., Roth, G. A., Mensah, G. A., Ezzati, M., Flaxman, A., Murray, C. J., and Naghavi, M. (2014). The global burden of ischemic heart disease in 1990 and 2010: the Global Burden of Disease 2010 study. Circulation 129, 1493-1501.

Moretti, A., Beilin, M., Welling, A., Jung, C. B., Lam, J. T., Bott-Flugel, L., Dorn, T., Goedel, A., Hohnke, C., Hofmann, F., et al. (2010). Patient-specific induced pluripotent stem-cell models forlong-QT syndrome. N Engl J Med 363, 1397-1409.

Ndubaku, C. O., Crawford, T. D., Chen, H., Boggs, J. W., Drobnick, J., Harris, S. F., Jesudason, R., McNamara, E., Nonomiya, J., Sambrone, A., et al. (2015). Structure-based design of GNE-495, a potent and selective MAP4K4 Inhibitor with efficacy in retinal angiogenesis. ACS Med Chem Lett 6, 913-918.

Newby, L. K., Marber, M. S., Melloni, C., Sarov-Blat, L., Aberle, L. H., Aylward, P. E., Cai, G., de Winter, R. J., Hamm, C. W., Heitner, J. F., et al. (2014). Losmapimod, a novel p38 mitogen-activated protein kinase inhibitor, in non-ST-segment elevation myocardial infarction: a randomised phase 2 trial. Lancet 384, 1187-1195.

O'Connor, M. S., Safari, A., Liu, D., Qin, J., and Songyang, Z. (2004). The human Rap1 protein complex and modulation of telomere length. J Biol Chem 279, 28585-28591.

Oh, H., Wang, S. C., Prahash, A., Sano, M., Moravec, C. S., Taffet, G. E., Michael, L. H., Youker, K. A., Entman, M. L., and Schneider, M. D. (2003). Telomere attrition and Chk2 activation in human heart failure. Proc Natl Acad Sci USA 100, 5378-5383.

Passier, R., Orlova, V., and Mummery, C. (2016). Complex tissue and disease modeling using hiPSCs. Cell Stem Cell 18, 309-321.

Piot, C., Croisille, P., Staat, P., Thibault, H., Rioufol, G., Mewton, N., Elbelghiti, R., Cung, T. T., Bonnefoy, E., Angoulvant, D., et al. (2008). Effect of cyclosporine on reperfusion injury in acute myocardial infarction. N Engl J Med 359, 473-481.

Rose, B. A., Force, T., and Wang, Y. (2010). Mitogen-activated protein kinase signaling in the heart: angels versus demons in a heart-breaking tale. Physiol Rev 90, 1507-1546.

Sakata, Y., Hoit, B. D., Liggett, S. B., Walsh, R. A., and Dorn, G. (1998). Decompensation of pressure-overload hypertrophy in G alpha q-overexpressing mice. Circulation 97, 1488-1495.

Sala, L., Yu, Z., Ward-van Oostwaard, D., van Veldhoven, J. P., Moretti, A., Laugwitz, K. L., Mummery, C. L., AP, I. J., and Beilin, M. (2016). A new hERG allosteric modulator rescues genetic and drug-induced long-QT syndrome phenotypes in cardiomyocytes from isogenic pairs of patient induced pluripotent stem cells. EMBO Mol Med 8, 1065-1081.

Sano, M., Wang, S. C., Shirai, M., Scaglia, F., Xie, M., Sakai, S., Tanaka, T., Kulkarni, P. A., Barger, P. M., Youker, K. A., et al. (2004). Activation of cardiac Cdk9 represses PGC-1 and confers a predisposition to heart failure. EMBO J 23, 3559-3569.

Schaaf, S., Shibamiya, A., Mewe, M., Eder, A., Stohr, A., Hirt, M. N., Rau, T., Zimmermann, W. H., Conradi, L., Eschenhagen, T., et al. (2011). Human engineered heart tissue as a versatile tool in basic research and preclinical toxicology. PLoS One 6, e26397.

Schroder P, Forster T, Kleine S, Becker C, Richters A, Ziegler S, Rauh D, Kumar K, Waldmann H (2015). Neuritogenic militarinone-inspired 4-hydroxypyridones target the stress pathway kinase map4k4. Angew Chem Int Ed Engl 54, 12398-12403.

Silva, J. M., Li, M. Z., Chang, K., Ge, W., Golding, M. C., Rickies, R. J., Siolas, D., Hu, G., Paddison, P. J., Schlabach, M. R., et al. (2005). Second-generation shRNA libraries covering the mouse and human genomes. Nat Genet 37, 1281-1288.

Sivasubramanian, N., Coker, M. L., Kurrelmeyer, K. M., MacLellan, W. R., DeMayo, F. J., Spinale, F. G., and Mann, D. L. (2001). Left ventricular remodeling in transgenic mice with cardiac restricted overexpression of tumor necrosis factor. Circulation 104, 826-831.

Song, W., Dyer, E., Stuckey, D. J., Copeland, O., Leung, M. C., Bayliss, C., Messer, A., Wilkinson, R., Tremoleda, J. L., Schneider, M. D., et al. (2011). Molecular mechanism of the E99K mutation in cardiac actin (ACTC gene) that causes apical hypertrophy in man and mouse. J Biol Chem 286, 27582-27593.

Stuckey, D. J., McSweeney, S. J., Thin, M. Z., Habib, J., Price, A. N., Fiedler, L. R., Gsell, W., Prasad, S. K., and Schneider, M. D. (2014). T1 mapping detects pharmacological retardation of diffuse cardiac fibrosis in mouse pressure-overload hypertrophy. Circ Cardiovasc Imaging 7, 240-249.

Su, Y. C., Treisman, J. E., and Skolnik, E. Y. (1998). The Drosophila Ste20-related kinase misshapen is required for embryonic dorsal closure and acts through a JNK MAPK module on an evolutionarily conserved signaling pathway. Genes Dev 12, 2371-2380.

Subramaniam, A., Jones, W. K., Gulick, J., Wert, S., Neumann, J., and Robbins, J. (1991). Tissue-specific regulation of the alpha-myosin heavy chain gene promoter in transgenic mice. J Biol Chem 266, 24613-24620.

Suematsu, N., Tsutsui, H., Wen, J., Kang, D., Ikeuchi, M., Ide, T., Hayashidani, S., Shiomi, T., Kubota, T., Hamasaki, N., et al. (2003). Oxidative stress mediates tumor necrosis factor -alpha-induced mitochondrial DNA damage and dysfunction in cardiac myocytes. Circulation 107, 1418-1423.

Taira, K., Umikawa, M., Takei, K., Myagmar, B. E., Shinzato, M., Machida, N., Uezato, H., Nonaka, S., and Kariya, K. (2004). The Traf2- and Nck-interacting kinase as a putative effector of Rap2 to regulate actin cytoskeleton. J Biol Chem 279, 49488-49496.

Vitorino, P., Yeung, S., Crow, A., Bakke, J., Smyczek, T., West, K., McNamara, E., Eastham-Anderson, J., Gould, S., Harris, S. F., et al. (2015). MAP4K4 regulates integrin-FERM binding to control endothelial cell motility. Nature 519, 425-430.

Wang M, Amano S U, Flach R J, Chawla A, Aouadi M, Czech M P (2013). Identification of MAP4K4 as a novel suppressor of skeletal muscle differentiation. Mol Cell Biol 33, 678-687.

Wei, J., Wang, W., Chopra, I., Li, H. F., Dougherty, C. J., Adi, J., Adi, N., Wang, H., and Webster, K. A. (2011). c-Jun N-terminal kinase (JNK-1) confers protection against brief but not extended ischemia during acute myocardial infarction. J Biol Chem 286, 13995-14006.

Whelan, R. S., Kaplinskiy, V., and Kitsis, R. N. (2010). Cell death in the pathogenesis of heart disease: mechanisms and significance. Annu Rev Physiol 72, 19-44.

White, B. J., Tarabishy, S., Venna, V. R., Manwani, B., Benashski, S., McCullough, L. D., and Li, J. (2012). Protection from cerebral ischemia by inhibition of TGF-beta-activated kinase. Exp Neurol 237, 238-245.

Xue, Y., Wang, X., Li, Z., Gotoh, N., Chapman, D., and Skolnik, E. Y. (2001). Mesodermal patterning defect in mice lacking the Ste20 NCK interacting kinase (NIK). Development 128, 1559-1572.

Yang, Y. M., Gupta, S. K., Kim, K. J., Powers, B. E., Cerqueira, A., Wainger, B. J., Ngo, H. D., Rosowski, K. A., Schein, P. A., Ackeifi, C. A., et al. (2013). A small molecule screen in stem-cell-derived motor neurons identifies a kinase inhibitor as a candidate therapeutic for ALS. Cell Stem Cell 12, 713-726.

Yao, Z., Zhou, G., Wang, X. S., Brown, A., Diener, K., Gan, H., and Tan, T. H. (1999). A novel human STE20-related protein kinase, HGK, that specifically activates the c-Jun N-terminal kinase signaling pathway. J Biol Chem 274, 2118-2125.

Yazawa, M., Hsueh, B., Jia, X., Pasca, A. M., Bernstein, J. A., Hallmayer, J., and Dolmetsch, R. E. (2011). Using induced pluripotent stem cells to investigate cardiac phenotypes in Timothy syndrome. Nature 471, 230-234.

Yue, J., Xie, M., Gou, X., Lee, P., Schneider, M. D., and Wu, X. (2014). Microtubules regulate focal adhesion dynamics through MAP4K4. Dev Cell 31, 572-585.

Zhang, D., Gaussin, V., Taffet, G. E., Belaguli, N. S., Yamada, M., Schwartz, R. J., Michael, L. H., Overbeek, P. A., and Schneider, M. D. (2000). TAK1 is activated in the myocardium after pressure overload and is sufficient to provoke heart failure in transgenic mice. Nat Med 6, 556-563.

Zohn, I. E., Li, Y., Skolnik, E. Y., Anderson, K. V., Han, J., and Niswander, L. (2006). p38 and a p38-interacting protein are critical for downregulation of E-cadherin during mouse gastrulation. Cell 125, 957-969.

The invention claimed is:

1. A compound of formula (I) or a pharmaceutically acceptable salt thereof, or a compound selected from List A, or a pharmaceutically acceptable salt thereof:

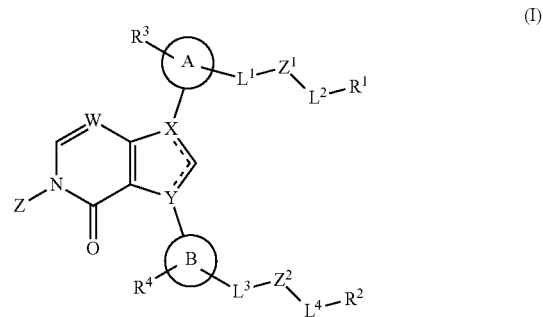

wherein

W is independently selected from N or C;

Z is independently selected from H or —CH$_2$OP(=O)(OH)$_2$;

either X is N and Y is C, or Y is N and X is C;

ring A is independently selected from an aryl and a 5 to 10 membered heterocyclic ring containing 1, 2 or 3 heteroatoms selected from N, O and S;

ring B is independently selected from an aryl and a 5 or 6 membered heterocyclic ring containing 1, 2 or 3 heteroatoms selected from N, O and S;

provided that ring A and ring B of the compound of formula (I) are not both phenyl;

L$^1$ and L$^3$ are independently selected from a bond, —(CR$^a$R$^b$)$_m$—, —O(CR$^a$R$^b$)$_m$— or —NH(CR$^a$R$^b$)$_m$—, wherein m is at each occurrence independently selected from 1, 2, 3, or 4;

Z$^1$ is a bond, —NR$^{5a}$—, —O—, —C(O)—, —SO$_2$—, —SO$_2$NR$^{5a}$—, —NR$^{5a}$SO$_2$—, —C(O)NR$^{5a}$—, —NR$^{5a}$C(O)—, —C(O)O—, or —NR$^{5a}$C(O)NR$^{5a}$—;

Z$^2$ is a bond, —NR$^{5b}$—, —O—, —C(O)—, —SO$_2$—, —SO$_2$NR$^{5a}$—, —NR$^{5a}$SO$_2$—, —C(O)NR$^{5a}$—, —NR$^{5b}$C(O)—, or —C(O)O—;

L$^2$ and L$^4$ are independently either a bond or —(CR$^c$R$^d$)$_n$—, wherein n is at each occurrence independently selected from 1, 2, 3, or 4;

R$^1$ is selected from H, halo, C$_{1-6}$ alkyl, C$_{2-6}$ alkenyl, C$_{1-6}$ haloalkyl, —NR$^{6a}$R$^{6b}$, —OR$^{6a}$, OP(=O)(OH)$_2$, —C(O)R$^{6a}$, 5 or 6 membered heteroaryl rings, or 3 to 8 membered heterocycloalkyl ring systems, wherein the heteroaryl and heterocycloalkyl rings are unsubstituted or substituted with 1 or 2 groups selected from: C$_{1-6}$ alkyl, oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$(O)R$^7$;

R$^2$ is selected from halo, C$_{1-6}$ alkyl, C$_{2-6}$ alkenyl, C$_{1-6}$ haloalkyl, —NR$^{6a}$R$^{6b}$, —OR$^{6a}$ OP(=O)(OH)$_2$, —C(O)R$^{6a}$, —NR$^{5b}$C(O)O—C$_{1-6}$ alkyl, phenyl, 5 or 6 membered heteroaryl rings, 3 to 8 membered cycloalkyl rings, or 3 to 8 membered heterocycloalkyl ring systems, wherein the phenyl, heteroaryl, cycloalkyl and heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, C(O)R$^{6a}$, —C(O)OR$^g$, and —NR$^8$C(O)R$^7$;

R$^3$ and R$^4$ are independently selected from H, halo, —CN and C$_{1-6}$ alkyl;

R$^{5a}$ and R$^{5b}$ are independently selected at each occurrence, from: H, C$_{1-6}$ alkyl, or C$_{3-6}$ cycloalkyl;

R$^{6a}$ and R$^{6b}$ are, independently selected at each occurrence, from: H, C$_{1-6}$ alkyl, C$_{1-6}$ alkyl substituted with –OR$^e$, C$_{1-6}$ alkyl substituted with —NR$^e$R$^f$, and C$_{3-6}$ cycloalkyl;

R$^7$ is selected from H, —OR$^8$, C$_{1-6}$ alkyl and C$_{3-6}$ cycloalkyl;

R$^8$ is selected from H and C$_{1-6}$ alkyl;

R$^a$, R$^b$, R$^c$ and R$^d$ are, at each occurrence, independently selected from: H, halo, C$_{1-6}$ alkyl, and —OR$^h$, or R$^a$ and R$^b$ or R$^c$ and R$^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and R$^e$, R$^f$, R$^g$ and R$^h$ are each independently selected at each occurrence from H or C$_{1-6}$ alkyl;

and wherein List A is a compound selected from the group consisting of:

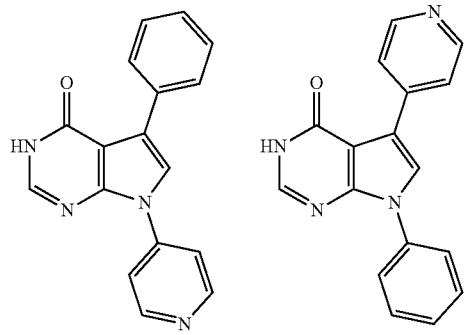

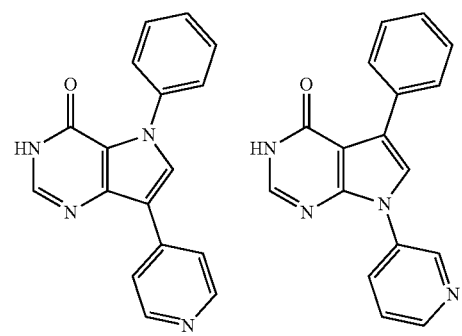

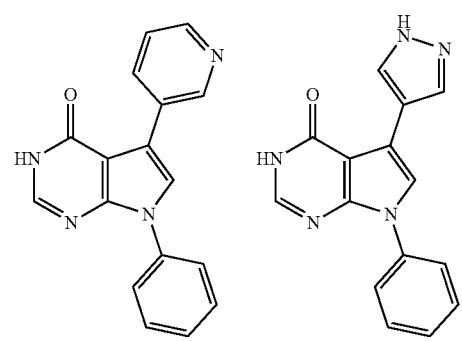

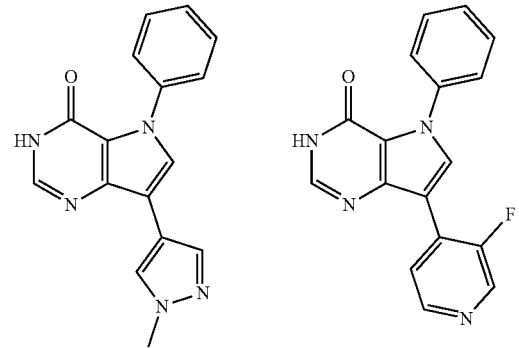

-continued
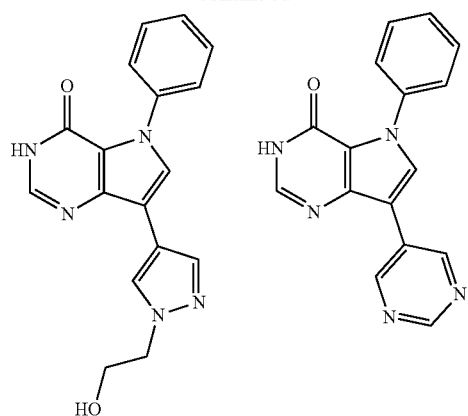
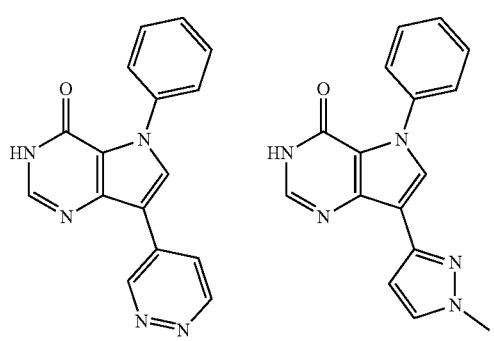
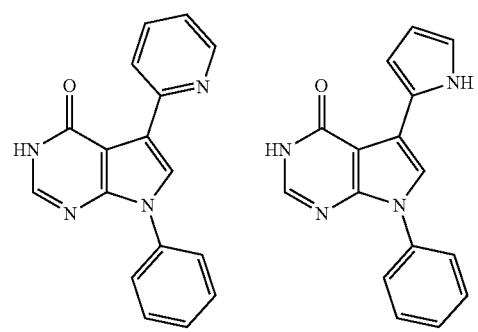
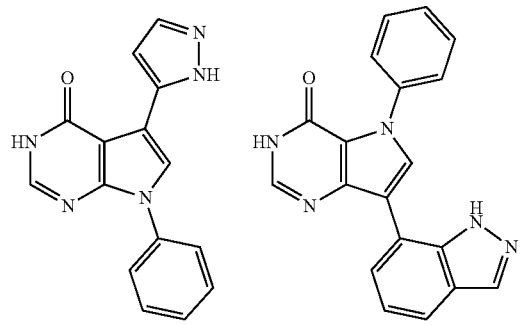
-continued
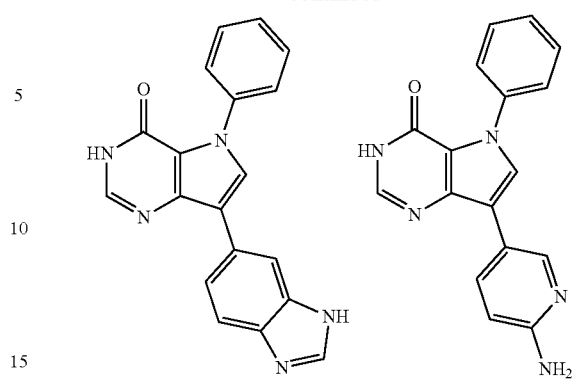
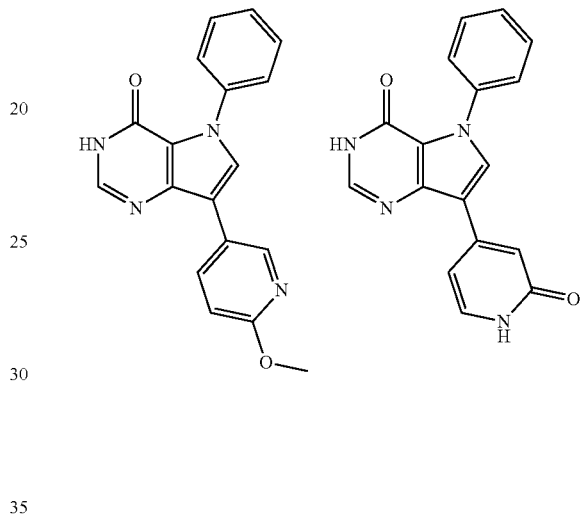
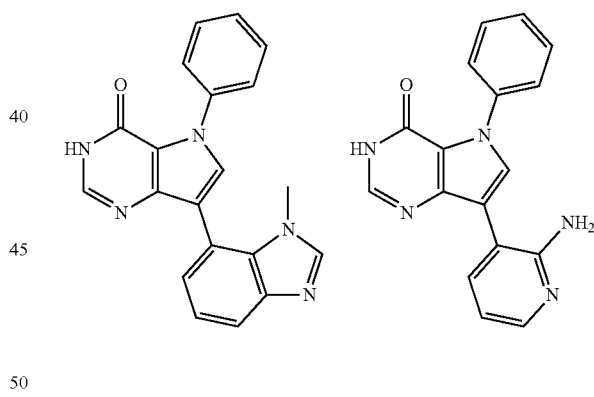
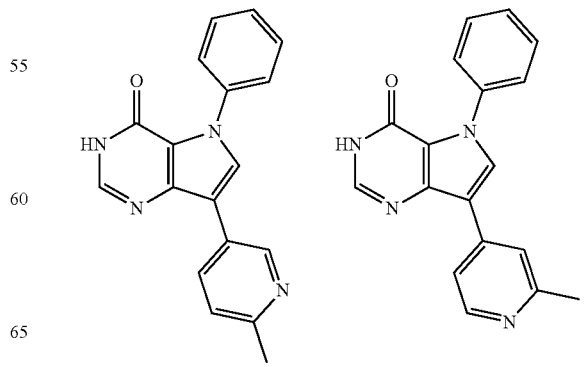

-continued

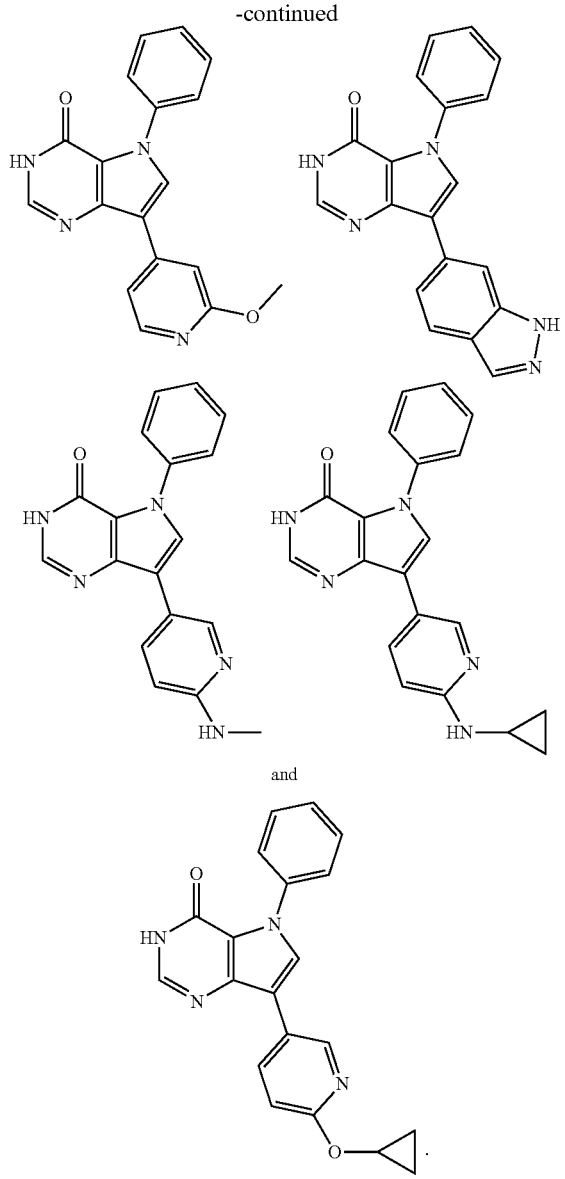

2. A compound of claim 1 wherein W is N.

3. A compound of claim 1, wherein A is independently selected from phenyl and a 5 to 10 membered heteroaryl ring containing 1, 2 or 3 heteroatoms selected from N, O and S; and ring B is independently selected from phenyl and a 5 or 6 membered heteroaryl ring containing 1, 2 or 3 heteroatoms selected from N, O and S.

4. A compound of claim 1, wherein ring A is a 5, 6 or 9 membered heterocyclic ring.

5. A compound of claim 1, wherein ring A is a 6 or 9 membered heteroaryl, optionally wherein the 9 membered ring is a fused bicyclic system comprising a 6 membered and 5 membered ring.

6. A compound of claim 1, wherein ring A is independently selected from pyrrole, 2H-pyrrole, furan, pyrrolidine, pyrroline, tetrahydrofuran, thiophene, tetrahydrothiophene, pyrazole, imidazole, oxazole, isoxazole, pyrazoline, imidazoline, pyrazolidine, imidazolidine, thiazole, isothiazole, thiazolidine, isoxazolidine, triazole, oxadiazole, furazan, thiadiazole, pyridine, pyridine N-oxide, pyran, dihydropyran, piperidine, pyridazine, pyrimidine, pyrazine, oxazine, dioxine, piperazine, morpholine, dioxane, thiazine, thiomorpholine, oxathiane, dithiane, triazine, phenyl, naphthalene, benzimidazole, and indazole.

7. A compound of claim 1, wherein ring B is a 5 or 6 membered heteroaryl.

8. A compound of claim 1, wherein ring B is selected from pyrrole, 2H-pyrrole, furan, pyrrolidine, pyrroline, tetrahydrofuran, thiophene, tetrahydrothiophene, pyrazole, imidazole, oxazole, isoxazole, pyrazoline, imidazoline, pyrazolidine, imidazolidine, thiazole, isothiazole, thiazolidine, isoxazolidine, triazole, oxadiazole, furazan, thiadiazole, pyridine, pyran, dihydropyran, piperidine, pyridazine, pyrimidine, pyrazine, oxazine, dioxine, piperazine, morpholine, dioxane, thiazine, thiomorpholine, oxathiane, dithiane, triazine, phenyl and naphthalene.

9. A compound of claim 1, wherein ring A is selected from:

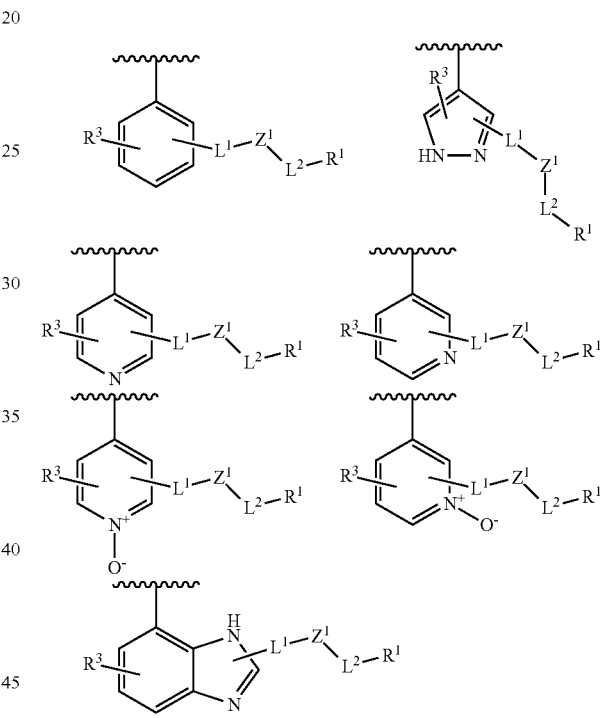

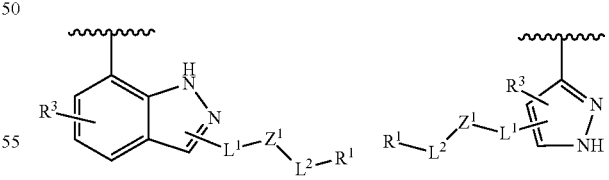

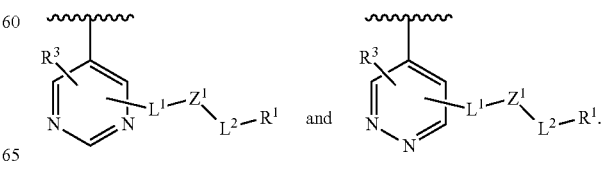

10. A compound of claim 1, wherein ring B is selected from:

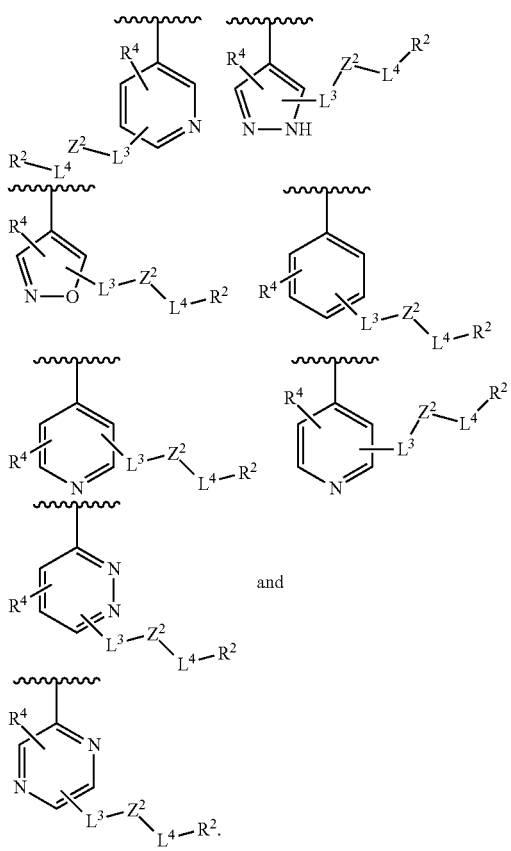

and

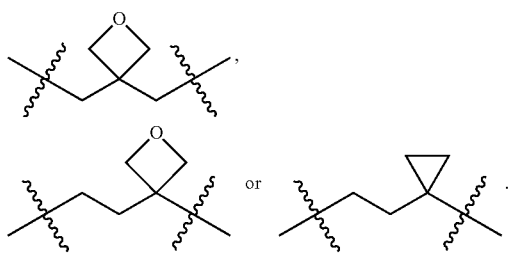

11. A compound of claim 1, wherein $L^1$ is represented by a bond or —CH$_2$—.

12. A compound of claim 1, wherein $Z^1$ is a bond, —O—, —C(O)—, —SO$_2$—, or —NR$^{5a}$C(O)—.

13. A compound of claim 1, wherein $L^2$ is bond, —CH$_2$—, —CH$_2$CH$_2$—, —(CH$_2$)$_3$—, —CH$_2$CH(OH)CH$_2$—, —CH$_2$CH(OH)C(CH$_3$)$_2$—, —CH$_2$CH(OCH$_3$)CH$_2$—, —CH$_2$C(CH$_3$)$_2$CH$_2$—, —CH$_2$C(CH$_3$)$_2$—, —CF$_2$CH$_2$—,

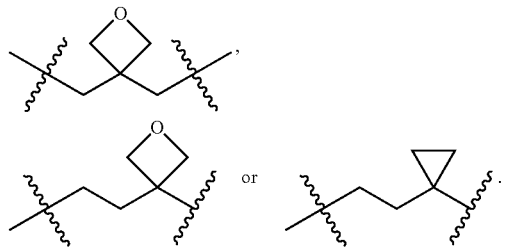

14. A compound of claim 1, wherein $R^1$ is selected from H, halo, C$_{1-6}$ alkyl, C$_{2-6}$ alkenyl, halo, C$_{1-6}$ alkyl, 5 or 6 membered heteroaryl rings, or 3 to 8 membered heterocycloalkyl ring systems (optionally 5 or 6 membered), wherein the heteroaryl and heterocycloalkyl rings are unsubstituted or substituted with 1 or 2 groups selected from: C$_{1-6}$ alkyl and oxo.

15. A compound of claim 1, wherein $L^3$ is represented by a bond or —CH$_2$—.

16. A compound of claim 1, wherein $Z^2$ is a bond, —NR$^{5b}$—, —O—, —C(O)—, or —NR$^{5a}$C(O)—.

17. A compound of claim 1, wherein $L^4$ is represented by a bond, —CH$_2$—, —CH$_2$CH$_2$—, —CH$_2$C(Me)$_2$-, —CH$_2$CH$_2$C(Me)$_2$-, —(CH$_2$)$_3$—, —CH$_2$CH(OH)CH$_2$—, —CH$_2$CH(OMe)CH$_2$—, —CH$_2$CH(OH)C(CH$_3$)$_2$—, —CH$_2$CH(OCH$_3$)CH$_2$—, —CH$_2$C(CH$_3$)$_2$CH$_2$—, —CH$_2$C(CH$_3$)$_2$—, —CF$_2$CH$_2$—,

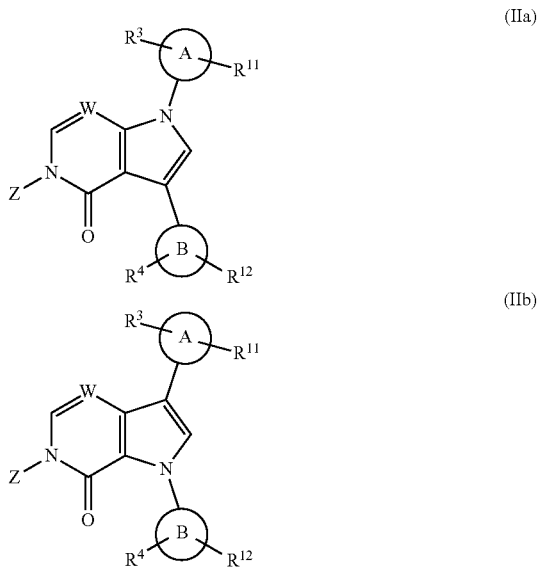

18. A compound of claim 1, wherein $R^2$ is selected from: halo, C$_{1-6}$ alkyl, C$_{2-6}$ alkenyl, —NR$^{6a}$R$^{6b}$, —OR$^{6a}$, —C(O)R$^{6a}$, —NR$^{5b}$C(O)O—C$_{1-6}$ alkyl, and 3 to 8 membered heterocycloalkyl ring systems,
wherein the heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$C(O)R$^7$.

19. A compound of claim 1, wherein the compound is a compound of formulae (IIa) or (IIb):

wherein
$R^{11}$ is selected from: H, halo, C$_{1-6}$ alkyl, C$_{2-6}$ alkenyl, —(CH$_2$)$_o$R$^Y$, —(CH$_2$)$_o$NR$^Z$R$^{6a}$, —(CH$_2$)$_o$OR$^Z$, —(CH$_2$)$_o$SO$_2$R$^{6a}$, —(CH$_2$)$_o$C(O)NR$^Z$R$^{6a}$, or —(CH$_2$)$_o$C(O)OR$^Z$, $R^Y$ is selected from 5 or 6 membered heteroaryl rings;

$R^Z$ is selected from H, C$_{1-6}$ alkyl, —C(O)R$^{6a}$, —C(O)OR$^{6a}$, —C(O)(CR$^a$R$^b$)$_p$NR$^{6a}$R$^{6b}$, (CR$^a$R$^b$)$_p$OR$^{6a}$, (CR$^a$R$^b$)$_p$NR$^{6a}$R$^{6b}$, (CR$^a$R$^b$)$_p$R$^V$; and $R^V$ is selected from 3 to 8 membered heterocycloalkyl ring systems, wherein the heterocycloalkyl ring is unsubstituted or substituted with 1 or 2 groups selected from: oxo, $C_{1-6}$ alkyl or halo, and $R^{12}$ is selected from: halo, $C_{1-6}$ alkyl, $C_{2-6}$ alkenyl, $-(CH_2)_oR^{Y2}$, $-(CH_2)_oNR^{Z2}R^{6a}$, $-(CH_2)_oOR^{Z2}$, $-(CH_2)_oC(O)NR22R^{6a}$, or $-(CH_2)_oC(O)OR^{Z2}$, $R^{Y2}$ is selected from 5 or 6 membered heteroaryl rings;

$R^{Z2}$ is selected from H, $C_{1-6}$ alkyl, $-C(O)R^{6a}$, $-C(O)OR^{6a}$, $-C(O)(CR^aR^b)_pNR^{6a}R^{6b}$, $(CR^aR^b)_pOR^{6a}$, $(CR^aR^b)_pNR^{6a}R^{6b}$, $(CR^aR^b)_pR^{Y2}$ or $-C(O)(CR^aR^b)_pR^{Y2}$;

$R^{Y2}$ is selected from 3 to 8 membered heterocycloalkyl ring systems, wherein the heterocycloalkyl ring is unsubstituted or substituted with 1 or 2 groups selected from: oxo, halo, $C_{1-6}$ alkyl, $C_{1-6}$ alkyl substituted with $NR^{6a}R^{6b}$, or $C_{1-6}$ alkyl substituted with $OR^{6a}$;

o is selected from 0, 1, 2 or 3; and p is selected from 0, 1, 2 or 3.

20. A compound of claim 1, wherein-$L^1$-$Z^1$-$L^2$-$R^1$ is selected from: H, $C_{1-6}$ alkyl, $-(CR^aR^b)_mOR^{6a}$, halo, $-OR^{6a}$, $-(CR^aR^b)_m$-5 or 6 membered heteroaryl rings, $-SO_2-C_{1-6}$ alkyl, $-C(O)OR^{6a}$, $-C(O)NR^{6a}R^{6b}$, $-O(CR^aR^b)$, $-NR^{6a}R^{6b}$, and $-O(CR^aR^b)_n$-3 to 8 membered heterocycloalkyl ring, wherein the heteroaryl and heterocycloalkyl rings are unsubstituted or substituted with 1 or 2 groups selected from: $C_{1-6}$ alkyl, oxo or halo.

21. A compound of claim 1, wherein-$L^3$-$Z^2$-$L^4$-$R^2$ is selected from: halo, $C_{1-6}$ alkyl, $C_{2-6}$ alkenyl, $-OR^{6a}$, $-NR^{6a}R^{6b}$, $-(CR^aR^b)_m$-phenyl, $-(CR^aR^b)_m$-5 or 6 membered heteroaryl rings, $-(CR^aR^b)_mNR^{6a}R^{6b}$, $-(CR^aR^b)_mOR^{6a}$, $-(CR^aR^b)_mOC(O)R^{6a}$, $-(CR^aR^b)_mC(O)OR^{6a}$, $-(CR^aR^b)_mC(O)NR^{6a}R^{6b}$, $-(CR^aR^b)_mNR^{5a}C(O)-C_{1-6}$ alkyl, $-(CR^aR^b)_mNR^{5a}C(O)OR^{6a}$, $-O(CR^aR^b)_nOR^{6a}$, $-O(CR^aR^b)_nNR^{5b}C(O)OC_{1-6}$ alkyl, 3 to 8 membered heterocycloalkyl ring, $-O(CR^aR^b)_n$-3 to 8 membered heterocycloalkyl ring, $-O(CR^aR^b)_n-NR^{6a}R^{6b}$, $-NR^{5a}(CR^cR^d)_nOR^{6a}$, $-C(O)NR^{6a}R^{6b}$, $-NR^{5b}C(O)-C_{1-6}$ alkyl, $-NR^{5b}C(O)(CR^cR^d)_nNR^{6a}R^{6b}$, $-NR^{5b}C(O)(CR^cR^d)_nOR^{6a}$, and $-NR^{5b}C(O)(CR^cR^d)_n$-3 to 8 membered heterocycloalkyl ring, wherein the phenyl, heteroaryl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, $-C(O)R^7$, and $-NR^8C(O)R^7$, Optionally, -$L^1$-$Z^1$-$L^2$-$R^1$ or $R^{11}$ may be H.

22. A compound of claim 1, wherein-$L^3$-$Z^2$-$L^4$-$R^2$ is selected from: F, Cl, —OMe, methyl, $NH_2$, —$CH_2$-phenyl, —$CH_2$-imidazolyl, —$CH_2NH_2$, —$CH_2NMe_2$, —$CH_2NHMe$, —$CH_2NHC(O)Me$, —$CH_2N(Me)C(O)Ot$-Bu, —$CH_2OH$, —$CH_2CH_2OH$, —$CH_2CH_2CH_2OH$, —$CH_2CH_2OMe$, —$CH_2CH_2CH_2OCH_3$, —$CH_2CH_2NHMe$, —$(CH_2)_3OH$, —$(CH_2)_3OMe$, —$CH_2C(Me_2)OH$, —$CH_2CH_2OC(O)Me$, —$CH_2C(O)OMe$, —$CH_2C(O)OH$, —$CH_2C(O)OEt$, —$CH_2C(O)$ $NH_2$, —OMe, —$OCH_2CH_2OH$, —$OCH_2CH_2OMe$, —$OCH_2C(Me)_2OH$, —$OCH_2CH_2C(Me)_2OH$, —$OCH_2CH(OH)CH_2OH$, —$OCH_2C(Me_2)OH$, —$OCH_2CH_2NH_2$, —$OCH_2CH_2NMe_2$, —$O(CH_2)_3NMe_2$, —$OCH_2CH(OH)CH_2NMe_2$, —$OCH_2CH_2NHC(O)O^tBu$, —$OCH_2$-azetidinyl, —$OCH_2$—N-methylazetindinyl, —O—N-ethylpiperadinyl, —$O(CH_2)_3$-morpholinyl, —$OCH_2CH(OH)CH_2$-morpholinyl, —$OCH_2CH(OMe)CH_2$-morpholinyl, —$O(CH_2)_3$—N-methylpiperazinyl, —$OCH_2CH(OH)CH_2$—N-methylpiperazinyl, —$OCH_2CH(OH)CH_2$—N-methylpiperazinonyl, —$O(CH_2)_3$—N-methylpiperazinonyl, —$OCH_2CH(OH)CH_2$-morpholinonyl, —$OCH_2CH(OH)CH_2$-morpholinonyl, —$OCH_2CH(OH)CH_2$-thiomorpholin-dionyl, —$NHCH_2CH_2OH$, —$N(Me)CH_2CH_2OH$, —$NHCH_2CH_2OMe$, —$C(O)NHCH_2CH_2NMe_2$, —$C(O)NHCH_2CH_2OH$, —$NHC(O)Me$, —$NHC(O)CH_2OH$, —$NHC(O)CH_2NH_2$, —$NHC(O)CH_2NHMe$, —$NHC(O)CH_2NMe_2$, —$NHC(O)CH_2CH_2NHMe$, —$NHC(O)(CH_2)_3NMe_2$, —$NHC(O)CH_2$-morpholinyl, —$NHC(O)CH_2$—N-oxetanyl, azetidinyl, hydroxypyrolidinyl, methylpiperazinyl, pyrolidinonyl, imidazolidinonyl, N-methylimidazolidinonyl, piperidinonyl,

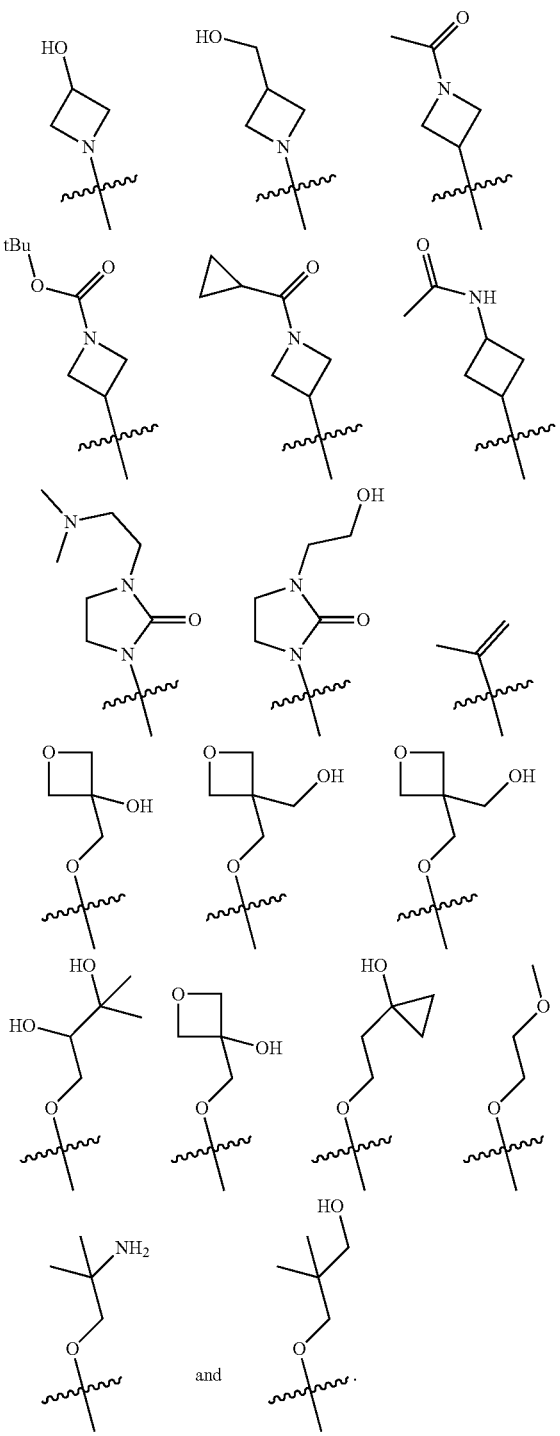

and

23. A compound of claim 1, wherein -L$^1$-Z$^1$-L$^2$-R$^1$ is —O(CR$^a$R$^b$)$_{1-3}$—R$^1$.
24. A compound of claim 1, wherein -L$^3$-Z$^2$-L$^4$-R$^2$ is —O(CR$^a$R$^b$)$_{1-3}$—R$^2$.
25. A compound of claim 1, wherein the compound of formula (I) is a compound selected from:
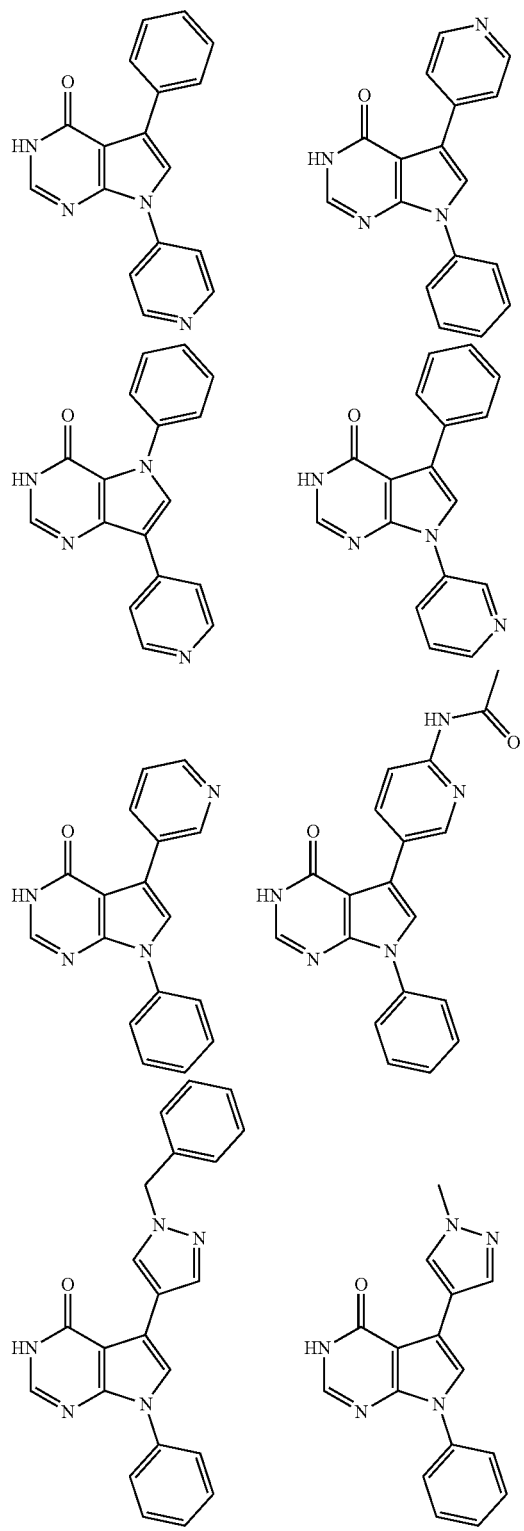
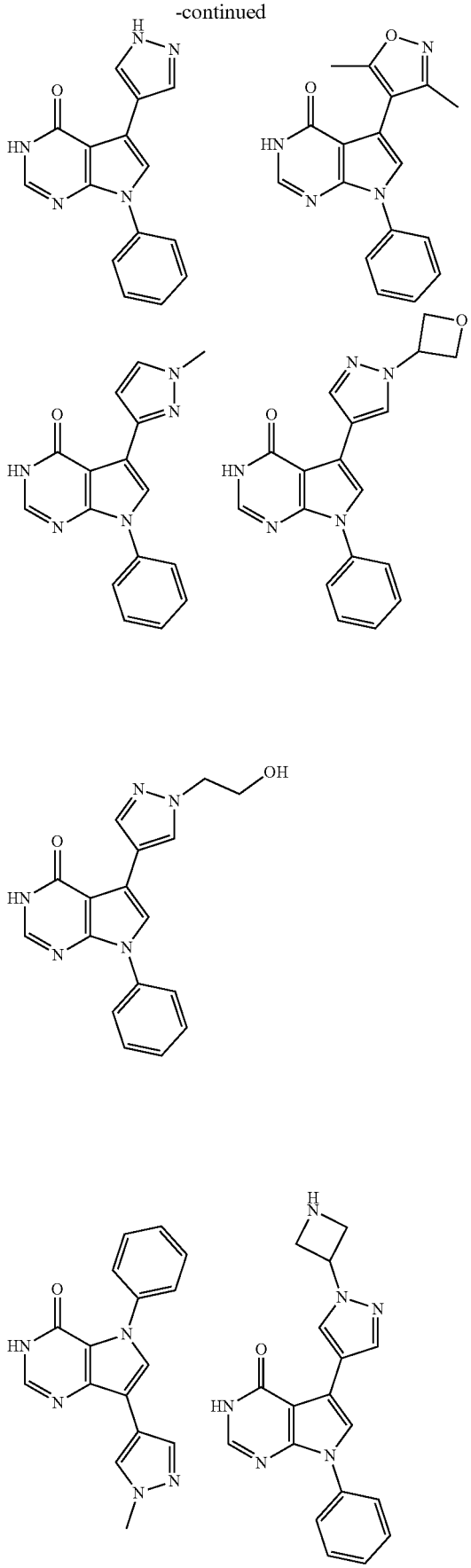

305
-continued
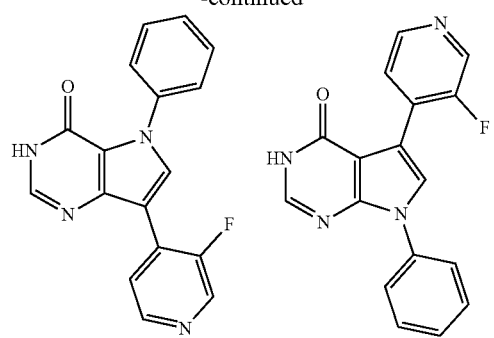
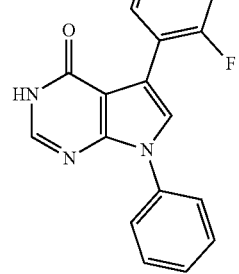
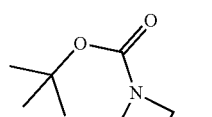
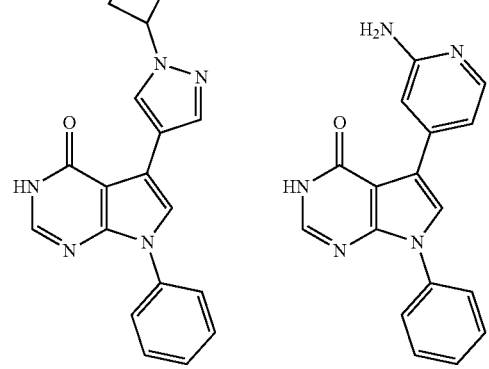
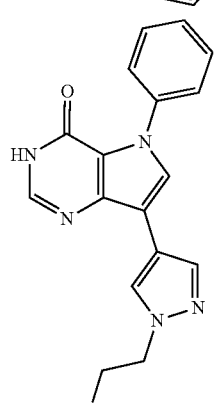
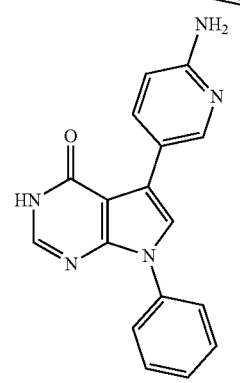
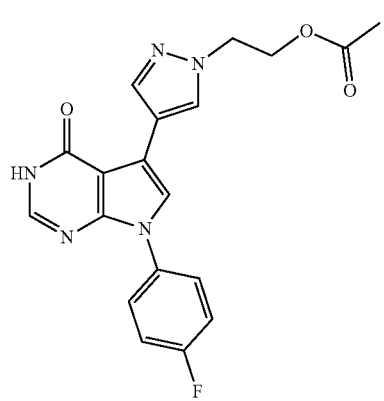
306
-continued
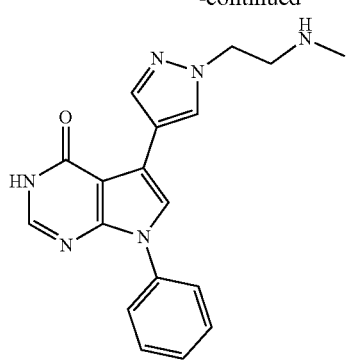
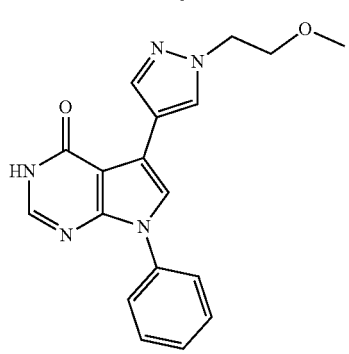
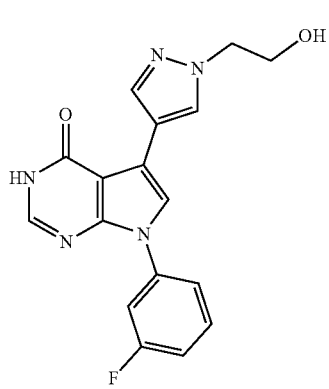
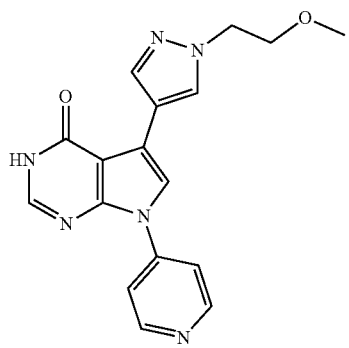

307
-continued
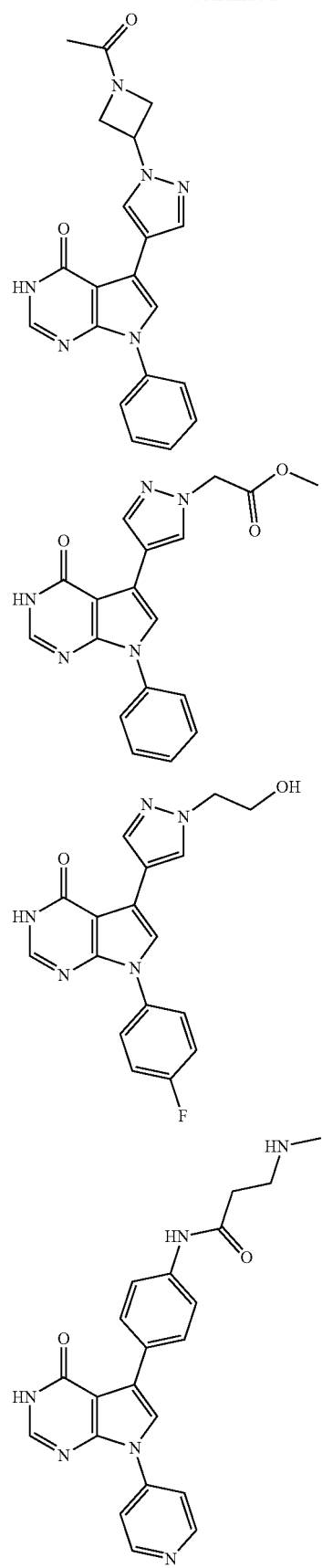
308
-continued
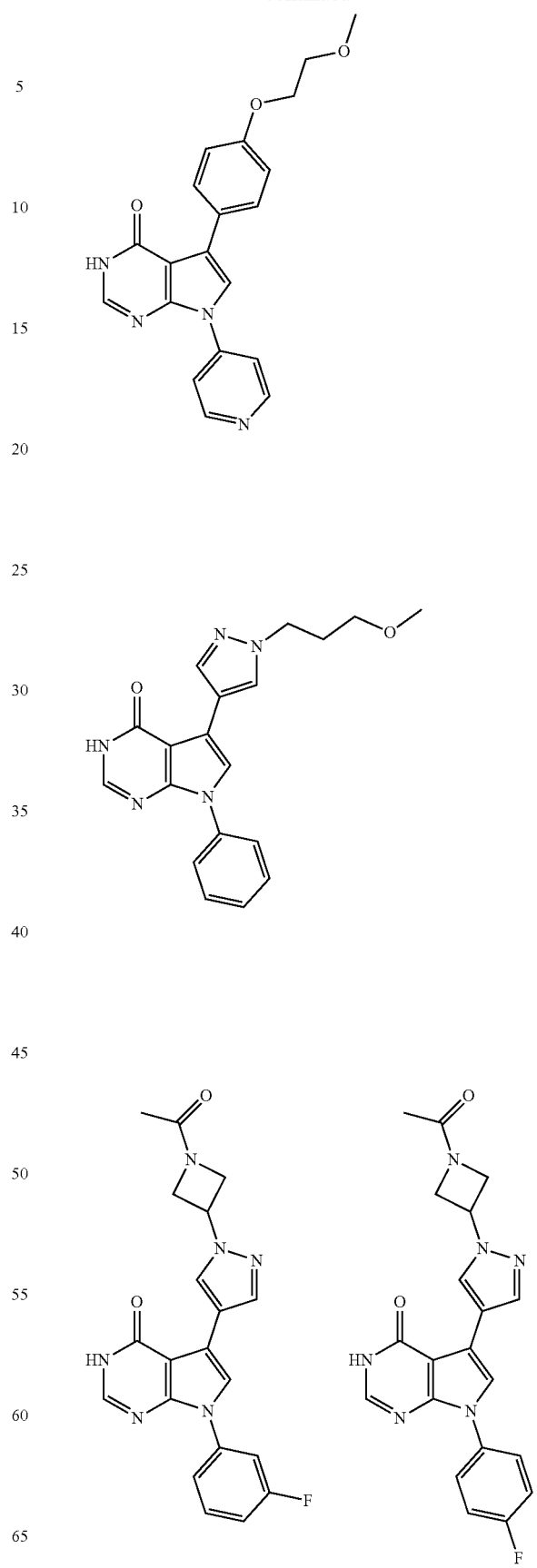

309
-continued
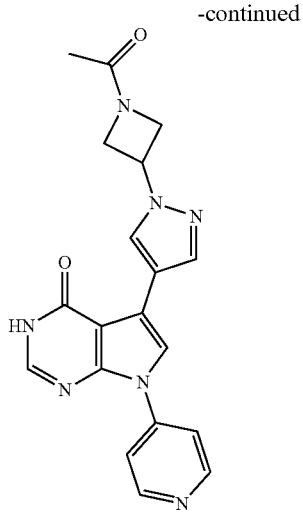
310
-continued
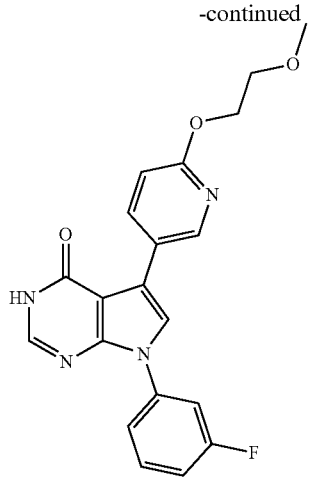
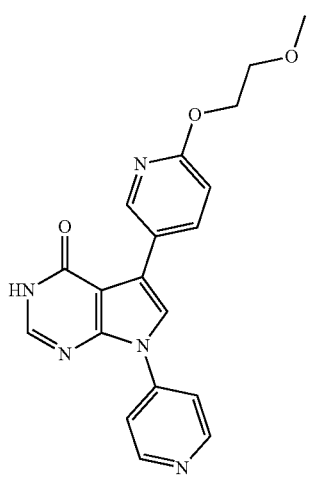
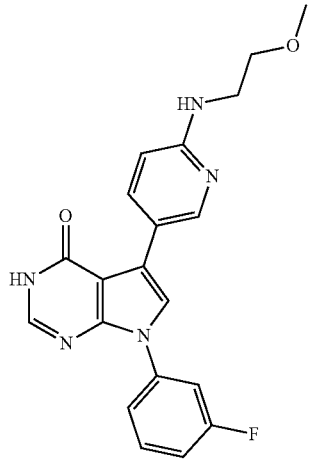
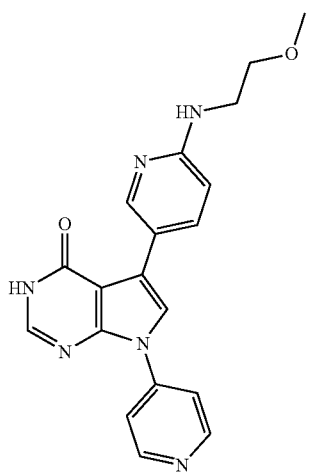

311
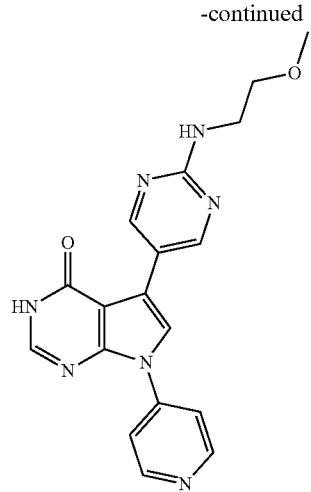
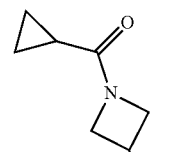
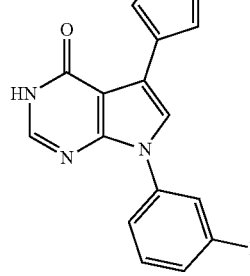
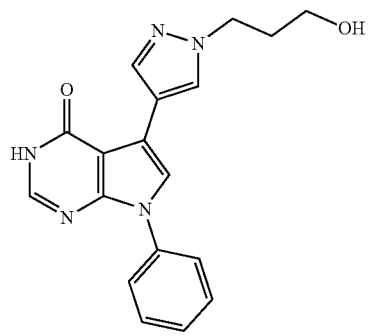
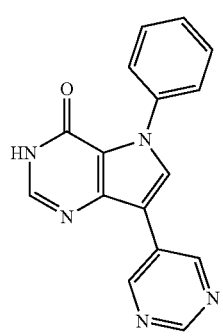
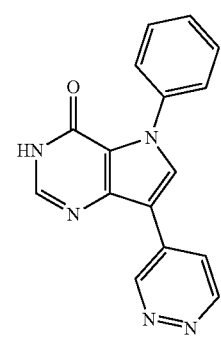
312
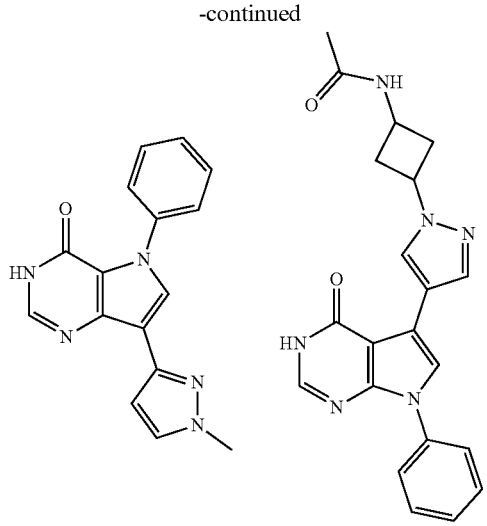
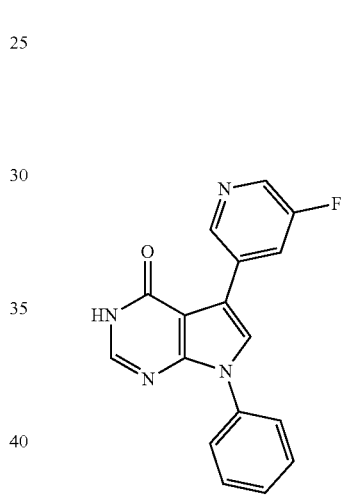
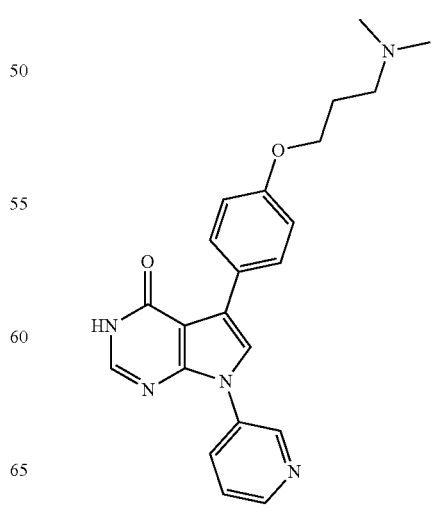

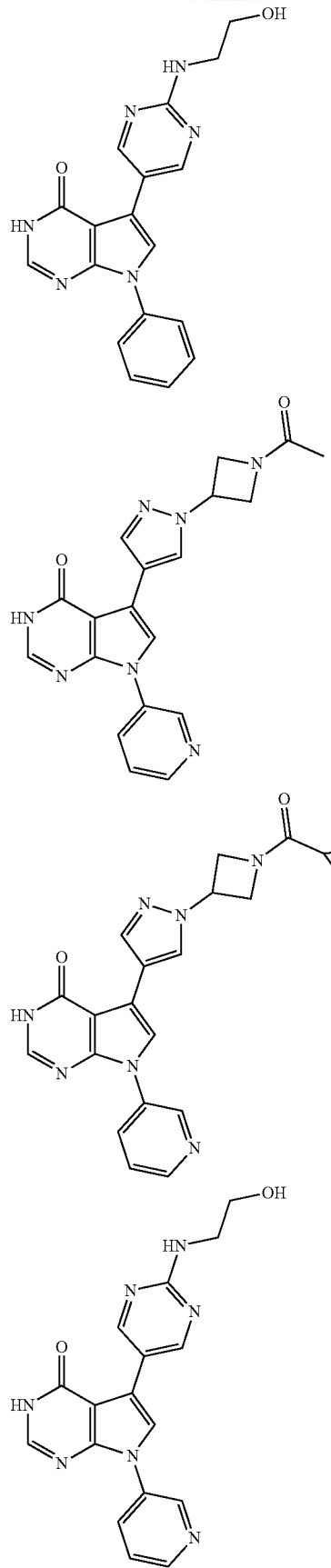

315
-continued
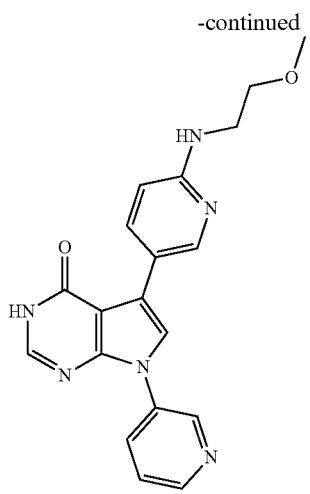
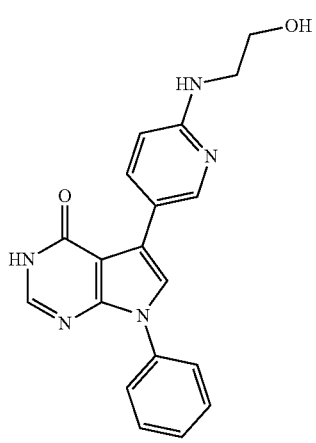
316
-continued
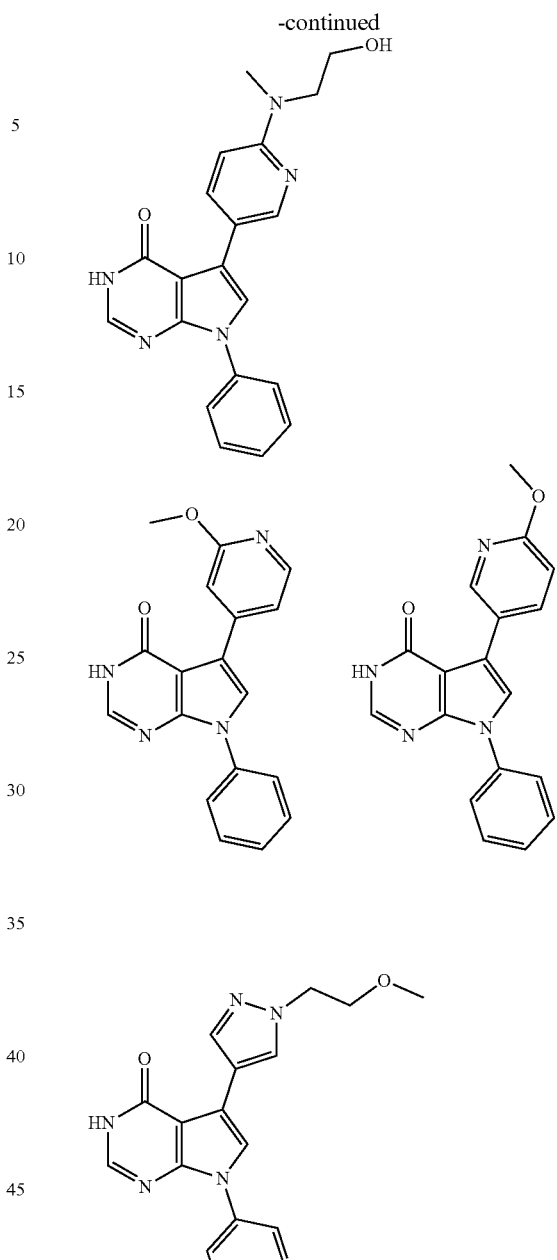

317
-continued
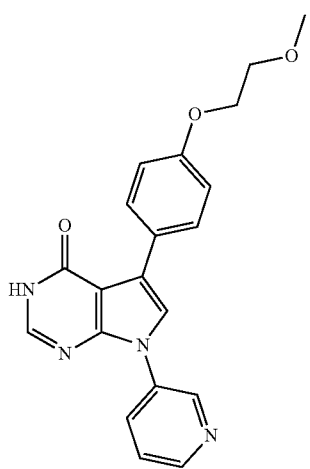
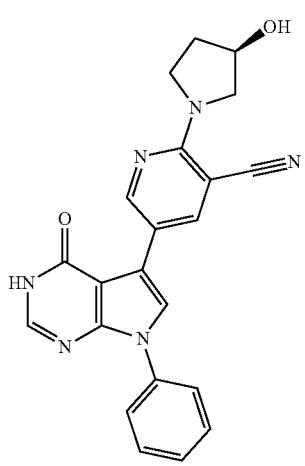
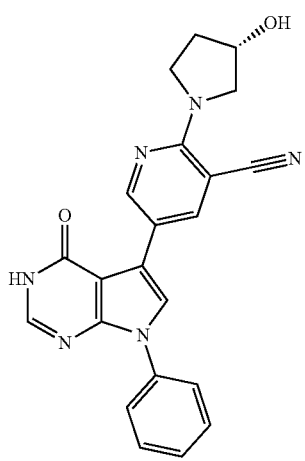
318
-continued
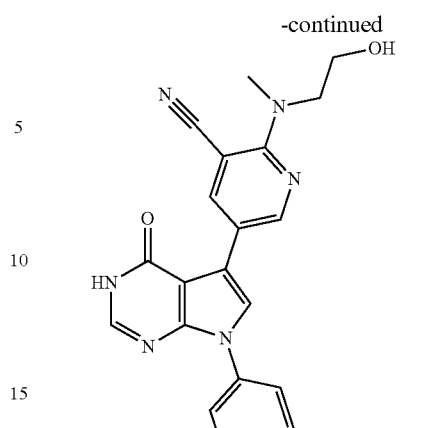
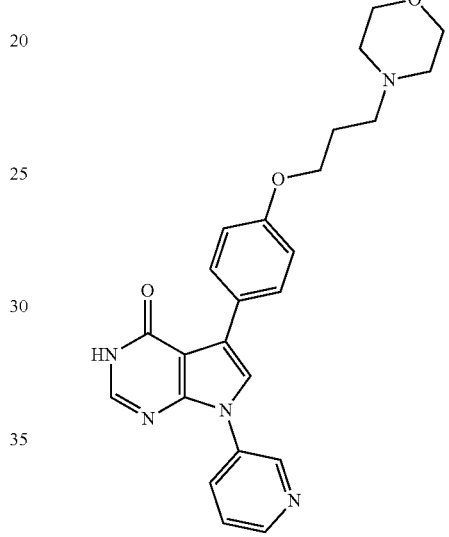
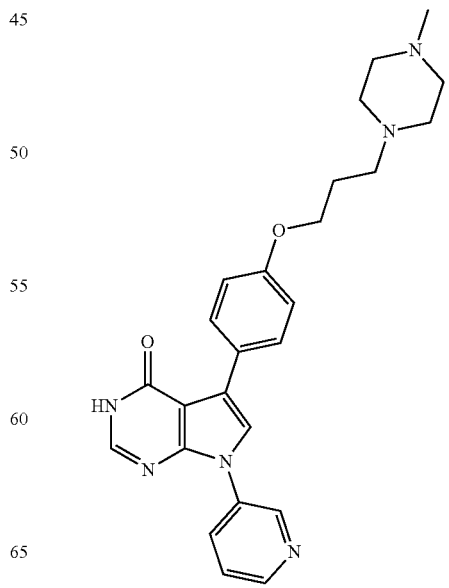

-continued
319
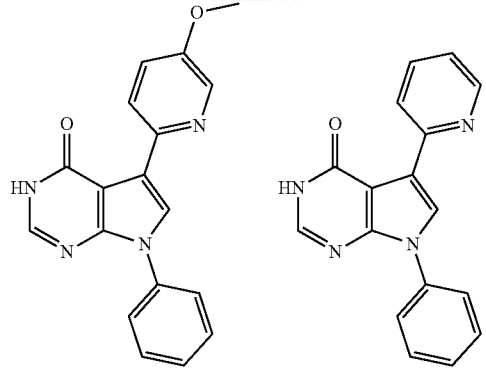
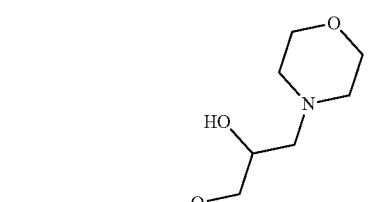
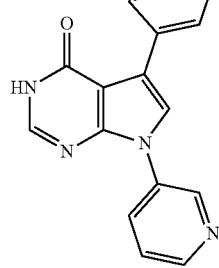
320
-continued
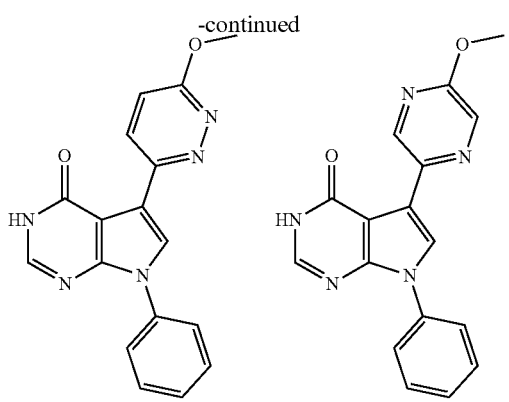
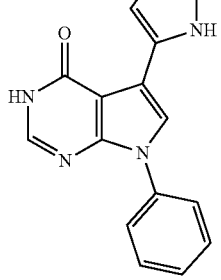
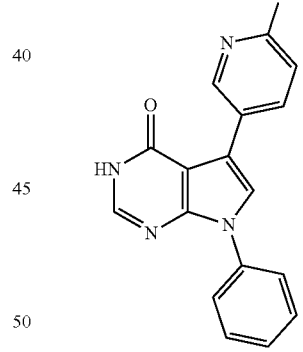
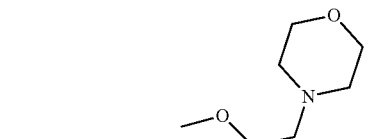
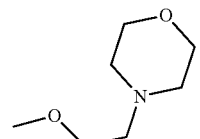
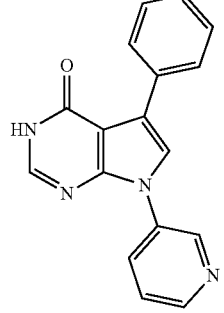
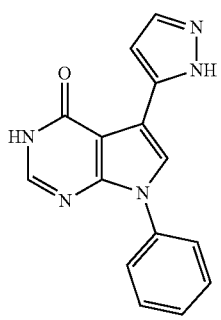

321
-continued
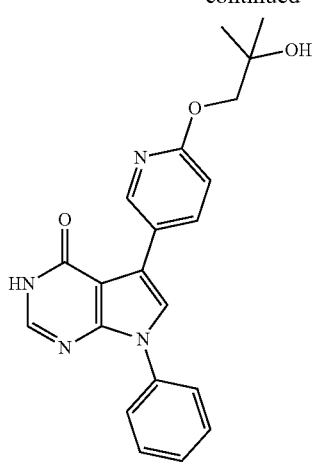
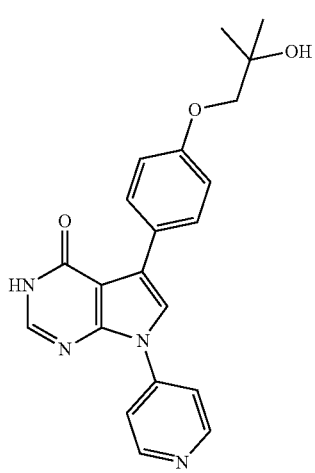
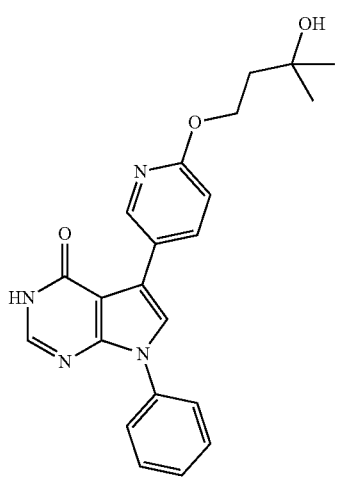
322
-continued
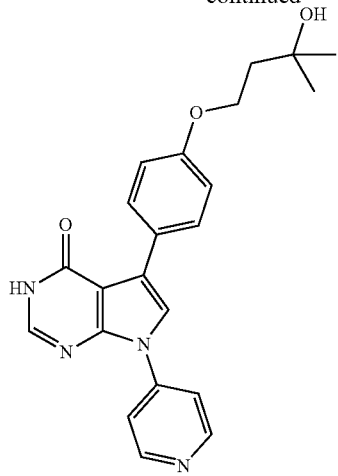
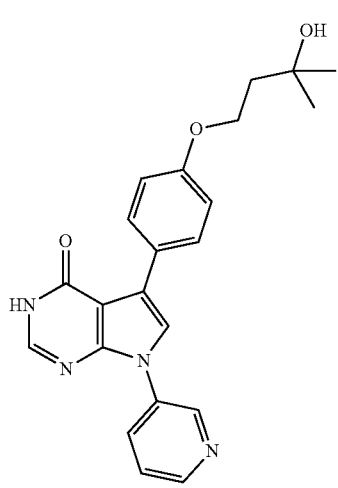
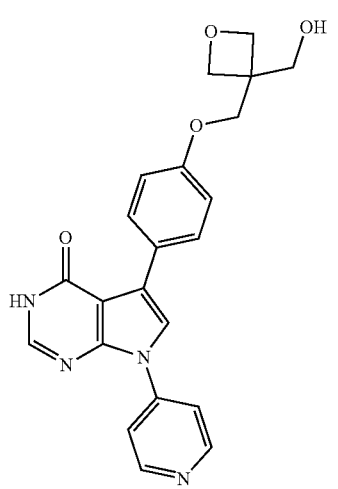

323
-continued
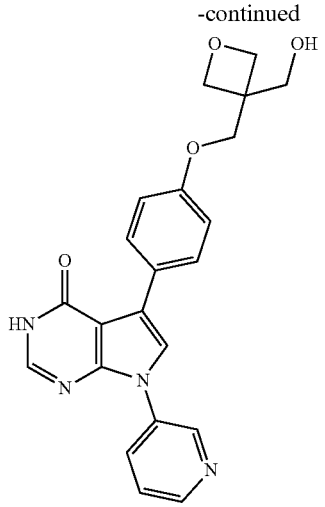
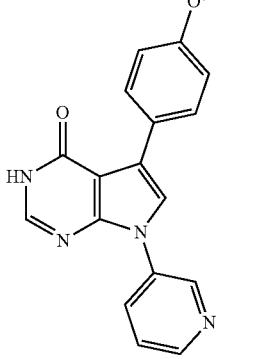
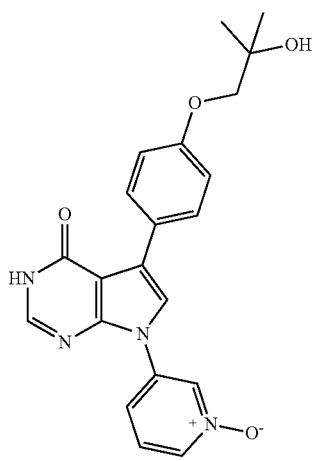
324
-continued
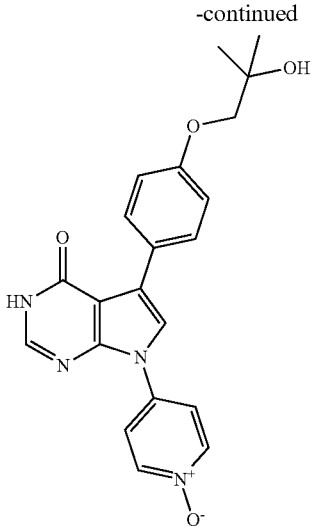
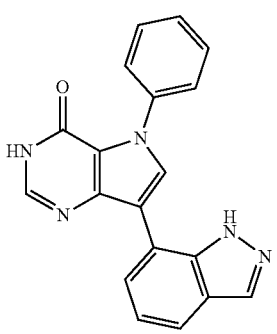
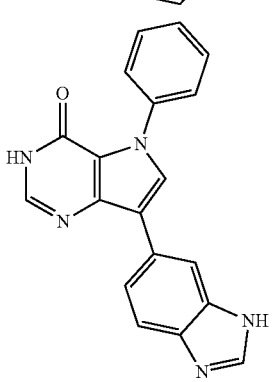
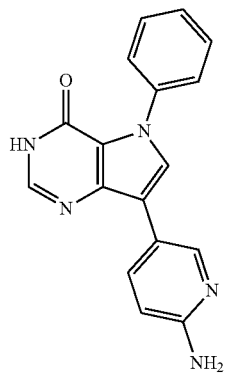

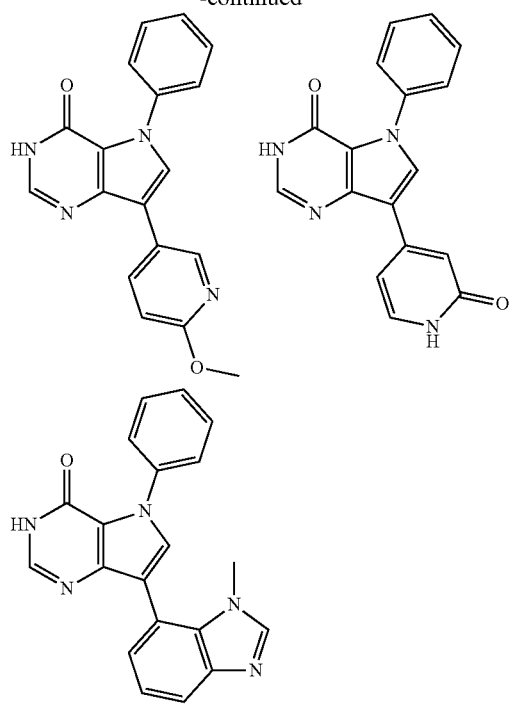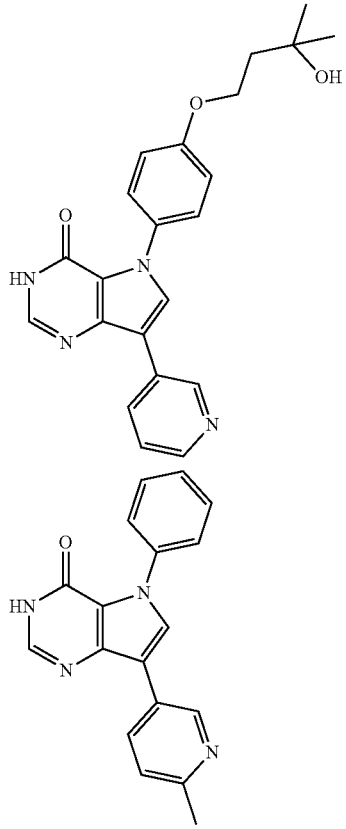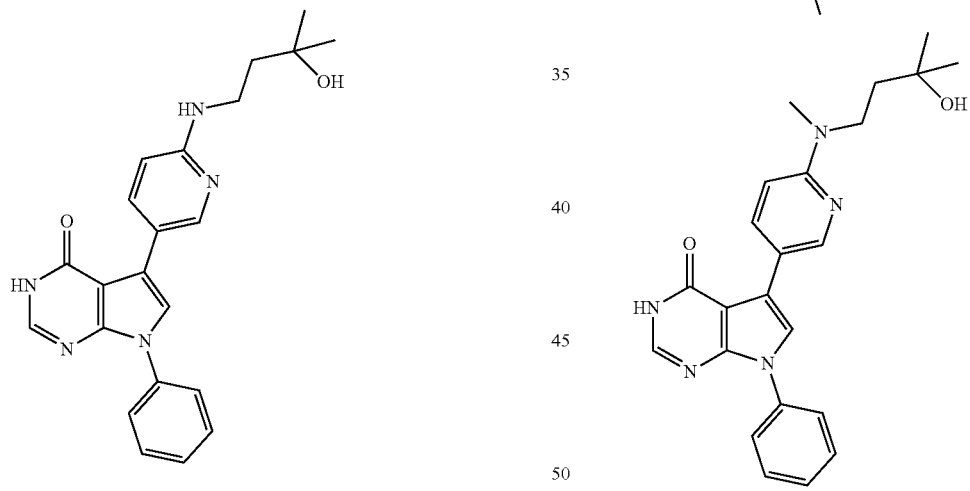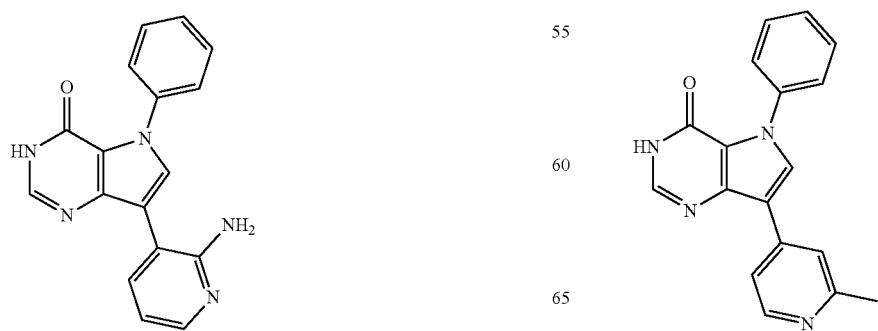

327
-continued
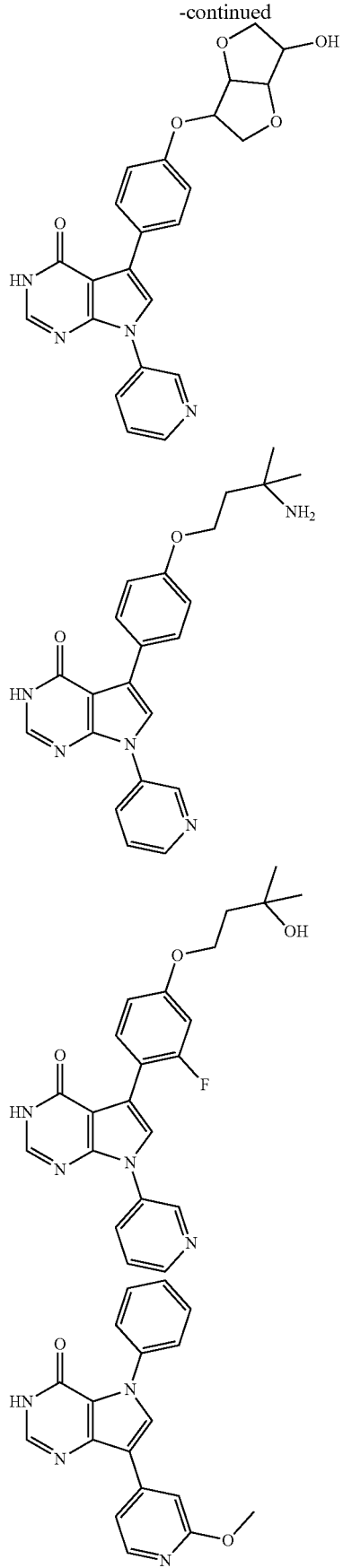
328
-continued
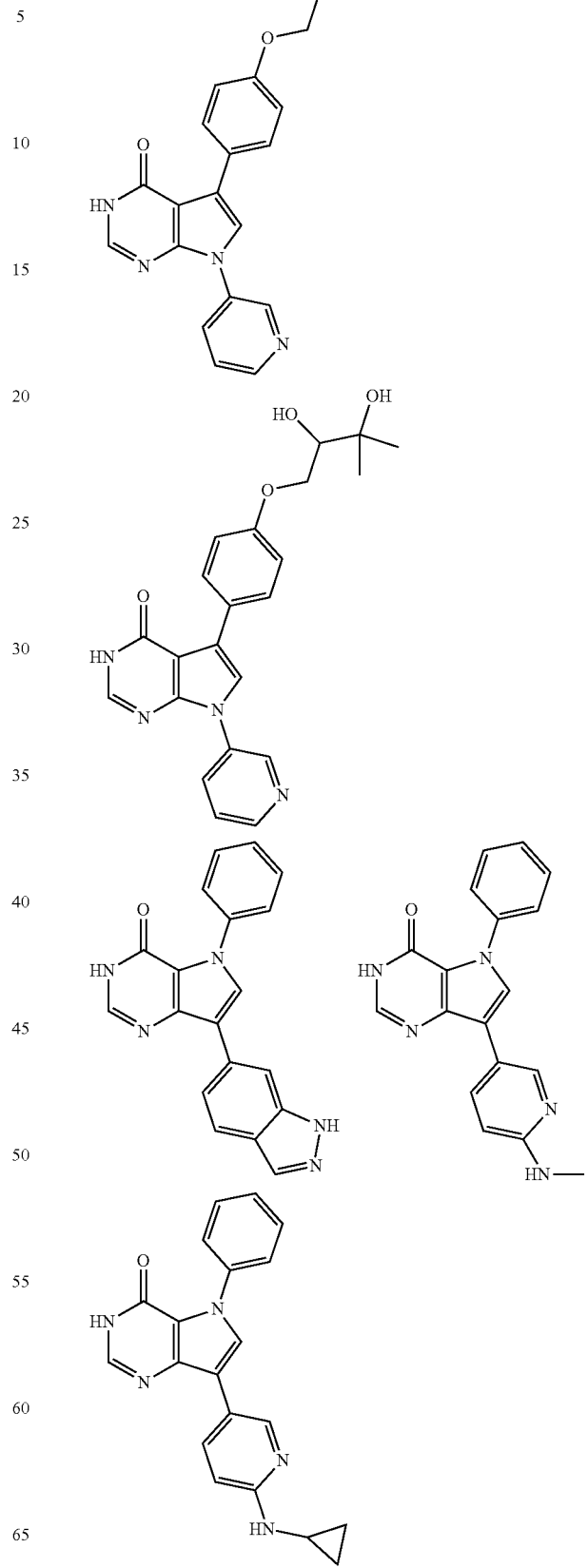

329
-continued
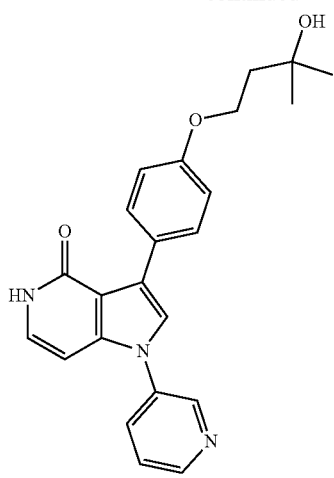
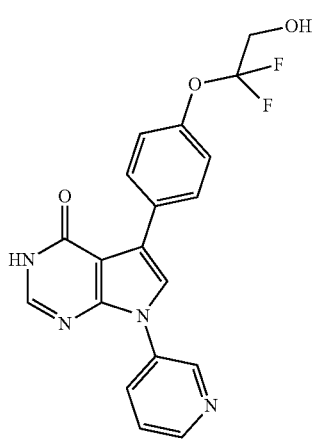
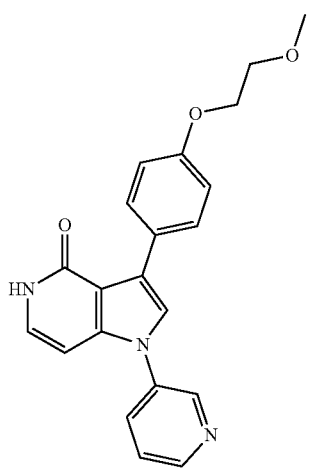
330
-continued
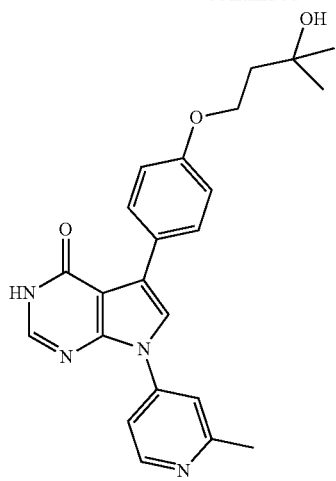
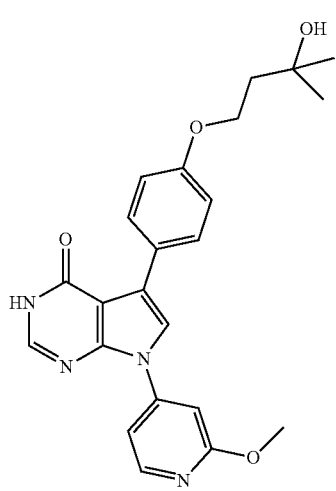
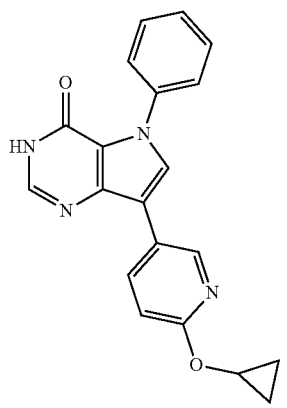

331
-continued
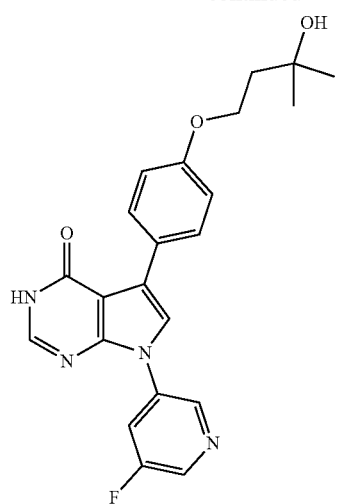
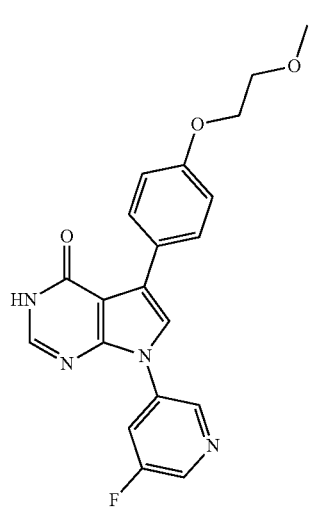
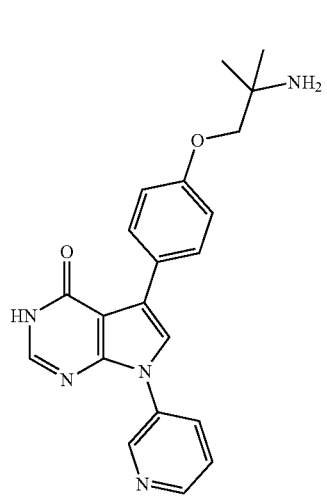
332
-continued
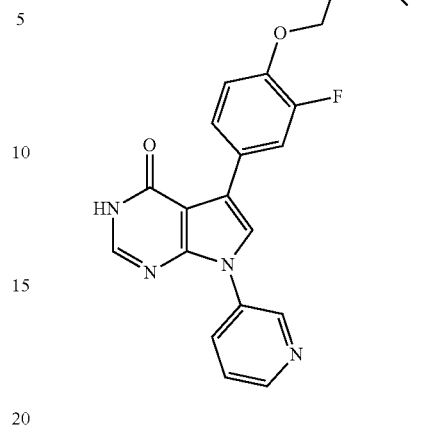
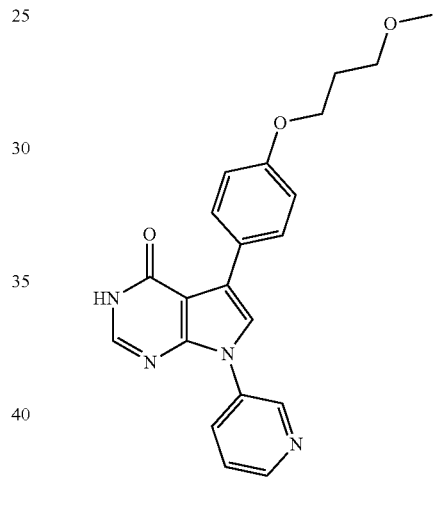
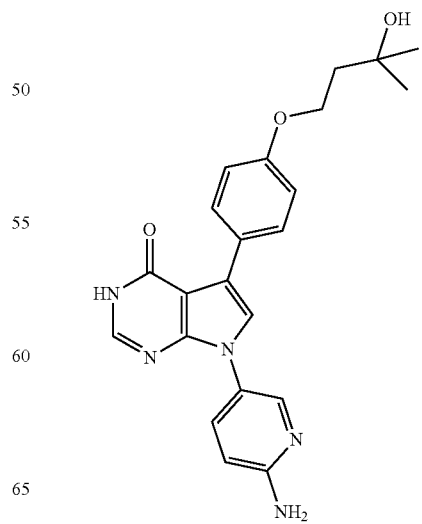

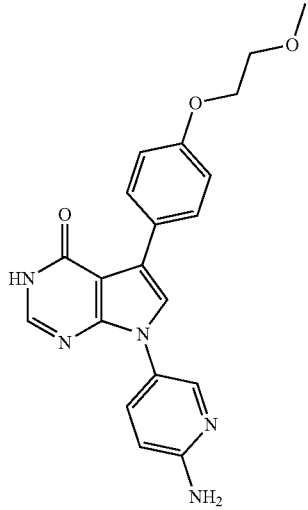
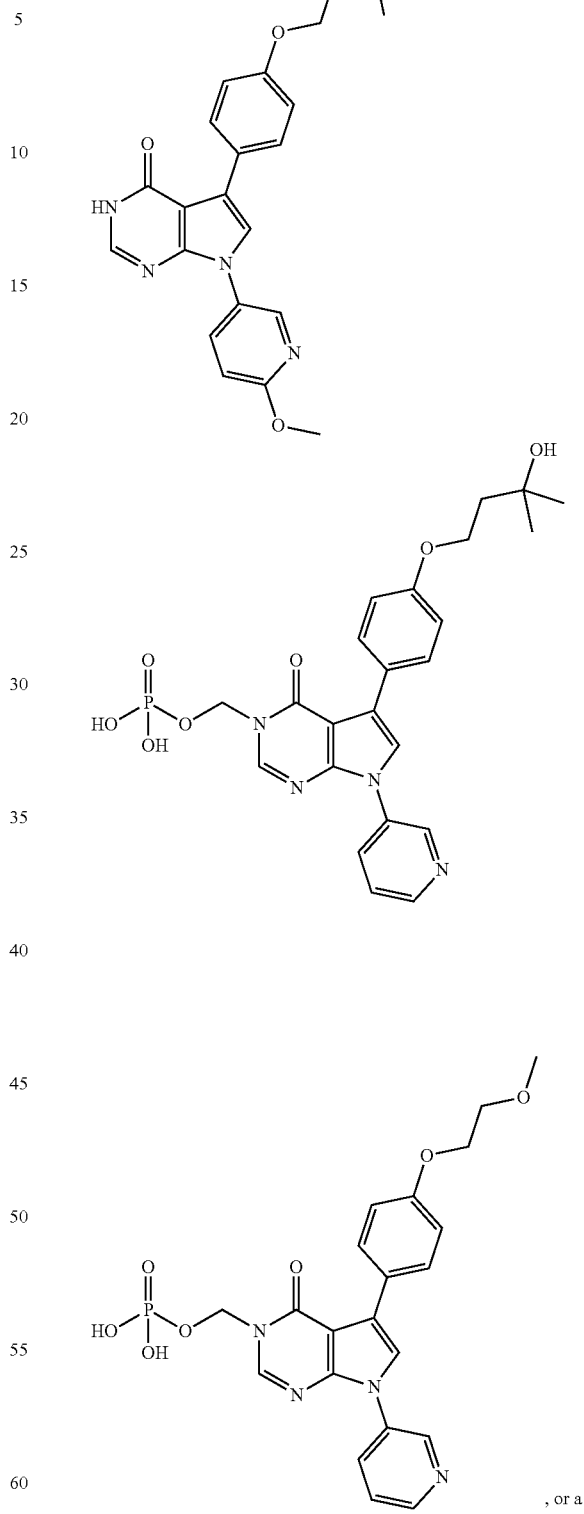
or a pharmaceutically acceptable salt thereof.
26. A pharmaceutical formulation comprising a compound of formula (I), or a pharmaceutically acceptable salt thereof, and a pharmaceutically acceptable excipient;

wherein the compound of formula (I) is:

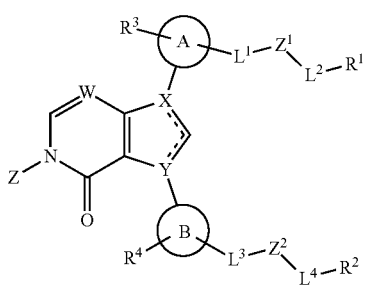

wherein
W is independently selected from N or C;
Z is independently selected from H or —CH$_2$OP (=O)(OH)$_2$;
either X is N and Y is C, or Y is N and X is C;
ring A is independently selected from an aryl and a 5 to 10 membered heterocyclic ring containing 1, 2 or 3 heteroatoms selected from N, O and S;
ring B is independently selected from an aryl and a 5 or 6 membered heterocyclic ring containing 1, 2 or 3 heteroatoms selected from N, O and S;
provided that ring A and ring B of the compound of formula (I) are not both phenyl;
L$^1$ and L$^3$ are independently selected from a bond, —(CR$^a$R$^b$)$_m$—, —(CR$^a$R$^b$)$_m$— or —NH(CR$^a$R$^b$)$_m$—, wherein m is at each occurrence independently selected from 1, 2, 3, or 4;
Z$^1$ is a bond, —NR$^{5a}$—, —O—, —C(O)—, —SO$_2$—, —SO$_2$NR$^{5a}$—, —NR$^{5a}$SO$_2$—, —C(O)NR$^{5a}$—, —NR$^{5a}$C(O)—, —C(O)O—, or —NR$^{5a}$C(O)NR$^{5a}$—;
Z$^2$ is a bond, —NR$^{5b}$—, —O—, —C(O)—, —SO$_2$—, —SO$_2$NR$^{5a}$—, —NR$^{5a}$SO$_2$—, —C(O)NR$^{5a}$—, —NR$^{5b}$C(O)—, or —C(O)O—;
L$^2$ and L$^4$ are independently either a bond or —(CR$^c$R$^d$)$_n$—, wherein n is at each occurrence independently selected from 1, 2, 3, or 4;
R$^1$ is selected from H, halo, C$_{1-6}$ alkyl, C$_{2-6}$ alkenyl, C$_{1-6}$ haloalkyl, —NR$^{6a}$R$^{6b}$, —OR$^{6a}$, OP(=O)(OH)$_2$, —C(O)R$^{6a}$, 5 or 6 membered heteroaryl rings, or 3 to 8 membered heterocycloalkyl ring systems,
wherein the heteroaryl and heterocycloalkyl rings are unsubstituted or substituted with 1 or 2 groups selected from: C$_{1-6}$ alkyl, oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, —C(O)R$^7$, and —NR$^8$(O)R$^7$;
R$^2$ is selected from H, halo, C$_{1-6}$ alkyl, C$_{2-6}$ alkenyl, C$_{1-6}$ haloalkyl, —NR$^{6a}$R$^{6b}$, —OR$^{6a}$ OP(=O)(OH)$_2$, —C(O)R$^{6a}$, —NR$^{5b}$C(O)O—C$_{1-6}$ alkyl, phenyl, 5 or 6 membered heteroaryl rings, 3 to 8 membered cycloalkyl rings, or 3 to 8 membered heterocycloalkyl ring systems,
wherein the phenyl, heteroaryl, cycloalkyl and heterocycloalkyl rings are unsubstituted or substituted with 1 or 2 groups selected from: oxo, halo, OR$^{6a}$, C$_{1-6}$ alkyl, C$_{1-6}$ alkyl substituted with NR$^{6a}$R$^{6b}$, C$_{1-6}$ alkyl substituted with OR$^{6a}$, C(O)R$^{6a}$, —C(O)OR$^g$, and —NR$^8$C(O)R$^7$;
R$^3$ and R$^4$ are independently selected from H, halo, —CN and C$_{1-6}$ alkyl;
R$^{5a}$ and R$^{5b}$ are independently selected at each occurrence, from: H, C$_{1-6}$ alkyl, or C$_{3-6}$ cycloalkyl;

R$^{6a}$ and R$^{6b}$ are, independently selected at each occurrence, from: H, C$_{1-6}$ alkyl, C$_{1-6}$ alkyl substituted with –OR$^e$, C$_{1-6}$ alkyl substituted with —NR$^e$R$^f$, and C$_{3-6}$ cycloalkyl;
R$^7$ is selected from H, —OR$^8$, C$_{1-6}$ alkyl and C$_{3-6}$ cycloalkyl;
R$^8$ is selected from H and C$_{1-6}$ alkyl;
R$^a$, R$^b$, R$^c$ and R$^d$ are, at each occurrence, independently selected from: H, halo, C$_{1-6}$ alkyl, and —OR$^h$, or R$^a$ and R$^b$ or R$^c$ and R$^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and
R$^e$, R$^f$, R$^g$ and R$^h$ are each independently selected at each occurrence from H or C$_{1-6}$ alkyl.

27. A method of treating a disease or medical condition mediated by MAP4K4, wherein the method comprises administering to a patient in need thereof a therapeutically effective amount of a compound of formula (I), or a pharmaceutically acceptable salt thereof:

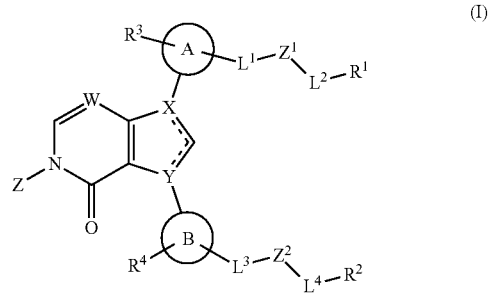

wherein
W is independently selected from N or C;
Z is independently selected from H or —CH$_2$OP (=O)(OH)$_2$;
either X is N and Y is C, or Y is N and X is C;
ring A is independently selected from an aryl and a 5 to 10 membered heterocyclic ring containing 1, 2 or 3 heteroatoms selected from N, O and S;
ring B is independently selected from an aryl and a 5 or 6 membered heterocyclic ring containing 1, 2 or 3 heteroatoms selected from N, O and S;
provided that ring A and ring B of the compound of formula (I) are not both phenyl;
L$^1$ and L$^3$ are independently selected from a bond, —(CR$^a$R$^b$)$_m$—, —(CR$^a$R$^b$)$_m$— or —NH(CR$^a$R$^b$)$_m$—, wherein m is at each occurrence independently selected from 1, 2, 3, or 4;
Z$^1$ is a bond, —NR$^{5a}$—, —O—, —C(O)—, —SO$_2$—, —SO$_2$NR$^{5a}$—, —NR$^{5a}$SO$_2$—, —C(O)NR$^{5a}$—, —NR$^{5a}$C(O)—, —C(O)O—, or —NR$^{5a}$C(O)NR$^{5a}$—;
Z$^2$ is a bond, —NR$^{5b}$—, —O—, —C(O)—, —SO$_2$—, —SO$_2$NR$^{5a}$—, —NR$^{5a}$SO$_2$—, —C(O)NR$^{5a}$—, —NR$^{5b}$C(O)—, or —C(O)O—;
L$^2$ and L$^4$ are independently either a bond or —(CR$^c$R$^d$)$_n$—, wherein n is at each occurrence independently selected from 1, 2, 3, or 4;
R$^1$ is selected from H, halo, C$_{1-6}$ alkyl, C$_{2-6}$ alkenyl, C$_{1-6}$ haloalkyl, —NR$^{6a}$R$^{6b}$, —OR$^{6a}$, OP(=O)(OH)$_2$, —C(O)R$^{6a}$, 5 or 6 membered heteroaryl rings, or 3 to 8 membered heterocycloalkyl ring systems, wherein the heteroaryl and heterocycloalkyl rings are unsubstituted or substituted with 1 or 2 groups selected from: $C_{1-6}$ alkyl, oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, —C(O)R$^7$, and —NR$^8$(O)R$^7$;

$R^2$ is selected from H, halo, $C_{1-6}$ alkyl, $C_{2-6}$ alkenyl, $C_{1-6}$ haloalkyl, —NR$^{6a}$R$^{6b}$, —OR$^{6a}$ OP(=O)(OH)$_2$, —C(O)R$^{6a}$, —NR$^{5b}$C(O)O—$C_{1-6}$ alkyl, phenyl, 5 or 6 membered heteroaryl rings, 3 to 8 membered cycloalkyl rings, or 3 to 8 membered heterocycloalkyl ring systems, wherein the phenyl, heteroaryl, cycloalkyl and heterocycloalkyl rings are unsubstituted or substituted with 1 or 2 groups selected from: oxo, halo, $OR^{6a}$, $C_{1-6}$ alkyl, $C_{1-6}$ alkyl substituted with $NR^{6a}R^{6b}$, $C_{1-6}$ alkyl substituted with $OR^{6a}$, C(O)R$^{6a}$, —C(O)OR$^g$, and —NR$^8$C(O)R$^7$;

$R^3$ and $R^4$ are independently selected from H, halo, —CN and $C_{1-6}$ alkyl;

$R^{5a}$ and $R^{5b}$ are independently selected at each occurrence, from: H, $C_{1-6}$ alkyl, or $C_{3-6}$ cycloalkyl;

$R^{6a}$ and $R^{6b}$ are, independently selected at each occurrence, from: H, $C_{1-6}$ alkyl, $C_{1-6}$ alkyl substituted with –OR$^e$, $C_{1-6}$ alkyl substituted with —NR$^e$R$^f$, and $C_{3-6}$ cycloalkyl;

$R^7$ is selected from H, —OR$^8$, $C_{1-6}$ alkyl and $C_{3-6}$ cycloalkyl;

$R^8$ is selected from H and $C_{1-6}$ alkyl;

$R^a$, $R^b$, $R^c$ and $R^d$ are, at each occurrence, independently selected from: H, halo, $C_{1-6}$ alkyl, and —OR$^h$, or $R^a$ and $R^b$ or $R^c$ and $R^d$ taken together with the atom to which they are attached form a 3 to 6 membered cycloalkyl ring or a 3 to 6 membered heterocycloalkyl ring containing 1 or 2 O, N or S atoms, wherein the cycloalkyl ring is unsubstituted or substituted with 1 or 2 halo groups; and $R^e$, $R^f$, $R^g$ and $R^h$ are each independently selected at each occurrence from H or $C_{1-6}$ alkyl.

28. The method of claim 27, wherein the disease or medical condition is myocardial infarction.

29. The method of claim 27 wherein the disease or medical condition is an infarct.

30. The method of claim 27 wherein the disease or medical condition is selected from: heart muscle cell injury, heart muscle cell injury due to cardiopulmonary bypass, chronic forms of heart muscle cell injury, hypertrophic cardiomyopathies, dilated cardiomyopathies, mitochondrial cardiomyopathies, cardiomyopathies due to genetic conditions; cardiomyopathies due to high blood pressure; cardiomyopathies due to heart tissue damage from a previous heart attack; cardiomyopathies due to chronic rapid heart rate; cardiomyopathies due to heart valve problems; cardiomyopathies due to metabolic disorders; cardiomyopathies due to nutritional deficiencies of essential vitamins or minerals; cardiomyopathies due to alcohol consumption; cardiomyopathies due to use of cocaine, amphetamines or anabolic steroids; cardiomyopathies due to radiotherapy to treat cancer; cardiomyopathies due to certain infections which may injure the heart and trigger cardiomyopathy; cardiomyopathies due to hemochromatosis; cardiomyopathies due to sarcoidosis; cardiomyopathies due to amyloidosis; cardiomyopathies due to connective tissue disorders; drug- or radiation-induced cardiomyopathies; idiopathic or cryptogenic cardiomyopathies; other forms of ischemic injury, including but not limited to ischemia-reperfusion injury, ischemia stroke, renal artery occlusion, and global ischemia-reperfusion injury (cardiac arrest); cardiac muscle cell necrosis; or cardiac muscle cell apoptosis.

\* \* \* \* \*